(12) United States Patent
Julien et al.

(10) Patent No.: US 7,732,186 B2
(45) Date of Patent: Jun. 8, 2010

(54) RECOMBINANT METHODS AND MATERIALS FOR PRODUCING EPOTHILONE AND EPOTHILONE DERIVATIVES

(75) Inventors: Bryan Julien, Oakland, CA (US); Leonard Katz, Hayward, CA (US); Chaitan Khosla, Palo Alto, CA (US); Li Tang, Foster City, CA (US); Rainer Ziermann, San Mateo, CA (US)

(73) Assignee: Kosan Biosciences, Inc., Princeton, NJ (US)

( * ) Notice: Subject to any disclaimer, the term of this patent is extended or adjusted under 35 U.S.C. 154(b) by 103 days.

(21) Appl. No.: 11/932,927

(22) Filed: Oct. 31, 2007

(65) Prior Publication Data

US 2009/0170172 A1    Jul. 2, 2009

Related U.S. Application Data

(63) Continuation of application No. 10/849,462, filed on May 18, 2004, now Pat. No. 7,402,421, which is a continuation of application No. 09/724,878, filed on Nov. 28, 2000, now Pat. No. 7,129,071, which is a continuation of application No. 09/443,501, filed on Nov. 19, 1999, now Pat. No. 6,303,342.

(60) Provisional application No. 60/130,560, filed on Apr. 22, 1999, provisional application No. 60/122,620, filed on Mar. 3, 1999, provisional application No. 60/119,386, filed on Feb. 10, 1999, provisional application No. 60/109,401, filed on Nov. 20, 1998.

(51) Int. Cl.
    C12N 1/20 (2006.01)

(52) U.S. Cl. .............................. 435/252.3; 435/252.34; 435/252.35

(58) Field of Classification Search .................. None
See application file for complete search history.

(56) References Cited

U.S. PATENT DOCUMENTS

| | | | |
|---|---|---|---|
| 4,916,138 A | 4/1990 | Ueda et al. |
| 5,605,793 A | 2/1997 | Stemmer |
| 5,672,491 A | 9/1997 | Khosla et al. |
| 5,686,295 A | 11/1997 | Jaoua et al. |
| 5,712,146 A | 1/1998 | Khosla et al. |
| 5,776,735 A | 7/1998 | Denoya et al. |

(Continued)

FOREIGN PATENT DOCUMENTS

DE    4138042    5/1993

(Continued)

OTHER PUBLICATIONS

An, J. and Kim, Y. (1998). Eur J. Biochem 274 (52): 395-402.

(Continued)

*Primary Examiner*—Manjunath N Rao
*Assistant Examiner*—William W Moore
(74) *Attorney, Agent, or Firm*—Hong Liu; Fox Rothschild LLP

(57) ABSTRACT

Recombinant nucleic acids that encode all or a portion of the epothilone polyketide synthase (PKS) are used to express recombinant PKS genes in host cells for the production of epothilones, epothilone derivatives, and polyketides that are useful as cancer chemotherapeutics, fungicides, and immunosuppressants.

10 Claims, 8 Drawing Sheets

U.S. PATENT DOCUMENTS

| | | | |
|---|---|---|---|
| 5,783,431 | A | 7/1998 | Peterson et al. |
| 5,811,238 | A | 9/1998 | Stemmer et al. |
| 5,824,513 | A | 10/1998 | Katz et al. |
| 5,830,721 | A | 11/1998 | Stemmer et al. |
| 5,830,750 | A | 11/1998 | Khosla et al. |
| 5,843,718 | A | 12/1998 | Khosla et al. |
| 5,969,145 | A | 10/1999 | Schinzer et al. |
| 6,022,731 | A | 2/2000 | Khosla et al. |
| 6,033,883 | A | 3/2000 | Barr et al. |
| 6,090,601 | A | 7/2000 | Gustafsson et al. |
| 6,121,029 | A | 9/2000 | Schupp et al. |
| 6,242,469 | B1 | 6/2001 | Danishefsky et al. |
| 6,280,999 | B1 * | 8/2001 | Gustafsson et al. ....... 435/252.3 |
| 6,300,355 | B1 | 10/2001 | Danishefsky et al. |
| 6,303,342 | B1 | 10/2001 | Julien et al. |
| 6,346,404 | B1 | 2/2002 | Schupp et al. |
| 6,355,457 | B1 | 3/2002 | Schupp et al. |
| 6,355,458 | B1 | 3/2002 | Schupp et al. |
| 6,355,459 | B1 | 3/2002 | Schupp et al. |
| 6,358,719 | B1 | 3/2002 | Schupp et al. |
| 6,383,787 | B1 | 5/2002 | Schupp et al. |
| 6,410,301 | B1 | 6/2002 | Julien et al. |
| 6,583,290 | B1 * | 6/2003 | Julien et al. .................. 548/203 |
| 6,858,411 | B1 * | 2/2005 | Julien et al. .................... 435/76 |
| 6,921,650 | B1 * | 7/2005 | Julien et al. .................... 435/76 |
| 7,129,071 | B1 * | 10/2006 | Julien et al. .................. 435/193 |
| 7,402,421 | B2 * | 7/2008 | Julien et al. ............... 435/252.3 |

FOREIGN PATENT DOCUMENTS

| | | |
|---|---|---|
| EP | 0423714 | 6/1994 |
| EP | 0428169 | 3/1995 |
| WO | WO 93/10121 | 5/1993 |
| WO | WO 97/02358 | 1/1997 |
| WO | WO 97/13845 | 4/1997 |
| WO | WO 97/19086 | 5/1997 |
| WO | WO 98/08849 | 3/1998 |
| WO | WO 98/22461 | 5/1998 |
| WO | WO 98/25929 | 6/1998 |
| WO | WO 98/27203 | 6/1998 |
| WO | WO 98/49315 | 11/1998 |
| WO | WO 99/01124 | 1/1999 |
| WO | WO 99/02514 | 1/1999 |
| WO | WO 99/02669 | 1/1999 |
| WO | WO 99/03986 | 1/1999 |
| WO | WO 99/07692 | 2/1999 |
| WO | WO 99/43320 | 2/1999 |
| WO | WO 99/15047 | 4/1999 |
| WO | WO 99/27890 | 6/1999 |
| WO | WO 99/39694 | 8/1999 |
| WO | WO 99/40047 | 8/1999 |
| WO | WO 99/42602 | 8/1999 |
| WO | WO 99/43653 | 9/1999 |
| WO | WO 99/54318 | 10/1999 |
| WO | WO 99/54319 | 10/1999 |
| WO | WO 99/54330 | 10/1999 |
| WO | WO 99/65913 | 12/1999 |
| WO | WO 99/66028 | 12/1999 |
| WO | WO 99/67252 | 12/1999 |
| WO | WO 99/67253 | 12/1999 |
| WO | WO 00/00485 | 1/2000 |
| WO | WO 00/01838 | 1/2000 |
| WO | WO 00/22139 | 4/2000 |
| WO | 00/31247 | 6/2000 |

OTHER PUBLICATIONS

Arslanian, R. L., et al. (2002). J. Natural Products 65(4):570-572.
Balog D., et al., (1996). Angew Chem Int Ed Engl 35 (23/24):2801-2803.
Balog D., et al., (1998). Angew Chem Int Ed Engl 37 (19):2675-2678.
Betlach, et al., (1998). Biochem 37: 14937.
Beyer et al., (1999), Biochimica et Biophysica Acta 1445 (2):185-195.
Bierman, et al., (1992). Gene 116:43-49.
Bollag, D. et al., (1995). Cancer Res 55:2325-2333.
Bretscher, A.P. et al, (1978). J. Bacteriology 133(2):763-768.
Campos and Zusman, (1975). Proc Natl Acad Sci USA 72:518-522.
Campos, et al., (1978). J. Mol Biol 119:167-168.
Caspers, et al., (1994). Cellular and Molecular Biology 40 (5): 635-644.
Chou, T.C. et al. (1998). Proc Natl Acad Sci USA 95 (16):9642-9647.
Gerth, K. et al. (1996). J. Antibiotics 49:560-563.
Frykman, S. et al. (2002). J. Industrial Microbiology & Biotechnology 28(1):17-20.
Hahn D., et al., (1991). J. Bact. 173:5573-5577.
Hamilton, C. et al. (1989). J. Bact 171(9):4617-4622.
Hodgkin and Kaiser. (1979). Mol Gen Genet 171:177-191.
Hofle, et al. (1996). Angew Chem Int Ed Engl. 35(13/14):1567-1569.
Hondo, T. et al. (1987). Transplantation Proceedings XIX(5) Suppl. 6:17-22.
Jacobsen, et al., (1998). Biochemistry 37:4928-4934.
Jaoua, et al. (1992). Plasmid 28:157-165.
Kafeshi, et al. (1995). Mol Microbiol 15:483-494.
Kaiser, (1979). Proc. Natl. Acad. Sci. USA 76:5952-5956.
Katz, et al., (1983). J. Gen Microbiol 129:2703-2714.
Keiser and Melton, (1988). Gene 65:83-91.
Lau, J. et al. (2002). Biotechnology and Bioengineering 79(3):280-288.
Link, A. et al. (1997). J Bact 179(20):6228-6237.
Lydiate, et al., (1985). Gene 35:223-235.
Magrini, et al. (1999). J Bact 181 (13):4062-4070.
Sheng, et al., (1995). Nucleic Acids Res 23:1990-1996.
Shimkets, L.J., (1993). Basic and Applied Molecular Genetics 5th ASM pp. 85-96.
Silakowski, B., et al., (199). J Biol Chem 274(52):37391-37399.
Smokvina, et al., (1990). Gene 94:53-59.
Stassi, et al., (1998). Appl Microbiol. Biotechnol 49:725-731.
Strong, S. et al. (1997). Nucleic Acids Res 19:3959-3961.
Su, et al., (1997). Angew Chem Int Ed Engl 36 (19): 2093-2096.
Su, et al., (1997). Angew Chem Int Ed Engl 36 (7): 757-759.
Tang, L. et al. (2000). Science 287:640-642.
Thompson, et al. (1982). Gene 20:51-62.
Ueki, T. et al. (1996). Gene 183:153-157.
Vara, et al., (1989). J Bacteriol 171:5782-5791.
Varon et al. (1992). Antimicrobial Agents and Chemotherapy 36(10):2316-2321.
Witkowski, et al., (1999). Biochem 38(36): 11643-11650.
Wu and Kaiser. (1997). J Bact 179 (24):7748-7758.
Meng, et al., (1997). JACS 119 (42):10073-10092.
Molnar, I., et al., (2000). Chemistry & Biology 7 (2):97-109.
Muth, et al., (1989). Mol Gen Genet 219:341-348.
Nicolaou, K. C., et al., (1997). Angew Chem Int Ed Engl 36:2097-2103.
Nicolaou, K. C., et al., (1998). Angew Chem Int Ed Engl 37(15):2014-2045.
Oliynyk et al. (1996). Chemistry & Biology 3:833-839.
Paitan et al., (1999). J. Molecular Biology 286:465-474.
Pfeifer, B. A., et al., (2001). Microbiology and Molecular Biology Reviews 65(1):106-118.
Regentin, R., et al., (2001). Abstracts of Papers American Chemical Society 221(1-2):BIOT 61.
Salmi, et al., (1998). J Bact 180 (3):614-621.
Scholz, et al. (1989). Gene 75:271-278.
Servin-Gonzales, (1993). Plasmid 30:131-140.

* cited by examiner

R=

X=CH₂,O,S
Y=CH₂,O,S

X=H,Me,Et,CH₂OH,Br
Y=O,S

X=H,Me,Et,Br,OH
Y=NH,O,S

X=NO₂,CN,Me,O-alkyl,halo,etc.
Y=CH,N

X=NO₂,CN,alkyl,aryl,halo,O-alkyl,etc.
Y=CH,N

X=NO₂,CN,alkyl,aryl,halo,O-alkyl,etc.
Y=CH,N

X=CH,N
Y=CH,N

X=CH₂,O,S,NH,N-alkyl,N-aryl
Y=CH₂,O,S,NH,N-alkyl,N-aryl

X=CH₂,O,S,NH,N-alkyl,N-aryl
Y=CH₂,O,S,NH,N-alkyl,N-aryl

RECOMBINANT METHODS AND MATERIALS FOR PRODUCING EPOTHILONE AND EPOTHILONE DERIVATIVES

CROSS-REFERENCE TO RELATED APPLICATIONS

This application is a continuation of U.S. Ser. No. 10/849,462, filed 18 May 2004, now issued as U.S. Pat. No. 7,402,421, which is a continuation of U.S. Ser. No. 09/724,878, filed 28 Nov. 2000, issued as U.S. Pat. No. 7,129,071, which is a continuation of U.S. Ser. No. 09/443,501, filed 19 Nov. 1999, issued as U.S. Pat. No. 6,303,342, which claims benefit of U.S. provisional application Ser. Nos. 60/130,560, filed 22 Apr. 1999; 60/122,620, filed 3 Mar. 1999; 60/119,386, filed 10 Feb. 1999; and 60/109,401, filed 20 Nov. 1998, each of which is incorporated herein by reference.

REFERENCE TO GOVERNMENT FUNDING

This invention was supported in part by SBIR grant 1R43-CA79228-01. The U.S. government has certain rights in this invention.

FIELD OF THE INVENTION

The present invention provides recombinant methods and materials for producing epothilone and epothilone derivatives. The invention relates to the fields of agriculture, chemistry, medicinal chemistry, medicine, molecular biology, and pharmacology.

BACKGROUND OF THE INVENTION

The epothilones were first identified by Gerhard Hofle and colleagues at the National Biotechnology Research Institute as an antifungal activity extracted from the myxobacterium *Sorangium cellulosum* (see K. Gerth et al., 1996, J. Antibiotics 49: 560-563 and Germany Patent No. DE 41 38 042). The epothilones were later found to have activity in a tubulin polymerization assay (see D. Bollag et al., 1995, Cancer Res. 55:2325-2333) to identify antitumor agents and have since been extensively studied as potential antitumor agents for the treatment of cancer.

The chemical structure of the epothilones produced by *Sorangium cellulosum* strain So ce 90 was described in Hofle et al., 1996, Epothilone A and B—novel 16-membered macrolides with cytotoxic activity: isolation, crystal structure, and conformation in solution, Angew. Chem. Int. Ed. Engl. 35(13/14): 1567-1569, incorporated herein by reference. The strain was found to produce two epothilone compounds, designated A (R=H) and B (R=CH$_3$), as shown below, which showed broad cytotoxic activity against eukaryotic cells and noticeable activity and selectivity against breast and colon tumor cell lines.

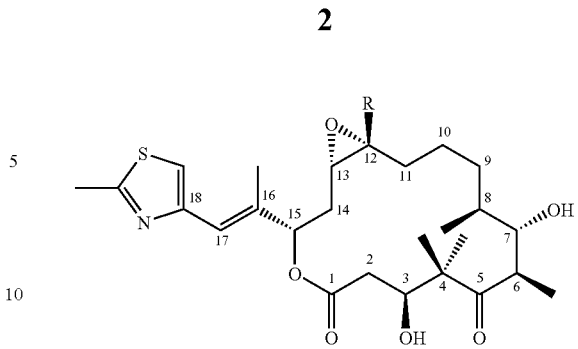

The desoxy counterparts of epothilones A and B, also known as epothilones C (R=H) and D (R=CH$_3$), are known to be less cytotoxic, and the structures of these epothilones are shown below.

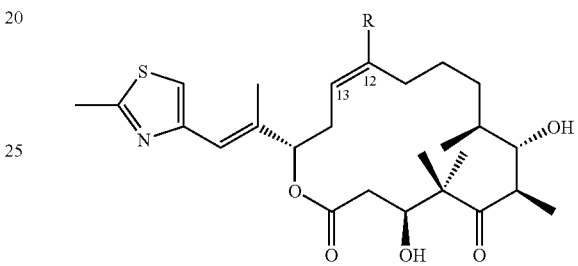

Two other naturally occurring epothilones have been described. These are epothilones E and F, in which the methyl side chain of the thiazole moiety of epothilones A and B has been hydroxylated to yield epothilones E and F, respectively.

Because of the potential for use of the epothilones as anticancer agents, and because of the low levels of epothilone produced by the native So ce 90 strain, a number of research teams undertook the effort to synthesize the epothilones. This effort has been successful (see Balog et al., 1996, Total synthesis of (−)-epothilone A, Angew. Chem. Int. Ed. Engl. 35(23/24): 2801-2803; Su et al., 1997, Total synthesis of (−)-epothilone B: an extension of the Suzuki coupling method and insights into structure-activity relationships of the epothilones, Angew. Chem. Int. Ed. Engl. 36(7): 757-759; Meng et al., 1997, Total syntheses of epothilones A and B, JACS 119(42): 10073-10092; and Balog et al., 1998, A novel aldol condensation with 2-methyl-4-pentenal and its application to an improved total synthesis of epothilone B, Angew. Chem. Int. Ed. Engl. 37(19): 2675-2678, each of which is incorporated herein by reference). Despite the success of these efforts, the chemical synthesis of the epothilones is tedious, time-consuming, and expensive. Indeed, the methods have been characterized as impractical for the full-scale pharmaceutical development of an epothilone.

A number of epothilone derivatives, as well as epothilones A-D, have been studied in vitro and in vivo (see Su et al., 1997, Structure-activity relationships of the epothilones and the first in vivo comparison with paclitaxel, Angew. Chem. Int. Ed. Engl. 36(19): 2093-2096; and Chou et al., August 1998, Desoxyepothilone B: an efficacious microtubule-targeted antitumor agent with a promising in vivo profile relative to epothilone B, Proc. Natl. Acad. Sci. USA 95: 9642-9647, each of which is incorporated herein by reference). Additional epothilone derivatives and methods for synthesizing epothilones and epothilone derivatives are described in PCT patent publication Nos. 99/54330, 99/54319, 99/54318, 99/43653, 99/43320, 99/42602, 99/40047, 99/27890, 99/07692, 99/02514, 99/01124, 98/25929, 98/22461, 98/08849, and 97/19086; U.S. Pat. No. 5,969,145; and Germany patent publication No. DE 41 38 042, each of which is incorporated herein by reference.

There remains a need for economical means to produce not only the naturally occurring epothilones but also the derivatives or precursors thereof, as well as new epothilone derivatives with improved properties. There remains a need for a host cell that produces epothilones or epothilone derivatives that is easier to manipulate and ferment than the natural producer Sorangium cellulosum. The present invention meets these and other needs.

SUMMARY OF THE INVENTION

In one embodiment, the present invention provides recombinant DNA compounds that encode the proteins required to produce epothilones A, B, C, and D. The present invention also provides recombinant DNA compounds that encode portions of these proteins. The present invention also provides recombinant DNA compounds that encode a hybrid protein, which hybrid protein includes all or a portion of a protein involved in epothilone biosynthesis and all or a portion of a protein involved in the biosynthesis of another polyketide or non-ribosomal-derived peptide. In a preferred embodiment, the recombinant DNA compounds of the invention are recombinant DNA cloning vectors that facilitate manipulation of the coding sequences or recombinant DNA expression vectors that code for the expression of one or more of the proteins of the invention in recombinant host cells.

In another embodiment, the present invention provides recombinant host cells that produce a desired epothilone or epothilone derivative. In one embodiment, the invention provides host cells that produce one or more of the epothilones or epothilone derivatives at higher levels than produced in the naturally occurring organisms that produce epothilones. In another embodiment, the invention provides host cells that produce mixtures of epothilones that are less complex than the mixtures produced by naturally occurring host cells. In another embodiment, the present invention provides non-Sorangium recombinant host cells that produce an epothilone or epothilone derivative.

In a preferred embodiment, the host cells of the invention produce less complex mixtures of epothilones than do naturally occurring cells that produce epothilones. Naturally occurring cells that produce epothilones typically produce a mixture of epothilones A, B, C, D, E, and F. The table below summarizes the epothilones produced in different illustrative host cells of the invention.

| Cell Type | Epothilones Produced | Epothilones Not Produced |
|---|---|---|
| 1 | A, B, C, D, E, F | — |
| 2 | A, C, E | B, D, F |
| 3 | B, D, F | A, C, E |
| 4 | A, B, C, D | E, F |
| 5 | A, C | B, D, E, F |
| 6 | C | A, B, D, E, F |
| 7 | B, D | A, C, E, F |
| 8 | D | A, B, C, E, F |

In addition, cell types may be constructed which produce only the newly discovered epothilones G and H, further discussed below, and one or the other of G and H or both in combination with the downstream epothilones. Thus, it is understood, based on the present invention, that the biosynthetic pathway which relates the naturally occurring epothilones is, respectively, G→C→A→E and H→D→B→F. Appropriate enzymes may also convert members of each pathway to the corresponding member of the other.

Thus, the recombinant host cells of the invention also include host cells that produce only one desired epothilone or epothilone derivative.

In another embodiment, the invention provides Sorangium host cells that have been modified genetically to produce epothilones either at levels greater than those observed in naturally occurring host cells or as less complex mixtures of epothilones than produced by naturally occurring host cells, or produce an epothilone derivative that is not produced in nature. In a preferred embodiment, the host cell produces the epothilones at equal to or greater than 20 mg/L.

In another embodiment, the recombinant host cells of the invention are host cells other than Sorangium cellulosum that have been modified genetically to produce an epothilone or an epothilone derivative. In a preferred embodiment, the host cell produces the epothilones at equal to or greater than 20 mg/L. In a more preferred embodiment, the recombinant host cells are Myxococcus, Pseudomonas, or Streptomyces host cells that produce the epothilones or an epothilone derivative at equal to or greater than 20 mg/L.

In another embodiment, the present invention provides novel compounds useful in agriculture, veterinary practice, and medicine. In one embodiment, the compounds are useful as fungicides. In another embodiment, the compounds are useful in cancer chemotherapy. In a preferred embodiment, the compound is an epothilone derivative that is at least as potent against tumor cells as epothilone B or D. In another embodiment, the compounds are useful as immunosuppressants. In another embodiment, the compounds are useful in the manufacture of another compound. In a preferred embodiment, the compounds are formulated in a mixture or solution for administration to a human or animal.

These and other embodiments of the invention are described in more detail in the following description, the examples, and claims set forth below.

DETAILED DESCRIPTION OF THE INVENTION

The present invention provides the genes and proteins that synthesize the epothilones in *Sorangium cellulosum* in recombinant and isolated form. As used herein, the term recombinant refers to a compound or composition produced by human intervention, typically by specific and directed manipulation of a gene or portion thereof. The term isolated refers to a compound or composition in a preparation that is substantially free of contaminating or undesired materials or, with respect to a compound or composition found in nature, substantially free of the materials with which that compound or composition is associated in its natural state. The epothilones (epothilone A, B, C, D, E, and F) and compounds structurally related thereto (epothilone derivatives) are potent cytotoxic agents specific for eukaryotic cells. These compounds have application as anti-fungals, cancer chemotherapeutics, and immunosuppressants. The epothilones are produced at very low levels in the naturally occurring *Sorangium cellulosum* cells in which they have been identified. Moreover, *S. cellulosum* is very slow growing, and fermentation of *S. cellulosum* strains is difficult and time-consuming. One important benefit conferred by the present invention is the ability simply to produce an epothilone or epothilone derivative in a non-*S. cellulosum* host cell. Another advantage of the present invention is the ability to produce the epothilones at higher levels and in greater amounts in the recombinant host cells provided by the invention than possible in the naturally occurring epothilone producer cells. Yet another advantage is the ability to produce an epothilone derivative in a recombinant host cell.

The isolation of recombinant DNA encoding the epothilone biosynthetic genes resulted from the probing of a genomic library of *Sorangium cellulosum* SMP44 DNA. As described more fully in Example 1 below, the library was prepared by partially digesting *S. cellulosum* genomic DNA with restriction enzyme SauIIIA1 and inserting the DNA fragments generated into BamHI-digested Supercos™ cosmid DNA (Stratagene). Cosmid clones containing epothilone gene sequences were identified by probing with DNA probes specific for sequences from PKS genes and reprobing with secondary probes comprising nucleotide sequences identified with the primary probes.

Figure 1:
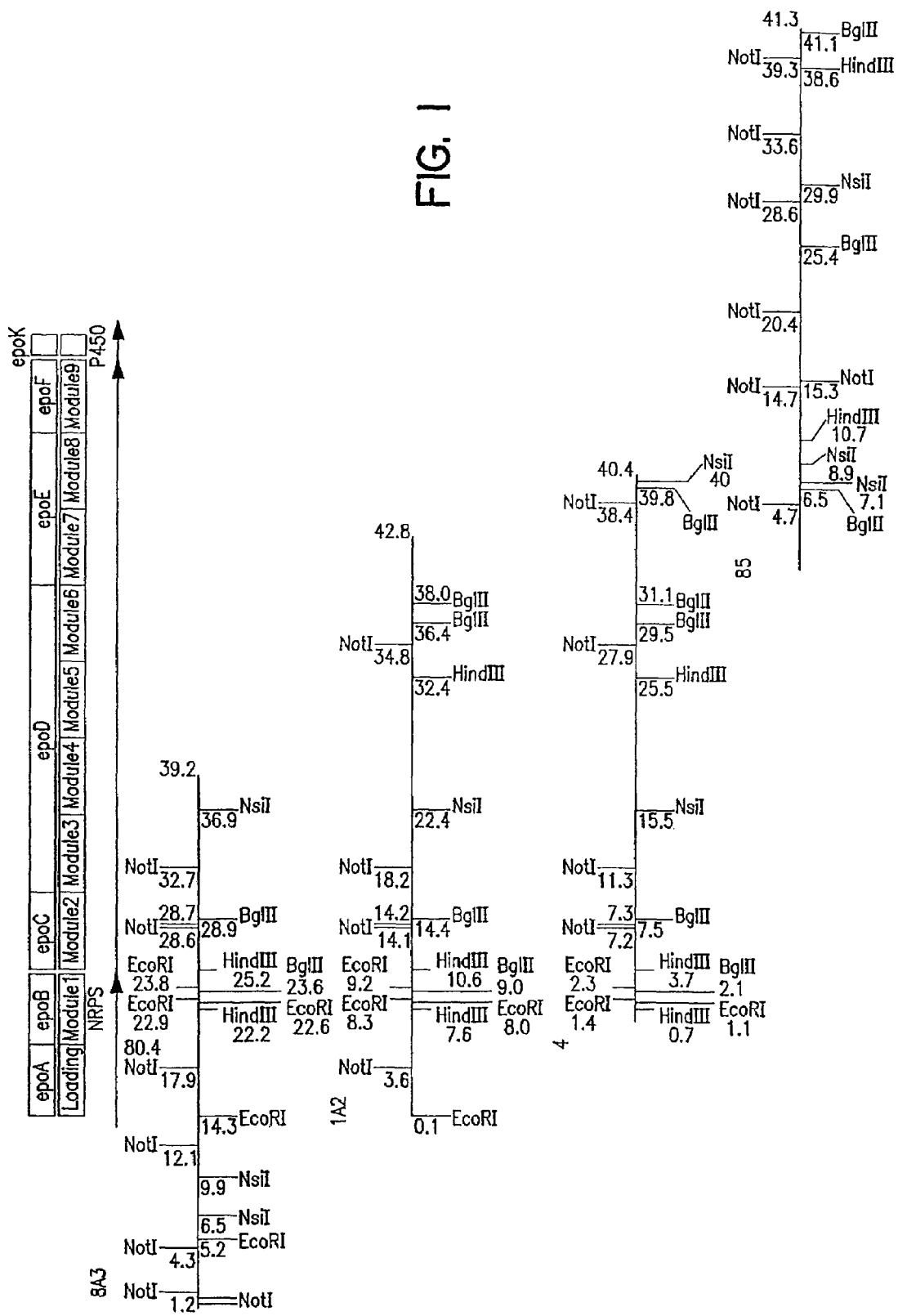
FIG. 1 shows a restriction site map of the insert Sorangium cellulosum genomic DNA in four overlapping cosmid clones (designated 8A3, 1A2, 4, and 85 and corresponding to pKOS35-70.8A3, pKOS35-70.1A2, pKOS35-70.4, and pKOS35-79.85, respectively) spanning the epothilone gene cluster. A functional map of the epothilone gene cluster is also shown. The loading domain (Loading, epoA), the non-ribosomal peptide synthase (NRPS, Module 1, epoB) module, and each module (Modules 2 through 9, epoC, epoD, epoE, and epoF) of the remaining eight modules of the epothilone synthase gene are shown, as is the location of the epoK gene that encodes a cytochrome P450-like epoxidation enzyme.

Four overlapping cosmid clones were identified by this effort. These four cosmids were deposited with the American Type Culture Collection (ATCC), Manassas, Va., USA, under the terms of the Budapest Treaty, and assigned ATCC accession numbers. The clones (and accession numbers) were designated as cosmids pKOS35-70.1A2 (ATCC 203782), pKOS35-70.4 (ATCC 203781), pKOS35-70.8A3 (ATCC 203783), and pKOS35-79.85 (ATCC 203780). The cosmids contain insert DNA that completely spans the epothilone gene cluster. A restriction site map of these cosmids is shown in FIG. 1. FIG. 1 also provides a function map of the epothilone gene cluster, showing the location of the six epothilone PKS genes and the epoK P450 epoxidase gene.

The epothilone PKS genes, like other PKS genes, are composed of coding sequences organized to encode a loading domain, a number of modules, and a thioesterase domain. As described more fully below, each of these domains and modules corresponds to a polypeptide with one or more specific functions. Generally, the loading domain is responsible for binding the first building block used to synthesize the polyketide and transferring it to the first module. The building blocks used to form complex polyketides are typically acylthioesters, most commonly acetyl, propionyl, malonyl, methylmalonyl, and ethylmalonyl CoA. Other building blocks include amino acid-like acylthioesters. PKSs catalyze the biosynthesis of polyketides through repeated, decarboxylative Claisen condensations between the acylthioester building blocks. Each module is responsible for binding a building block, performing one or more functions on that building block, and transferring the resulting compound to the next module. The next module, in turn, is responsible for attaching the next building block and transferring the growing compound to the next module until synthesis is complete. At that point, an enzymatic thioesterase (TE) activity cleaves the polyketide from the PKS.

Such modular organization is characteristic of the class of PKS enzymes that synthesize complex polyketides and is well known in the art. Recombinant methods for manipulating modular PKS genes are described in U.S. Pat. Nos. 5,672,491; 5,712,146; 5,830,750; and 5,843,718; and in PCT patent publication Nos. 98/49315 and 97/02358, each of which is incorporated herein by reference. The polyketide known as 6-deoxyerythronolide B (6-dEB) is synthesized by a PKS that is a prototypical modular PKS enzyme. The genes, known as eryAI, eryAI, and eryAII, that code for the multi-subunit protein known as deoxyerythronolide B synthase or DEBS (each subunit is known as DEBS1, DEBS2, or DEBS3) that synthesizes 6-dEB are described in U.S. Pat. Nos. 5,712,146 and 5,824,513, incorporated herein by reference.

The loading domain of the DEBS PKS consists of an acyltransferase (AT) and an acyl carrier protein (ACP). The AT of the DEBS loading domain recognizes propionyl CoA (other loading domain ATs can recognize other acyl-CoAs, such as acetyl, malonyl, methylmalonyl, or butyryl CoA) and transfers it as a thioester to the ACP of the loading domain. Concurrently, the AT on each of the six extender modules recognizes a methylmalonyl CoA (other extender module ATs can recognize other CoAs, such as malonyl or alpha-substituted malonyl CoAs, i.e., malonyl, ethylmalonyl, and 2-hydroxymalonyl CoA) and transfers it to the ACP of that module to form a thioester. Once DEBS is primed with acyl- and methylmalonyl-ACPs, the acyl group of the loading domain migrates to form a thioester (trans-esterification) at the KS of the first module; at this stage, module one possesses an acyl-KS adjacent to a methylmalonyl ACP. The acyl group derived from the DEBS loading domain is then covalently attached to the alpha-carbon of the extender group to form a carbon-carbon bond, driven by concomitant decarboxylation, and generating a new acyl-ACP that has a backbone two carbons longer than the loading unit (elongation or extension). The growing polyketide chain is transferred from the ACP to the KS of the next module of DEBS, and the process continues.

The polyketide chain, growing by two carbons for each module of DEBS, is sequentially passed as a covalently bound thioester from module to module, in an assembly line-like process. The carbon chain produced by this process alone would possess a ketone at every other carbon atom, producing a polyketone, from which the name polyketide arises. Commonly, however, additional enzymatic activities modify the beta keto group of each two carbon unit just after it has been added to the growing polyketide chain but before it is transferred to the next module. Thus, in addition to the minimal module containing KS, AT, and ACP necessary to form the carbon-carbon bond, modules may contain a ketoreductase (KR) that reduces the keto group to an alcohol. Modules may also contain a KR plus a dehydratase (DH) that dehydrates the alcohol to a double bond. Modules may also contain a KR, a DH, and an enoylreductase (ER) that converts the double bond to a saturated single bond using the beta carbon as a methylene function. The DEBS modules include those with only a KR domain, only an inactive KR domain, and with all three KR, DH, and ER domains.

Once a polyketide chain traverses the final module of a PKS, it encounters the releasing domain or thioesterase found at the carboxyl end of most PKSs. Here, the polyketide is cleaved from the enzyme and, for most but not all polyketides, cyclized. The polyketide can be modified further by tailoring or modification enzymes; these enzymes add carbohydrate groups or methyl groups, or make other modifications, i.e., oxidation or reduction, on the polyketide core molecule. For example, 6-dEB is hydroxylated, methylated, and glycosylated (glycosidated) to yield the well known antibiotic erythromycin A in the *Saccharopolyspora erythraea* cells in which it is produced naturally.

While the above description applies generally to modular PKS enzymes and specifically to DEBS, there are a number of variations that exist in nature. For example, many PKS enzymes comprise loading domains that, unlike the loading domain of DEBS, comprise an "inactive" KS domain that functions as a decarboxylase. This inactive KS is in most instances called $KS^Q$, where the superscript is the single-letter abbreviation for the amino acid (glutamine) that is present instead of the active site cysteine required for ketosynthase activity. The epothilone PKS loading domain contains a $KS^Y$ domain not present in other PKS enzymes for which amino acid sequence is currently available in which the amino acid tyrosine has replaced the cysteine. The present invention provides recombinant DNA coding sequences for this novel KS domain.

Another important variation in PKS enzymes relates to the type of building block incorporated. Some polyketides, including epothilone, incorporate an amino acid derived building block. PKS enzymes that make such polyketides require specialized modules for incorporation. Such modules are called non-ribosomal peptide synthetase (NRPS) modules. The epothilone PKS, for example, contains an NRPS module. Another example of a variation relates to additional activities in a module. For example, one module of the epothilone PKS contains a methyltransferase (MT) domain, a heretofore unknown domain of PKS enzymes that make modular polyketides.

The complete nucleotide sequence of the coding sequence of the open reading frames (ORFs) of the epothilone PKS genes and epothilone tailoring (modification) enzyme genes is provided in Example 1, below. This sequence information together with the information provided below regarding the locations of the open reading frames of the genes within that sequence provides the amino acid sequence of the encoded proteins. Those of skill in the art will recognize that, due to the degenerate nature of the genetic code, a variety of DNA compounds differing in their nucleotide sequences can be used to encode a given amino acid sequence of the invention. The native DNA sequence encoding the epothilone PKS and epothilone modification enzymes of *Sorangium cellulosum* is shown herein merely to illustrate a preferred embodiment of the invention. The present invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity and, in some instances, even an improvement of a desired activity. The present invention includes such polypeptides with alternate amino acid sequences, and the amino acid sequences shown merely illustrate preferred embodiments of the invention.

The present invention provides recombinant genes for the production of epothilones. The invention is exemplified by the cloning, characterization, and manipulation of the epothilone PKS and modification enzymes of *Sorangium cellulosum* SMP44. The description of the invention and the recombinant vectors deposited in connection with that description enable the identification, cloning, and manipulation of epothilone PKS and modification enzymes from any naturally occurring host cell that produces an epothilone. Such host cells include other *S. cellulosum* strains, such as So ce 90, other *Sorangium* species, and non-*Sorangium* cells. Such identification, cloning, and characterization can be conducted by those of ordinary skill in accordance with the present invention using standard methodology for identifying homologous DNA sequences and for identifying genes that encode a protein of function similar to a known protein. Moreover, the present invention provides recombinant epothilone PKS and modification enzyme genes that are synthesized de novo or are assembled from non-epothilone PKS genes to provide an ordered array of domains and modules in one or more proteins that assemble to form a PKS that produces epothilone or an epothilone derivative.

The recombinant nucleic acids, proteins, and peptides of the invention are many and diverse. To facilitate an understanding of the invention and the diverse compounds and methods provided thereby, the following discussion describes various regions of the epothilone PKS and corresponding coding sequences. This discussion begins with a general discussion of the genes that encode the PKS, the location of the various domains and modules in those genes, and the location of the various domains in those modules. Then, a more detailed discussion follows, focusing first on the loading domain, followed by the NRPS module, and then the remaining eight modules of the epothilone PKS.

There are six epothilone PKS genes. The epoA gene encodes the 149 kDa loading domain (which can also be referred to as a loading module). The epoB gene encodes module 1, the 158 kDa NRPS module. The epoC gene encodes the 193 kDa module 2. The epoD gene encodes a 765 kDa protein that comprises modules 3 through 6, inclusive. The epoE gene encodes a 405 kDa protein that comprises modules 7 and 8. The epoF gene encodes a 257 kDa protein that comprises module 9 and the thioesterase domain. Immediately downstream of the epoF gene is epoK, the P450 epoxidase gene which encodes a 47 kDa protein, followed immediately by the epoL gene, which may encode a 24 kDa dehydratase. The epoL gene is followed by a number of ORFs that include genes believed to encode proteins involved in transport and regulation.

The sequences of these genes are shown in Example 1 in one contiguous sequence or contig of 71,989 nucleotides (SEQ ID NO: 2). This contig also contains two genes that appear to originate from a transposon and are identified below as ORF A and ORF B. These two genes are believed not to be involved in epothilone biosynthesis but could possibly contain sequences that function as a promoter or enhancer. The contig also contains more than 12 additional ORFs, only 12 of which, designated ORF2 through ORF12 and ORF2 complement, are identified below. As noted, ORF2 actually is two ORFs, because the complement of the strand shown also comprises an ORF. The function of the corresponding gene product, if any, of these ORFs has not yet been established. The Table below provides the location of various open reading frames, module-coding sequences, and domain encoding sequences within the contig sequence shown in Example 1. Those of skill in the art will recognize, upon consideration of the sequence shown in Example 1, that the actual start locations of several of the genes could differ from the start locations shown in the table, because of the presence in frame codons for methionine or valine in close proximity to the codon indicated as the start codon. The actual start codon can be confirmed by amino acid sequencing of the proteins expressed from the genes.

| Start | Stop | Comment |
| --- | --- | --- |
| 3 | 992 | transposase gene ORF A, not part of the PKS |
| 989 | 1501 | transposase gene ORF B, not part of the PKS |
| 1998 | 6263 | epoA gene, encodes the loading domain |
| 2031 | 3548 | $KS^Y$ of the loading domain |
| 3621 | 4661 | AT of the loading domain |
| 4917 | 5810 | ER of the loading domain, potentially involved in formation of the thiazole moiety |
| 5856 | 6155 | ACP of the loading domain |
| 6260 | 10493 | epoB gene, encodes module 1, the NRPS module |
| 6620 | 6649 | condensation domain C2 of the NRPS module |
| 6861 | 6887 | heterocyclization signature sequence |
| 6962 | 6982 | condensation domain C4 of the NRPS module |
| 7358 | 7366 | condensation domain C7 (partial) of the NRPS module |
| 7898 | 7921 | adenylation domain A1 of the NRPS module |
| 8261 | 8308 | adenylation domain A3 of the NRPS module |
| 8411 | 8422 | adenylation domain A4 of the NRPS module |
| 8861 | 8905 | adenylation domain A6 of the NRPS module |
| 8966 | 8983 | adenylation domain A7 of the NRPS module |
| 9090 | 9179 | adenylation domain A8 of the NRPS module |
| 9183 | 9992 | oxidation region for forming thiazole |
| 10121 | 10138 | Adenylation domain A10 of the NRPS module |
| 10261 | 10306 | Thiolation domain (PCP) of the NRPS module |
| 10639 | 16137 | epoC gene, encodes module 2 |
| 10654 | 12033 | KS2, the KS domain of module 2 |
| 12250 | 13287 | AT2, the AT domain of module 2 |
| 13327 | 13899 | DH2, the DH domain of module 2 |
| 14962 | 15756 | KR2, the KR domain of module 2 |
| 15763 | 16008 | ACP2, the ACP domain of module 2 |
| 16134 | 37907 | epoD gene, encodes modules 3-6 |
| 16425 | 17606 | KS3 |
| 17817 | 18857 | AT3 |
| 19581 | 20396 | KR3 |
| 20424 | 20642 | ACP3 |
| 20706 | 22082 | KS4 |
| 22296 | 23336 | AT4 |
| 24069 | 24647 | KR4 |
| 24867 | 25151 | ACP4 |
| 25203 | 26576 | KS5 |
| 26793 | 27833 | AT5 |
| 27966 | 28574 | DH5 |
| 29433 | 30287 | ER5 |
| 30321 | 30869 | KR5 |
| 31077 | 31373 | ACP5 |
| 31440 | 32807 | KS6 |
| 33018 | 34067 | AT6 |
| 34107 | 34676 | DH6 |
| 35760 | 36641 | ER6 |
| 36705 | 37256 | KR6 |
| 37470 | 37769 | ACP6 |
| 37912 | 49308 | epoE gene, encodes modules 7 and 8 |
| 38014 | 39375 | KS7 |
| 39589 | 40626 | AT7 |
| 41341 | 41922 | KR7 |
| 42181 | 42423 | ACP7 |

-continued

| Start | Stop | Comment |
| --- | --- | --- |
| 42478 | 43851 | KS8 |
| 44065 | 45102 | AT8 |
| 45262 | 45810 | DH (inactive) |
| 46072 | 47172 | MT8, the methyltransferase domain of module 8 |
| 48103 | 48636 | KR8, this domain is inactive |
| 48850 | 49149 | ACP8 |
| 49323 | 56642 | epoF gene, encodes module 9 and the TE domain |
| 49416 | 50774 | KS9 |
| 50985 | 52025 | AT9 |
| 52173 | 53414 | DH (inactive) |
| 54747 | 55313 | KR9 |
| 55593 | 55805 | ACP9 |
| 55878 | 56600 | TE9, the thioesterase domain |
| 56757 | 58016 | epoK gene, encodes the P450 epoxidase |
| 58194 | 58733 | epoL gene (putative dehydratase) |
| 59405 | 59974 | ORF2 complement, complement of strand shown |
| 59460 | 60249 | ORF2 |
| 60271 | 60738 | ORF3, complement of strand shown |
| 61730 | 62647 | ORF4 (putative transporter) |
| 63725 | 64333 | ORF5 |
| 64372 | 65643 | ORF6 |
| 66237 | 67472 | ORF7 (putative oxidoreductase) |
| 67572 | 68837 | ORF8 (putative oxidoreductase membrane subunit) |
| 68837 | 69373 | ORF9 |
| 69993 | 71174 | ORF10 (putative transporter) |
| 71171 | 71542 | ORF11 |
| 71557 | 71989 | ORF12 |

With this overview of the organization and sequence of the epothilone gene cluster, one can better appreciate the many different recombinant DNA compounds provided by the present invention.

The epothilone PKS is multiprotein complex composed of the gene products of the epoA, epoB, epoC, epoD, epoE, and epoF genes. To confer the ability to produce epothilones to a host cell, one provides the host cell with the recombinant epoA, epoB, epoC, epoD, epoE, and epoF genes of the present invention, and optionally other genes, capable of expression in that host cell. Those of skill in the art will appreciate that, while the epothilone and other PKS enzymes may be referred to as a single entity herein, these enzymes are typically multisubunit proteins. Thus, one can make a derivative PKS (a PKS that differs from a naturally occurring PKS by deletion or mutation) or hybrid PKS (a PKS that is composed of portions of two different PKS enzymes) by altering one or more genes that encode one or more of the multiple proteins that constitute the PKS.

The post-PKS modification or tailoring of epothilone includes multiple steps mediated by multiple enzymes. These enzymes are referred to herein as tailoring or modification enzymes. Surprisingly, the products of the domains of the epothilone PKS predicted to be functional by analysis of the genes that encode them are compounds that have not been previously reported. These compounds are referred to herein as epothilones G and H. Epothilones G and H lack the C-12-C-13 π-bond of epothilones C and D and the C-12-C-13 epoxide of epothilones A and B, having instead a hydrogen and hydroxyl group at C-13, a single bond between C-12 and C-13, and a hydrogen and H or methyl group at C-12. These compounds are predicted to result from the epothilone PKS, because the DNA and corresponding amino acid sequence for module 4 of the epothilone PKS does not appear to include a DH domain.

As described below, however, expression of the epothilone PKS genes epoA, epoB, epoC, epoD, epoE, and epoF in certain heterologous host cells that do not express epoK or epoL leads to the production of epothilones C and D, which lack the C-13 hydroxyl and have a double bond between C-12 and C-13. The dehydration reaction that mediates the formation of this double bond may be due to the action of an as yet unrecognized domain of the epothilone PKS (for example, dehydration could occur in the next module, which possesses an active DH domain and could generate a conjugated diene precursor prior to its dehydrogenation by an ER domain) or an endogenous enzyme in the heterologous host cells (*Streptomyces coelicolor*) in which it was observed. In the latter event, epothilones G and H may be produced in *Sorangium cellulosum* or other host cells and, to be converted to epothilones C and D, by the action of a dehydratase, which may be encoded by the epoL gene. In any event, epothilones C and D are converted to epothilones A and B by an epoxidase encoded by the epoK gene. Epothilones A and B are converted to epothilones E and F by a hydroxylase gene, which may be encoded by one of the ORFs identified above or by another gene endogenous to *Sorangium cellulosum*. Thus, one can produce an epothilone or epothilone derivative modified as desired in a host cell by providing that host cell with one or more of the recombinant modification enzyme genes provided by the invention or by utilizing a host cell that naturally expresses (or does not express) the modification enzyme. Thus, in general, by utilizing the appropriate host and by appropriate inactivation, if desired, of modification enzymes, one may interrupt the progression of G→C→A→E or the corresponding downstream processing of epothilone H at any desired point; by controlling methylation, one or both of the pathways can be selected.

Thus, the present invention provides a wide variety of recombinant DNA compounds and host cells for expressing the naturally occurring epothilones A, B, C, and D and derivatives thereof. The invention also provides recombinant host cells, particularly *Sorangium cellulosum* host cells that produce epothilone derivatives modified in a manner similar to epothilones E and F. Moreover, the invention provides host cells that can produce the heretofore unknown epothilones G and H, either by expression of the epothilone PKS genes in host cells that do not express the dehydratase that converts epothilones G and H to C and D or by mutating or altering the PKS to abolish the dehydratase function, if it is present in the epothilone PKS.

The macrolide compounds that are products of the PKS cluster can thus be modified in various ways. In addition to the modifications described above, the PKS products can be glycosylated, hydroxylated, dehydroxylated, oxidized, methylated and demethylated using appropriate enzymes. Thus, in addition to modifying the product of the PKS cluster by altering the number, functionality, or specificity of the modules contained in the PKS, additional compounds within the scope of the invention can be produced by additional enzyme-catalyzed activity either provided by a host cell in which the polyketide synthases are produced or by modifying these cells to contain additional enzymes or by additional in vitro modification using purified enzymes or crude extracts or, indeed, by chemical modification.

The present invention also provides a wide variety of recombinant DNA compounds and host cells that make epothilone derivatives. As used herein, the phrase "epothilone derivative" refers to a compound that is produced by a recombinant epothilone PKS in which at least one domain has been either rendered inactive, mutated to alter its catalytic function, or replaced by a domain with a different function or in which a domain has been inserted. In any event, the "epothilone derivative PKS" functions to produce a compound that differs in structure from a naturally occurring epothilone but retains its ring backbone structure and so is called an "epothilone derivative." To faciliate a better understanding of the recombinant DNA compounds and host cells provided by the invention, a detailed discussion of the loading domain and each of the modules of the epothilone PKS, as well as novel recombinant derivatives thereof, is provided below.

The loading domain of the epothilone PKS includes an inactive KS domain, $KS^Y$, an AT domain specific for malonyl CoA (which is believed to be decarboxylated by the $KS^Y$ domain to yield an acetyl group), and an ACP domain. The present invention provides recombinant DNA compounds that encode the epothilone loading domain. The loading domain coding sequence is contained within an ~8.3 kb EcoRI restriction fragment of cosmid pKOS35-70.8A3. The KS domain is referred to as inactive, because the active site region "TAYSSSL" (SEQ ID NO: 20) of the KS domain of the loading domain has a Y residue in place of the cysteine required for ketosynthase activity; this domain does have decarboxylase activity. See Witkowski et al., 7 Sep. 1999, Biochem. 38(36): 11643-11650, incorporated herein by reference.

The presence of the Y residue in place of a Q residue (which occurs typically in an inactive loading domain KS) may make the KS domain less efficient at decarboxylation. The present invention provides a recombinant epothilone PKS loading domain and corresponding DNA sequences that encode an epothilone PKS loading domain in which the Y residue has been changed to a Q residue by changing the codon therefor in the coding sequence of the loading domain. The present invention also provides recombinant PKS enzymes comprising such loading domains and host cells for producing such enzymes and the polyketides produced thereby. These recombinant loading domains include those in which just the Y residue has been changed, those in which amino acids surrounding and including the Y domain have been changed, and those in which the complete $KS^Y$ domain has been replaced by a complete $KS^Q$ domain. The latter embodiment includes but is not limited to a recombinant epothilone loading domain in which the $KS^Y$ domain has been replaced by the $KS^Q$ domain of the oleandolide PKS or the narbonolide PKS (see the references cited below in connection with the oleandomycin, narbomycin, and picromycin PKS and modification enzymes).

The epothilone loading domain also contains an AT domain believed to bind malonyl CoA. The sequence "QTAFTQPALFTFEYALAALW . . . GHSIG" (SEQ ID NO: 1) in the AT domain is consistent with malonyl CoA specificity. As noted above, the malonyl CoA is believed to be decarboxylated by the $KS^Y$ domain to yield acetyl CoA. The present invention provides recombinant epothilone derivative loading domains or their encoding DNA sequences in which the malonyl specific AT domain or its encoding sequence has been changed to another specificity, such as methylmalonyl CoA, ethylmalonyl CoA, and 2-hydroxymalonyl CoA. When expressed with the other proteins of the epothilone PKS, such loading domains lead to the production of epothilones in which the methyl substituent of the thiazole ring of epothilone is replaced with, respectively, ethyl, propyl, and hydroxymethyl. The present invention provides recombinant PKS enzymes comprising such loading domains and host cells for producing such enzymes and the polyketides produced thereby.

Those of skill in the art will recognize that an AT domain that is specific for 2-hydroxymalonyl CoA will result in a polyketide with a hydroxyl group at the corresponding location in the polyketide produced, and that the hydroxyl group can be methylated to yield a methoxy group by polyketide modification enzymes. See, e.g., the patent applications cited in connection with the FK-520 PKS in the table below. Consequently, reference to a PKS that has a 2-hydroxymalonyl specific AT domain herein similarly refers to polyketides produced by that PKS that have either a hydroxyl or methoxyl group at the corresponding location in the polyketide.

The loading domain of the epothilone PKS also comprises an ER domain. While, this ER domain may be involved in forming one of the double bonds in the thiazole moiety in epothilone (in the reverse of its normal reaction), or it may be non-functional. In either event, the invention provides recombinant DNA compounds that encode the epothilone PKS loading domain with and without the ER region, as well as hybrid loading domains that contain an ER domain from another PKS (either active or inactive, with or without accompanying KR and DH domains) in place of the ER domain of the epothilone loading domain. The present invention also provides recombinant PKS enzymes comprising such loading domains and host cells for producing such enzymes and the polyketides produced thereby.

The recombinant nucleic acid compounds of the invention that encode the loading domain of the epothilone PKS and the corresponding polypeptides encoded thereby are useful for a variety of applications. In one embodiment, a DNA compound comprising a sequence that encodes the epothilone loading domain is coexpressed with the proteins of a heterologous PKS. As used herein, reference to a heterologous modular PKS (or to the coding sequence therefor) refers to all or part of a PKS, including each of the multiple proteins constituting the PKS, that synthesizes a polyketide other than an epothilone or epothilone derivative (or to the coding sequences therefor). This coexpression can be in one of two forms. The epothilone loading domain can be coexpressed as a discrete protein with the other proteins of the heterologous PKS or as a fusion protein in which the loading domain is fused to one or more modules of the heterologous PKS. In either event, the hybrid PKS formed, in which the loading domain of the heterologous PKS is replaced by the epothilone loading domain, provides a novel PKS. Examples of a heterologous PKS that can be used to prepare such hybrid PKS enzymes of the invention include but are not limited to DEBS and the picromycin (narbonolide), oleandolide, rapamycin, FK-506, FK-520, rifamycin, and avermectin PKS enzymes and their corresponding coding sequences.

In another embodiment, a nucleic acid compound comprising a sequence that encodes the epothilone loading domain is coexpressed with the proteins that constitute the remainder of the epothilone PKS (i.e., the epoB, epoC, epoD, epoE, and epoF gene products) or a recombinant epothilone PKS that produces an epothilone derivative due to an alteration or mutation in one or more of the epoB, epoC, epoD, epoE, and epoF genes. As used herein, reference to an epothilone or a PKS that produces an epothilone derivative (or to the coding sequence therefor) refers to all or any one of the proteins that comprise the PKS (or to the coding sequences therefor).

In another embodiment, the invention provides recombinant nucleic acid compounds that encode a loading domain composed of part of the epothilone loading domain and part of a heterologous PKS. In this embodiment, the invention provides, for example, either replacing the malonyl CoA specific AT with a methylmalonyl CoA, ethylmalonyl CoA, or 2-hydroxymalonyl CoA specific AT. This replacement, like the others described herein, is typically mediated by replacing the coding sequences therefor to provide a recombinant DNA compound of the invention; the recombinant DNA is used to prepare the corresponding protein. Such changes (including not only replacements but also deletions and insertions) may be referred to herein either at the DNA or protein level.

The compounds of the invention also include those in which both the $KS^Y$ and AT domains of the epothilone loading domain have been replaced but the ACP and/or linker regions of the epothilone loading domain are left intact. Linker regions are those segments of amino acids between domains in the loading domain and modules of a PKS that help form the tertiary structure of the protein and are involved in correct alignment and positioning of the domains of a PKS. These compounds include, for example, a recombinant loading domain coding sequence in which the $KS^Y$ and AT domain coding sequences of the epothilone PKS have been replaced by the coding sequences for the $KS^Q$ and AT domains of, for example, the oleandolide PKS or the narbonolide PKS. There are also PKS enzymes that do not employ a $KS^Q$ domain but instead merely utilize an AT domain that binds acetyl CoA, propionyl CoA, or butyryl CoA (the DEBS loading domain) or isobutyryl CoA (the avermectin loading domain). Thus, the compounds of the invention also include, for example, a recombinant loading domain coding sequence in which the $KS^Y$ and AT domain coding sequences of the epothilone PKS have been replaced by an AT domain of the DEBS or avermectin PKS. The present invention also provides recombinant DNA compounds encoding loading domains in which the ACP domain or any of the linker regions of the epothilone loading domain has been replaced by another ACP or linker region.

Any of the above loading domain coding sequences is coexpressed with the other proteins that constitute a PKS that synthesizes epothilone, an epothilone derivative, or another polyketide to provide a PKS of the invention. If the product desired is epothilone or an epothilone derivative, then the loading domain coding sequence is typically expressed as a discrete protein, as is the loading domain in the naturally occurring epothilone PKS. If the product desired is produced by the loading domain of the invention and proteins from one or more non-epothilone PKS enzymes, then the loading domain is expressed either as a discrete protein or as a fusion protein with one or more modules of the heterologous PKS.

The present invention also provides hybrid PKS enzymes in which the epothilone loading domain has been replaced in its entirety by a loading domain from a heterologous PKS with the remainder of the PKS proteins provided by modified or unmodified epothilone PKS proteins. The present invention also provides recombinant expression vectors and host cells for producing such enzymes and the polyketides produced thereby. In one embodiment, the heterologous loading domain is expressed as a discrete protein in a host cell that expresses the epoB, epoC, epoD, epoE, and epoF gene products. In another embodiment, the heterologous loading domain is expressed as a fusion protein with the epoB gene product in a host cell that expresses the epoC, epoD, epoE, and epoF gene products. In a related embodiment, the present invention provides recombinant epothilone PKS enzymes in which the loading domain has been deleted and replaced by an NRPS module and corresponding recombinant DNA compounds and expression vectors. In this embodiment, the recombinant PKS enzymes thus produce an epothilone derivative that comprises a dipeptide moiety, as in the compound leinamycin. The invention provides such enzymes in which the remainder of the epothilone PKS is identical in function to the native epothilone PKS as well as those in which the remainder is a recombinant PKS that produces an epothilone derivative of the invention.

The present invention also provides reagents and methods useful in deleting the loading domain coding sequence or any portion thereof from the chromosome of a host cell, such as *Sorangium cellulosum*, or replacing those sequences or any portion thereof with sequences encoding a recombinant loading domain. Using a recombinant vector that comprises DNA complementary to the DNA including and/or flanking the loading domain coding sequence in the *Sorangium chromosome*, one can employ the vector and homologous recombination to replace the native loading domain coding sequence with a recombinant loading domain coding sequence or to delete the sequence altogether.

Moreover, while the above discussion focuses on deleting or replacing the epothilone loading domain coding sequences, those of skill in the art will recognize that the present invention provides recombinant DNA compounds, vectors, and methods useful in deleting or replacing all or any portion of an epothilone PKS gene or an epothilone modification enzyme gene. Such methods and materials are useful for a variety of purposes. One purpose is to construct a host cell that does not make a naturally occurring epothilone or epothilone derivative. For example, a host cell that has been modified to not produce a naturally occurring epothilone may be particularly preferred for making epothilone derivatives or other polyketides free of any naturally occurring epothilone. Another purpose is to replace the deleted gene with a gene that has been altered so as to provide a different product or to produce more of one product than another.

If the epothilone loading domain coding sequence has been deleted or otherwise rendered non-functional in a *Sorangium cellulosum* host cell, then the resulting host cell will produce a non-functional epothilone PKS. This PKS could still bind and process extender units, but the thiazole moiety of epothilone would not form, leading to the production of a novel epothilone derivative. Because this derivative would predictably contain a free amino group, it would be produced at most in low quantities. As noted above, however, provision of a heterologous or other recombinant loading domain to the host cell would result in the production of an epothilone derivative with a structure determined by the loading domain provided.

The loading domain of the epothilone PKS is followed by the first module of the PKS, which is an NRPS module specific for cysteine. This NRPS module is naturally expressed as a discrete protein, the product of the epoB gene. The present invention provides the epoB gene in recombinant form. The recombinant nucleic acid compounds of the invention that encode the NRPS module of the epothilone PKS and the corresponding polypeptides encoded thereby are useful for a variety of applications. In one embodiment, a nucleic acid compound comprising a sequence that encodes the epothilone NRPS module is coexpressed with genes encoding one or more proteins of a heterologous PKS. The NRPS module can be expressed as a discrete protein or as a fusion protein with one of the proteins of the heterologous PKS. The resulting PKS, in which at least a module of the heterologous PKS is replaced by the epothilone NRPS module or the NRPS module is in effect added as a module to the heterologous PKS, provides a novel PKS. In another embodiment, a DNA compound comprising a sequence that encodes the epothilone NRPS module is coexpressed with the other epothilone PKS proteins or modified versions thereof to provide a recombinant epothilone PKS that produces an epothilone or an epothilone derivative.

Two hybrid PKS enzymes provided by the invention illustrate this aspect. Both hybrid PKS enzymes are hybrids of DEBS and the epothilone NRPS module. The first hybrid PKS is composed of four proteins: (i) DEBS1; (ii) a fusion protein composed of the KS domain of module 3 of DEBS and all but the KS domain of the loading domain of the epothilone PKS; (iii) the epothilone NRPS module; and (iv) a fusion protein composed of the KS domain of module 2 of the epothilone PKS fused to the AT domain of module 5 of DEBS and the rest of DEBS3. This hybrid PKS produces a novel polyketide with a thiazole moiety incorporated into the macrolactone ring and a molecular weight of 413.53 when expressed in *Streptomyces coelicolor*. Glycosylated, hydroxylated, and methylated derivatives can be produced by expression of the hybrid PKS in *Saccharopolyspora erythraea*.

Diagrammatically, the construct is represented:

The structure of the product is:

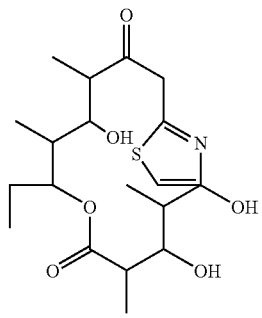

The second hybrid PKS illustrating this aspect of the invention is composed of five proteins: (i) DEBS1; (ii) a fusion protein composed of the KS domain of module 3 of DEBS and all but the KS domain of the loading domain of the epothilone PKS; (iii) the epothilone NRPS module; and (iv) a fusion protein composed of the KS domain of module 2 of the epothilone PKS fused to the AT domain of module 4 of DEBS and the rest of DEBS2; and (v) DEBS3. This hybrid PKS produces a novel polyketide with a thiazole moiety incorporated into the macrolactone ring and a molecular weight of 455.61 when expressed in *Streptomyces coelicolor*. Glycosylated, hydroxylated, and methylated derivatives can be produced by expression of the hybrid PKS in *Saccharopolyspora erythraea*.

Diagrammatically, the construct is represented:

The structure of the product is:

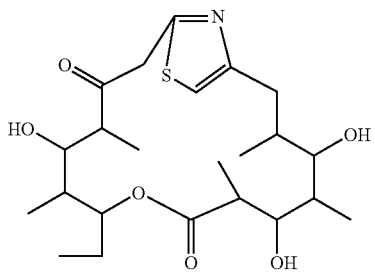

In another embodiment, a portion of the NRPS module coding sequence is utilized in conjunction with a heterologous coding sequence. In this embodiment, the invention provides, for example, changing the specificity of the NRPS module of the epothilone PKS from a cysteine to another amino acid. This change is accomplished by constructing a coding sequence in which all or a portion of the epothilone PKS NRPS module coding sequences have been replaced by those coding for an NRPS module of a different specificity. In one illustrative embodiment, the specificity of the epothilone NRPS module is changed from cysteine to serine or threonine. When the thus modified NRPS module is expressed with the other proteins of the epothilone PKS, the recombinant PKS produces an epothilone derivative in which the thiazole moiety of epothilone (or an epothilone derivative) is changed to an oxazole or 5-methyloxazole moiety, respectively. Alternatively, the present invention provides recombinant PKS enzymes composed of the products of the epoA, epoC, epoD, epoE, and epoF genes (or modified versions thereof) without an NRPS module or with an NRPS module from a heterologous PKS. The heterologous NRPS module can be expressed as a discrete protein or as a fusion protein with either the epoA or epoC genes.

The invention also provides methods and reagents useful in changing the specificity of a heterologous NRPS module from another amino acid to cysteine. This change is accomplished by constructing a coding sequence in which the sequences that determine the specificity of the heterologous NRPS module have been replaced by those that specify cysteine from the epothilone NRPS module coding sequence. The resulting heterologous NRPS module is typically coexpressed in conjunction with the proteins constituting a heterologous PKS that synthesizes a polyketide other than epothilone or an epothilone derivative, although the heterologous NRPS module can also be used to produce epothilone or an epothilone derivative.

In another embodiment, the invention provides recombinant epothilone PKS enzymes and corresponding recombinant nucleic acid compounds and vectors in which the NRPS module has been inactivated or deleted. Such enzymes, compounds, and vectors are constructed generally in accordance with the teaching for deleting or inactivating the epothilone PKS or modification enzyme genes above. Inactive NRPS module proteins and the coding sequences therefore provided by the invention include those in which the peptidyl carrier protein (PCP) domain has been wholly or partially deleted or otherwise rendered inactive by changing the active site serine (the site for phosphopantetheinylation) to another amino acid, such as alanine, or the adenylation domains have been deleted or otherwise rendered inactive. In one embodiment, both the loading domain and the NRPS have been deleted or rendered inactive. In any event, the resulting epothilone PKS can then function only if provided a substrate that binds to the KS domain of module 2 (or a subsequent module) of the epothilone PKS or a PKS for an epothilone derivative. In a method provided by the invention, the thus modified cells are then fed activated acylthioesters that are bound by preferably the second, but potentially any subsequent, module and processed into novel epothilone derivatives.

Thus, in one embodiment, the invention provides *Sorangium* and non-*Sorangium* host cells that express an epothilone PKS (or a PKS that produces an epothilone derivative) with an inactive NRPS. The host cell is fed activated acylthioesters to produce novel epothilone derivatives of the invention. The host cells expressing, or cell free extracts containing, the PKS can be fed or supplied with N-acylcysteamine thioesters (NACS) of novel precursor molecules to prepare epothilone derivatives. See U.S. patent application Ser. No. 60/117,384, filed 27 Jan. 1999, and PCT patent publication No. US99/03986, both of which are incorporated herein by reference, and Example 6, below.

The second (first non-NRPS) module of the epothilone PKS includes a KS, an AT specific for methylmalonyl CoA, a DH, a KR, and an ACP. This module is encoded by a sequence within an ~13.1 kb EcoRI-NsiI restriction fragment of cosmid pKOS35-70.8A3.

The recombinant nucleic acid compounds of the invention that encode the second module of the epothilone PKS and the corresponding polypeptides encoded thereby are useful for a variety of applications. The second module of the epothilone PKS is produced as a discrete protein by the epoC gene. The present invention provides the epoC gene in recombinant form. In one embodiment, a DNA compound comprising a sequence that encodes the epothilone second module is coexpressed with the proteins constituting a heterologous PKS either as a discrete protein or as a fusion protein with one or more modules of the heterologous PKS. The resulting PKS, in which a module of the heterologous PKS is either replaced by the second module of the epothilone PKS or the latter is merely added to the modules of the heterologous PKS, provides a novel PKS. In another embodiment, a DNA compound comprising a sequence that encodes the second module of the epothilone PKS is coexpressed with the other proteins constituting the epothilone PKS or a recombinant epothilone PKS that produces an epothilone derivative.

In another embodiment, all or only a portion of the second module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with a DH or KR or both that specify a different stereochemistry; and/or inserting an ER. Generally, any reference herein to inserting or replacing a PKS KR, DH, and/or ER domain includes the replacement of the associated KR, DH, or ER domains in that module, typically with corresponding domains from the module from which the inserted or replacing domain is obtained. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a gene for a PKS that produces a polyketide other than epothilone, or from chemical synthesis. The resulting heterologous second module coding sequence can be coexpressed with the other proteins that constitute a PKS that synthesizes epothilone, an epothilone derivative, or another polyketide. Alternatively, one can delete or replace the second module of the epothilone PKS with a module from a heterologous PKS, which can be expressed as a discrete protein or as a fusion protein fused to either the epoB or epoD gene product.

Illustrative recombinant PKS genes of the invention include those in which the AT domain encoding sequences for the second module of the epothilone PKS have been altered or replaced to change the AT domain encoded thereby from a methylmalonyl specific AT to a malonyl specific AT. Such malonyl specific AT domain encoding nucleic acids can be isolated, for example and without limitation, from the PKS genes encoding the narbonolide PKS, the rapamycin PKS (i.e., modules 2 and 12), and the FK-520 PKS (i.e., modules 3, 7, and 8). When such a hybrid second module is coexpressed with the other proteins constituting the epothilone PKS, the resulting epothilone derivative produced is a 16-desmethyl epothilone derivative.

In addition, the invention provides DNA compounds and vectors encoding recombinant epothilone PKS enzymes and the corresponding recombinant proteins in which the KS domain of the second (or subsequent) module has been inactivated or deleted. In a preferred embodiment, this inactivation is accomplished by changing the codon for the active site cysteine to an alanine codon. As with the corresponding variants described above for the NRPS module, the resulting recombinant epothilone PKS enzymes are unable to produce an epothilone or epothilone derivative unless supplied a precursor that can be bound and extended by the remaining domains and modules of the recombinant PKS enzyme. Illustrative diketides are described in Example 6, below.

The third module of the epothilone PKS includes a KS, an AT specific for malonyl CoA, a KR, and an ACP. This module is encoded by a sequence within an ~8 kb BglI-NsiI restriction fragment of cosmid pKOS35-70.8A3.

The recombinant DNA compounds of the invention that encode the third module of the epothilone PKS and the corresponding polypeptides encoded thereby are useful for a variety of applications. The third module of the epothilone PKS is expressed in a protein, the product of the epoD gene, which also contains modules 4, 5, and 6. The present invention provides the epoD gene in recombinant form. The present invention also provides recombinant DNA compounds that encode each of the epothilone PKS modules 3, 4, 5, and 6, as discrete coding sequences without coding sequences for the other epothilone modules. In one embodiment, a DNA compound comprising a sequence that encodes the epothilone third module is coexpressed with proteins constituting a heterologous PKS. The third module of the epothilone PKS can be expressed either as a discrete protein or as a fusion protein fused to one or more modules of the heterologous PKS. The resulting PKS, in which a module of the heterologous PKS is either replaced by that for the third module of the epothilone PKS or the latter is merely added to the modules of the heterologous PKS, provides a novel PKS. In another embodiment, a DNA compound comprising a sequence that encodes the third module of the epothilone PKS is coexpressed with proteins comprising the remainder of the epothilone PKS or a recombinant epothilone PKS that produces an epothilone derivative, typically as a protein comprising not only the third but also the fourth, fifth, and sixth modules.

In another embodiment, all or a portion of the third module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR; replacing the KR with a KR that specifies a different stereochemistry; and/or inserting a DH or a DH and an ER. As above, the reference to inserting a DH or a DH and an ER includes the replacement of the KR with a DH and KR or an ER, DH, and KR. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting heterologous third module coding sequence can be utilized in conjunction with a coding sequence for a PKS that synthesizes epothilone, an epothilone derivative, or another polyketide.

Illustrative recombinant PKS genes of the invention include those in which the AT domain encoding sequences for the third module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When coexpressed with the remaining modules and proteins of the epothilone PKS or an epothilone PKS derivative, the recombinant PKS produces the 14-methyl epothilone derivatives of the invention.

Those of skill in the art will recognize that the KR domain of the third module of the PKS is responsible for forming the hydroxyl group involved in cyclization of epothilone. Consequently, abolishing the KR domain of the third module or adding a DH or DH and ER domains will interfere with the cyclization, leading either to a linear molecule or to a molecule cyclized at a different location than is epothilone.

The fourth module of the epothilone PKS includes a KS, an AT that can bind either malonyl CoA or methylmalonyl CoA, a KR, and an ACP. This module is encoded by a sequence within an ~10 kb NsiI-HindIII restriction fragment of cosmid pKOS35-70.1A2.

The recombinant DNA compounds of the invention that encode the fourth module of the epothilone PKS and the corresponding polypeptides encoded thereby are useful for a variety of applications. In one embodiment, a DNA compound comprising a sequence that encodes the epothilone fourth module is inserted into a DNA compound that comprises the coding sequence for one or more modules of a heterologous PKS. The resulting construct encodes a protein in which a module of the heterologous PKS is either replaced by that for the fourth module of the epothilone PKS or the latter is merely added to the modules of the heterologous PKS. Together with other proteins that constitute the heterologous PKS, this protein provides a novel PKS. In another embodiment, a DNA compound comprising a sequence that encodes the fourth module of the epothilone PKS is expressed in a host cell that also expresses the remaining modules and proteins of the epothilone PKS or a recombinant epothilone PKS that produces an epothilone derivative. For making epothilone or epothilone derivatives, the recombinant fourth module is usually expressed in a protein that also contains the epothilone third, fifth, and sixth modules or modified versions thereof.

In another embodiment, all or a portion of the fourth module coding sequence is utilized in conjunction with other PKS coding sequences to create a hybrid module. In this embodiment, the invention provides, for example, either replacing the malonyl CoA and methylmalonyl specific AT with a malonyl CoA, methylmalonyl CoA, ethylmalonyl CoA, or 2-hydroxymalonyl CoA specific AT; deleting the KR; and/or replacing the KR, including, optionally, to specify a different stereochemistry; and/or inserting a DH or a DH and ER. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a gene for a PKS that produces a polyketide other than epothilone, or from chemical synthesis. The resulting heterologous fourth module coding sequence is incorporated into a protein subunit of a recombinant PKS that synthesizes epothilone, an epothilone derivative, or another polyketide. If the desired polyketide is an epothilone or epothilone derivative, the recombinant fourth module is typically expressed as a protein that also contains the third, fifth, and sixth modules of the epothilone PKS or modified versions thereof. Alternatively, the invention provides recombinant PKS enzymes for epothilones and epothilone derivatives in which the entire fourth module has been deleted or replaced by a module from a heterologous PKS.

In a preferred embodiment, the invention provides recombinant DNA compounds comprising the coding sequence for the fourth module of the epothilone PKS modified to encode an AT that binds methylmalonyl CoA and not malonyl CoA. These recombinant molecules are used to express a protein that is a recombinant derivative of the epoD protein that comprises the modified fourth module as well as modules 3, 5, and 6, any one or more of which can optionally be in derivative form, of the epothilone PKS. In another preferred embodiment, the invention provides recombinant DNA compounds comprising the coding sequence for the fourth module of the epothilone PKS modified to encode an AT that binds malonyl CoA and not methylmalonyl CoA. These recombinant molecules are used to express a protein that is a recombinant derivative of the epoD protein that comprises the modified fourth module as well as modules 3, 5, and 6, any one or more of which can optionally be in derivative form, of the epothilone PKS.

Prior to the present invention, it was known that *Sorangium cellulosum* produced epothilones A, B, C, D, E, and F and that epothilones A, C, and E had a hydrogen at C-12, while epothilones B, D, and F had a methyl group at this position. Unappreciated prior to the present invention was the order in which these compounds were synthesized in *S. cellulosum*, and the mechanism by which some of the compounds had a hydrogen at C-12 where others had a methyl group at this position. The present disclosure reveals that epothilones A and B are derived from epothilones C and D by action of the epoK gene product and that the presence of a hydrogen or methyl moiety at C-12 is due to the AT domain of module 4 of the epothilone PKS. This domain can bind either malonyl or methylmalonyl CoA and, consistent with its having greater similarity to malonyl specific AT domains than to methylmalonyl specific AT domains, binds malonyl CoA more often than methylmalonyl CoA.

Thus, the invention provides recombinant DNA compounds and expression vectors and the corresponding recombinant PKS in which the hybrid fourth module with a methylmalonyl specific AT has been incorporated. The methylmalonyl specific AT coding sequence can originate, for example and without limitation, from coding sequences for the oleandolide PKS, DEBS, the narbonolide PKS, the rapamycin PKS, or any other PKS that comprises a methylmalonyl specific AT domain. In accordance with the invention, the hybrid fourth module expressed from this coding sequence is incorporated into the epothilone PKS (or the PKS for an epothilone derivative), typically as a derivative epoD gene product. The resulting recombinant epothilone PKS produces epothilones with a methyl moiety at C-12, i.e., epothilone H (or an epothilone H derivative) if there is no dehydratase activity to form the C-12-C-13 alkene; epothilone D (or an epothilone D derivative), if the dehydratase activity but not the epoxidase activity is present; epothilone B (or an epothilone B derivative), if both the dehydratase and epoxidase activity but not the hydroxylase activity are present; and epothilone F (or an epothilone F derivative), if all three dehydratase, epoxidase, and hydroxylase activities are present. As indicated parenthetically above, the cell will produce the corresponding epothilone derivative if there have been other changes to the epothilone PKS.

If the recombinant PKS comprising the hybrid methylmalonyl specific fourth module is expressed in, for example, *Sorangium cellulosum*, the appropriate modifying enzymes are present (unless they have been rendered inactive in accordance with the methods herein), and epothilones D, B, and/or F are produced. Such production is typically carried out in a recombinant *S. cellulosum* provided by the present invention in which the native epothilone PKS is unable to function at all or unable to function except in conjunction with the recombinant fourth module provided. In an illustrative example, one can use the methods and reagents of the invention to render inactive the epoD gene in the native host. Then, one can transform that host with a vector comprising the recombinant epoD gene containing the hybrid fourth module coding sequence. The recombinant vector can exist as an extrachromosomal element or as a segment of DNA integrated into the host cell chromosome. In the latter embodiment, the invention provides that one can simply integrate the recombinant methylmalonyl specific module 4 coding sequence into wild-type *S. cellulosum* by homologous recombination with the native epoD gene to ensure that only the desired epothilone is produced. The invention provides that the *S. cellulosum* host can either express or not express (by mutation or homologous recombination of the native genes therefor) the dehydratase, epoxidase, and/or oxidase gene products and thus form or not form the corresponding epothilone D, B, and F compounds, as the practitioner elects.

*Sorangium cellulosum* modified as described above is only one of the recombinant host cells provided by the invention. In a preferred embodiment, the recombinant methylmalonyl specific epothilone fourth module coding sequences are used in accordance with the methods of invention to produce epothilone D, B, and F (or their corresponding derivatives) in heterologous host cells. Thus, the invention provides reagents and methods for introducing the epothilone or epothilone derivative PKS and epothilone dehydratase, epoxidase, and hydroxylase genes and combinations thereof into heterologous host cells.

The recombinant methylmalonyl specific epothilone fourth module coding sequences provided by the invention afford important alternative methods for producing desired epothilone compounds in host cells. Thus, the invention provides a hybrid fourth module coding sequence in which, in addition to the replacement of the endogenous AT coding sequence with a coding sequence for an AT specific for methylmalonyl Co A, coding sequences for a DH and KR for, for example and without limitation, module 10 of the rapamycin PKS or modules 1 or 5 of the FK-520 PKS have replaced the endogenous KR coding sequences. When the gene product comprising the hybrid fourth module and epothilone PKS modules 3, 5, and 6 (or derivatives thereof) encoded by this coding sequence is incorporated into a PKS comprising the other epothilone PKS proteins (or derivatives thereof) produced in a host cell, the cell makes either epothilone D or its trans stereoisomer (or derivatives thereof), depending on the stereochemical specificity of the inserted DH and KR domains.

Similarly, and as noted above, the invention provides recombinant DNA compounds comprising the coding sequence for the fourth module of the epothilone PKS modified to encode an AT that binds malonyl CoA and not methylmalonyl CoA. The invention provides recombinant DNA compounds and vectors and the corresponding recombinant PKS in which this hybrid fourth module has been incorporated into a derivative epoD gene product. When incorporated into the epothilone PKS (or the PKS for an epothilone derivative), the resulting recombinant epothilone PKS produces epothilones C, A, and E, depending, again, on whether epothilone modification enzymes are present. As noted above, depending on the host, whether the fourth module includes a KR and DH domain, and on whether and which of the dehydratase, epoxidase, and oxidase activities are present, the practitioner of the invention can produce one or more of the epothilone G, C, A, and E compounds and derivatives thereof using the compounds, host cells, and methods of the invention.

The fifth module of the epothilone PKS includes a KS, an AT that binds malonyl CoA, a DH, an ER, a KR, and an ACP. This module is encoded by a sequence within an ~12.4 kb NsiI-NotI restriction fragment of cosmid pKOS35-70.1A2.

The recombinant DNA compounds of the invention that encode the fifth module of the epothilone PKS and the corresponding polypeptides encoded thereby are useful for a variety of applications. In one embodiment, a DNA compound comprising a sequence that encodes the epothilone fifth module is inserted into a DNA compound that comprises the coding sequence for one or more modules of a heterologous PKS. The resulting construct, in which the coding sequence for a module of the heterologous PKS is either replaced by that for the fifth module of the epothilone PKS or the latter is merely added to coding sequences for the modules of the heterologous PKS, can be incorporated into an expression vector and used to produce the recombinant protein encoded thereby. When the recombinant protein is combined with the other proteins of the heterologous PKS, a novel PKS is produced. In another embodiment, a DNA compound comprising a sequence that encodes the fifth module of the epothilone PKS is inserted into a DNA compound that comprises coding sequences for the epothilone PKS or a recombinant epothilone PKS that produces an epothilone derivative. In the latter constructs, the epothilone fifth module is typically expressed as a protein comprising the third, fourth, and sixth modules of the epothilone PKS or derivatives thereof.

In another embodiment, a portion of the fifth module coding sequence is utilized in conjunction with other PKS coding sequences to create a hybrid module coding sequence and the hybrid module encoded thereby. In this embodiment, the invention provides, for example, either replacing the malonyl CoA specific AT with a methylmalonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting hybrid fifth module coding sequence can be utilized in conjunction with a coding sequence for a PKS that synthesizes epothilone, an epothilone derivative, or another polyketide. Alternatively, the fifth module of the epothilone PKS can be deleted or replaced in its entirety by a module of a heterologous PKS to produce a protein that in combination with the other proteins of the epothilone PKS or derivatives thereof constitutes a PKS that produces an epothilone derivative.

Illustrative recombinant PKS genes of the invention include recombinant epoD gene derivatives in which the AT domain encoding sequences for the fifth module of the epothilone PKS have been altered or replaced to change the AT domain encoded thereby from a malonyl specific AT to a methylmalonyl specific AT. Such methylmalonyl specific AT domain encoding nucleic acids can be isolated, for example and without limitation, from the PKS genes encoding DEBS, the narbonolide PKS, the rapamycin PKS, and the FK-520 PKS. When such recombinant epoD gene derivatives are coexpressed with the epoA, epoB, epoC, epoE, and epoF genes (or derivatives thereof), the PKS composed thereof produces the 10-methyl epothilones or derivatives thereof. Another recombinant epoD gene derivative provided by the invention includes not only this altered module 5 coding sequence but also module 4 coding sequences that encode an AT domain that binds only methylmalonyl CoA. When incorporated into a PKS with the epoA, epoB, epoC, epoE, and epoF genes, the recombinant epoD gene derivative product leads to the production of 10-methyl epothilone B and/or D derivatives.

Other illustrative recombinant epoD gene derivatives of the invention include those in which the ER, DH, and KR domain encoding sequences for the fifth module of the epothilone PKS have been replaced with those encoding (i) a KR and DH domain; (ii) a KR domain; and (iii) an inactive KR domain. These recombinant epoD gene derivatives of the invention are coexpressed with the epoA, epoB, epoC, epoE, and epoF genes to produce a recombinant PKS that makes the corresponding (i) C-11 alkene, (ii) C-11 hydroxy, and (iii) C-11 keto epothilone derivatives. These recombinant epoD gene derivatives can also be coexpressed with recombinant epo genes containing other alterations or can themselves be further altered to produce a PKS that makes the corresponding C-11 epothilone derivatives. For example, one recombinant epoD gene derivative provided by the invention also includes module 4 coding sequences that encode an AT domain that binds only methylmalonyl CoA. When incorporated into a PKS with the epoA, epoB, epoC, epoE, and epoF genes, the recombinant epoD gene derivative product leads to the production of the corresponding C-11 epothilone B and/or D derivatives.

Functionally similar epoD genes for producing the epothilone C-11 derivatives can also be made by inactivation of one, two, or all three of the ER, DH, and KR domains of the epothilone fifth module. However, the preferred mode for altering such domains in any module is by replacement with the complete set of desired domains taken from another module of the same or a heterologous PKS coding sequence. In this manner, the natural architecture of the PKS is conserved. Also, when present, KR and DH or KR, DH, and ER domains that function together in a native PKS are preferably used in the recombinant PKS. Illustrative replacement domains for the substitutions described above include, for example and without limitation, the inactive KR domain from the rapamycin PKS module 3 to form the ketone, the KR domain from the rapamycin PKS module 5 to form the alcohol, and the KR and DH domains from the rapamycin PKS module 4 to form the alkene. Other such inactive KR, active KR, and active KR and DH domain encoding nucleic acids can be isolated from, for example and without limitation, the PKS genes encoding DEBS, the narbonolide PKS, and the FK-520 PKS. Each of the resulting PKS enzymes produces a polyketide compound that comprises a functional group at the C-11 position that can be further derivatized in vitro by standard chemical methodology to yield semi-synthetic epothilone derivatives of the invention.

The sixth module of the epothilone PKS includes a KS, an AT that binds methylmalonyl CoA, a DH, an ER, a KR, and an ACP. This module is encoded by a sequence within an ~14.5 kb HindIII-NsiI restriction fragment of cosmid pKOS35-70.1A2.

The recombinant DNA compounds of the invention that encode the sixth module of the epothilone PKS and the corresponding polypeptides encoded thereby are useful for a variety of applications. In one embodiment, a DNA compound comprising a sequence that encodes the epothilone sixth module is inserted into a DNA compound that comprises the coding sequence for one or more modules of a heterologous PKS. The resulting protein encoded by the construct, in which the coding sequence for a module of the heterologous PKS is either replaced by that for the sixth module of the epothilone PKS or the latter is merely added to coding sequences for the modules of the heterologous PKS, provides a novel PKS when coexpressed with the other proteins comprising the PKS. In another embodiment, a DNA compound comprising a sequence that encodes the sixth module of the epothilone PKS is inserted into a DNA compound that comprises the coding sequence for modules 3, 4, and 5 of the epothilone PKS or a recombinant epothilone PKS that produces an epothilone derivative and coexpressed with the other proteins of the epothilone or epothilone derivative PKS to produce a PKS that makes epothilone or an epothilone derivative in a host cell.

In another embodiment, a portion of the sixth module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the ER, DH, and KR; and/or replacing any one, two, or all three of the ER, DH, and KR with either a KR, a DH and KR, or a KR, DH, and ER, including, optionally, to specify a different stereochemistry. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting heterologous sixth module coding sequence can be utilized in conjunction with a coding sequence for a protein subunit of a PKS that makes epothilone, an epothilone derivative, or another polyketide. If the PKS makes epothilone or an epothilone derivative, the hybrid sixth module is typically expressed as a protein comprising modules 3, 4, and 5 of the epothilone PKS or derivatives thereof. Alternatively, the sixth module of the epothilone PKS can be deleted or replaced in its entirety by a module from a heterologous PKS to produce a PKS for an epothilone derivative.

Illustrative recombinant PKS genes of the invention include those in which the AT domain encoding sequences for the sixth module of the epothilone PKS have been altered or replaced to change the AT domain encoded thereby from a methylmalonyl specific AT to a malonyl specific AT. Such malonyl specific AT domain encoding nucleic acids can be isolated from, for example and without limitation, the PKS genes encoding the narbonolide PKS, the rapamycin PKS, and the FK-520 PKS. When a recombinant epoD gene of the invention encoding such a hybrid module 6 is coexpressed with the other epothilone PKS genes, the recombinant PKS makes the 8-desmethyl epothilone derivatives. This recombinant epoD gene derivative can also be coexpressed with recombinant epo gene derivatives containing other alterations or can itself be further altered to produce a PKS that makes the corresponding 8-desmethyl epothilone derivatives. For example, one recombinant epoD gene provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the 8-desmethyl derivatives of epothilones B and D.

Other illustrative recombinant epoD gene derivatives of the invention include those in which the ER, DH, and KR domain encoding sequences for the sixth module of the epothilone PKS have been replaced with those that encode (i) a KR and DH domain; (ii) a KR domain; and (iii) an inactive KR domain. These recombinant epoD gene derivatives of the invention, when coexpressed with the other epothilone PKS genes make the corresponding (i) C-9 alkene, (ii) C-9 hydroxy, and (iii) C-9 keto epothilone derivatives. These recombinant epoD gene derivatives can also be coexpressed with other recombinant epo gene derivatives containing other alterations or can themselves be further altered to produce a PKS that makes the corresponding C-9 epothilone derivatives. For example, one recombinant epoD gene derivative provided by the invention also includes module 4 coding sequences that encode an AT domain that binds only methylmalonyl CoA. When incorporated into a PKS with the epoA, epoB, epoC, epoE, and epoF genes, the recombinant epoD gene product leads to the production of the C-9 derivatives of epothilones B and D.

Functionally equivalent sixth modules can also be made by inactivation of one, two, or all three of the ER, DH, and KR domains of the epothilone sixth module. The preferred mode for altering such domains in any module is by replacement with the complete set of desired domains taken from another module of the same or a heterologous PKS coding sequence. Illustrative replacement domains for the substitutions described above include but are not limited to the inactive KR domain from the rapamycin PKS module 3 to form the ketone, the KR domain from the rapamycin PKS module 5 to form the alcohol, and the KR and DH domains from the rapamycin PKS module 4 to form the alkene. Other such inactive KR, active KR, and active KR and DH domain encoding nucleic acids can be isolated from for example and without limitation the PKS genes encoding DEBS, the narbonolide PKS, and the FK-520 PKS. Each of the resulting PKSs produces a polyketide compound that comprises a functional group at the C-9 position that can be further derivatized in vitro by standard chemical methodology to yield semi-synthetic epothilone derivatives of the invention.

The seventh module of the epothilone PKS includes a KS, an AT specific for methylmalonyl CoA, a KR, and an ACP. This module is encoded by a sequence within an ~8.7 kb BglII restriction fragment from cosmid pKOS35-70.4.

The recombinant DNA compounds of the invention that encode the seventh module of the epothilone PKS and the corresponding polypeptides encoded thereby are useful for a variety of applications. The seventh module of the epothilone PKS is contained in the gene product of the epoE gene, which also contains the eighth module. The present invention provides the epoE gene in recombinant form, but also provides DNA compounds that encode the seventh module without coding sequences for the eighth module as well as DNA compounds that encode the eighth module without coding sequences for the seventh module. In one embodiment, a DNA compound comprising a sequence that encodes the epothilone seventh module is inserted into a DNA compound that comprises the coding sequence for one or more modules of a heterologous PKS. The resulting construct, in which the coding sequence for a module of the heterologous PKS is either replaced by that for the seventh module of the epothilone PKS or the latter is merely added to coding sequences for the modules of the heterologous PKS, provides a novel PKS coding sequence that can be expressed in a host cell. Alternatively, the epothilone seventh module can be expressed as a discrete protein. In another embodiment, a DNA compound comprising a sequence that encodes the seventh module of the epothilone PKS is expressed to form a protein that, together with other proteins, constitutes the epothilone PKS or a PKS that produces an epothilone derivative. In these embodiments, the seventh module is typically expressed as a protein comprising the eighth module of the epothilone PKS or a derivative thereof and coexpressed with the epoA, epoB, epoC, epoD, and epoF genes or derivatives thereof to constitute the PKS.

In another embodiment, a portion or all of the seventh module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR; replacing the KR with a KR that specifies a different stereochemistry; and/or inserting a DH or a DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting heterologous seventh module coding sequence is utilized, optionally in conjunction with other coding sequences, to express a protein that together with other proteins constitutes a PKS that synthesizes epothilone, an epothilone derivative, or another polyketide. When used to prepare epothilone or an epothilone derivative, the seventh module is typically expressed as a protein comprising the eighth module or derivative thereof and coexpressed with the epoA, epoB, epoC, epoD, and epoF genes or derivatives thereof to constitute the PKS. Alternatively, the coding sequences for the seventh module in the epoE gene can be deleted or replaced by those for a heterologous module to prepare a recombinant epoE gene derivative that, together with the epoA, epoB, epoC, epoD, and epoF genes, can be expressed to make a PKS for an epothilone derivative.

Illustrative recombinant epoE gene derivatives of the invention include those in which the AT domain encoding sequences for the seventh module of the epothilone PKS have been altered or replaced to change the AT domain encoded thereby from a methylmalonyl specific AT to a malonyl specific AT. Such malonyl specific AT domain encoding nucleic acids can be isolated from for example and without limitation the PKS genes encoding the narbonolide PKS, the rapamycin PKS, and the FK-520 PKS. When coexpressed with the other epothilone PKS genes, epoA, epoB, epoC, epoD, and epoF, or derivatives thereof, a PKS for an epothilone derivative with a C-6 hydrogen, instead of a C-6 methyl, is produced. Thus, if the genes contain no other alterations, the compounds produced are the 6-desmethyl epothilones.

The eighth module of the epothilone PKS includes a KS, an AT specific for methylmalonyl CoA, inactive KR and DH domains, a methyltransferase (MT) domain, and an ACP. This module is encoded by a sequence within an ~10 kb NotI restriction fragment of cosmid pKOS35-79.85.

The recombinant DNA compounds of the invention that encode the eighth module of the epothilone PKS and the corresponding polypeptides encoded thereby are useful for a variety of applications. In one embodiment, a DNA compound comprising a sequence that encodes the epothilone eighth module is inserted into a DNA compound that comprises the coding sequence for one or more modules of a heterologous PKS. The resulting construct, in which the coding sequence for a module of the heterologous PKS is either replaced by that for the eighth module of the epothilone PKS or the latter is merely added to coding sequences for modules of the heterologous PKS, provides a novel PKS coding sequence that is expressed with the other proteins constituting the PKS to provide a novel PKS. Alternatively, the eighth module can be expressed as a discrete protein that can associate with other PKS proteins to constitute a novel PKS. In another embodiment, a DNA compound comprising a sequence that encodes the eighth module of the epothilone PKS is coexpressed with the other proteins constituting the epothilone PKS or a PKS that produces an epothilone derivative. In these embodiments, the eighth module is typically expressed as a protein that also comprises the seventh module or a derivative thereof.

In another embodiment, a portion or all of the eighth module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the inactive KR and/or the inactive DH; replacing the inactive KR and/or DH with an active KR and/or DH; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting heterologous eighth module coding sequence is expressed as a protein that is utilized in conjunction with the other proteins that constitute a PKS that synthesizes epothilone, an epothilone derivative, or another polyketide. When used to prepare epothilone or an epothilone derivative, the heterologous or hybrid eighth module is typically expressed as a recombinant epoE gene product that also contains the seventh module. Alternatively, the coding sequences for the eighth module in the epoE gene can be deleted or replaced by those for a heterologous module to prepare a recombinant epoE gene that, together with the epoA, epoB, epoC, epoD, and epoF genes, can be expressed to make a PKS for an epothilone derivative.

The eighth module of the epothilone PKS also comprises a methylation or methyltransferase (MT) domain with an activity that methylates the epothilone precursor. This function can be deleted to produce a recombinant epod gene derivative of the invention, which can be expressed with the other epothilone PKS genes or derivatives thereof that makes an epothilone derivative that lacks one or both methyl groups, depending on whether the AT domain of the eighth module has been changed to a malonyl specific AT domain, at the corresponding C-4 position of the epothilone molecule. In another important embodiment, the present invention provides recombinant DNA compounds that encode a polypeptide with this methylation domain and activity and a variety of recombinant PKS coding sequences that encode recombinant PKS enzymes that incorporate this polypeptide. The availability of this MT domain and the coding sequences therefor provides a significant number of new polyketides that differ from known polyketides by the presence of at least an additional methyl group. The MT domain of the invention can in effect be added to any PKS module to direct the methylation at the corresponding location in the polyketide produced by the PKS. As but one illustrative example, the present invention provides the recombinant nucleic acid compounds resulting from inserting the coding sequence for this MT activity into a coding sequence for any one or more of the six modules of the DEBS enzyme to produce a recombinant DEBS that synthesizes a 6-deoxyerythronolide B derivative that comprises one or more additional methyl groups at the C-2, C-4, C-6, C-8, C-10, and/or C-12 positions. In such constructs, the MT domain can be inserted adjacent to the AT or the ACP.

The ninth module of the epothilone PKS includes a KS, an AT specific for malonyl CoA, a KR, an inactive DH, and an ACP. This module is encoded by a sequence within an ~14.7 HindIII-BglII kb restriction fragment of cosmid pKOS35-79.85.

The recombinant DNA compounds of the invention that encode the ninth module of the epothilone PKS and the corresponding polypeptides encoded thereby are useful for a variety of applications. The ninth module of the epothilone PKS is expressed as a protein, the product of the epoF gene, that also contains the TE domain of the epothilone PKS. The present invention provides the epoF gene in recombinant form, as well as DNA compounds that encode the ninth module without the coding sequences for the TE domain and DNA compounds that encode the TE domain without the coding sequences for the ninth module. In one embodiment, a DNA compound comprising a sequence that encodes the epothilone ninth module is inserted into a DNA compound that comprises the coding sequence for one, or more modules of a heterologous PKS. The resulting construct, in which the coding sequence for a module of the heterologous PKS is either replaced by that for the ninth module of the epothilone PKS or the latter is merely added to coding sequences for the modules of the heterologous PKS, provides a novel PKS protein coding sequence that when coexpressed with the other proteins constituting a PKS provides a novel PKS. The ninth module coding sequence can also be expressed as a discrete protein with or without an attached TE domain. In another embodiment, a DNA compound comprising a sequence that encodes the ninth module of the epothilone PKS is expressed as a protein together with other proteins to constitute an epothilone PKS or a PKS that produces an epothilone derivative. In these embodiments, the ninth module is typically expressed as a protein that also contains the TE domain of either the epothilone PKS or a heterologous PKS.

In another embodiment, a portion or all of the ninth module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxy malonyl CoA specific AT; deleting the KR; replacing the KR with a KR that specifies a different stereochemistry; and/or inserting a DH or a DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the epothilone PKS, from a coding sequence for a PKS that produces a polyketide other than epothilone, or from chemical synthesis. The resulting heterologous ninth module coding sequence is coexpressed with the other proteins constituting a PKS that synthesizes epothilone, an epothilone derivative, or another polyketide. Alternatively, the present invention provides a PKS for an epothilone or epothilone derivative in which the ninth module has been replaced by a module from a heterologous PKS or has been deleted in its entirety. In the latter embodiment, the TE domain is expressed as a discrete protein or fused to the eighth module.

The ninth module of the epothilone PKS is followed by a thioesterase domain. This domain is encoded in the ~14.7 kb HindIII-BglII restriction comprising the ninth module coding sequence. The present invention provides recombinant DNA compounds that encode hybrid PKS enzymes in which the ninth module of the epothilone PKS is fused to a heterologous thioesterase or one or more modules of a heterologous PKS are fused to the epothilone PKS thioesterase. Thus, for example, a thioesterase domain coding sequence from another PKS can be inserted at the end of the ninth module ACP coding sequence in recombinant DNA compounds of the invention. Recombinant DNA compounds encoding this thioesterase domain are therefore useful in constructing DNA compounds that encode a protein of the epothilone PKS, a PKS that produces an epothilone derivative, and a PKS that produces a polyketide other than epothilone or an epothilone derivative.

In one important embodiment, the present invention thus provides a hybrid PKS and the corresponding recombinant DNA compounds that encode the proteins constituting those hybrid PKS enzymes. For purposes of the present invention a hybrid PKS is a recombinant PKS that comprises all or part of one or more modules, loading domain, and thioesterase/cyclase domain of a first PKS and all or part of one or more modules, loading domain, and thioesterase/cyclase domain of a second PKS. In one preferred embodiment, the first PKS is most but not all of the epothilone PKS, and the second PKS is only a portion or all of a non-epothilone PKS. An illustrative example of such a hybrid PKS includes an epothilone PKS in which the natural loading domain has been replaced with a loading domain of another PKS. Another example of such a hybrid PKS is an epothilone PKS in which the AT domain of module four is replaced with an AT domain from a heterologous PKS that binds only methylmalonyl CoA. In another preferred embodiment, the first PKS is most but not all of a non-epothilone PKS, and the second PKS is only a portion or all of the epothilone PKS. An illustrative example of such a hybrid PKS includes an erythromycin PKS in which an AT specific for methylmalonyl CoA is replaced with an AT from the epothilone PKS specific for malonyl CoA. Another example is an erythromycin PKS that includes the MT domain of the epothilone PKS.

Those of skill in the art will recognize that all or part of either the first or second PKS in a hybrid PKS of the invention need not be isolated from a naturally occurring source. For example, only a small portion of an AT domain determines its specificity. See U.S. patent application Ser. No. 09/346,860 and PCT patent application No. WO US99/15047, each of which is incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

The following Table lists references describing illustrative PKS genes and corresponding enzymes that can be utilized in the construction of the recombinant PKSs and the corresponding DNA compounds that encode them of the invention. Also presented are various references describing polyketide tailoring and modification enzymes and corresponding genes that can be employed to make the recombinant DNA compounds of the present invention.

Avermectin
U.S. Pat. No. 5,252,474 to Merck.
MacNeil et al., 1993, *Industrial Microorganisms: Basic and Applied Molecular Genetics*, Baltz, Hegeman, & Skatrud, eds. (ASM), pp. 245-256, A Comparison of the Genes Encoding the Polyketide Synthases for Avermectin, Erythromycin, and Nemadectin.
MacNeil et al., 1992, Gene 115: 119-125, Complex Organization of the *Streptomyces avermitilis* genes encoding the avermectin polyketide synthase.
Ikeda and Omura, 1997, Chem. Res. 97: 2599-2609, Avermectin biosynthesis.

Candicidin (FR008)
Hu et al., 1994, Mol. Microbiol. 14: 163-172.

Erythromycin
PCT Pub. No. 93/13663 to Abbott.
U.S. Pat. No. 5,824,513 to Abbott.
Donadio et al., 1991, Science 252:675-9.
Cortes et al., 8 Nov. 1990, Nature 348:176-8, An unusually large multifunctional polypeptide in the erythromycin producing polyketide synthase of *Saccharopolyspora erythraea*.
Glycosylation Enzymes
PCT Pat. App. Pub. No. 97/23630 to Abbott.

FK-506
Motamedi et al., 1998, The biosynthetic gene cluster for the macrolactone ring of the immunosuppressant FK-506, Eur. J. Biochem. 256: 528-534.
Motamedi et al., 1997, Structural organization of a multifunctional polyketide synthase involved in the biosynthesis of the macrolide immunosuppressant FK-506, Eur. J. Biochem. 244: 74-80.

Methyltransferase
U.S. Pat. No. 5,264,355, issued 23 Nov. 1993, Methylating enzyme from *Streptomyces* MA6858. 31-O-desmethyl-FK-506 methyltransferase.
Motamedi et al., 1996, Characterization of methyltransferase and hydroxylase genes involved in the biosynthesis of the immunosuppressants FK-506 and FK-520, J. Bacteriol. 178: 5243-5248.

FK-520
U.S. patent application Ser. No. 09/154,083, filed 16 Sep. 1998.
U.S. patent application Ser. No. 09/410,551, filed 1 Oct. 1999.
Nielsen et al., 1991, Biochem. 30:5789-96.

Lovastatin
U.S. Pat. No. 5,744,350 to Merck.

Narbomycin
U.S. patent application Ser. No. 60/107,093, filed 5 Nov. 1998.

Nemadectin
MacNeil et al., 1993, supra.

Niddamycin
Kakavas et al., 1997, Identification and characterization of the niddamycin polyketide synthase genes from *Streptomyces caelestis*, J. Bacteriol. 179: 7515-7522.

Oleandomycin
Swan et al., 1994, Characterisation of a *Streptomyces antibioticus* gene encoding a type I polyketide synthase which has an unusual coding sequence, Mol. Gen. Genet. 242: 358-362.
U.S. patent application Ser. No. 60/120,254, filed 16 Feb. 1999, Ser. No. 60/106,100, filed 28 Oct. 1999, claiming priority thereto by inventors S. Shah, M. Betlach, R. McDaniel, and L. Tang.
Olano et al., 1998, Analysis of a *Streptomyces antibioticus* chromosomal region involved in oleandomycin biosynthesis, which encodes two glycosyltransferases responsible for glycosylation of the macrolactone ring, Mol. Gen. Genet. 259 (3): 299-308.

Picromycin
PCT patent application No. WO US99/11814, filed 28 May 1999.
U.S. patent application Ser. No. 09/320,878, filed 27 May 1999.
U.S. patent application Ser. No. 09/141,908, filed 28 Aug. 1998.
Xue et al., 1998, Hydroxylation of macrolactones YC-17 and narbomycin is mediated by the pikC-encoded cytochrome P450 in *Streptomyces venezuelae*, Chemistry & Biology 5(11): 661-667.
Xue et al., October 1998, A gene cluster for macrolide antibiotic biosynthesis in *Streptomyces venezuelae*: Architecture of metabolic diversity, Proc. Natl. Acad. Sci. USA 95: 12111 12116.

Platenolide
EP Pat. App. Pub. No. 791,656 to Lilly.

Pradimicin
PCT Pat. Pub. No. WO 98/11230 to Bristol-Myers Squibb.

Rapamycin
Schwecke et al., August 1995, The biosynthetic gene cluster for the polyketide rapamycin, Proc. Natl. Acad. Sci. USA 92:7839-7843.

Aparicio et al., 1996, Organization of the biosynthetic gene cluster for rapamycin in *Streptomyces hygroscopicus*: analysis of the enzymatic domains in the modular polyketide synthase, Gene 169: 9-16.

Rifamycin

PCT Pat. Pub. No. WO 98/07868 to Novartis.

August et al., 13 Feb. 1998, Biosynthesis of the ansamycin antibiotic rifamycin: deductions from the molecular analysis of the rifbiosynthetic gene cluster of Amycolatopsis mediterranei S669, Chemistry & Biology, 5(2): 69-79.

*Sorangium* PKS

U.S. patent application Ser. No. 09/144,085, filed 31 Aug. 1998.

Soraphen

U.S. Pat. No. 5,716,849 to Novartis.

Schupp et al., 1995, J. Bacteriology 177: 3673-3679. A *Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

U.S. Pat. No. 5,876,991 to Lilly.

EP Pub. No. 791,655 to Lilly.

Kuhstoss et al., 1996, Gene 183:231-6., Production of a novel polyketide through the construction of a hybrid polyketide synthase.

Tailoring Enzymes

Merson-Davies and Cundliffe, 1994, Mol. Microbiol. 13: 349-355. Analysis of five tylosin biosynthetic genes from the tylBA region of the *Streptomyces fradiae* genome.

As the above Table illustrates, there are a wide variety of PKS genes that serve as readily available sources of DNA and sequence information for use in constructing the hybrid PKS-encoding DNA compounds of the invention. Methods for constructing hybrid PKS-encoding DNA compounds are described without reference to the epothilone PKS in U.S. Pat. Nos. 5,672,491 and 5,712,146 and U.S. patent application Ser. No. 09/073,538, filed 6 May 1998, and 09/141,908, filed 28 Aug. 1998, each of which is incorporated herein by reference. Preferred PKS enzymes and coding sequences for the proteins which constitute them for purposes of isolating heterologous PKS domain coding sequences for constructing hybrid PKS enzymes of the invention are the soraphen PKS and the PKS described as a *Sorangium* PKS in the above table.

To summarize the functions of the genes cloned and sequenced in Example 1:

| Gene | Protein | Modules | Domains Present |
|------|---------|---------|-----------------|
| epoA | EpoA | Load | Ks$^y$ mAT ER ACP |
| epoB | EpoB | 1 | NRPS, condensation, heterocyclization, adenylation, thiolation, PCP |
| epoC | EpoC | 2 | KS mmAT DH KR ACP |
| epoD | EpoD | 3 | KS mAT KR ACP |
|      |      | 4 | KS mAT KR ACP |
|      |      | 5 | KS mAT DH ER KR ACP |
|      |      | 6 | KS mmAT DH ER KR ACP |

-continued

| Gene | Protein | Modules | Domains Present |
|------|---------|---------|-----------------|
| epoE | EpoE | 7 | KS mmAT KR ACP |
|      |      | 8 | KS mmAT MT DH* KR* ACP |
| epoF | EpoF | 9 | KS mAT KR DH* ACP TE |

NRPS—non-ribosomal peptide synthetase;
KS—ketosynthase;
mAT—malonyl CoA specifying acyltransferase;
mmAT—methylmalonyl CoA specifying acyltransferase;
DH—dehydratase;
ER—enoylreductase;
KR—ketoreductase;
MT—methyltransferase;
TE thioesterase;
*—inactive domain.

The hybrid PKS-encoding DNA compounds of the invention can be and often are hybrids of more than two PKS genes. Even where only two genes are used, there are often two or more modules in the hybrid gene in which all or part of the module is derived from a second (or third) PKS gene. Illustrative examples of recombinant epothilone derivative PKS genes of the invention, which are identified by listing the specificities of the hybrid modules (the other modules having the same specificity as the epothilone PKS), include:

(a) module 4 with methylmalonyl specific AT (mm AT) and a KR and module 2 with a malonyl specific AT (m AT) and a KR;

(b) module 4 with mM AT and a KR and module 3 with mM AT and a KR;

(c) module 4 with mM AT and a KR and module 5 with mM AT and a ER, DH, and KR;

(d) module 4 with mM AT and a KR and module 5 with mM AT and a DH and KR;

(e) module 4 with mM AT and a KR and module 5 with mM AT and a KR;

(f) module 4 with mM AT and a KR and module 5 with mM AT and an inactive KR;

(g) module 4 with mM AT and a KR and module 6 with m AT and a ER, DH, and KR;

(h) module 4 with mM AT and a KR and module 6 with m AT and a DH and KR;

(i) module 4 with mM AT and a KR and module 6 with m AT and a KR;

(j) module 4 with mM AT and a KR and module 6 with m AT and an inactive KR;

(k) module 4 with mM AT and a KR and module 7 with m AT;

(l) hybrids (c) through (f), except that module 5 has a m AT;

(m) hybrids (g) through (O) except that module 6 has a mM AT; and (n) hybrids (a) through (m) except that module 4 has a m AT.

The above list is illustrative only and should not be construed as limiting the invention, which includes other recombinant epothilone PKS genes and enzymes with not only two hybrid modules other than those shown but also with three or more hybrid modules.

Those of skill in the art will appreciate that a hybrid PKS of the invention includes but is not limited to a PKS of any of the following types: (i) an epothilone or epothilone derivative PKS that contains a module in which at least one of the domains is from a heterologous module; (ii) an epothilone or epothilone derivative PKS that contains a module from a heterologous PKS; (iii) an epothilone or epothilone derivative PKS that contains a protein from a heterologous PKS; and (iv) combinations of the foregoing.

While an important embodiment of the present invention relates to hybrid PKS genes, the present invention also provides recombinant epothilone PKS genes in which there is no second PKS gene sequence present but which differ from the epothilone PKS gene by one or more deletions. The deletions can encompass one or more modules and/or can be limited to a partial deletion within one or more modules. When a deletion encompasses an entire module other than the NRPS module, the resulting epothilone derivative is at least two carbons shorter than the compound produced from the PKS from which the deleted version was derived. The deletion can also encompass the NRPS module and/or the loading domain, as noted above. When a deletion is within a module, the deletion typically encompasses a KR, DH, or ER domain, or both DH and ER domains, or both KR and DH domains, or all three KR, DH, and ER domains.

The catalytic properties of the domains and modules of the epothilone PKS and of epothilone modification enzymes can also be altered by random or site specific mutagenesis of the corresponding genes. A wide variety of mutagenizing agents and methods are known in the art and are suitable for this purpose. The technique known as DNA shuffling can also be employed. See, e.g., U.S. Pat. Nos. 5,830,721; 5,811,238; and 5,605,793; and references cited therein, each of which is incorporated herein by reference.

Recombinant Manipulations

To construct a hybrid PKS or epothilone derivative PKS gene of the invention, or simply to express unmodified epothilone biosynthetic genes, one can employ a technique, described in PCT Pub. No. 98/27203 and U.S. patent application Ser. No. 08/989,332, filed 11 Dec. 1997, and 60/129, 731, filed 16 Apr. 1999, each of which is incorporated herein by reference, in which the various genes of the PKS are divided into two or more, often three, segments, and each segment is placed on a separate expression vector. In this manner, the full complement of genes can be assembled and manipulated more readily for heterologous expression, and each of the segments of the gene can be altered, and various altered segments can be combined in a single host cell to provide a recombinant PKS of the invention. This technique makes more efficient the construction of large libraries of recombinant PKS genes, vectors for expressing those genes, and host cells comprising those vectors. In this and other contexts, the genes encoding the desired PKS are not only present on two or more vectors, but also can be ordered or arranged differently than in the native producer organism from which the genes were derived. Various examples of this technique as applied to the epothilone PKS are described in the Examples below. In one embodiment, the epoA, epoB, epoC, and epoD genes are present on a first plasmid, and the epoE and epoF and optionally either the epoK or the epoK and epoL genes are present on a second (or third) plasmid.

Thus, in one important embodiment, the recombinant nucleic acid compounds of the invention are expression vectors. As used herein, the term "expression vector" refers to any nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA that is translated into a polypeptide in the cell or cell extract. Thus, the vector typically includes a promoter to enhance gene expression but alternatively may serve to incorporate the relevant coding sequence under the control of an endogenous promoter. Furthermore, expression vectors may typically contain additional functional elements, such as resistance-conferring genes to act as selectable markers and regulatory genes to enhance promoter activity.

The various components of an expression vector can vary widely, depending on the intended use of the vector. In particular, the components depend on the host cell(s) in which the vector will be used or is intended to function. Vector components for expression and maintenance of vectors in *E. coli* are widely known and commercially available, as are vector components for other commonly used organisms, such as yeast cells and *Streptomyces* cells.

In one embodiment, the vectors of the invention are used to transform *Sorangium* host cells to provide the recombinant *Sorangium* host cells of the invention. U.S. Pat. No. 5,686, 295, incorporated herein by reference, describes a method for transforming *Sorangium* host cells, although other methods may also be employed. *Sorangium* is a convenient host for expressing epothilone derivatives of the invention in which the recombinant PKS that produces such derivatives is expressed from a recombinant vector in which the epothilone PKS gene promoter is positioned to drive expression of the recombinant coding sequence. The epothilone PKS gene promoter is provided in recombinant form by the present invention and is an important embodiment thereof. The promoter is contained within an ~500 nucleotide sequence between the end of the transposon sequences and the start site of the open reading frame of the epoA gene. Optionally, one can include sequences from further upstream of this ~500 bp region in the promoter. Those of skill in the art will recognize that, if a *Sorangium* host that produces epothilone is used as the host cell, the recombinant vector need drive expression of only a portion of the PKS containing the altered sequences. Thus, such a vector may comprise only a single altered epothilone PKS gene, with the remainder of the epothilone PKS polypeptides provided by the genes in the host cell chromosomal DNA. If the host cell naturally produces an epothilone, the epothilone derivative will thus be produced in a mixture containing the naturally occurring epothilone(s).

Those of skill will also recognize that the recombinant DNA compounds of the invention can be used to construct *Sorangium* host cells in which one or more genes involved in epothilone biosynthesis have been rendered inactive. Thus, the invention provides such *Sorangium* host cells, which may be preferred host cells for expressing epothilone derivatives of the invention so that complex mixtures of epothilones are avoided. Particularly preferred host cells of this type include those in which one or more of any of the epothilone PKS gene ORFs has been disrupted, and/or those in which any or more of the epothilone modification enzyme genes have been disrupted. Such host cells are typically constructed by a process involving homologous recombination using a vector that contains DNA homologous to the regions flanking the gene segment to be altered and positioned so that the desired homologous double crossover recombination event desired will occur.

Homologous recombination can thus be used to delete, disrupt, or alter a gene. In a preferred illustrative embodiment, the present invention provides a recombinant epothilone producing *Sorangium cellulosum* host cell in which the epoK gene has been deleted or disrupted by homologous recombination using a recombinant DNA vector of the invention. This host cell, unable to make the epoK epoxidase gene product is unable to make epothilones A and B and so is a preferred source of epothilones C and D.

Homologous recombination can also be used to alter the specificity of a PKS module by replacing coding sequences for the module or domain of a module to be altered with those specifying a module or domain of the desired specificity. In another preferred illustrative embodiment, the present invention provides a recombinant epothilone producing *Sorangium cellulosum* host cell in which the coding sequence for the AT domain of module 4 encoded by the epoD gene has been altered by homologous recombination using a recombinant DNA vector of the invention to encode an AT domain that binds only methylmalonyl CoA. This host cell, unable to make epothilones A, C, and E is a preferred source of epothilones B, D, and F. The invention also provides recombinant *Sorangium* host cells in which both alterations and deletions of epothilone biosynthetic genes have been made. For example, the invention provides recombinant *Sorangium cellulosum* host cells in which both of the foregoing alteration and deletion have been made, producing a host cell that makes only epothilone D.

In similar fashion, those of skill in the art will appreciate the present invention provides a wide variety of recombinant *Sorangium cellulosum* host cells that make less complex mixtures of the epothilones than do the wild type producing cells as well as those that make one or more epothilone derivatives. Such host cells include those that make only epothilones A, C, and E; those that make only epothilones B, D, and F, those that make only epothilone D; and those that make only epothilone C.

In another preferred embodiment, the present invention provides expression vectors and recombinant *Myxococcus*, preferably *M. xanthus*, host cells containing those expression vectors that express a recombinant epothilone PKS or a PKS for an epothilone derivative. Presently, vectors that replicate extrachromosomally in *M. xanthus* are not known. There are, however, a number of phage known to integrate into *M. xanthus* chromosomal DNA, including Mx8, Mx9, Mx81, and Mx82. The integration and attachment function of these phages can be placed on plasmids to create phage-based expression vectors that integrate into the *M. xanthus* chromosomal DNA. Of these, phage Mx9 and Mx8 are preferred for purposes of the present invention. Plasmid pPLH343, described in Salmi et al., February 1998, Genetic determinants of immunity and integration of temperate *Myxococcus xanthus* phage Mx8, J. Bact. 180(3): 614-621, is a plasmid that replicates in *E. coli* and comprises the phage Mx8 genes that encode the attachment and integration functions.

The promoter of the epothilone PKS gene functions in *Myxococcus xanthus* host cells. Thus, in one embodiment, the present invention provides a recombinant promoter for use in recombinant host cells derived from the promoter of the *Sorangium cellulosum* epothilone PKS gene. The promoter can be used to drive expression of one or more epothilone PKS genes or another useful gene product in recombinant host cells. The invention also provides an epothilone PKS expression vector in which one or more of the epothilone PKS or epothilone modification enzyme genes are under the control of their own promoter. Another preferred promoter for use in *Myxococcus xanthus* host cells for purposes of expressing a recombinant PKS of the invention is the promoter of the pilA gene of *M. xanthus*. This promoter, as well as two *M. xanthus* strains that express high levels of gene products from genes controlled by the pilA promoter, a pilA deletion strain and a pilS deletion strain, are described in Wu and Kaiser, December 1997, Regulation of expression of the pilA gene in *Myxococcus xanthus*, J. Bact. 179(24):7748-7758, incorporated herein by reference. Optionally, the invention provides recombinant *Myxococcus* host cells comprising both the pilA and pilS deletions. Another preferred promoter is the starvation dependent promoter of the sdcK gene.

Selectable markers for use in *Myxococcus xanthus* include kanamycin, tetracycline, chloramphenicol, zeocin, spectinomycin, and streptomycin resistance conferring genes. The recombinant DNA expression vectors of the invention for use in *Myxococcus* typically include such a selectable marker and may further comprise the promoter derived from an epothilone PKS or epothilone modification enzyme gene.

Figure 3:
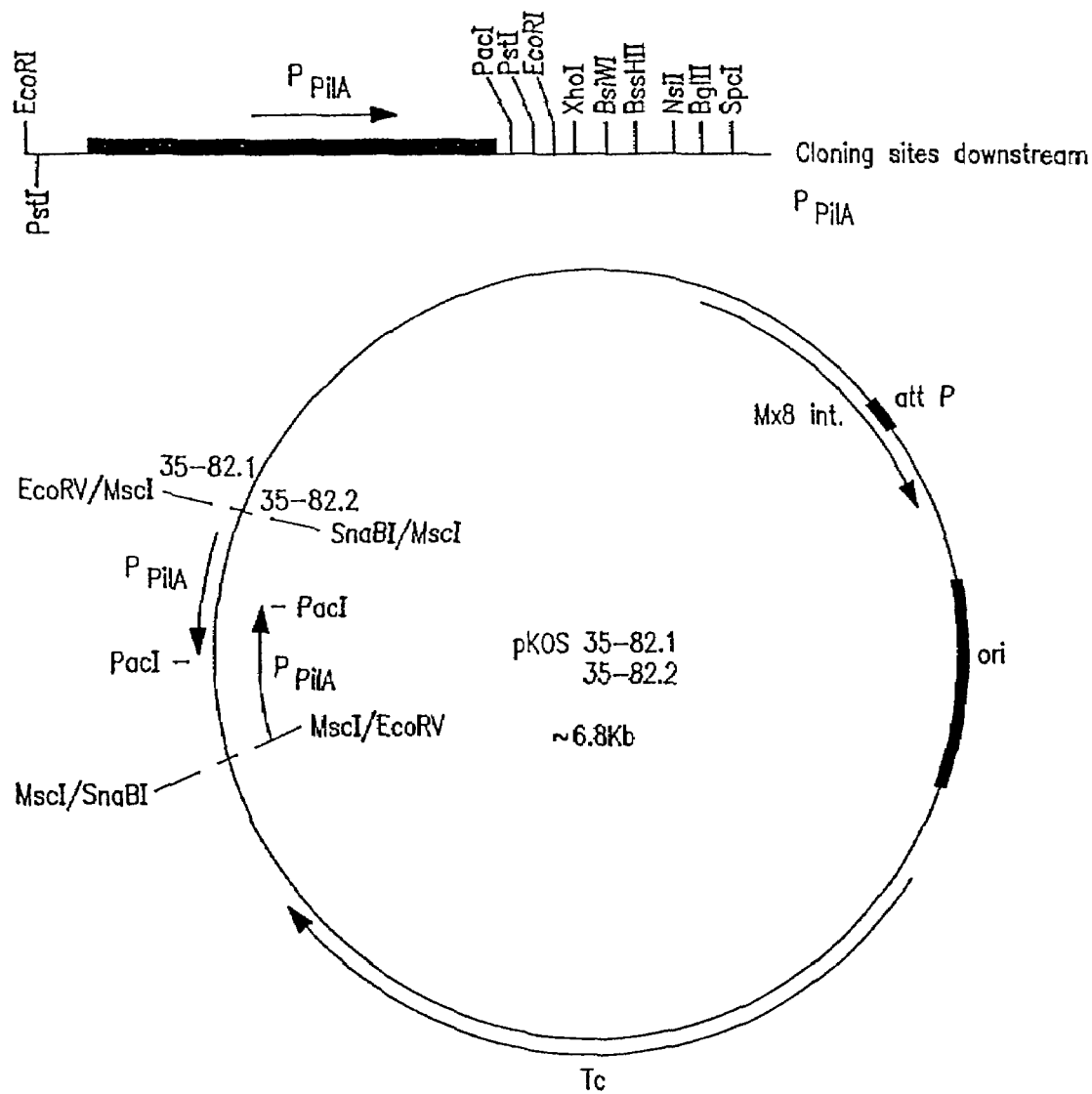
FIG. 3 shows restriction site and function maps of plasmids pKOS35-82.1 and pKOS35-82.2.

The present invention provides preferred expression vectors for use in preparing the recombinant *Myxococcus xanthus* expression vectors and host cells of the invention. These vectors, designated plasmids pKOS35-82.1 and pKOS35-82.2 (FIG. 3), are able to replicate in *E. coli* host cells as well as integrate into the chromosomal DNA of *M. xanthus*. The vectors comprise the Mx8 attachment and integration genes as well as the pilA promoter with restriction enzyme recognition sites placed conveniently downstream. The two vectors differ from one another merely in the orientation of the pilA promoter on the vector and can be readily modified to include the epothilone PKS and modification enzyme genes of the invention. The construction of the vectors is described in Example 2.

Especially preferred *Myxococcus* host cells of the invention are those that produce an epothilone or epothilone derivative or mixtures of epothilones or epothilone derivatives at equal to or greater than 20 mg/L, more preferably at equal to or greater than 200 mg/L, and most preferably at equal to or greater than 1 g/L. Especially preferred are *M. xanthus* host cells that produce at these levels. *M. xanthus* host cells that can be employed for purposes of the invention include the DZ1 (Campos et al., 1978, J. Mol. Biol. 119: 167-178, incorporated herein by reference), the TA-producing cell line ATCC 31046, DK1219 (Hodgkin and Kaiser, 1979, Mol. Gen. Genet. 171: 177-191, incorporated herein by reference), and the DK1622 cell lines (Kaiser, 1979, Proc. Natl. Acad. Sci. USA 76: 5952-5956, incorporated herein by reference).

In another preferred embodiment, the present invention provides expression vectors and recombinant *Pseudomonas fluorescens* host cells that contain those expression vectors and express a recombinant PKS of the invention. A plasmid for use in constructing the *P. fluorescens* expression vectors and host cells of the invention is plasmid pRSF1010, which replicates in *E. coli* and *P. fluorescens* host cells (see Scholz et al., 1989, Gene 75:271-8, incorporated herein by reference). Low copy number replicons and vectors can also be used. As noted above, the invention also provides the promoter of the *Sorangium cellulosum* epothilone PKS and epothilone modification enzyme genes in recombinant form. The promoter can be used to drive expression of an epothilone PKS gene or other gene in *P. fluorescens* host cells. Also, the promoter of the soraphen PKS genes can be used in any host cell in which a *Sorangium* promoter functions. Thus, in one embodiment, the present invention provides an epothilone PKS expression vector for use in *P. fluorescens* host cells.

In another preferred embodiment, the expression vectors of the invention are used to construct recombinant *Streptomyces* host cells that express a recombinant PKS of the invention. *Streptomyces* host cells useful in accordance with the invention include *S. coelicolor, S. lividans, S. venezuelae, S. ambofaciens, S. fradiae*, and the like. Preferred *Streptomyces* host cell/vector combinations of the invention include *S. coelicolor* CH999 and *S. lividans* K4-114 and K4-155 host cells, which do not produce actinorhodin, and expression vectors derived from the pRM1 and pRM5 vectors, as described in U.S. Pat. No. 5,830,750 and U.S. patent application Ser. No. 08/828,898, filed 31 Mar. 1997, and 09/181,833, filed 28 Oct.

1998. Especially preferred *Streptomyces* host cells of the invention are those that produce an epothilone or epothilone derivative or mixtures of epothilones or epothilone derivatives at equal to or greater than 20 mg/L, more preferably at equal to or greater than 200 mg/L, and most preferably at equal to or greater than 1 g/L. Especially preferred are *S. coelicolor* and *S. lividans* host cells that produce at these levels. Also, species of the closely related genus *Saccharopolyspora* can be used to produce epothilones, including but not limited to *S. erythraea*.

The present invention provides a wide variety of expression vectors for use in *Streptomyces*. For replicating vectors, the origin of replication can be, for example and without limitation, a low copy number replicon and vectors comprising the same, such as SCP2* (see Hopwood et al., Genetic Manipulation of *Streptomyces*: A Laboratory manual (The John Innes Foundation, Norwich, U.K., 1985); Lydiate et al., 1985, Gene 35: 223-235; and Kieser and Melton, 1988, Gene 65: 83-91, each of which is incorporated herein by reference), SLP 1.2 (Thompson et al., 1982, Gene 20: 51-62, incorporated herein by reference), and pSG5(ts) (Muth et al., 1989, Mol. Gen. Genet. 219: 341-348, and Bierman et al., 1992, Gene 116: 43-49, each of which is incorporated herein by reference), or a high copy number replicon and vectors comprising the same, such as pIJ101 and pJV1 (see Katz et al., 1983, J. Gen. Microbiol. 129: 2703-2714; Vara et al., 1989, J. Bacteriol. 171: 5782-5781; and Servin-Gonzalez, 1993, Plasmid 30: 131-140, each of which is incorporated herein by reference). High copy number vectors are generally, however, not preferred for expression of large genes or multiple genes. For non-replicating and integrating vectors and generally for any vector, it is useful to include at least an *E. coli* origin of replication, such as from pUC, p1P, p1I, and pBR. For phage based vectors, the phage phiC31 and its derivative KC515 can be employed (see Hopwood et al., supra). Also, plasmid pSET152, plasmid pSAM, plasmids pSE101 and pSE211, all of which integrate site-specifically in the chromosomal DNA of *S. lividans*, can be employed.

Typically, the expression vector will comprise one or more marker genes by which host cells containing the vector can be identified and/or selected. Useful antibiotic resistance conferring genes for use in *Streptomyces* host cells include the ermE (confers resistance to erythromycin and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

The recombinant PKS gene on the vector will be under the control of a promoter, typically with an attendant ribosome binding site sequence. A preferred promoter is the actI promoter and its attendant activator gene actII-ORF4, which is provided in the pRM1 and pRM5 expression vectors, supra. This promoter is activated in the stationary phase of growth when secondary metabolites are normally synthesized. Other useful *Streptomyces* promoters include without limitation those from the ermE gene and the melC1 gene, which act constitutively, and the tipA gene and the merA gene, which can be induced at any growth stage. In addition, the T7 RNA polymerase system has been transferred to *Streptomyces* and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene discussed above include dnrI, redD, and ptpA genes (see U.S. patent application Ser. No. 09/181,833, supra), which can be employed with their cognate promoters to drive expression of a recombinant gene of the invention.

The present invention also provides recombinant expression vectors that drive expression of the epothilone PKS and PKS enzymes that produce epothilone or epothilone derivatives in plant cells. Such vectors are constructed in accordance with the teachings in U.S. patent application Ser. No. 09/114,083, filed 10 Jul. 1998, and PCT patent publication No. 99/02669, each of which is incorporated herein by reference. Plants and plant cells expressing epothilone are disease resistant and able to resist fungal infection. For improved production of an epothilone or epothilone derivative in any heterologous host cells, including plant, Myxococcus, *Pseudomonas*, and *Streptomyces* host cells, one can also transform the cell to express a heterologous phosphopantetheinyl transferase. See U.S. patent application Ser. No. 08/728,742, filed 11 Oct. 1996, and PCT patent publication No. 97/13845, both of which are incorporated herein by reference.

In addition to providing recombinant expression vectors that encode the epothilone or an epothilone derivative PKS, the present invention also provides, as discussed above, DNA compounds that encode epothilone modification enzyme genes. As discussed above, these gene products convert epothilones C and D to epothilones A and B, and convert epothilones A and B to epothilones E and F. The present invention also provides recombinant expression vectors and host cells transformed with those vectors that express any one or more of those genes and so produce the corresponding epothilone or epothilone derivative. In one aspect, the present invention provides the epoK gene in recombinant form and host cells that express the gene product thereof, which converts epothilones C and D to epothilones A and B, respectively.

In another important embodiment, and as noted above, the present invention provides vectors for disrupting the function of any one or more of the epoL, epoK, and any of the ORFs associated with the epothilone PKS gene cluster in *Sorangium* cells. The invention also provides recombinant *Sorangium* host cells lacking (or containing inactivated forms of) any one or more of these genes. These cells can be used to produce the corresponding epothilones and epothilone derivatives that result from the absence of any one or more of these genes.

The invention also provides non-*Sorangium* host cells that contain a recombinant epothilone PKS or a PKS for an epothilone derivative but do not contain (or contain non-functional forms of) any epothilone modification enzyme genes. These host cells of the invention are expected produce epothilones G and H in the absence of a dehydratase activity capable of forming the C-12-C-13 alkene of epothilones C and D. This dehydration reaction is believed to take place in the absence of the epoL gene product in *Streptomyces* host cells. The host cells produce epothilones C and D (or the corresponding epothilone C and D derivative) when the dehydratase activity is present and the P450 epoxidase and hydroxylase (that converts epothilones A and B to epothilones E and F, respectively) genes are absent. The host cells also produce epothilones A and B (or the corresponding epothilone A and B derivatives) when the hydroxylase gene only is absent. Preferred for expression in these host cells is the recombinant epothilone PKS enzymes of the invention that contain the hybrid module 4 with an AT specific for methylnalonlyl CoA only, optionally in combination with one or more additional hybrid modules. Also preferred for expression in these host cells is the recombinant epothilone PKS enzymes of the invention that contain the hybrid module 4 with an AT specific for malonyl CoA only, optionally in combination with one or more additional hybrid modules.

The recombinant host cells of the invention can also include other genes and corresponding gene products that enhance production of a desired epothilone or epothilone derivative. As but one non-limiting example, the epothilone PKS proteins require phosphopantetheinylation of the ACP domains of the loading domain and modules 2 through 9 as well as of the PCP domain of the NRPS. Phosphopantetheinylation is mediated by enzymes that are called phosphopantetheinyl transferases (PPTases). To produce functional PKS enzyme in host cells that do not naturally express a PPTase able to act on the desired PKS enzyme or to increase amounts of functional PKS enzyme in host cells in which the PPTase is rate-limiting, one can introduce a heterologous PPTase, including but not limited to Sfp, as described in PCT Pat. Pub. Nos. 97/13845 and 98/27203, and U.S. patent application Ser. No. 08/728,742, filed 11 Oct. 1996, and 08/989,332, each of which is incorporated herein by reference.

The host cells of the invention can be grown and fermented under conditions known in the art for other purposes to produce the compounds of the invention. The compounds of the invention can be isolated from the fermentation broths of these cultured cells and purified by standard procedures. Fermentation conditions for producing the compounds of the invention from *Sorangium* host cells can be based on the protocols described in PCT patent publication Nos. 93/10121, 97/19086, 98/22461, and 99/42602, each of which is incorporated herein by reference. The novel epothilone analogs of the present invention, as well as the epothilones produced by the host cells of the invention, can be derivatized and formulated as described in PCT patent publication Nos. 93/10121, 97/19086, 98/08849, 98/22461, 98/25929, 99/01124, 99/02514, 99/07692, 99/27890, 99/39694, 99/40047, 99/42602, 99/43653, 99/43320, 99/54319, 99/54319, and 99/54330, and U.S. Pat. No. 5,969,145, each of which is incorporated herein by reference.

Invention Compounds

Preferred compounds of the invention include the 14-methyl epothilone derivatives (made by utilization of the hybrid module 3 of the invention that has an AT that binds methylmalonyl CoA instead of malonyl CoA); the 8,9-dehydro epothilone derivatives (made by utilization of the hybrid module 6 of the invention that has a DH and KR instead of an ER, DH, and KR); the 10-methyl epothilone derivatives (made by utilization of the hybrid module 5 of the invention that has an AT that binds methylmalonyl CoA instead of malonyl CoA); the 9-hydroxy epothilone derivatives (made by utilization of the hybrid module 6 of the invention that has a KR instead of an ER, DH, and KR); the 8-desmethyl-14-methyl epothilone derivatives (made by utilization of the hybrid module 3 of the invention that has an AT that binds methylmalonyl CoA instead of malonyl CoA and a hybrid module 6 that binds malonyl CoA instead of methylmalonyl CoA); and the 8-desmethyl-8,9-dehydro epothilone derivatives (made by utilization of the hybrid module 6 of the invention that has a DH and KR instead of an ER, DH, and KR and an AT that specifies malonyl CoA instead of methylmalonyl CoA).

More generally, preferred epothilone derivative compounds of the invention are those that can be produced by altering the epothilone PKS genes as described herein and optionally by action of epothilone modification enzymes and/ or by chemically modifying the resulting epothilones produced when those genes are expressed. Thus, the present invention provides compounds of the formula:

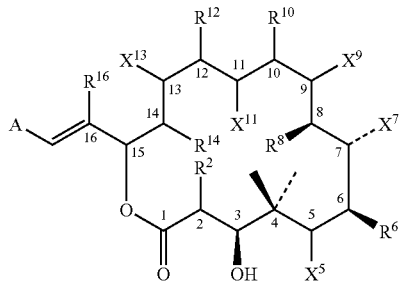

(1)

including the glycosylated forms thereof and stereoisomeric forms where the stereochemistry is not shown, wherein A is a substituted or unsubstituted straight, branched chain or cyclic alkyl, alkenyl or alkynyl residue optionally containing 1-3 heteroatoms selected from O, S and N; or wherein A comprises a substituted or unsubstituted aromatic residue;

$R^2$ represents H,H, or H,lower alkyl, or lower alkyl,lower alkyl;

$X^5$ represents =O or a derivative thereof, or H,OH or H,NR$_2$ wherein R is H, or alkyl, or acyl or H,OCOR or H,OCONR$_2$ wherein R is H, or alkyl, or is H,H;

$R^6$ represents H or lower alkyl, and the remaining substituent on the corresponding carbon is H;

$X^7$ represents OR, NR$_2$, wherein R is H, or alkyl or acyl or is OCOR, or OCONR$_2$ wherein R is H or alkyl or $X^7$ taken together with $X^9$ forms a carbonate or carbamate cycle, and wherein the remaining substituent on the corresponding carbon is H;

$R^8$ represents H or lower alkyl and the remaining substituent on the carbon is H;

$X^9$ represents =O or a derivative thereof, or is H,OR or H,NR$_2$, wherein R is H, or alkyl or acyl or is H,OCOR or H,OCONR$_2$ wherein R is H or alkyl, or represents H,H or wherein $X^9$ together with $X^7$ or with $X^{11}$ can form a cyclic carbonate or carbamate;

$R_{10}$ is H,H or H,lower alkyl, or lower alkyl,lower alkyl;

$X^{11}$ is =O or a derivative thereof, or is H,OR, or H,NR$_2$ wherein R is H, or alkyl or acyl or is H,OCOR or H,OCONR$_2$ wherein R is H or alkyl, or is H,H or wherein $X^{11}$ in combination with $X^9$ may form a cyclic carbonate or carbamate;

$R^{12}$ is H,H, or H,lower alkyl, or lower alkyl,lower alkyl;

$X^{13}$ is =O or a derivative thereof, or H,OR or H,NR$_2$ wherein R is H, alkyl or acyl or is H,OCOR or H,OCONR$_2$ wherein R is H or alkyl;

$R^{14}$ is H,H, or H,lower alkyl, or lower alkyl,lower alkyl;

$R^{16}$ is H or lower alkyl; and wherein optionally H or another substituent may be removed from positions 12 and 13 and/or 8 and 9 to form a double bond, wherein said double bond may optionally be converted to an epoxide.

Particularly preferred are compounds of the formulas

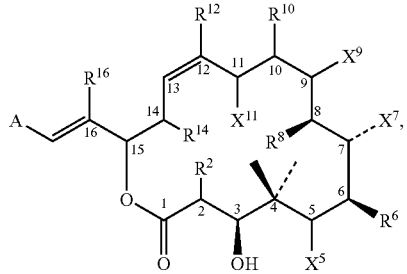

1(a)

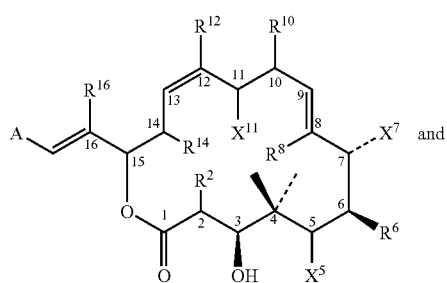

1(b) and

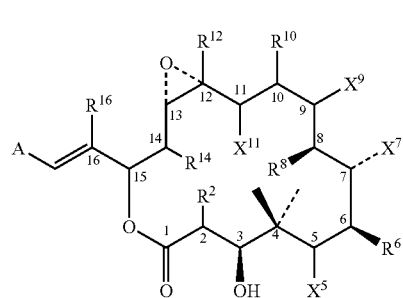

1(c)

wherein the noted substituents are as defined above.

Especially preferred are compounds of the formulas

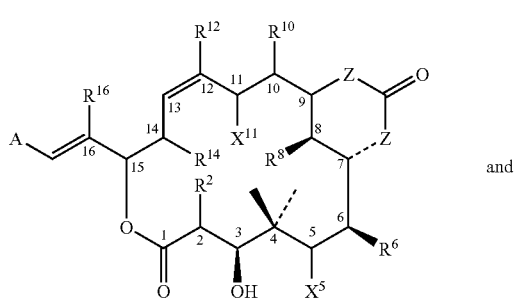

1(d) and

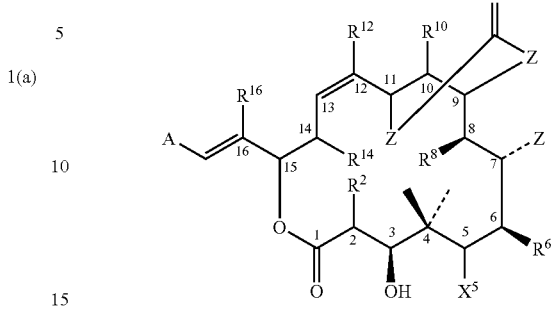

1(e)

wherein both Z are O or one Z is N and the other Z is O, and the remaining substituents are as defined above.

As used herein, a substituent which "comprises an aromatic moiety" contains at least one aromatic ring, such as phenyl, pyridyl, pyrimidyl, thiophenyl, or thiazolyl. The substituent may also include fused aromatic residues such as naphthyl, indolyl, benzothiazolyl, and the like. The aromatic moiety may also be fused to a nonaromatic ring and/or may be coupled to the remainder of the compound in which it is a substituent through a nonaromatic, for example, alkylene residue. The aromatic moiety may be substituted or unsubstituted as may the remainder of the substituent.

Figure 2:
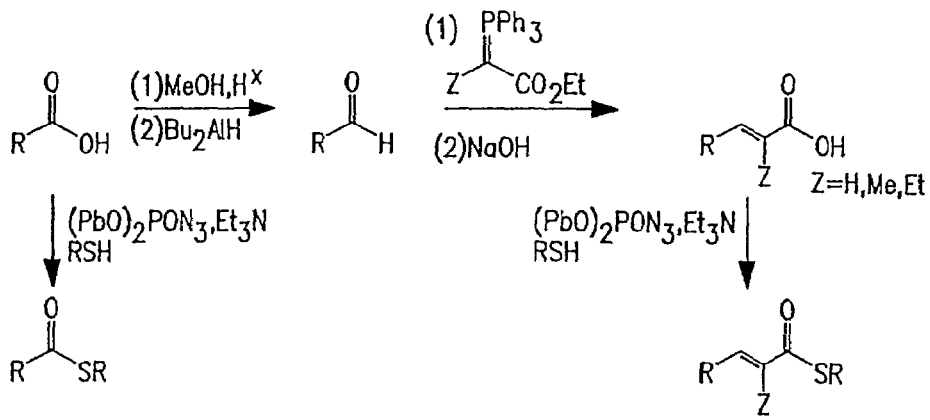
FIG. 2 shows a number of precursor compounds to N-acyl-cysteamine thioester derivatives that can be supplied to an epothilone PKS of the invention in which the NRPS-like module 1 or module 2 KS domain has been inactivated to produce a novel epothilone derivative. A general synthetic procedure for making such compounds is also shown.
Figure 2:
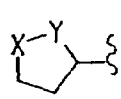
Figure 2:
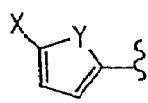
Figure 2:
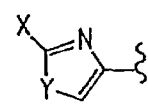
Figure 2:
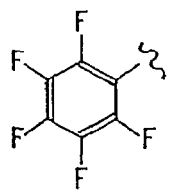
Figure 2:
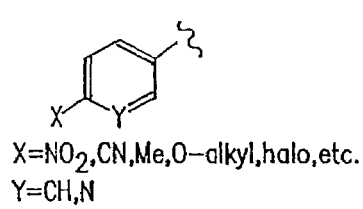
Figure 2:
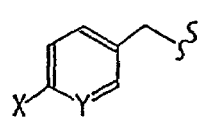
Figure 2:
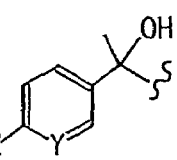
Figure 2:
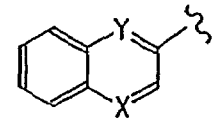
Figure 2:
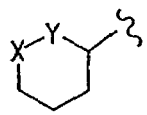
Figure 2:
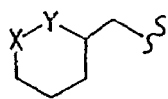

Preferred embodiments of A include the "R" groups shown in FIG. 2.

As used herein, the term alkyl refers to a $C_1$-$C_8$ saturated, straight or branched chain hydrocarbon radical derived from a hydrocarbon moiety by removal of a single hydrogen atom. Alkenyl and alkynyl refer to the corresponding unsaturated forms. Examples of alkyl include but are not limited to methyl, ethyl, propyl, isopropyl, n-butyl, tert-butyl, neopentyl, i-hexyl, n-heptyl, n-octyl. Lower alkyl (or alkenyl or alkynyl) refers to a 1-4C radical. Methyl is preferred. Acyl refers to alkylCO, alkenylCO or alkynylCO.

The terms halo and halogen as used herein refer to an atom selected from fluorine, chlorine, bromine, and iodine. The term haloalkyl as used herein denotes an alkyl group to which one, two, or three halogen atoms are attached to any one carbon and includes without limitation chloromethyl, bromoethyl, trifluoromethyl, and the like.

The term heteroaryl as used herein refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, and the like.

The term heterocyle includes but is not limited to pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "substituted" as used herein refers to a group substituted by independent replacement of any of the hydrogen atoms thereon with, for example, Cl, Br, F, I, OH, CN, alkyl, alkoxy, alkoxy substituted with aryl, haloalkyl, alkylthio, amino, alkylamino, dialkylamino, mercapto, nitro, carboxaldehyde, carboxy, alkoxycarbonyl, or carboxamide. Any one substituent may be an aryl, heteroaryl, or heterocycloalkyl group.

It will apparent that the nature of the substituents at positions 2, 4, 6, 8, 10, 12, 14 and 16 in formula (1) is determined at least initially by the specificity of the AT catalytic domain of modules 9, 8, 7, 6, 5, 4, 3 and 2, respectively. Because AT domains that accept malonyl CoA, methylmalonyl CoA, ethylmalonyl CoA (and in general, lower alkyl malonyl CoA), as well as hydroxymalonyl CoA, are available, one of the substituents at these positions may be H, and the other may be H, lower alkyl, especially methyl and ethyl, or OH. Further reaction at these positions, e.g., a methyl transferase reaction such as that catalyzed by module 8 of the epothilone PKS, may be used to replace H at these positions as well. Further, an H,OH embodiment may be oxidized to =O or, with the adjacent ring C, be dehydrated to form a π-bond. Both OH and =O are readily derivatized as further described below.

Thus, a wide variety of embodiments of $R^2$, $R^6$, $R^8$, $R^{10}$, $R^{12}$, $R^{14}$ and $R^{16}$ is synthetically available. The restrictions set forth with regard to embodiments of these substituents set forth in the definitions with respect to Formula (1) above reflect the information described in the SAR description in Example 8 below.

Similarly, β-carbonyl modifications (or absence of modification) can readily be controlled by modifying the epothilone PKS gene cluster to include the appropriate sequences in the corresponding positions of the epothilone gene cluster which will or will not contain active KR, DH and/or ER domains. Thus, the embodiments of $X^5$, $X^7$, $X^9$, $X^{11}$ and $X^{13}$ synthetically available are numerous, including the formation of π-bonds with the adjacent ring positions.

Positions occupied by OH are readily converted to ethers or esters by means well known in the art; protection of OH at positions not to be derivatized may be required. Further, a hydroxyl may be converted to a leaving group, such as a tosylate, and replaced by an amino or halo substituent. A wide variety of "hydroxyl derivatives" such as those discussed above is known in the art.

Similarly, ring positions which contain oxo groups may be converted to "carbonyl derivatives" such as oximes, ketals, and the like. Initial reaction products with the oxo moieties may be further reacted to obtain more complex derivatives. As described in Example 8, such derivatives may ultimately result in a cyclic substituent linking two ring positions.

The enzymes useful in modification of the polyketide initially synthesized, such as transmethylases, dehydratases, oxidases, glycosylation enzymes and the like, can be supplied endogenously by a host cell when the polyketide is synthesized intracellularly, by modifying a host to contain the recombinant materials for the production of these modifying enzymes, or can be supplied in a cell-free system, either in purified forms or as relatively crude extracts. Thus, for example, the epoxidation of the π-bond at position 12-13 may be effected using the protein product of the epoK gene directly in vitro.

The nature of A is most conveniently controlled by employing an epothilone PKS which comprises an inactivated module 1 NRPS (using a module 2 substrate) or a KS2 knockout (using a module 3 substrate) as described in Example 6, hereinbelow. Limited variation can be obtained by altering the AT catalytic specificity of the loading module; further variation is accomplished by replacing the NRPS of module 1 with an NRPS of different specificity or with a conventional PKS module. However, at present, variants are more readily prepared by feeding the synthetic module 2 substrate precursors and module 3 substrate precursors to the appropriately altered epothilone PKS as described in Example 6.

Pharmaceutical Compositions

The compounds can be readily formulated to provide the pharmaceutical compositions of the invention. The pharmaceutical compositions of the invention can be used in the form of a pharmaceutical preparation, for example, in solid, semi-solid, or liquid form. This preparation will contain one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987, Transplantation Proceedings XIX, Supp. 6: 17-22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases caused by infection, immune system disorder (or to suppress immune function), or cancer, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intrathecal, intramuscular, and intrasternal injection or infusion techniques.

Dosage levels of the compounds of the present invention are of the order from about 0.01 mg to about 100 mg per kilogram of body weight per day, preferably from about 0.1 mg to about 50-mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 gm of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention may be formulated within the range of, for example, 0.00001% to 60% by weight, preferably from 0.001% to 10% by weight, and most preferably from about 0.005% to 0.8% by weight.

It will be understood, however, that the specific dose level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

EXAMPLE 1

DNA Sequencing of Cosmid Clones and Subclones Thereof

The epothilone producing strain, *Sorangium cellulosum* SMP44, was grown on a cellulose-containing medium, see Bollag et al., 1995, Cancer Research 55: 2325-2333, incorporated herein by reference, and epothilone production was confirmed by LC/MS analysis of the culture supernatant. Total DNA was prepared from this strain using the procedure described by Jaoua et al., 1992, Plasmid 28: 157-165, incorporated herein by reference. To prepare a cosmid library, *S. cellulosum* genomic DNA was partially digested with Sau3AI and ligated with BamHI-digested pSupercos (Stratagene). The DNA was packaged in lambda phage as recommended by the manufacturer and the mixture then used to infect *E. coli* XL1-Blue MR cells. This procedure yielded approximately 3,000 isolated colonies on LB-ampicillin plates. Because the size of the *S. cellulosum* genome is estimated to be circa $10^7$ nucleotides, the DNA inserts present among 3000 colonies would correspond to circa 10 *S. cellulosum* genomes.

To screen the library, two segments of KS domains were used to design oligonucleotide primers for a PCR with *Sorangium cellulosum* genomic DNA as template. The fragment generated was then used as a probe to screen the library. This approach was chosen, because it was found, from the examination of over a dozen PKS genes, that KS domains are the most highly conserved (at the amino acid level) of all the PKS domains examined. Therefore, it was expected that the probes produced would detect not only the epothilone PKS genes but also other PKS gene clusters represented in the library. The two degenerate oligonucleotides synthesized using conserved regions within the ketosynthase (KS) domains compiled from the DEBS and soraphen PKS gene sequences were (standard nomenclature for degenerate positions is used): CTSGTSKCSSTBCACCTSGCSTGC (SEQ ID NO: 21) and TGAYRTGSGCGTTSGTSCCGSWGA (SEQ ID NO: 22). A single band of 750 bp, corresponding to the predicted size, was seen in an agarose gel after PCR employing the oligos as primers and *S. cellulosum* SMP44 genomic DNA as template. The fragment was removed from the gel and cloned in the HincII site of pUC118 (which is a derivative of pUC18 with an insert sequence for making single stranded DNA). After transformation of *E. coli*, plasmid DNA from ten independent clones was isolated and sequenced. The analysis revealed nine unique sequences that each corresponded to a common segment of KS domains in PKS genes. Of the nine, three were identical to a polyketide synthase gene cluster previously isolated from this organism and determined not to belong to the epothilone gene cluster from the analysis of the modules. The remaining six KS fragments were excised from the vector, pooled, end-labeled with $^{32}P$ and used as probe in hybridizations with the colonies containing the cosmid library under high stringency conditions.

The screen identified 15 cosmids that hybridized to the pooled KS probes. DNA was prepared from each cosmid, digested with NotI, separated on an agarose gel, and transferred to a nitrocellulose membrane for Southern hybridization using the pooled KS fragments as probe. The results revealed that two of the cosmids did not contain KS-hybridizing inserts, leaving 13 cosmids to analyze further. The blot was stripped of the label and re-probed, under less stringent conditions, with labeled DNA containing the sequence corresponding to the enoylreductase domain from module four of the DEBS gene cluster. Because it was anticipated that the epothilone PKS gene cluster would encode two consecutive modules that contain an ER domain, and because not all PKS gene clusters have ER domain containing modules, hybridization with the ER probe was predicted to identify cosmids containing insert DNA from the epothilone PKS gene cluster. Two cosmids were found to hybridize strongly to the ER probe, one hybridized moderately, and a final cosmid hybridized weakly. Analysis of the restriction pattern of the NotI fragments indicated that the two cosmids that hybridized strongly with the ER probe overlapped one another. The nucleotide sequence was also obtained from the ends of each of the 13 cosmids using the T7 and T3 primer binding sites. All contained sequences that showed homology to PKS genes. In FIG. 1, the T7 site is to the left side of cosmid 8A3 and to the right side of cosmids 1A2 and 4. The PKS gene sequence is to the left of cosmid 1A2, because the sequences generated from the left of cosmid 8A3 are non-PKS sequences. Sequence from one of the cosmids that hybridized strongly to the ER probe showed homology to NRPs and, in particular, to the adenylation domain of an NRPS. Because it was anticipated that the thiazole moiety of epothilone might be derived from the formation of an amide bond between an acetate and cysteine molecule (with a subsequent cyclization step), the presence of an NRPS domain in a cosmid that also contained ER domain(s) supported the prediction that this cosmid might contain all or part of the epothilone PKS gene cluster.

Preliminary restriction analysis of the 12 remaining cosmids suggested that three might overlap with the cosmid of interest. To verify this, oligonucleotides were synthesized for each end of the four cosmids (determined from the end sequencing described above) and used as primer sets in PCRs with each of the four cosmid DNAs. Overlap would be indicated by the appearance of a band from a non-cognate primer-template reaction. The results of this experiment verified that two of the cosmids overlapped with the cosmid containing the NRPS. Restriction mapping of the three cosmids revealed that the cosmids did, in fact, overlap. Furthermore, because PKS sequences extended to the end of the insert in the last overlapping fragment, based on the assumption that the NRPS would map to the 5'-end of the cluster, the results also indicated that the 3' end of the gene cluster had not been isolated among the clones identified.

To isolate the remaining segment of the epothilone biosynthesis genes, a PCR fragment was generated from the cosmid containing the most 3'-terminal region of the putative gene cluster. This fragment was used as a probe to screen a newly prepared cosmid library of *Sorangium cellulosum* genomic DNA of again approximately 3000 colonies. Several hybridizing clones were identified; DNA was made from six of them. Analysis of NotI-digested fragments indicated that all contained overlapping regions. The cosmid containing the largest insert DNA that also had the shortest overlap with the cosmid used to make the probe was selected for further analysis.

Restriction maps were created for the four cosmids, as shown in FIG. 1. Sequence obtained from one of the ends of cosmid pKOS35-70.8A3 showed no homology to PKS sequences or any associated modifying enzymes. Similarly, sequence from one end of cosmid pKOS35-79.85 also did not contain sequences corresponding to a PKS region. These findings supported the observation that the epothilone cluster was contained within the ~70 kb region encompassed by the four cosmid inserts.

(A) The right (T3) side of cosmid 8A3 was sequenced, and the complement of the sequence generated is shown below, followed by the encoded amino acid sequence, which is from a ketosynthase domain.

T3 end Reverse and complement from the original sequence (SEQ ID NO: 23)
TCCTGGGTCTGCACGGCCCGACGCTGGCCATGGATACGGCGTGCTCGTCC
TCCCTGGTCGCGCTGCACCTCGCCTGCCAGAGCCTGCGACTGGGCGAGTG
CGATCAAGCGCTGGTTGGCGGGGTCAACGTGCTGCTCGCGCCGGAGACCT
TCGTGCTGCTCTCACGGATGCGCGCGCTTTCGCCCGACGGGCGGTGCAAG
ACGTTCTCGGCCGACGCGGACGGCTACGCGCGGGGCGAGGGGTGCGCCGT
GGTGGTGCTCAAGCGGCTGCGCAATGCGCAGCGCGCTCGGCG.

Protein translation (SEQ ID NO: 24)
Leu Gly Leu His Gly Pro Thr Leu Ala Met Asp Thr
Ala Cys Ser Ser Ser Leu Val Ala Leu His Leu Ala
Cys Gln Ser Leu Arg Leu Gly Glu Cys Asp Gln Ala
Leu Val Gly Gly Val Asn Val Leu Leu Ala Pro Glu
Thr Phe Val Leu Leu Ser Arg Met Arg Ala Leu Ser
Pro Asp Gly Arg Cys Lys Thr Phe Ser Ala Asp Ala
Asp Gly Tyr Ala Arg Gly Glu Gly Cys Ala Val Val
Val Leu Lys Arg Leu Arg Asn Ala Gln Arg Ala Arg.

(B) The left (T3) side of cosmid 1A2 was sequenced, and the sequence generated is shown below, followed by the encoded amino acid sequence, which is from a ketosynthase domain.

T3 end (SEQ ID NO: 25)
CATAGATCGTAAGCTGTGCTAGTGATCTGCCTTACGTTACGTCTTCCGCA
CCTCGAGCGAATTCTCTCGGATAACTTTCAAGTTTTCTGAGGGGCTTGG
TCTCTGGTTCCTCAGGAAGCCTGATCGGGACGAGCTAATTCCCATCCATT
TTTTTGAGACTCTGCTCAAAGGGATTAGACCGAGTGAGACAGTTCTTTTG
CAGTGAGCGAAGAACCTGGGGCTCGACCGGAGGACGATCGACGTCCGCGA
GCGGGTCAGCCGCTGAGGATGTGCCCGTCGTGGCGGATCGTCCCATCGAG
CGCGCAGCCGAAGATCCGATTGCGATCGTCGGAGCGGGCTGCCGTCTGCC
CGGTGGCGTGATCGATCTGAGCGGGTTCTGGACGCTCCTCGAGGGCTCGC
GCGACACCGTCGGGCAAGTCCCCGCCGAACGCTGG Protein translation (SEQ ID NO: 26)
His Arg Ser STP Ala Val Leu Val Ile Cys Leu Thr
Leu Arg Leu Pro His Leu Glu Arg Ile Leu Ser Asp
Asn Phe Gln Val Phe STP (SEQ ID NO: 27)
Gly Gly Leu Val Ser Gly Ser Ser Gly Ser Leu Ile
Gly Thr Ser STP (SEQ ID NO: 28)
Phe Pro Ser Ile Phe Leu Arg Leu Cys Ser Lys Gly
Leu Asp Arg Val Arg Gln Phe Phe Cys Ser Glu Arg
Arg Thr Trp Gly Ser Thr Gly Gly Arg Ser Thr Ser
Ala Ser Gly Ser Ala Ala Gln Asp Val Pro Val Val
Ala Asp Arg Pro Ile Glu Arg Ala Ala Glu Asp Pro
Ile Ala Ile Val Gly Ala Gly Cys Arg Leu Pro Gly
Gly Val Ile Asp Leu Ser Gly Phe Trp Thr Leu Leu
Glu Gly Ser Arg Asp Thr Val Gly Gln Val Pro Ala
Glu Arg Trp.

(C) The right (T7) side of cosmid 1A2 was sequenced, and the complement of the sequence generated is shown below, followed by the encoded amino acid sequence, which is from an acyltransferase-ketoreductase domain junction.

T7 end Reverse and complement from the original sequence (SEQ ID NO: 29)
GACGCGCGGACTTTCCTGCACGGTGCTTCATGCGTCGGCTGACGCCTCCA
CCGTCGCCGAGCAGGTATCCGAAGCTGCCAGTCGCCGAAACGACTGGCAG
GGAGTCCTCTACCTGTGGGGCCTCGACGCCGTCGTCGATGCTGGGGCATC
GGCCGACGAAGTCAGCGAGGCTACCCGCCGTGCCACCGCACCCGTCCTTG
GGCTGGTTCGATTCCTGAGCGCTGCGCCCCATCCTCCTCGCTTCTGGGTG
GTGACCCGCGGGCATGCACGGTGGGCGGCGAGCCAGAGGTCTCTCTTTG
CCAAGCGGCGTTGTGGGGCCTCGCGCGCGTCGTGGCGCTGGAGCATCCCG
CTGCCTGTGGGTGGCC.

Protein translation (SEQ ID NO: 30)
Thr Arg Gly Leu Ser Cys Thr Val Leu His Ala Ser
Ala Asp Ala Ser Thr Val Ala Glu Gln Val Ser Glu
Ala Ala Ser Arg Arg Asn Asp Trp Gln Gly Val Leu
Tyr Leu Trp Gly Leu Asp Ala Val Val Asp Ala Gly
Ala Ser Ala Asp Glu Val Ser Glu Ala Thr Arg Arg -continued

```
Ala Thr Ala Pro Val Leu Gly Leu Val Arg Phe Leu

Ser Ala Ala Pro His Pro Pro Arg Phe Trp Val Val

Thr Arg Gly Ala Cys Thr Val Gly Gly Glu Pro Glu

Val Ser Leu Cys Gln Ala Ala Leu Trp Gly Leu Ala

Arg Val Val Ala Leu Glu His Pro Ala Ala Cys Gly

Trp.
```

(D) The left (T3) side of cosmid 4 was sequenced, and the sequence generated is shown below, followed by the encoded amino acid sequence, which is from an adenylation domain of the non-ribosomal peptide synthase portion of the epothilone PKS.

T3 end.

(SEQ ID NO: 31)
```
CGTCCAGCCTGCGCGATCCGGCGCATTGGGCGCGTTGATCGAACGAGAGA

AGGTGACGGTGTGGAACTCGGTGCCGGCGCTGATGCGGATGCTCGTCGAG

CATTCCGAGGGTCGCCCCGATTCGCTCGCTAGGTCTCCTGCGGCTTTCGC

TGCTGAGCGGCGACTGGATCCCGGTGGGCCTGCCTGGCGAGCTCCAGGCC

ATCAGGCCCGGCGTGTCGGTGATCAGCCTGGGCGGGGCCACCGAAGCGTC

GATCTGGTCCATCGGGTACCCCGTGAGGAACGTCGATCCATCGTGGGCGA

GCATCCCCTACGGCCGTCCGCTGCGCAACCAGACGTTCCACGTGCTCGAT

GAGGCGCTCGAACCGCGCCCGGTCTGGGTTCCGGGGCAACTCTACATTGG

CGGGGTCGGACTGGCACTGGGCTACTGGCGCGATGAAGAGAAGACGCGCA

CAGCT.
```

Protein translation (SEQ ID NO: 32)
```
Val Gln Pro Ala Arg Ser Gly Ala Leu Gly Ala Leu Ile Glu Arg Glu Lys Val Thr Val Trp Asn Ser Val Pro Ala Leu Met Arg Met Leu Val Glu His Ser Glu Gly Arg Pro Asp Ser Leu Ala Arg Ser Leu Arg Leu Ser Leu Leu Ser Gly Asp Trp Ile Pro Val Gly Leu Pro Gly Glu Leu Gln Ala Ile Arg Pro Gly Val Ser Val Ile Ser Leu Gly Gly Ala Thr Glu Ala Ser Ile Trp Ser Ile Gly Tyr Pro Val Arg Asn Val Asp Pro Ser Trp Ala Ser Ile Pro Tyr Gly Arg Pro Leu Arg Asn Gln Thr Phe His Val Leu Asp Glu Ala Leu Glu Pro Arg Pro Val Trp Val Pro Gly Gln Leu Tyr Ile Gly Gly Val Gly Leu Ala Leu Gly Tyr Trp Arg Asp Glu Glu Lys Thr Arg Thr Ala.
```

(E) The right (T7) side of cosmid 4 was sequenced, and the complement of the sequence generated is shown below, followed by the encoded amino acid sequence, which is from a dehydratase domain.

T7 end Reverse and complement from the original sequence (SEQ ID NO: 33)
```
GGCCCGGTCGGGCCTCATTCCAGGTATCGAGCCGTGAGGAGGCAGGTAGA

AGCTGGGTTCGGCACGCCACGGGGCACGTGTGTAGCGACCAGAGCTCAGC

AGTGGGAGCGTTGAAGGAAGCTCCGTGGGAGATTCAACAGCGATGTCCGA

GCGTCCTGTCGTCGGAGGCGCTCTATCCGCTGCTCAACGAGCACGCCCTC

GACTATGGCCCCTGCTTCCAGGGTGTGGAGCAGGTGTGGCTCGOCACGGG

GGAGGTGCTCGGCCGGGTACGCTTGCCAGAAGACATGGCATCCTCAAGTG

GCGCCTATCGGATTCATCCCGCCTTGTTGGATGCAGTTTTCATAGTGCTG

ACCGCGCTGCTCGACCACGCCGGAATCCATCGT.
```

Protein translation (SEQ ID NO: 34)
```
Pro Gly Arg Ala Ser Phe Gln Val Ser Ser Arg Glu Glu Ala Gly Arg Ser Trp Val Arg His Ala Thr Gly His Val Cys Ser Asp Gln Ser Ser Ala Val Gly Ala Leu Lys Glu Ala Pro Trp Glu Ile Gln Gln Arg Cys Pro Ser Val Leu Ser Ser Glu Ala Leu Tyr Pro Leu Leu Asn Glu His Ala Leu Asp Tyr Gly Pro Cys Phe Gln Gly Val Glu Gln Val Trp Leu Gly Thr Gly Glu Val Leu Gly Arg Val Arg Leu Pro Glu Asp Met Ala Ser Ser Ser Gly Ala Tyr Arg Ile His Pro Ala Leu Leu Asp Ala Val Phe Ile Val Leu Thr Ala Leu Leu Asp His Ala Gly Ile His Arg.
```

To sequence the inserts in the cosmids, each of the NotI restriction fragments from the four cosmids was cloned into the NotI site of the commercially available pBluescript plasmid. Initial sequencing was performed on the ends of each of the clones. Analysis of the sequences allowed the prediction, before having the complete sequence, that there would be 10 modules in this PKS gene cluster, a loading domain plus 9 modules.

Sequence was obtained for the complete PKS as follows. Each of the 13 non-overlapping NotI fragments was isolated and subjected to partial HinPI digestion. Fragments of ~2 to 4 kb in length were removed from an agarose gel and cloned in the AccI site of pUC118. Sufficient clones from each library of the NotI fragments were sequenced to provide at least 4-fold coverage of each. To sequence across each of the NotI sites, a set of oligos, one 5' and the other 3' to each NotI site, was made and used as primers in PCR amplification of a fragment that contained each NotI site. Each fragment produced in this manner was cloned and sequenced.

The nucleotide sequence was determined for a linear segment corresponding to ~72 kb. Analysis revealed a PKS gene cluster with a loading domain and nine modules. Downstream of the PKS sequence is an ORF, designated epoK, that shows strong homology to cytochrome P450 oxidase genes and encodes the epothilone epoxidase. The nucleotide sequence of 15 kb downstream of epoK has also been determined: a number of additional ORFs have been identified but an ORF that shows homology to any known dehydratase has not been identified. The epoL gene may encode a dehydratase activity, but this activity may instead be resident within the epothilone PKS or encoded by another gene.

The PKS genes are organized in 6 open reading frames. At the polypeptide level, the loading domain and modules 1, 2, and 9 appear on individual polypeptides; their corresponding genes are designated epoA, epoB, epoC and epoF respectively. Modules 3, 4, 5, and 6 are contained on a single polypeptide whose gene is designated epoD, and modules 7 and 8 are on another polypeptide whose gene is designated epoE. It is clear from the spacing between ORFs that epoC, epoD, epoE and epoF constitute an operon. The epoA, epoB, and epoK gene may be also part of the large operon, but there are spaces of approximately 100 bp between epoB and epoC and 115 bp between epoF and epoK which could contain a promoter. The present invention provides the intergenic sequences in recombinant form. At least one, but potentially more than one, promoter is used to express all of the epothilone genes. The epothilone PKS gene cluster is shown schematically below.

the presence of a DH domain. Although the sequence of the AT domain appears to resemble those that specify malonate loading, it can also load methylmalonate, thereby accounting in part for the mixture of epothilones found in the fermentation broths of the naturally producing organisms.

A significant departure from the expected array of functions was found in module 4. This module was expected to contain a DH domain, thereby directing the synthesis of epothilones C and D as the products of the PKS. Rigorous analysis revealed that the space between the AT and KR domains of module 4 was not large enough to accommodate a functional DH domain. Thus, the extent of reduction at module 4 does not proceed beyond the ketoreduction of the beta-keto formed after the condensation directed by module 4. Because the C-12,13 unsaturation has been demonstrated (epothilones C and D), there must be an additional dehydratase function that introduces the double bond, and this function is believed to be in the PKS itself or resident in an ORF in the epothilone biosynthetic gene cluster.

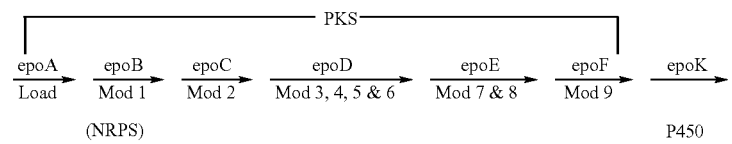

A detailed examination of the modules shows an organization and composition that is consistent with one able to be used for the biosynthesis of epothilone. The description that follows is at the polypeptide level. The sequence of the AT domain in the loading module and in modules 3, 4, 5, and 9 shows similarity to the consensus sequence for malonyl loading domains, consistent with the presence of an H side chain at C-14, C-12 (epothilones A and C), C-10, and C-2, respectively, as well as the loading region. The AT domains in modules 2, 6, 7, and 8 resemble the consensus sequence for methylmalonyl specifying AT domains, again consistent with the presence of methyl side chains at C-16, C-8, C-6, and C-4 respectively.

The loading module contains a KS domain in which the cysteine residue usually present at the active site is instead a tyrosine. This domain is designated as $KS^y$ and serves as a decarboxylase, which is part of its normal function, but cannot function as a condensing enzyme. Thus, the loading domain is expected to load malonyl CoA, move it to the ACP, and decarboxylate it to yield the acetyl residue required for condensation with cysteine.

Module 1 is the non-ribosomal peptide synthetase that activates cysteine and catalyzes the condensation with acetate on the loading module. The sequence contains segments highly similar to ATP-binding and ATPase domains, required for activation of amino acids, a phosphopantotheinylation site, and an elongation domain. In database searches, module 1 shows very high similarity to a number of previously identified peptide synthetases.

Module 2 determines the structure of epothilone at C-15-C-17. The presence of the DH domain in module 2 yields the C-16-17 dehydro moiety in the molecule. The domains in module 3 are consistent with the structure of epothilone at C-14 and C-15; the OH that comes from the action of the KR is employed in the lactonization of the molecule.

Module 4 controls the structure at C-12 and C-13 where a double bond is found in epothilones C and D, consistent with Thus, the action of the dehydratase could occur either during the synthesis of the polyketide or after cyclization has taken place. In the former case, the compounds produced at the end of acyl chain growth would be epothilones C and D. If the C-12,13 dehydration were a post-polyketide event, the completed acyl chain would have a hydroxyl group at C-13, as shown below. The names epothilones G and H have been assigned to the 13-hydroxy compounds produced in the absence of or prior to the action of the dehydratase.

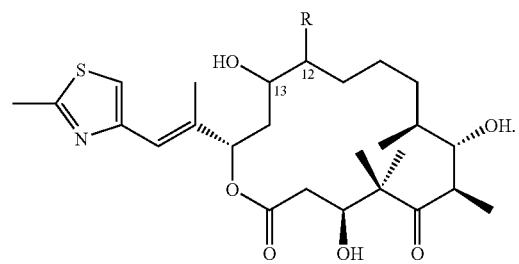

Epothilones G (R = H) and H (R = CH₃)

Modules 5 and 6 each have the full set of reduction domains (KR, DH and ER) to yield the methylene functions at C-11 and C-9. Modules 7 and 9 have KR domains to yield the hydroxyls at C-7 and C-3, and module 8 does not have a functional KR domain, consistent with the presence of the keto group at C-5. Module 8 also contains a methyltransferase (MT) domain that results in the presence of the geminal dimethyl function at C-4. Module 9 has a thioesterase domain that terminates polyketide synthesis and catalyzes ring closure. The genes, proteins, modules, and domains of the epothilone PKS are summarized in the Table hereinabove.

Inspection of the sequence has revealed translational coupling between epoA and epoB (loading domain and module 1) and between epoC and epoD. Very small gaps are seen between epoD and epoE and epoE and epoF but gaps exceeding 100 bp are found between epoB and epoC and epoF and epoK. These intergenic regions may contain promoters. Sequencing efforts have not revealed the presence of regulatory genes, and it is possible that epothilone synthesis is not regulated by operon specific regulation in *Sorangium cellulosum*.

The sequence of the epothilone PKS and flanking regions has been compiled into a single contig, as shown below (SEQ ID NO: 2).

```
   1 TCGTGCGCGG GCACGTCGAG GCGTTTGCCG ACTTCGGCGG CGTCCCGCGC GTGCTGCTCT
  61 ACGACAACCT CAAGAACGCC GTCGTCGAGC GCCACGGCGA CGCGATCCGG TTCCACCCCA
 121 CGCTGCTGGC TCTGTCGGCG GATTACCGCT TCGAGCCGCG CCCCGTCGCC GTCGCCCGCG
 181 GCAACGAGAA GGGCCGCGTC GAGCGCGCCA TCCGCTACGT CCGCGAGGGC TTCTTCGAGG
 241 CCCGGGCCTA CGCCGACCTC GGAGACCTCA ACCGCCAAGC GACCGAGTGG ACCAGCTCCG
 301 CGGCGCTCGA TCGCTCCTGG GTCGAGGACC GCGCCCGCAC CGTGCGTCAG GCCTTCGACG
 361 ACGAGCGCAG CGTGCTGCTG CGACACCCTG ACACACCGTT TCCGGACCAC GAGCGCGTCG
 421 AGGTCGAGGT CGGAAAGACC CCCTACGCGC GCTTCGATCT CAACGACTAC TCGGTCCCCC
 481 ACGACCGGAC GCGCCGCACG CTGGTCGTCC TCGCCGACCT CAGTCAGGTA CGCATCGCCG
 541 ACGGCAACCA GATCGTCGCG ACCCACGTCC GTTCGTGGGA CCGCGGCCAG CAGATCGAGC
 601 AGCCCGAGCA CCTCCAGCGC CTGGTCGACG AGAAGCGCCG CGCCCGCGAG CACCGCGGCC
 661 TTGATCGCCT CGCGCGCGCC GCCCGCAGCA GCCAGGCATT CCTGCGCATC GTCGCCGAGC
 721 GCGGCGATAA CGTCGGCAGC GCGATCGCCC GGCTTCTGCA ACTGCTCGAC GCCGTGGGCG
 781 CCGCCGAGCT CGAAGAGGCC CTGGTCGAGG TGCTTGAGCG CGACACCATC CACATCGGTG
 841 CCGTCCGCCA GGTGATCGAC CGCCGCCGCT CCGAGCGCCA CCTGCCGCCT CCAGTCTCAA
 901 TCCCCGTCAC CCGCGGCGAG CACGCCGCCC TCGTCGTCAC GCCGCATTCC CTCACCACCT
 961 ACGACGCCCT GAAGAAGGAC CCGACGCCAT GACCGACCTG ACGCCCACCG AGACCAAAGA
1021 CCGGCTCAAG AGCCTCGGCC TCTTCGGCCT GCTCGCCTGC TGGGAGCAGC TCGCCGACAA
1081 GCCCTGGCTT CGCGAGGTGC TCGCCATCGA GGAGCGCGAG CGCCACAAGC GCAGCCTCGA
1141 ACGCCGCCTG AAGAACTCCC GCGTCGCCGC CTTCAAGCCC ATGACCGACT TCGACTCGTC
1201 CTGGCCCAAG AAGATCGACC GCGAGGCCGT CGACGACCTC TACGATAGCC GCTACGCGGA
1261 CCTGCTCTTC GAGGTCGTCA CCCGTCGCTA CGACGCGCAG AAGCCGCTCT TGCTCAGCAC
1321 GAACAAGGCA TTCGCCGACT GGGGCCAGGT CTTCCCGCAC GCCGCGTGCG TCGTCACGCT
1381 CGTCGACCGG CTCGTGCACC GCGCCGAGGT GATCGAGATC GAGGCCGAGA GCTACCGGCT
1441 GAAGGAAGCC AAGGAGCTCA ACGCCACCCG CACCAAGCAG CGCCGCACCA AGAAGCACTG
1501 AGCGGCATTT TCACCGGTGA ACTTCACCGA AATCCCGCGT GTTGCCGAGA TCATCTACAG
1561 GCGGATCGAG ACCGTGCTCA CGGCGTGGAC GACATGGCGC GGAAACGTCG TCGTAACTGC
1621 CCAGCAATGT CATGGGAATG GCCCCTTGAG GGGCTGGCCG GGGTCGACGA TATCGCGCGA
1681 TCTCCCCGTC AATTCCCGAG CGTAAAAGAA AAATTTGTCA TAGATCGTAA GCTGTGCTAG
1741 TGATCTGCCT TACGTTACGT CTTCCGCACC TCGAGCGAAT TCTCTCGGAT AACTTTCAAG
1801 TTTTCTGAGG GGGCTTGGTC TCTGGTTCCT CAGGAAGCCT GATCGGGACG AGCTAATTCC
1861 CATCCATTTT TTTGAGACTC TGCTCAAAGG GATTAGACCG AGTGAGACAG TTCTTTTGCA
1921 GTGAGCGAAG AACCTGGGGC TCGACCGGAG GACGATCGAC GTCCGCGAGC GGGTCAGCCG
1981 CTGAGGATGT GCCCGTCGTG GCGGATCGTC CCATCGAGCG CGCAGCCGAA GATCCGATTG
2041 CGATCGTCGG AGCGGGCTGC CGTCTGCCCG GTGGCGTGAT CGATCTGAGC GGGTTCTGGA
```

```
                   -continued
2101 CGCTCCTCGA GGGCTCGCGC GACACCGTCG GGCAAGTCCC CGCCGAACGC TGGGATGCAG

2161 CAGCGTGGTT TGATCCCGAC CTCGATGCCC CGGGGAAGAC GCCCGTTACG CGCGCATCTT

2221 TCCTGAGCGA CGTAGCCTGC TTCGACGCCT CCTTCTTCGG CATCTCGCCT CGCGAAGCGC

2281 TGCGGATGGA CCCTGCACAT CGACTCTTGC TGGAGGTGTG CTGGGAGGCG CTGGAGAACG

2341 CCGCGATCGC TCCATCGGCG CTCGTCGGTA CGGAAACGGG AGTGTTCATC GGGATCGGCC

2401 CGTCCGAATA TGAGGCCGCG CTGCCGCGAG CGACGGCGTC CGCAGAGATC GACGCTCATG

2461 GCGGGCTGGG GACGATGCCC AGCGTCGGAG CGGGCCGAAT CTCGTATGTC CTCGGGCTGC

2521 GAGGGCCGTG TGTCGCGGTG GATACGGCCT ATTCGTCCTC GCTCGTGGCC GTTCATCTGG

2581 CCTGTCAGAG CTTGCGCTCC GGGGAATGCT CCACGGCCCT GGCTGGTGGG GTATCGCTGA

2641 TGTTGTCGCC GAGCACCCTC GTGTGGCTCT CGAAGACCCG CGCGCTGGCC ACGGACGGTC

2701 GCTGCAAGGC GTTTTCGGCG GAGGCCGATG GGTTCGGACG AGGCGAAGGG TGCGCCGTCG

2761 TGGTCCTCAA GCGGCTCAGT GGAGCCCGCG CGGACGGCGA CCGGATATTG GCGGTGATTC

2821 GAGGATCCGC GATCAATCAC GACGGAGCGA GCAGCGGTCT GACCGTGCCG AACGGGAGCT

2881 CCCAAGAAAT CGTGCTGAAA CGGGCCCTGG CGGACGCAGG CTGCGCCGCG TCTTCGGTGG

2941 GTTATGTCGA GGCACACGGC ACGGGCACGA CGCTTGGTGA CCCCATCGAA ATCCAAGCTC

3001 TGAATGCGGT ATACGGCCTC GGGCGAGACG TCGCCACGCC GCTGCTGATC GGGTCGGTGA

3061 AGACCAACCT TGGCCATCCT GAGTATGCGT CGGGGATCAC TGGGCTGCTG AAGGTCGTCT

3121 TGTCCCTTCA GCACGGGCAG ATTCCTGCGC ACCTCCACGC GCAGGCGCTG AACCCCCGGA

3181 TCTCATGGGG TGATCTTCGG CTGACCGTCA CGCGCGCCCG GACACCGTGG CCGGACTGGA

3241 ATACGCCGCG ACGGGCGGGG GTGAGCTCGT TCGGCATGAG CGGGACCAAC GCGCACGTGG

3301 TGCTGGAAGA GGCGCCGGCG GCGACGTGCA CACCGCCGGC GCCGGAGCGG CCGGCAGAGC

3361 TGCTGGTGCT GTCGGCAAGG ACCGCGGCAG CCTTGGATGC ACACGCGGCG CGGCTGCGCG

3421 ACCATCTGGA GACCTACCCT TCGCAGTGTC TGGGCGATGT GGCGTTCAGT CTGGCGACGA

3481 CGCGCAGCGC GATGGAGCAC CGGCTCGCGG TGGCGGCGAC GTCGAGCGAG GGGCTGCGGG

3541 CAGCCCTGGA CGCTGCGGCG CAGGGACAGA CGCCGCCCGG TGTGGTGCGC GGTATCGCCG

3601 ATTCCTCACG CGGCAAGCTC GCCTTTCTCT TCACCGGACA GGGGGCGCAG ACGCTGGGCA

3661 TGGGCCGTGG GCTGTATGAT GTATGGCCCG CGTTCCGCGA GGCGTTCGAC CTGTGCGTGA

3721 GGCTGTTCAA CCAGGAGCTC GACCGGCCGC TCCGCGAGGT GATGTGGGCC GAACCGGCCA

3781 GCGTCGACGC CGCGCTGCTC GACCAGACAG CCTTTACCCA GCCGGCGCTG TTCACCTTCG

3841 AGTATGCGCT CGCCGCGCTG TGGCGGTCGT GGGGCGTAGA GCCGGAGTTG GTCGCTGGCC

3901 ATAGCATCGG TGAGCTGGTG GCTGCCTGCG TGGCGGGCGT GTTCTCGCTT GAGGACGCGG

3961 TGTTCCTGGT GGCTGCGCGC GGGCGCCTGA TGCAGGCGCT GCCGGCCGGC GGGGCGATGG

4021 TGTCGATCGC GGCGCCGGAG GCCGATGTGG CTGCTGCGGT GGCGCCGCAC GCAGCGTCGG

4081 TGTCGATCGC CGCGGTCAAC GGTCCGGACC AGGTGGTCAT CGCGGGCGCC GGGCAACCCG

4141 TGCATGCGAT CGCGGCGGCG ATGGCCGCGC GCGGGGCGCG AACCAAGGCG CTCCACGTCT

4201 CGCATGCGTT CCACTCACCG CTCATGGCCC CGATGCTGGA GGCGTTCGGG CGTGTGGCCG

4261 AGTCGGTGAG CTACCGGCGG CCGTCGATCG TCCTGGTCAG CAATCTGAGC GGGAAGGCTG

4321 GCACAGACGA GGTGAGCTCG CCGGGCTATT GGGTGCGCCA CGCGCGAGAG GTGGTGCGCT

4381 TCGCGGATGG AGTGAAGGCG CTGCACGCGG CCGGTGCGGG CACCTTCGTC GAGGTCGGTC

4441 CGAAATCGAC GCTGCTCGGC CTGGTGCCTG CCTGCCTGCC GGACGCCCGG CCGGCGCTGC
```

```
                    -continued
4501 TCGCATCGTC GCGCGCTGGG CGTGACGAGC CAGCGACCGT GCTCGAGGCG CTCGGCGGGC

4561 TCTGGGCCGT CGGTGGCCTG GTCTCCTGGG CCGGCCTCTT CCCCTCAGGG GGGCGGCGGG

4621 TGCCGCTGCC CACGTACCCT TGGCAGCGCG AGCGCTACTG GATCGACACG AAAGCCGACG

4681 ACGCGGCGCG TGGCGACCGC CGTGCTCCGG GAGCGGGTCA CGACGAGGTC GAGAAGGGGG

4741 GCGCGGTGCG CGGCGGCGAC CGGCGCAGCG CTCGGCTCGA CCATCCGCCG CCCGAGAGCG

4801 GACGCCGGGA GAAGGTCGAG GCCGCCGGCG ACCGTCCGTT CCGGCTCGAG ATCGATGAGC

4861 CAGGCGTGCT CGATCGCCTG GTGCTTCGGG TCACGGAGCG CGCGCCCCT GGTCTTGGCG

4921 AGGTCGAGAT CGCCGTCGAC GCGGCGGGGC TCAGCTTCAA TGATGTCCAG CTCGCGCTGG

4981 GCATGGTGCC CGACGACCTG CCGGGAAAGC CCAACCCTCC GCTGCTGCTC GGAGGCGAGT

5041 GCGCCGGGCG CATCGTCGCC GTGGGCGAGG GCGTGAACGG CCTTGTGGTG GGCCAACCGG

5101 TCATCGCCCT TTCGGCGGGA GCGTTTGCTA CCCACGTCAC CACGTCGGCT GCGCTGGTGC

5161 TGCCTCGGCC TCAGGCGCTC TCGGCGACCG AGGCGGCCGC CATGCCCGTC GCGTACCTGA

5221 CGGCATGGTA CGCGCTCGAC GGAATAGCCC GCCTTCAGCC GGGGGAGCGG GTGCTGATCC

5281 ACGCGGCGAC CGGCGGGGTC GGTCTCGCCG CGGTGCAGTG GGCGCAGCAC GTGGGAGCCG

5341 AGGTCCATGC GACGGCCGGC ACGCCCGAGA AGCGCGCCTA CCTGGAGTCG CTGGGCGTGC

5401 GGTATGTGAG CGATTCCCGC TCGGACCGGT TCGTCGCCGA CGTGCGCGCG TGGACGGGCG

5461 GCGAGGGAGT AGACGTCGTG CTCAACTCGC TTTCGGGCGA GCTGATCGAC AAGAGTTTCA

5521 ATCTCCTGCG ATCGCACGGC CGGTTTGTGG AGCTCGGCAA GCGCGACTGT TACGCGGATA

5581 ACCAGCTCGG GCTGCGGCCG TTCCTGCGCA ATCTCTCCTT CTCGCTGGTG GATCTCCGGG

5641 GGATGATGCT CGAGCGGCCG GCGCGGGTCC GTGCGCTCTT CGAGGAGCTC CTCGGCCTGA

5701 TCGCGGCAGG CGTGTTCACC CCTCCCCCCA TCGCGACGCT CCCGATCGCT CGTGTCGCCG

5761 ATGCGTTCCG GAGCATGGCG CAGGCGCAGC ATCTTGGGAA GCTCGTACTC ACGCTGGGTG

5821 ACCCGGAGGT CCAGATCCGT ATTCCGACCC ACGCAGGCGC CGGCCCGTCC ACCGGGGATC

5881 GGGATCTGCT CGACAGGCTC GCGTCAGCTG CGCCGGCCGC GCGCGCGGCG GCGCTGGAGG

5941 CGTTCCTCCG TACGCAGGTC TCGCAGGTGC TGCGCACGCC CGAAATCAAG GTCGGCGCGG

6001 AGGCGCTGTT CACCCGCCTC GGCATGGACT CGCTCATGGC CGTGGAGCTG CGCAATCGTA

6061 TCGAGGCGAG CCTCAAGCTG AAGCTGTCGA CGACGTTCCT GTCCACGTCC CCCAATATCG

6121 CCTTGTTGAC CCAAAACCTG TTGGATGCTC TCGCCACAGC TCTCTCCTTG GAGCGGGTGG

6181 CGGCGGAGAA CCTACGGGCA GGCGTGCAAA GCGACTTCGT CTCATCGGGC GCAGATCAAG

6241 ACTGGGAAAT CATTGCCCTA TGACGATCAA TCAGCTTCTG AACGAGCTCG AGCACCAGGG

6301 TGTCAAGCTG GCGGCCGATG GGAGCGCCT CCAGATACAG GCCCCAAGA ACGCCCTGAA

6361 CCCGAACCTG CTCGCTCGAA TCTCCGAGCA CAAAAGCACG ATCCTGACGA TGCTCCGTCA

6421 GAGACTCCCC GCAGAGTCCA TCGTGCCCGC CCCAGCCGAG CGGCACGTTC CGTTTCCTCT

6481 CACAGACATC CAAGGATCCT ACTGGCTGGG TCGGACAGGA GCGTTTACGG TCCCCAGCGG

6541 GATCCACGCC TATCGCGAAT ACGACTGTAC GGATCTCGAC GTGGCGAGGC TGAGCCGCGC

6601 CTTTCGGAAA GTCGTCGCGC GGCACGACAT GCTTCGGGCC CACACGCTGC CGACATGAT

6661 GCAGGTGATC GAGCCTAAAG TCGACGCCGA CATCGAGATC ATCGATCTGC GCGGGCTCGA

6721 CCGGAGCACA CGGGAAGCGA GGCTCGTATC GTTGCGAGAT GCGATGTCGC ACCGCATCTA

6781 TGACACCGAG CGCCCTCCGC TCTATCACGT CGTCGCCGTT CGGCTGGACG AGCAGCAAAC

6841 CCGTCTCGTG CTCAGTATCG ATCTCATTAA CGTTGACCTA GGCAGCCTGT CCATCATCTT
```

```
6901 CAAGGATTGG CTCAGCTTCT ACGAAGATCC CGAGACCTCT CTCCCTGTCC TGGAGCTCTC
6961 GTACCGCGAC TATGTGCTCG CGCTGGAGTC TCGCAAGAAG TCTGAGGCGC ATCAACGATC
7021 GATGGATTAC TGGAAGCGGC GCGTCGCCGA GCTCCCACCT CCGCCGATGC TTCCGATGAA
7081 GGCCGATCCA TCTACCCTGA GGGAGATCCG CTTCCGGCAC ACGGAGCAAT GGCTGCCGTC
7141 GGACTCCTGG AGTCGATTGA AGCAGCGTGT CGGGGAGCGC GGGCTGACCC CGACGGGCGT
7201 CATTCTGGCT GCATTTTCCG AGGTGATCGG GCGCTGGAGC GCGAGCCCCC GGTTTACGCT
7261 CAACATAACG CTCTTCAACC GGCTCCCCGT CCATCCGCGC GTGAACGATA TCACCGGGGA
7321 CTTCACGTCG ATGGTCCTCC TGGACATCGA CACCACTCGC GACAAGAGCT CGAACAGCG
7381 CGCTAAGCGT ATTCAAGAGC AGCTGTGGGA AGCGATGGAT CACTGCGACG TAAGCGGTAT
7441 CGAGGTCCAG CGAGAGGCCG CCCGGGTCCT GGGGATCCAA CGAGGCGCAT TGTTCCCCGT
7501 GGTGCTCACG AGCGCGCTCA ACCAGCAAGT CGTTGGTGTC ACCTCGCTGC AGAGGCTCGG
7561 CACTCCGGTG TACACCAGCA CGCAGACTCC TCAGCTGCTG CTGGATCATC AGCTCTACGA
7621 GCACGATGGG GACCTCGTCC TCGCGTGGGA CATCGTCGAC GGAGTGTTCC CGCCCGACCT
7681 TCTGGACGAC ATGCTCGAAG CGTACGTCGC TTTTCTCCGG CGGCTCACTG AGGAACCATG
7741 GAGTGAACAG ATGCGCTGTT CGCTTCCGCC TGCCCAGCTA GAAGCGCGGG CGAGCGCAAA
7801 CGAGACCAAC TCGCTGCTGA GCGAGCATAC GCTGCACGGC CTGTTCGCGG CGCGGGTCGA
7861 GCAGCTGCCT ATGCAGCTCG CCGTGGTGTC GGCGCGCAAG ACGCTCAGGT ACGAAGAGCT
7921 TTCGCGCCGT TCGCGGCGAC TTGGCGCGCG GCTGCGCGAG CAGGGGCAC GCCCGAACAC
7981 ATTGGTCGCG GTGGTGATGG AGAAAGGCTG GGAGCAGGTT GTCGCGGTTC TCGCGGTGCT
8041 CGAGTCAGGC GCGGCCTACG TGCCGATCGA TGCCGACCTA CCGGCGGAGC GTATCCACTA
8101 CCTCCTCGAT CATGGTGAGG TAAAGCTCGT GCTGACGCAG CCATGGCTGG ATGGCAAACT
8161 GTCATGGCCG CCGGGGATCC AGCGGCTGCT CGTGAGCGAT GCCGGCGTCG AAGGCGACGG
8221 CGACCAGCTT CCGATGATGC CCATTCAGAC ACCTTCGGAT CTCGCGTATG TCATCTACAC
8281 CTCGGGATCC ACAGGGTTGC CAAGGGGGT GATGATCGAT CATCGGGGTG CCGTCAACAC
8341 CATCCTGGAC ATCAACGAGC GCTTCGAAAT AGGGCCCGGA GACAGAGTGC TGGCGCTCTC
8401 CTCGCTGAGC TTCGATCTCT CGGTCTACGA TGTGTTCGGG ATCCTGGCGG CGGGCGGTAC
8461 GATCGTGGTG CCGGACGCGT CCAAGCTGCG CGATCCGGCG CATTGGGCAG CGTTGATCGA
8521 ACGAGAGAAG GTGACGGTGT GGAACTCGGT GCCGGCGCTG ATGCGGATGC TCGTCGAGCA
8581 TTCCGAGGGT CGCCCCGATT CGCTCGCTAG GTCTCTGCGG CTTTCGCTGC TGAGCGGCGA
8641 CTGGATCCCG GTGGGCCTGC CTGGCGAGCT CCAGGCCATC AGGCCCGGCG TGTCGGTGAT
8701 CAGCCTGGGC GGGGCCACCG AAGCGTCGAT CTGGTCCATC GGGTACCCCG TGAGGAACGT
8761 CGATCCATCG TGGGCGAGCA TCCCCTACGG CCGTCCGCTG CGCAACCAGA CGTTCCACGT
8821 GCTCGATGAG GCGCTCGAAC CGCGCCCGGT CTGGGTTCCG GGGCAACTCT ACATTGGCGG
8881 GGTCGGACTG GCACTGGGCT ACTGGCGCGA TGAAGAGAAG ACGCGCAACA GCTTCCTCGT
8941 GCACCCCGAG ACCGGGGAGC GCCTCTACAA GACCGGCGAT CTGGGCCGCT ACCTGCCCGA
9001 TGGAAACATC GAGTTCATGG GGCGGGAGGA CAACCAAATC AAGCTTCGCG GATACCGCGT
9061 TGAGCTCGGG GAAATCGAGG AAACGCTCAA GTCGCATCCG AACGTACGCG ACGCGGTGAT
9121 TGTGCCCGTC GGGAACGACG CGGCGAACAA GCTCCTTCTA GCCTATGTGG TCCCGGAAGG
9181 CACACGGAGA CGCGCTGCCG AGCAGGACGC GAGCCTCAAG ACCGAGCGGG TCGACGCGAG
9241 AGCACACGCC GCCAAAGCGG ACGGATTGAG CGACGGCGAG AGGGTGCAGT CAAGCTCGC
```

```
                       -continued
 9301   TCGACACGGA CTCCGGAGGG ATCTGGACGG AAAGCCCGTC GTCGATCTGA CCGGGCTGGT

9361   TCCGCGGGAG GCGGGGCTGG ACGTCTACGC GCGTCGCCGT AGCGTCCGAA CGTTCCTCGA

9421   GGCCCCGATT CCATTTGTTG AATTCGGCCG ATTCCTGAGC TGCCTGAGCA GCGTGGAGCC

9481   CGACGGCGCG GCCCTTCCCA AATTCCGTTA TCCATCGGCT GGCAGCACGT ACCCGGTGCA

9541   AACCTACGCG TACGCCAAAT CCGGCCGCAT CGAGGGCGTG GACGAGGGCT TCTATTATTA

9601   CCACCCGTTC GAGCACCGTT TGCTGAAGGT CTCCGATCAC GGGATCGAGC GCGGAGCGCA

9661   CGTTCCGCAA AACTTCGACG TGTTCGATGA AGCGGCGTTC GGCCTCCTGT TCGTGGGCAG

9721   GATCGATGCC ATCGAGTCGC TGTATGGATC GTTGTCACGA GAATTCTGCC TGCTGGAGGC

9781   CGGATATATG GCGCAGCTCC TGATGGAGCA GGCGCCTTCC TGCAACATCG GCGTCTGTCC

9841   GGTGGGTCAA TTCGATTTTG AACAGGTTCG GCCGGTTCTC GACCTGCGGC ATTCGGACGT

9901   TTACGTGCAC GGCATGCTGG GCGGGCGGGT AGACCCGCGG CAGTTCCAGG TCTGTACGCT

9961   CGGTCAGGAT TCCTCACCGA GGCGCGCCAC GACGCGCGGC GCCCCTCCCG GCCGCGATCA

10021   GCACTTCGCC GATATCCTTC GCGACTTCTT GAGGACCAAA CTACCCGAGT ACATGGTGCC

10081   TACAGTCTTC GTGGAGCTCG ATGCGTTGCC GCTGACGTCC AACGGCAAGG TCGATCGTAA

10141   GGCCCTGCGC GAGCGGAAGG ATACCTCGTC GCCGCGGCAT TCGGGGCACA CGGCGCCACG

10201   GGACGCCTTG GAGGAGATCC TCGTTGCGGT CGTACGGGAG GTGCTCGGGC TGGAGGTGGT

10261   TGGGCTCCAG CAGAGCTTCG TCGATCTTGG TGCGACATCG ATTCACATCG TTCGCATGAG

10321   GAGTCTGTTG CAGAAGAGGC TGGATAGGGA GATCGCCATC ACCGAGTTGT TCCAGTACCC

10381   GAACCTCGGC TCGCTGGCGT CCGGTTTGCG CCGAGACTCG AAAGATCTAG AGCAGCGGCC

10441   GAACATGCAG GACCGAGTGG AGGCTCGGCG CAAGGGCAGG AGACGTAGCT AAGAGCGCCG

10501   AACAAAACCA GGCCGAGCGG GCCAATGAAC CGCAAGCCCG CCTGCGTCAC CCTGGGACTC

10561   ATCTGATCTG ATCGCGGGTA CGCGTCGCGG GTGTGCGCGT TGACCCGTGT TGCTCGAACG

10621   CTGAGGAACG GTGAGCTCAT GGAAGAACAA GAGTCCTCCG CTATCGCAGT CATCGGCATG

10681   TCGGGCCGTT TTCCGGGGGC GCGGGATCTG GACGAATTCT GGAGGAACCT TCGAGACGGC

10741   ACGGAGGCCG TGCAGCGCTT CTCCGAGCAG GAGCTCGCGG CGTCCGGAGT CGACCCAGCG

10801   CTGGTGCTGG ACCCGAACTA CGTCCGGGCG GCAGCGTGC TGGAAGATGT CGACCGGTTC

10861   GACGCTGCTT TCTTCGGCAT CAGCCCGCGC GAGGCAGAGC TCATGGATCC GCAGCACCGC

10921   ATCTTCATGG AATGCGCCTG GGAGGCGCTG GAGAACGCCG GATACGACCC GACAGCCTAC

10981   GAGGGCTCTA TCGGCGTGTA CGCCGGCGCC AACATGAGCT CGTACTTGAC GTCGAACCTC

11041   CACGAGCACC CAGCGATGAT GCGGTGGCCC GGCTGGTTTC AGACGTTGAT CGGCAACGAC

11101   AAGGATTACC TCGCGACCCA CGTCTCCTAC AGGCTGAATC TGAGAGGGCC GAGCATCTCC

11161   GTTCAAACTG CCTGCTCTAC CTCGCTCGTG GCGGTTCACT TGGCGTGCAT GAGCCTCCTG

11221   GACCGCGAGT GCGACATGGC GCTGGCCGGC GGGATTACCG TCCGGATCCC CCATCGAGCC

11281   GGCTATGTAT ATGCTGAGGG GGGCATCTTC TCTCCCGACG GCCATTGCCG GGCCTTCGAC

11341   GCCAAGGCGA ACGGCACGAT CATGGGCAAC GGCTGCGGGG TTGTCCTCCT GAAGCCGCTG

11401   GACCGGGCGC TCTCCGATGG TGATCCCGTC CGCGCGGTCA TCCTTGGGTC TGCCACAAAC

11461   AACGACGGAG CGAGGAAGAT CGGGTTCACT GCGCCCAGTG AGGTGGGCCA GGCGCAAGCG

11521   ATCATGGAGG CGCTGGCGCT GGCAGGGGTC GAGGCCCGGT CCATCCAATA CATCGAGACC

11581   CACGGGACCG GCACGCTGCT CGGAGACGCC ATCGAGACGG CGGCGTTGCG GCGGGTGTTC

11641   GATCGCGACG CTTCGACCCG GAGGTCTTGC GCGATCGGCT CCGTGAAGAC CGGCATCGGA
```

```
-continued
11701  CACCTCGAAT CGGCGGCTGG CATCGCCGGT TTGATCAAGA CGGTCTTGGC GCTGGAGCAC
11761  CGGCAGCTGC CGCCCAGCCT GAACTTCGAG TCTCCTAACC CATCGATCGA TTTCGCGAGC
11821  AGCCCGTTCT ACGTCAATAC CTCTCTTAAG GATTGGAATA CCGGCTCGAC TCCGCGGCGG
11881  GCCGGCGTCA GCTCGTTCGG GATCGGCGGC ACCAACGCCC ATGTCGTGCT GGAGGAAGCA
11941  CCCGCGGCGA AGCTTCCAGC CGCGGCGCCG GCGCGCTCTG CCGAGCTCTT CGTCGTCTCG
12001  GCCAAGAGCG CAGCGGCGCT GGATGCCGCG GCGGCACGGC TACGAGATCA TCTGCAGGCG
12061  CACCAGGGGC TTTCGTTGGG CGACGTCGCC TTCAGCCTGG CGACGACGCG CAGTCCCATG
12121  GAGCACCGGC TCGCGATGGC GGCACCGTCG CGCGAGGCGT TGCGAGAGGG GCTCGACGCA
12181  GCGGCGCGAG GCCAGACCCC GCCGGGCGCC GTGCGTGGCC GCTGCTCCCC AGGCAACGTG
12241  CCGAAGGTGG TCTTCGTCTT TCCCGGCCAG GGCTCTCAGT GGGTCGGTAT GGGCCGTCAG
12301  CTCCTGGCTG AGGAACCCGT CTTCCACGCG GCGCTTTCGG CGTGCGACCG GGCCATCCAG
12361  GCCGAAGCTG GTTGGTCGCT GCTCGCCGAG CTCGCCGCCG ACGAAGGGTC GTCCCAGATC
12421  GAGCGCATCG ACGTGGTGCA GCCGGTGCTG TTCGCGCTCG CGGTGGCATT TGCGGCGCTG
12481  TGGCGGTCGT GGGGTGTCGG GCCCGACGTC GTGATCGGCC ACAGCATGGG CGAGGTAGCC
12541  GCCGCGCATG TGGCCGGGGC GCTGTCGCTC GAGGATGCGG TGGCGATCAT CTGCCGGCGC
12601  AGCCGGCTGC TCCGGCGCAT CAGCGGTCAG GGCGAGATGG CGGTGACCGA GCTGTCGCTG
12661  GCCGAGGCCG AGGCAGCGCT CCGAGGCTAC GAGGATCGGG TGAGCGTGGC CGTGAGCAAC
12721  AGCCCGCGCT CGACGGTGCT CTCGGGCGAG CCGGCAGCGA TCGCGAGGT GCTGTCGTCC
12781  CTGAACGCGA AGGGGGTGTT CTGCCGTCGG GTGAAGGTGG ATGTCGCCAG CCACAGCCCG
12841  CAGGTCGACC CGCTGCGCGA GGACCTCTTG GCAGCGCTGG GCGGGCTCCG GCCGCGTGCG
12901  GCTGCGGTGC CGATGCGCTC GACGGTGACG GGCGCCATGG TAGCGGGCCC GGAGCTCGGA
12961  GCGAATTACT GGATGAACAA TCTCAGGCAG CCTGTGCGCT TCGCCGAGGT AGTCCAGGCG
13021  CAGCTCCAAG GCGGCCACGG TCTGTTCGTG GAGATGAGCC CGCATCCGAT CCTAACGACT
13081  TCGGTCGAGG AGATGCGGCG CGCGGCCCAG CGGGCGGGCG CAGCGGTGGG CTCGCTGCGG
13141  CGAGGGCAGG ACGAGCGCCC GGCGATGCTG GAGGCGCTGG GCGCGCTGTG GGCGCAGGGC
13201  TACCCTGTAC CCTGGGGGCG GCTGTTTCCC GCGGGGGGGC GGCGGGTACC GCTGCCGACC
13261  TATCCCTGGC AGCGCGAGCG GTACTGGATC GAAGCGCCGG CCAAGAGCGC CGCGGGCGAT
13321  CGCCGCGGCG TGCGTGCGGG CGGTCACCCG CTCCTCGGTG AAATGCAGAC CCTATCAACC
13381  CAGACGAGCA CGCGGCTGTG GGAGACGACG CTGGATCTCA AGCGGCTGCC GTGGCTCGGC
13441  GACCACCGGG TGCAGGGAGC GGTCGTGTTT CCGGGCGCGG CGTACCTGGA GATGGCGATT
13501  TCGTCGGGGG CCGAGGCTTT GGGCGATGGC CCATTGCAGA TAACCGACGT GGTGCTCGCC
13561  GAGGCGCTGG CCTTCGCGGG CGACGCGGCG GTGTTGGTCC AGGTGGTGAC GACGGAGCAG
13621  CCGTCGGGAC GGCTGCAGTT CCAGATCGCG AGCCGGGCGC CGGGCGCTGG CCACGCGTCC
13681  TTCCGGGTCC ACGCTCGCGG CGCGTTGCTC CGAGTGGAGC GCACCGAGGT CCCGGCTGGG
13741  CTTACGCTTT CCGCCGTGCG CGCACGGCTC CAGGCCAGCA TGCCCGCCGC GGCCACCTAC
13801  GCGGAGCTGA CCGAGATGGG GCTGCAGTAC GGCCCTGCCT TCCAGGGGAT TGCTGAGCTA
13861  TGGCGCGGTG AGGGCGAGGC GCTGGGACGG GTACGCCTGC CCGACGCGGC CGGCTCGGCA
13921  GCGGAGTATC GGTTGCATCC TGCGCTGCTG GACGCGTGCT TCCAGGTCGT CGGCAGCCTC
13981  TTCGCCGGCG GTGGCGAGGC GACGCCGTGG GTGCCCGTGG AAGTGGGCTC GCTGCGGCTC
14041  TTGCAGCGGC CTTCGGGGGA GCTGTGGTGC CATGCGCGCG TCGTGAACCA CGGGCGCCAA
```

-continued

```
14101  ACCCCCGATC GGCAGGGCGC CGACTTTTGG GTGGTCGACA GCTCGGGTGC AGTGGTCGCC

14161  GAAGTCAGCG GGCTCGTGGC GCAGCGGCTT CCGGGAGGGG TGCGCCGGCG CGAAGAAGAC

14221  GATTGGTTCC TGGAGCTCGA GTGGGAACCC GCAGCGGTCG GCACAGCCAA GGTCAACGCG

14281  GGCCGGTGGC TGCTCCTCGG CGGCGGCGGT GGGCTCGGCG CCGCGTTGCG CTCGATGCTG

14341  GAGGCCGGCG GCCATGCCGT CGTCCATGCG GCAGAGAGCA ACACGAGCGC TGCCGGCGTA

14401  CGCGCGCTCC TGGCAAAGGC CTTTGACGGC CAGGCTCCGA CGGCGGTGGT GCACCTCGGC

14461  AGCCTCGATG GGGGTGGCGA GCTCGACCCA GGGCTCGGGG CGCAAGGCGC ATTGGACGCG

14521  CCCCGGAGCG CCGACGTCAG TCCCGATGCC CTCGATCCGG CGCTGGTACG TGGCTGTGAC

14581  AGCGTGCTCT GGACCGTGCA GGCCCTGGCC GGCATGGGCT TTCGAGACGC CCCGCGATTG

14641  TGGCTTCTGA CCCGCGGCGC ACAGGCCGTC GGCGCCGGCG ACGTCTCCGT GACACAGGCA

14701  CCGCTGCTGG GGCTGGGCCG CGTCATCGCC ATGGAGCACG CGGATCTGCG CTGCGCTCGG

14761  GTCGACCTCG ATCCGACCCG GCCCGATGGG GAGCTCGGTG CCCTGCTGGC CGAGCTGCTG

14821  GCCGACGACG CCGAAGCGGA AGTCGCGTTG CGCGGTGGCG AGCGATGCGT CGCTCGGATC

14881  GTCCGCCGGC AGCCCGAGAC CCGGCCCCGG GGGAGGATCG AGAGCTGCGT TCCGACCGAC

14941  GTCACCATCC GCGCGGACAG CACCTACCTT GTGACCGGCG GTCTGGGTGG GCTCGGTCTG

15001  AGCGTGGCCG GATGGCTGGC CGAGCGCGGC GCTGGTCACC TGGTGCTGGT GGGCCGCTCC

15061  GGCGCGGCGA GCGTGGAGCA ACGGGCAGCC GTCGCGGCGC TCGAGGCCCG CGGCGCGCGC

15121  GTCACCGTGG CGAAGGCAGA TGTCGCCGAT CGGGCGCAGC TCGAGCGGAT CCTCCGCGAG

15181  GTTACCACGT CGGGGATGCC GCTGCGGGGC GTCGTCCATG CGGCCGGCAT CTTGGACGAC

15241  GGGCTGCTGA TGCAGCAGAC TCCCGCGCGG TTTCGTAAGG TGATGGCGCC CAAGGTCCAG

15301  GGGGCCTTGC ACCTGCACGC GTTGACGCGC GAAGCGCCGC TTTCCTTCTT CGTGCTGTAC

15361  GCTTCGGGAG TAGGGCTCTT GGGCTCGCCG GGCCAGGGCA ACTACGCCGC GGCCAACACG

15421  TTCCTCGACG CTCTGGCGCA CCACCGGAGG GCGCAGGGGC TGCCAGCGTT GAGCGTCGAC

15481  TGGGGCCTGT TCGCGGAGGT GGGCATGGCG GCCGCGCAGG AAGATCGCGG CGCGCGGCTG

15541  GTCTCCCGCG GAATGCGGAG CCTCACCCCC GACGAGGGGC TGTCCGCTCT GGCACGGCTG

15601  CTCGAAAGCG GCCGCGTGCA GGTGGGGGTG ATGCCGGTGA ACCCGCGGCT GTGGGTGGAG

15661  CTCTACCCCG CGGCGGCGTC TTCGCGAATG TTGTCGCGCC TGGTGACGGC GCATCGCGCG

15721  AGCGCCGGCG GGCCAGCCGG GGACGGGGAC CTGCTCCGCC GCCTCGCTGC TGCCGAGCCG

15781  AGCGCGCGGA GCGGGCTCCT GGAGCCGCTC CTCCGCGCGC AGATCTCGCA GGTGCTGCGC

15841  CTCCCCGAGG GCAAGATCGA GGTGGACGCC CCGCTCACGA GCCTGGGCAT GAACTCGCTG

15901  ATGGGGCTCG AGCTGCGCAA CCGCATCGAG GCCATGCTGG GCATCACCGT ACCGGCAACG

15961  CTGTTGTGGA CCTATCCCAC GGTGGCGGCG CTGAGCGGGC ATCTGGCGCG GGAGGCATGC

16021  GAAGCCGCTC CTGTGGAGTC ACCGCACACC ACCGCCGATT CTGCTGTCGA GATCGAGGAG

16081  ATGTCGCAGG ACGATCTGAC GCAGTTGATC GCAGCAAAAT TCAAGGCGCT TACATGACTA

16141  CTCGCGGTCC TACGGCACAG CAGAATCCGC TGAAACAAGC GGCCATCATC ATTCAGCGGC

16201  TGGAGGAGCG GCTCGCTGGG CTCGCACAGG CGGAGCTGGA ACGGACCGAG CCGATCGCCA

16261  TCGTCGGTAT CGGCTGCCGC TTCCCTGGCG GTGCGGACGC TCCGGAAGCG TTTTGGGAGC

16321  TGCTCGACGC GGAGCGCGAC GCGGTCCAGC CGCTCGACAG GCGCTGGGCG CTGGTAGGTG

16381  TCGCTCCCGT CGAGGCCGTG CCGCACTGGG CGGGGCTGCT CACCGAGCCG ATAGATTGCT

16441  TCGATGCTGC GTTCTTCGGC ATCTCGCCTC GGGAGGCGCG ATCGCTCGAC CCGCAGCATC
```

```
-continued
16501  GTCTGTTGCT GGAGGTCGCT TGGGAGGGGC TCGAGGACGC CGGTATCCCG CCCCGGTCCA
16561  TCGACGGGAG CCGCACCGGT GTGTTCGTCG GCGCTTTCAC GGCGGACTAC GCGCGCACGG
16621  TCGCTCGGTT GCCGCGCGAG GAGCGAGACG CGTACAGCGC CACCGGCAAC ATGCTCAGCA
16681  TCGCCGCCGG ACGGCTGTCG TACACGCTGG GGCTGCAGGG ACCTTGCCTG ACCGTCGACA
16741  CGGCGTGCTC GTCATCGCTG GTGGCGATTC ACCTCGCCTG CCGCAGCCTG CGCGCAGGAG
16801  AGAGCGATCT CGCGTTGGCG GGAGGGGTCA GCACGCTCCT CTCCCCCGAC ATGATGGAAG
16861  CCGCGGCGCG CACGCAAGCG CTGTCGCCCG ATGGTCGTTG CCGGACCTTC GATGCTTCGG
16921  CCAACGGGTT CGTCCGTGGC GAGGGCTGTG GCCTGGTCGT CCTCAAACGG CTCTCCGACG
16981  CGCAACGGGA TGGCGACCGC ATCTGGGCGC TGATCCGGGG CTCGGCCATC AACCATGATG
17041  GCCGGTCGAC CGGGTTGACC GCGCCCAACG TGCTGGCTCA GGAGACGGTC TTGCGCGAGG
17101  CGCTGCGGAG CGCCCACGTC GAAGCTGGGG CCGTCGATTA CGTCGAGACC CACGGAACAG
17161  GGACCTCGCT GGGCGATCCC ATCGAGGTCG AGGCGCTGCG GGCGACGGTG GGGCCGGCGC
17221  GCTCCGACGG CACACGCTGC GTGCTGGGCG CGGTGAAGAC CAACATCGGC CATCTCGAGG
17281  CCGCGGCAGG CGTAGCGGGC CTGATCAAGG CAGCGCTTTC GCTGACGCAC GAGCGCATCC
17341  CGAGAAACCT CAACTTCCGC ACGCTCAATC CGCGGATCCG GCTCGAGGGC AGCGCGCTCG
17401  CGTTGGCGAC CGAGCCGGTG CCGTGGCCGC GCACGGACCG TCCGCGCTTC GCGGGGGTGA
17461  GCTCGTTCGG GATGAGCGGA ACGAACGCGC ATGTGGTGCT GGAAGAGGCG CCGGCGGTGG
17521  AGCTGTGGCC TGCCGCGCCG GAGCGCTCGG CGGAGCTTTT GGTGCTGTCG GGCAAGAGCG
17581  AGGGGGCGCT CGACGCGCAG GCGGCGCGGC TGCGCGAGCA CCTGGACATG CACCCGGAGC
17641  TCGGGCTCGG GGACGTGGCG TTCAGCCTGG CGACGACGCG CAGCGCGATG ACCCACCGGC
17701  TCGdGGTGGC GGTGACGTCG CGCGAGGGGC TGCTGGCGGC GCTTTCGGCC GTGGCGCAGG
17761  GGCAGACGCC GGCGGGGGCG GCGCGCTGCA TCGCGAGCTC CTCGCGCGGC AAGCTGGCGT
17821  TGCTGTTCAC CGGACAGGGC GCGCAGACGC CGGGCATGGG CCGGGGGCTC TGCGCGGCGT
17881  GGCCAGCGTT CCGGGAGGCG TTCGACCGGT GCGTGACGCT GTTCGACCGG GAGCTGGACC
17941  GCCCGCTGCG CGAGGTGATG TGGGCGGAGG CGGGGAGCGC CGAGTCGTTG TTGCTGGACC
18001  AGACGGCGTT CACCCAGCCC GCGCTCTTCG CGGTGGAGTA CGCGCTGACG GCGCTGTGGC
18061  GGTCGTGGGG CGTAGAGCCG GAGCTCCTGG TTGGGCATAG CATCGGGGAG CTGGTGGCGG
18121  CGTGCGTGGC GGGGGTGTTC TCGCTGGAAG ATGGGGTGAG GCTCGTGGCG GCGCGCGGGC
18181  GGCTGATGCA GGGGCTCTCG GCGGGCGGCG CGATGGTGTC GCTCGGAGCG CCGGAGGCGG
18241  AGGTGGCCGC GGCGGTGGCG CCGCACGCGG CGTGGGTGTC GATCGCGGCG GTCAATGGGC
18301  CGGAGCAGGT GGTGATCGCG GGCGTGGAGC AAGCGGTGCA GGCGATCGCG GCGGGGTTCG
18361  CGGCGCGCGG CGTGCGCACC AAGCGGCTGC ATGTCTCGCA CGCGTTCCAC TCGCCGCTGA
18421  TGGAACCGAT GCTGGAGGAG TTCGGGCGGG TGGCGGCGTC GGTGACGTAC CGGCGGCCAA
18481  GCGTTTCGCT GGTGAGCAAC CTGAGCGGGA AGGTGGTCAC GGACGAGCTG AGCGCGCCGG
18541  GCTACTGGGT GCGGCACGTG CGGGAGGCGG TGCGCTTCGC GGACGGGGTG AAGGCGCTGC
18601  ACGAAGCCGG CGCGGGCACG TTCCTCGAAG TGGGCCCGAA GCCGACGCTG CTCGGCCTGT
18661  TGCCAGCTTG CCTGCCGGAG GCGGAGCCGA CGTTGCTGGC GTCGTTGCGC GCCGGGCGCG
18721  AGGAGGCTGC GGGGGTGCTC GAGGCGCTGG GCAGGCTGTG GCCGCTGGC GGCTCGGTCA
18781  GCTGGCCGGG CGTCTTCCCC ACGGCTGGGC GGCGGGTGCC GCTGCCGACC TATCCGTGGC
18841  AGCGGCAGCG GTACTGGATC GAGGCGCCGG CCGAAGGGCT CGGAGCCACG GCCGCCGATG
```

```
18901  CGCTGGCGCA GTGGTTCTAC CGGGTGGACT GGCCCGAGAT GCCTCGCTCA TCCGTGGATT
18961  CGCGGCGAGC CCGGTCCGGC GGGTGGCTGG TGCTGGCCGA CCGGGGTGGA GTCGGGGAGG
19021  CGGCCGCGGC GGCGCTTTCG TCGCAGGGAT GTTCGTGCGC CGTGCTCCAT GCGCCCGCCG
19081  AGGCCTCCGC GGTCGCCGAG CAGGTGACCC AGGCCCTCGG TGGCCGCAAC GACTGGCAGG
19141  GGGTGCTGTA CCTGTGGGGT CTGGACGCCG TCGTGGAGGC GGGGGCATCG GCCGAAGAGG
19201  TCGGCAAAGT CACCCATCTT GCCACGGCGC CGGTGCTCGC GCTGATTCAG GCGGTGGGCA
19261  CGGGGCCGCG CTCACCCCGG CTCTGGATCG TGACCCGAGG GGCCTGCACG GTGGGCGGCG
19321  AGCCTGACGC TGCCCCCTGT CAGGCGGCGC TGTGGGGTAT GGGCCGGGTC GCGGCGCTGG
19381  AGCATCCCGG CTCCTGGGGC GGGCTCGTGG ACCTGGATCC GGAGGAGAGC CCGACGGAGG
19441  TCGAGGCCCT GGTGGCCGAG CTGCTTTCGC CGGACGCCGA GGATCAGCTG GCATTCCGCC
19501  AGGGGCGCCG GCGCGCAGCG CGGCTCGTGG CCGCCCCACC GGAGGGAAAC GCAGCGCCGG
19561  TGTCGCTGTC TGCGGAGGGG AGTTACTTGG TGACGGGTGG GCTGGGCGCC CTTGGCCTCC
19621  TCGTTGCGCG GTGGTTGGTG GAGCGCGGGG CGGGGCACCT TGTGCTGATC AGCCGGCACG
19681  GATTGCCCGA CCGCGAGGAA TGGGGCCGAG ATCAGCCGCC AGAGGTGCGC GCGCGCATTG
19741  CGGCGATCGA GGCGCTGGAG GCGCAGGGCG CGCGGGTCAC CGTGGCGGCG GTCGACGTGG
19801  CCGATGCCGA AGGCATGGCG GCGCTCTTGG CGGCCGTCGA GCCGCCGCTG CGGGGGGTCG
19861  TGCACGCCGC GGGTCTGCTC GACGACGGGC TGCTGGCCCA CCAGGACGCC GGTCGGCTCG
19921  CCCGGGTGTT GCGCCCCAAG GTGGAGGGGG CATGGGTGCT GCACACCCTT ACCCGCGAGC
19981  AGCCGCTGGA CCTCTTCGTA CTGTTTTCCT CGGCGTCGGG CGTCTTCGGC TCGATCGGCC
20041  AGGGCAGCTA CGCGGCAGGC AATGCCTTTT TGGACGCGCT GGCGGACCTC CGTCGAACGC
20101  AGGGGCTCGC CGCCCTGAGC ATCGCCTGGG GCCTGTGGGC GGAGGGGGGG ATGGGCTCGC
20161  AGGCGCAGCG CCGGGAACAT GAGGCATCGG GAATCTGGGC GATGCCGACG AGTCGTGCCC
20221  TGGCGGCGAT GGAATGGCTG CTCGGTACGC GCGCGACGCA GCGCGTGGTC ATCCAGATGG
20281  ATTGGGCCCA TGCGGGAGCG GCTCCGCGCG ACGCGAGCCG AGGCCGCTTC TGGGATCGGC
20341  TGGTAACTGT CACGAAAGCG GCCTCCTCCT CGGCCGTGCC AGCTGTAGAG CGCTGGCGCA
20401  ACGCGTCTGT TGTGGAGACC CGCTCGGCGC TCTACGAGCT TGTGCGCGGC GTGGTCGCCG
20461  GGGTGATGGG CTTTACCGAC CAAGGCACGC TCGACGTGCG ACGAGGCTTC GCCGAGCAGG
20521  GCCTCGACTC CCTGATGGCT GTGGAGATCC GCAAACGGCT TCAGGGTGAG CTGGGTATGC
20581  CGCTGTCGGC GACGCTGGCG TTCGACCATC CGACCGTGGA GCGGCTGGTG GAATACTTGC
20641  TGAGCCAGGC GCTGGAGCTG CAGGACCGCA CCGACGTGCG AAGCGTTCGG TTGCCGGCGA
20701  CAGAGGACCC GATCGCCATC GTGGGTGCCG CCTGCCGCTT CCCGGGCGGG GTCGAGGACC
20761  TGGAGTCCTA CTGGCAGCTG TTGACCGAGG GCGTGGTGGT CAGCACCGAG GTGCCGGCCG
20821  ACCGGTGGAA TGGGGCAGAC GGGCGCGGCC CCGGCTCGGG AGAGGCTCCG AGACAGACCT
20881  ACGTGCCCAG GGGTGGCTTT CTGCGCGAGG TGGAGACGTT CGATGCGGCG TTCTTCCACA
20941  TCTCGCCCTC GGAGGCGATG AGCCTGGACC CGCAACAGCG GCTGCTGCTG GAAGTGAGCT
21001  GGGAGGCGAT CGAGCGCGCG GGCCAGGACC CGTCGGCGCT GCGCGAGAGC CCCACGGGCG
21061  TGTTCGTGGG CGCGGGCCCC AACGAATATG CCGAGCGGGT GCAGGACCTC GCCGATGAGG
21121  CGGCGGGGCT CTACAGCGGC ACCGGCAACA TGCTCAGCGT TGCGGCGGGA CGGCTGTCAT
21181  TTTTCCTGGG CCTGCACGGG CCGACCCTGG CTGTGGATAC GGCGTGCTCC TCGTCGCTCG
21241  TGGCGCTGCA CCTCGGCTGC CAGAGCTTGC GACGGGGCGA GTGCGACCAA GCCCTGGTTG
```

```
-continued
21301  GCGGGGTCAA CATGCTGCTC TCGCCGAAGA CCTTCGCGCT GCTCTCACGG ATGCACGCGC
21361  TTTCGCCCGG CGGGCGGTGC AAGACGTTCT CGGCCGACGC GGACGGCTAC GCGCGGGCCG
21421  AGGGCTGCGC CGTGGTGGTG CTCAAGCGGC TCTCCGACGC GCAGCGCGAC CGCGACCCCA
21481  TCCTGGCGGT GATCCGGGGT ACGGCGATCA ATCATGATGG CCCGAGCAGC GGGCTGACAG
21541  TGCCCAGCGG CCCTGCCCAG GAGGCGCTGT TACGCCAGGC GCTGGCGCAC GCAGGGGTGG
21601  TTCCGGCCGA CGTCGATTTC GTGGAATGCC ACGGGACCGG GACGGCGCTG GGCGACCCGA
21661  TCGAGGTGCG GGCGCTGAGC GACGTGTACG GCAAGCCCG CCCTGCGGAC CGACCGCTGA
21721  TCCTGGGAGC CGCCAAGGCC AACCTTGGGC ACATGGAGCC CGCGGCGGGC CTGGCCGGCT
21781  TGCTCAAGGC GGTGCTCGCG CTGGGGCAAG AGCAAATACC AGCCCAGCCG GAGCTGGGCG
21841  AGCTCAACCC GCTCTTGCCG TGGAGGCGC TGCCGGTGGC GGTGGCCCGC GCAGCGGTGC
21901  CGTGGCCGCG CACGGACCGT CCGCGCTTCG CGGGGGTGAG CTCGTTCGGG ATGAGCGGAA
21961  CGAACGCGCA TGTGGTGCTG AAGAGGCGC CGGCGGTGGA CTGTGGCCT GCCGCGCCGG
22021  AGCGCTCGGC GGAGCTTTTG GTGCTGTCGG GCAAGAGCGA GGGGGCGCTC GACGCGCAGG
22081  CGGCGCGGCT GCGCGAGCAC CTGGACATGC ACCCGGAGCT CGGGCTCGGG GACGTGGCGT
22141  TCAGCCTGGC GACGACGCGC AGCGCGATGA ACCACCGGCT CGCGGTGGCG GTGACGTCGC
22201  GCGAGGGGCT GCTGGCGGCG CTTTCGGCCG TGGCGCAGGG GCAGACGCCG CCGGGGGCGG
22261  CGCGCTGCAT CGCGAGCTCG TCGCGCGGCA AGCTGGCGTT CCTGTTCACC GGACAGGGCG
22321  CGCAGACGCC GGGCATGGGC CGGGGGCTTT GCGCGGCGTG GCCAGCGTTC CGAGAGGCGT
22381  TCGACCGGTG CGTGGCGCTG TTCGACCGGG AGCTGGACCG CCCGCTGTGC GAGGTGATGT
22441  GGGCGGAGCC GGGGAGCGCC GAGTCGTTGT TGCTCGACCA GACGGCGTTC ACCCAGCCCG
22501  CGCTCTTCAC GGTGGAGTAC GCGCTGACGG CGCTGTGGCG GTCGTGGGGC GTAGAGCCGG
22561  AGCTGGTGGC TGGGCATAGC GCCGGGGAGC TGGTGGCGGC GTGCGTGGCG GGGGTGTTCT
22621  CGCTGGAAGA TGGGGTGAGG CTCGTGGCGG CGCGCGGGCG GCTGATGCAG GGGCTCTCGG
22681  CGGGCGGCGC GATGGTGTCG CTCGGAGCGC CGGAGGCGGA GGTGGCCGCG GCGGTGGCGC
22741  CGCACGCGGC GTGGGTGTCG ATCGCGGCGG TCAATGGGCC GGAGCAGGTG GTGATCGCGG
22801  GCGTGGAGCA AGCGGTGCAG GCGATCGCGG CGGGGTTCGC GGCGCGCGGC GTGCGCACCA
22861  AGCGGCTGCA TGTCTCGCAC GCATCCCACT CGCCGCTGAT GGAACCGATG CTGGAGGAGT
22921  TCGGGCGGGT GGCGGCGTCG GTGACGTACC GGCGGCCAAG CGTTTCGCTG GTGAGCAACC
22981  TGAGCGGGAA GGTGGTCACG GACGAGCTGA GCGCGCCGGG CTACTGGGTG CGGCACGTGC
23041  GGGAGGCGGT GCGCTTCGCG GACGGGGTGA AGGCGCTGCA CGAAGCCGGC GCGGGGACGT
23101  TCCTCGAAGT GGGCCCGAAG CCGACGCTGC TCGGCCTGTT GCCAGCTTGC CTGCCGGAGG
23161  CGGAGCCGAC GCTGCTGGCG TCGTTGCGCG CCGGGCGCGA GGAGGCTGCG GGGGTGCTCG
23221  AGGCGCTGGG CAGGCTGTGG GCCGCCGGCG GCTCGGTCAG CTGGCCGGGC GTCTTCCCCA
23281  CGGCTGGGCG GCGGGTGCCG CTGCCGACCT ATCCGTGGCA GCGGCAGCGG TACTGGCCCG
23341  ACATCGAGCC TGACAGCCGT CGCCACGCAG CCGCGGATCC GACCCAAGGC TGGTTCTATC
23401  GCGTGGACTG GCCGGAGATA CCTCGCAGCC TCCAGAAATC AGAGGAGGCG AGCCGCGGGA
23461  GCTGGCTGGT ATTGGCGGAT AAGGGTGGAG TCGGCGAGGC GGTCGCTGCA GCGCTGTCGA
23521  CACGTGGACT TCCATGCGTC GTGCTCCATG CGCCGGCAGA GACATCCGCG ACCGCCGAGC
23581  TGGTGACCGA GGCTGCCGGC GGTCGAAGCG ATTGGCAGGT AGTGCTCTAC CTGTGGGGTC
23641  TGGACGCCGT CGTCGGCGCG GAGGCGTCGA TCGATGAGAT CGGCGACGCG ACCCGTCGTG
```

```
23701  CTACCGCGCC GGTGCTCGGC TTGGCTCGGT TTCTGAGCAC CGTGTCTTGT TCGCCCCGAC
23761  TCTGGGTCGT GACCCGGGGG GCATGCATCG TTGGCGACGA GCCTGCGATC GCCCCTTGTC
23821  AGGCGGCGTT ATGGGGCATG GGCCGGGTGG CGGCGCTCGA GCATCCCGGG GCCTGGGGCG
23881  GGCTCGTGGA CCTGGATCCC CGAGCGAGCC CGCCCCAAGC CAGCCCGATC GACGGCGAGA
23941  TGCTCGTCAC CGAGCTATTG TCGCAGGAGA CCGAGGACCA GCTCGCCTTC CGCCATGGGC
24001  GCCGGCACGC GGCACGGCTG GTGGCCGCCC CGCCACGGGG GAAGCGGCA CCGGCGTCGC
24061  TGTCTGCGGA GGCGAGCTAC CTGGTGACGG GAGGCCTCGG TGGGCTGGGC CTGATCGTGG
24121  CCCAGTGGCT GGTGGAGCTG GGAGCGCGGC ACTTGGTGCT GACCAGCCGG CGCGGGTTGC
24181  CCGACCGGCA GGCGTGGCGC GAGCAGCAGC CGCCTGAGAT CCGCGCGCGG ATCGCAGCGG
24241  TCGAGGCGCT GGAGGCGCGG GGTGCACGGG TGACCGTGGC AGCGGTGGAC GTGGCCGACG
24301  TCGAACCGAT GACAGCGCTG GTTTCGTCGG TCGAGCCCCC GCTGCGAGGG GTGGTGCACG
24361  CCGCTGGCGT CAGCGTCATG CGTCCACTGG CGGAGACGGA CGAGACCCTG CTCGAGTCGG
24421  TGCTCCGTCC CAAGGTGGCC GGGAGCTGGC TGCTGCACCG GCTGCTGCAC GGCCGGCCTC
24481  TCGACCTGTT CGTGCTGTTC TCGTCGGGCG CAGCGGTGTG GGGTAGCCAT AGCCAGGGTG
24541  CGTACGCGGC GGCCAACGCT TTCCTCGACG GGCTCGCGCA TCTTCGGCGT TCGCAATCGC
24601  TGCCTGCGTT GAGCGTCGCG TGGGGTCTGT GGGCCGAGGG AGGCATGGCG GACGCGGAGG
24661  CTCATGCACG TCTGAGCGAC ATCGGGGTTC TGCCCATGTC GACGTCGGCA GCGTTGTCGG
24721  CGCTCCAGCG CCTGGTGGAG ACCGGCGCGG CTCAGCGCAC GGTGACCCGG ATGGACTGGG
24781  CGCGCTTCGC GCCGGTGTAC ACCGCTCGAG GGCGTCGCAA CCTGCTTTCG GCGCTGGTCG
24841  CAGGGCGCGA CATCATCGCG CCTTCCCCTC CGGCGGCAGC AACCCGGAAC TGGCGTGGCC
24901  TGTCCGTTGC GGAAGCCCGC ATGGCTCTGC ACGAGGTCGT CCATGGGGCC GTCGCTCGGG
24961  TGCTGGGCTT CCTCGACCCG AGCGCGCTCG ATCCTGGGAT GGGGTTCAAT GAGCAGGGCC
25021  TCGACTCGTT GATGGCGGTG GAGATCCGCA ACCTCCTTCA GGCTGAGCTG GACGTGCGGC
25081  TTTCGACGAC GCTGGCCTTT GATCATCCGA CGGTACAGCG GCTGGTGGAG CATCTGCTCG
25141  TCGATGTACT GAAGCTGGAG GATCGCAGCG ACACCCAGCA TGTTCGGTCG TTGGCGTCAG
25201  ACGAGCCCAT CGCCATCGTG GGAGCCGCCT GCCGCTTCCC GGGCGGGGTG GAGGACCTGG
25261  AGTCCTACTG GCAGCTGTTG GCCGAGGGCG TGGTGGTCAG CGCCGAGGTG CCGGCCGACC
25321  GGTGGGATGC GGCGGACTGG TACGACCCTG ATCCGGAGAT CCCAGGCCGG ACTTACGTGA
25381  CCAAAGGCGC CTTCCTGCGC GATTTGCAGA GATTGGATGC GACCTTCTTC CGCATCTCGC
25441  CTCGCGAGGC GATGAGCCTC GACCCGCAGC AGCGGTTGCT CCTGGAGGTA AGCTGGGAGG
25501  CGCTCGAGAG CGCGGGTATC GCTCCGGATA CGCTGCGAGA TAGCCCCACC GGGGTGTTCG
25561  TGGGTGCGGG GCCCAATGAG TACTACACGC AGCGGCTGCG AGGCTTCACC GACGGAGCGG
25621  CAGGGCTGTA CGGCGGCACC GGGAACATGC TCAGCGTTGC GGCTGGACGG CTGTCGTTTT
25681  TCCTGGGTCT GCACGGCCCG ACGCTGGCCA TGGATACGGC GTGCTCGTCC TCCCTGGTCG
25741  CGCTGCACCT CGCCTGCCAG AGCCTGCGAC TGGGCGAGTG CGATCAAGCG CTGGTTGGCG
25801  GGGTCAACGT GCTGCTCGCG CCGGAGACCT TCGTGCTGCT CTCACGGATG CGCGCGCTTT
25861  CGCCCGACGG GCGGTGCAAG ACGTTCTCGG CCGACGCGGA CGGCTACGCG CGGGGCGAGG
25921  GGTGCGCCGT GGTGGTGCTC AAGCGGCTGC GCGATGCGCA GCGCGCCGGC GACTCCATCC
25981  TGGCGCTGAT CCGGGGAAGC GCGGTGAACC ACGACGGCCC GAGCAGCGGG CTGACCGTGC
26041  CCAACGGACC CGCCCAGCAA GCATTGCTGC GCCAGGCGCT TTCGCAAGCA GGCGTGTCTC
```

-continued

```
26101 CGGTCGACGT TGATTTTGTG GAGTGTCACG GGACAGGGAC GGCGCTGGGC GACCCGATCG

26161 AGGTGCAGGC GCTGAGCGAG GTGTATGGTC CAGGGCGCTC CGAGGATCGA CCGCTGGTGC

26221 TGGGGGCCGT CAAGGCCAAC GTCGCGCATC TGGAGGCGGC ATCCGGCTTG CCAGCCTGC

26281 TCAAGGCCGT GCTTGCGCTG CGGCACGAGC AGATCCCGGC CCAGCCGGAG CTGGGGGAGC

26341 TCAACCCGCA CTTGCCGTGG AACACGCTGC CGGTGGCGGT GCCACGTAAG GCGGTGCCGT

26401 GGGGGCGCGG CGCACGGCCG CGTCGGGCCG GCGTGAGCGC GTTCGGGTTG AGCGGAACCA

26461 ACGTGCATGT CGTGCTGGAG GAGGCACCGG AGGTGGAGCT GGTGCCCGCG GCGCCGGCGC

26521 GACCGGTGGA GCTGGTTGTG CTATCGGCCA AGAGCGCGGC GGCGCTGGAC GCCGCGGCGG

26581 AACGGCTCTC GGCGCACCTG TCCGCGCACC CGGAGCTGAG CCTCGGCGAC GTGGCGTTCA

26641 GCCTGGCGAC GACGCGCAGC CCGATGGAGC ACCGGCTCGC CATCGCGACG ACCTCGCGCG

26701 AGGCCCTGCG AGGCGCGCTG GACGCCGCGG CGCAGCGGCA GACGCCGCAG GGCGCGGTGC

26761 GCGGCAAGGC CGTGTCCTCA CGCGGTAAGT TGGCTTTCCT GTTCACCGGA CAGGGCGCGC

26821 AAATGCCGGG CATGGGCCGT GGGCTGTACG AGGCGTGGCC AGCGTTCCGG GAGGCGTTCG

26881 ACCGGTGCGT GGCGCTCTTC GATCGGGAGC TCGACCAGCC TCTGCGCGAG GTGATGTGGG

26941 CTGCGCCGGG CCTCGCTCAG GCGGCGCGGC TCGATCAGAC CGCGTACGCG CAGCCGGCTC

27001 TCTTTGCGCT GGAGTACGCG CTGGCTGCCC TGTGGCGTTC GTGGGCGTG GAGCCGCACG

27061 TACTCCTCGG TCATAGCATC GGCGAGCTGG TCGCCGCCTG CGTGGCGGGC GTGTTCTCGC

27121 TCGAAGACGC GGTGAGGTTG GTGGCCGCGC GCGGGCGGCT GATGCAGGCG CTGCCCGCCG

27181 GCGGTGCCAT GGTCGCCATC GCAGCGTCCG AGGCCGAGGT GGCCGCCTCC GTGGCACCCC

27241 ACGCCGCCAC GGTGTCGATC GCCGCGGTCA ACGGTCCTGA CGCCGTCGTG ATCGCTGGCG

27301 CCGAGGTACA GGTGCTCGCC CTCGGCGCGA CGTTCGCGGC GCGTGGGATA CGCACGAAGA

27361 GGCTCGCCGT CTCCCATGCG TTCCACTCGC CGCTCATGGA TCCGATGCTG GAAGACTTCC

27421 AGCGGGTCGC TGCGACGATC GCGTACCGCG CGCCAGACCG CCCGGTGGTG TCGAATGTCA

27481 CCGGCCACGT CGCAGGCCCC GAGATCGCCA CGCCCGAGTA TTGGGTCCGG CATGTGCGAA

27541 GCGCCGTGCG CTTCGGCGAT GGGGCAAAGG CGTTGCATGC CGCGGGTGCC GCCACGTTCG

27601 TCGAGATTGG CCCGAAGCCG GTCCTGCTCG GGCTATTGCC AGCGTGCCTC GGGGAAGCGG

27661 ACGCGGTCCT CGTGCCGTCG CTACGCGCGG ACCGCTCGGA ATGCGAGGTG GTCCTCGCGG

27721 CGCTCGGGAC TTGGTATGCC TGGGGGGGTG CGCTCGACTG GAAGGGCGTG TTCCCCGATG

27781 GCGCGCGCCG CGTGGCTCTG CCCATGTATC CATGGCAGCG TGAGCGCCAT TGGATGGACC

27841 TCACCCCGCG AAGCGCCGCG CCTGCAGGGA TCGCAGGTCG CTGGCCGCTG GCTGGTGTCG

27901 GGCTCTGCAT GCCCGGCGCT GTGTTGCACC ACGTGCTCTC GATCGGACCA CGCCATCAGC

27961 CCTTCCTCGG TGATCACCTC GTGTTTGGCA AGGTGGTGGT GCCCGGCGCC TTTCATGTCG

28021 CGGTGATCCT CAGCATCGCC GCCGAGCGCT GGCCCGAGCG GGCGATCGAG CTGACAGGCG

28081 TGGAGTTCCT GAAGGCGATC GCGATGGAGC CCGACCAGGA GGTCGAGCTC CACGCCGTGC

28141 TCACCCCCGA AGCCGCCGGG GATGGCTACC TGTTCGAGCT GGCGACCCTG GCGGCGCCGG

28201 AGACCGAACG CCGATGGACG ACCCACGCCC GCGGTCGGGT GCAGCCGACA GACGGCGCGC

28261 CCGGCGCGTT GCCGCGCCTC GAGGTGCTGG AGGACCGCGC GATCCAGCCC CTCGACTTCG

28321 CCGGATTCCT CGACAGGTTA TCGGCGGTGC GGATCGGCTG GGGTCCGCTT TGGCGATGGC

28381 TGCAGGACGG GCGCGTCGGC GACGAGGCCT CGCTTGCCAC CCTCGTGCCG ACCTATCCGA

28441 ACGCCCACGA CGTGGCGCCC TTGCACCCGA TCCTGCTGGA CAACGGCTTT GCGGTGAGCC
```

```
                          -continued
28501   TGCTGGCAAC CCGGAGCGAG CCGGAGGACG ACGGGACGCC CCCGCTGCCG TTCGCCGTGG

28561   AACGGGTGCG GTGGTGGCGG GCGCCGGTTG GAAGGGTGCG GTGTGGCGGC GTGCCGCGGT

28621   CGCAGGCATT CGGTGTCTCG AGCTTCGTGC TGGTCGACGA AACTGGCGAG GTGGTCGCTG

28681   AGGTGGAGGG ATTTGTTTGC CGCCGGGCGC CGCGAGAGGT GTTCCTGCGG CAGGAGTCGG

28741   GCGCGTCGAC TGCAGCCTTG TACCGCCTCG ACTGGCCCGA AGCCCCCTTG CCCGATGCGC

28801   CTGCGGAACG GATGGAGGAG AGCTGGGTCG TGGTGGCAGC ACCTGGCTCG GAGATGGCCG

28861   CGGCGCTCGC AACACGGCTC AACCGCTGCG TACTCGCCGA ACCCAAAGGC CTCGAGGCGG

28921   CCCTCGCGGG GGTGTCTCCC GCAGGTGTGA TCTGCCTCTG GAACCTGGA GCCCACGAGG

28981   AAGCTCCGGC GGCGGCGCAG CGTGTGGCGA CCGAGGGCCT TTCGGTGGTG CAGGCGCTCA

29041   GGGATCGCGC GGTGCGCCTG TGGTGGGTGA CCACGGGCGC CGTGGCTGTC GAGGCCGGTG

29101   AGCGGGTGCA GGTCGCCACA GCGCCGGTAT GGGGCCTGGG CCGGACAGTG ATGCAGGAGC

29161   GCCCGGAGCT CAGCTGCACT CTGGTGGATT TGGAGCCGGA GGTCGATGCC GCGCGTTCAG

29221   CTGACGTTCT GCTGCGGGAG CTCGGTCGCG CTGACGACGA GACCCAGGTG GTTTTCCGTT

29281   CCGGAGAGCG CCGCGTAGCG CGGCTGGTCA AAGCGACAAC CCCCGAAGGG CTCTTGGTCC

29341   CTGACGCAGA ATCCTATCGA CTGGAGGCTG GGCAGAAGGG CACATTGGAC CAGCTCCGCC

29401   TCGCGCCGGC ACAGCGCCGG GCACCCGGCC CGGGCGAGGT CGAGATCAAG GTAACCGCCT

29461   CGGGGCTCAA CTTCCGGACC GTCCTCGCTG TGCTGGGAAT GTATCCGGGC GACGCTGGGC

29521   CGATGGGCGG AGATTGTGCC GGTATCGTCA CGGCGGTGGG CCAGGGGGTG CACCACCTCT

29581   CGGTCGGCGA TGCTGTCATG ACGCTGGGGA CGTTGCATCG ATTCGTCACG GTCGACGCGC

29641   GGCTGGTGGT CCGGCAGCCT GCAGGGCTGA CTCCCGCGCA GGCAGCTACG GTGCCGGTTG

29701   CGTTCCTGAC GGCCTGGCTC GCTCTGCACG ACCTGGGGAA TCTGCGGCGC GGCGAGCGGG

29761   TGCTGATCCA TGCTGCGGCC GGCGGCGTGG GCATGGCCGC GGTGCAAATC GCCCGATGGA

29821   TAGGGGCCGA GGTGTTCGCC ACGGCGAGCC CGTCCAAGTG GGCAGCGGTT CAGGCCATGG

29881   GCGTGCCGCG CACGCACATC GCCAGCTCGC GGACGCTGGA GTTTGCTGAG ACGTTCCGGC

29941   AGGTCACCGG CGGCCGGGGC GTGGACGTGG TGCTCAACGC GCTGGCCGGC GAGTTCGTGG

30001   ACGCGAGCCT GTCCCTGCTG ACGACGGGCG GCGGTTCCT CGAGATGGGC AAGACCGACA

30061   TACGGGATCG AGCCGCGGTC GCGGCGGCGC ATCCCGGTGT TCGCTATCGG GTATTCGACA

30121   TCCTGGAGCT CGCTCCGGAT CGAACTCGAG AGATCCTCGA GCGCGTGGTC GAGGGCTTTG

30181   CTGCGGGACA TCTGCGCGCA TTGCCGGTGC ATGCGTTCGC GATCACCAAG GCCGAGGCAG

30241   CGTTTCGGTT CATGGCGCAA GCGCGGCATC AGGGCAAGGT CGTGCTGCTG CCGGCGCCCT

30301   CCGCAGCGCC CTTGGCGCCG ACGGGCACCG TACTGCTGAC CGGTGGGCTG GGAGCGTTGG

30361   GGCTCCACGT GGCCCGCTGG CTCGCCCAGC AGGGCGCGCC GCACATGGTG CTCACAGGTC

30421   GGCGGGGCCT GGATACGCCG GGCGCTGCCA AAGCCGTCGC GGAGATCGAA GCGCTCGGCG

30481   CTCGGGTGAC GATCGCGGCG TCGGATGTCG CCGATCGGAA CGCGCTGGAG GCTGTGCTCC

30541   AGGCCATTCC GGCGGAGTGG CCGTTACAGG GCGTGATCCA TGCAGCCGGA GCGCTCGATG

30601   ATGGTGTGCT TGATGAGCAG ACCACCGACC GCTTCTCGCG GGTGCTGGCA CCGAAGGTGA

30661   CTGGCGCCTG GAATCTGCAT GAGCTCACGG CGGGCAACGA TCTCGCTTTC TTCGTGCTGT

30721   TCTCCTCCAT GTCGGGGCTC TTGGGCTCGG CCGGGCAGTC CAACTATGCG GCGGCCAACA

30781   CCTTCCTCGA CGCGCTGGCC GCGCATCGGC GGGCCGAAGG CCTGGCGGCG CAGAGCCTCG

30841   CGTGGGGCCC ATGGTCGGAC GGAGGCATGG CAGCGGGGCT CAGCGCGGCG CTGCAGGCGC
```

-continued

```
30901 GGCTCGCTCG GCATGGGATG GGAGCGCTGT CGCCCGCTCA GGGCACCGCG CTGCTCGGGC

30961 AGGCGCTGGC TCGGCCGGAA ACGCAGCTCG GGGCGATGTC GCTCGACGTG CGTGCGGCAA

31021 GCCAAGCTTC GGGAGCGGCA GTGCCGCCTG TGTGGCGCGC GCTGGTGCGC GCGGAGGCGC

31081 GCCATGCGGC GGCTGGGGCG CAGGGGGCAT TGGCCGCGCG CCTTGGGGCG CTGCCCGAGG

31141 CGCGTCGCGC CGACGAGGTG CGCAAGGTCG TGCAGGCCGA GATCGCGCGC GTGCTTTCAT

31201 GGGGCGCCGC GAGCGCCGTG CCCGTCGATC GGCCGCTGTC GGACTTGGGC CTCGACTCGC

31261 TCACGGCGGT GGAGCTGCGC AACGTGCTCG GCCAGCGGGT GGGTGCGACG CTGCCGGCGA

31321 CGCTGGCATT CGATCACCCG ACGGTCGACG CGCTCACGCG CTGGCTGCTC GATAAGGTCC

31381 TGGCCGTGGC CGAGCCGAGC GTATCGCCCG CAAAGTCGTC GCCGCAGGTC GCCCTCGACG

31441 AGCCCATTGC GGTGATCGGC ATCGGCTGCC GTTTCCCAGG CGGCGTGACC GATCCGGAGT

31501 CGTTTTGGCG GCTGCTCGAA GAGGGCAGCG ATGCCGTCGT CGAGGTGCCG CATGAGCGAT

31561 GGGACATCGA CGCGTTCTAT GATCCGGATC CGGATGTGCG CGGCAAGATG ACGACACGCT

31621 TTGGCGGCTT CCTGTCCGAT ATCGACCGGT TCGAGCCGGC CTTCTTCGGC ATCTCGCCGC

31681 GCGAAGCGAC GACCATGGAT CCGCAGCAGC GGCTGCTCCT GGAGACGAGC TGGGAGGCGT

31741 TCGAGCGCGC CGGGATTTTG CCCGAGCGGC TGATGGGCAG CGATACCGGC GTGTTCGTGG

31801 GGCTCTTGTA CCAGGAGTAC GCTGCGCTCG CCGGCGGCAT CGAGGCGTTC GATGGCTATC

31861 TAGGCACCGG CACCACGGCC AGCGTCGCCT CGGGCAGGAT CTCTTATGTG CTCGGGCTAA

31921 AGGGGCCGAG CCTGACGGTG GACACCGCGT GCTCCTCGTC GCTGGTCGCG GTGCACCTGG

31981 CCTGCCAGGC GCTGCGGCGG GGCGAGTGTT CGGTGGCGCT GGCCGGCGGC GTGGCGCTGA

32041 TGCTCACGCC GGCGACGTTC GTGGAGTTCA GCCGGCTGCG AGGCCTGGCT CCCGACGGAC

32101 GGTGCAAGAG CTTCTCGGCC GCAGCCGACG GCGTGGGGTG GAGCGAAGGC TGCGCCATGC

32161 TCCTGCTCAA ACCGCTTCGC GATGCTCAGC GCGATGGGGA TCCGATCCTG GCGGTGATCC

32221 GCGGCACCGC GGTGAACCAG GATGGGCGCA GCAACGGGCT GACGGCGCCC AACGGGTCGT

32281 CGCAGCAAGA GGTGATCCGT CGGGCCCTGG AGCAGGCGGG GCTGGCTCCG GCGGACGTCA

32341 GCTACGTCGA GTGCCACGGC ACCGGCACGA CGTTGGGCGA CCCCATCGAA GTGCAGGCCC

32401 TGGGCGCCGT GCTGGCACAG GGGCGACCCT CGGACCGGCC GCTCGTGATC GGGTCGGTGA

32461 AGTCCAATAT CGGACATACG CAGGCTGCGG CGGGCGTGGC CGGTGTCATC AAGGTGGCGC

32521 TGGCGCTCGA GCGCGGGCTT ATCCCGAGGA GCCTGCATTT CGACGCGCCC AATCCGCACA

32581 TTCCGTGGTC GGAGCTCGCC GTGCAGGTGG CCGCCAAACC CGTCGAATGG ACGAGAAACG

32641 GCGCGCCGCG ACGAGCCGGG GTGAGCTCGT TGGCGTCAG CGGGACCAAC GCGCACGTGG

32701 TGCTGGAGGA GGCGCCAGCG GCGGCGTTCG CGCCCGCGGC GGCGCGTTCA GCGGAGCTTT

32761 TCGTGCTGTC GGCGAAGAGC GCCGCGGCGC TGGACGCGCA GGCGGCGCGG CTTTCGGCGC

32821 ATGTCGTTGC GCACCCGGAG CTCGGCCTCG GCGACCTGGC GTTCAGCCTG GCGACGACCC

32881 GCAGCCCGAT GACGTACCGG CTCGCGGTGG CGGCGACCTC GCGCGAGGCG CTGTCTGCGG

32941 CGCTCGACAC AGCGGCGCAG GGGCAGGCGC CGCCCGCAGC GGCTCGCGGC CACGCTTCCA

33001 CAGGCAGCGC CCCAAAGGTG GTTTTCGTCT TTCCTGGCCA GGGCTCCCAG TGGCTGGGCA

33061 TGGGCCAAAA GCTCCTCTCG GAGGAGCCCG TCTTCCGCGA CGCGCTCTCG GCGTGTGACC

33121 GAGCGATTCA GGCCGAAGCC GGCTGGTCGC TGCTCGCCGA GCTCGCGGCC GATGAGACCA

33181 CCTCGCAGCT CGGCCGCATC GACGTGGTGC AGCCGGCGCT GTTCGCGATC GAGGTCGCGC

33241 TGTCGGCGCT GTGGCGGTCG TGGGGCGTCG AGCCGGATGC AGTGGTAGGC CACAGCATGG
```

-continued

```
33301  GCGAAGTGGC GGCCGCGCAC GTCGCCGGCG CCCTGTCGCT CGAGGATGCT GTAGCGATCA
33361  TCTGCCGGCG CAGCCTGCTG CTGCGGCGGA TCAGCGGCCA AGGCGAGATG GCGGTCGTCG
33421  AGCTCTCCCT GGCCGAGGCC GAGGCAGCGC TCCTGGGCTA CGAAGATCGG CTCAGCGTGG
33481  CGGTGAGCAA CAGCCCGCGA TCGACGGTGC TGGCGGGCGA GCCGGCAGCG CTCGCAGAGG
33541  TGCTGGCGAT CCTTGCGGCA AAGGGGGTGT TCTGCCGTCG AGTCAAGGTG GACGTCGCCA
33601  GCCACAGCCC ACAGATCGAC CCGCTGCGCG ACGAGCTATT GGCAGCATTG GGCGAGCTCG
33661  AGCCGCGACA AGCGACCGTG TCGATGCGCT CGACGGTGAC GAGCACGATC GTGGCGGGCC
33721  CGGAGCTCGT GGCGAGCTAC TGGGCGGACA ACGTTCGACA GCCGGTGCGC TTCGCCGAAG
33781  CGGTGCAATC GTTGATGGAA GGCGGTCATG GGCTGTTCGT GGAGATGAGC CCGCATCCGA
33841  TCCTGACGAC GTCGGTCGAG GAGATCCGAC GGGCGACGAA GCGGGAGGGA GTCGCGGTGG
33901  GCTCGTTGCG GCGTGGACAG GACGAGCGCC TGTCCATGTT GGAGGCGCTG GGAGCGCTCT
33961  GGGTACACGG CCAGGCGGTG GGCTGGGAGC GGCTGTTCTC CGCGGGCGGC GCGGGCCTCC
34021  GTCGCGTGCC GCTGCCGACC TATCCCTGGC AGCGCGAGCG GTACTGGGTC GAAGCGCCGA
34081  CCGGCGGCGC GGCGAGCGGC AGCCGCTTTG CTCATGCGGG CAGTCACCCG CTCCTGGGTG
34141  AAATGCAGAC CCTGTCGACC CAGAGGAGCA CGCGCGTGTG GGAGACGACG CTGGATCTCA
34201  AACGGCTGCC GTGGCTCGGC GATCACCGGG TGCAGGGGGC GGTCGTGTTC CCGGGCGCGG
34261  CGTACCTGGA GATGGCGCTT TCGTCTGGGG CCGAGGCCTT GGGTGACGGT CCGCTCCAGG
34321  TCAGCGATGT GGTGCTCGCC GAGGCGCTGG CCTTCGCGGA TGATACGCCG GTGGCGGTGC
34381  AGGTCATGGC GACCGAGGAG CGACCAGGCC GCCTGCAATT CCACGTTGCG AGCCGGGTGC
34441  CGGGCCACGG CCGTGCTGCC TTTCGAAGCC ATGCCCGCGG GGTGCTGCGC CAGACCGAGC
34501  GCGCCGAGGT CCCGGCGAGG CTGGATCTGG CCGCGCTTCG TGCCCGGCTT CAGGCCAGCG
34561  CACCCGCTGC GGCTACCTAT GCGGCGCTGG CCGAGATGGG GCTCGAGTAC GGCCCAGCGT
34621  TCCAGGGGCT TGTCGAGCTG TGGCGGGGGG AGGGCGAGGC GCTGGGACGT GTGCGGCTCC
34681  CCGAGGCCGC CGGCTCCCCA GCCGCGTGCC GGCTCCACCC CGCGCTCTTG GATGCGTGCT
34741  TCCACGTGAG CAGCGCCTTC GCTGACCGCG GCGAGGCGAC GCCATGGGTA CCCGTCGAAA
34801  TCGGCTCGCT GCGGTGGTTC CAGCGGCCGT CGGGGGAGCT GTGGTGTCAT GCGCGGAGCG
34861  TGAGCCACGG AAAGCCAACA CCCGATCGGC GGAGTACCGA CTTTTGGGTG GTCGACAGCA
34921  CGGGCGCGAT CGTCGCCGAG ATCTCCGGGC TCGTGGCGCA GCGGCTCGCG GGAGGTGTAC
34981  GCCGGCGCGA AGAAGACGAC TGGTTCATGG AGCCGGCTTG GGAACCGACC GCGGTCCCCG
35041  GATCCGAGGT CACGGCGGGC CGGTGGCTGC TCATCGGCTC GGGCGGCGGG CTCGGCGCTG
35101  CGCTCTACTC GGCGCTGACG GAAGCTGGCC ATTCCGTCGT CCACGCGACA GGGCACGGCA
35161  CGAGCGCCGC CGGGTTGCAG GCACTCCTGA CGGCGTCCTT CGACGGCCAG GCCCCGACGT
35221  CGGTGGTGCA CCTCGGCAGC CTCGATGAGC GTGGCGTGCT CGACGCGGAT GCCCCCTTCG
35281  ACGCCGATGC CCTCGAGGAG TCGCTGGTGC GCGGCTGCGA CAGCGTGCTC TGGACCGTGC
35341  AGGCCGTGGC CGGGGCGGGC TTCCGAGATC CTCCGCGGTT GTGGCTCGTG ACACGCGGCG
35401  CTCAGGCCAT CGGCGCCGGC GACGTCTCCG TGGCGCAAGC GCCGCTCCTG GGGCTGGGCC
35461  GCGTTATCGC CTTGGAGCAC GCCGAGCTGC GCTGCGCTCG GATCGACCTC GATCCAGCGC
35521  GGCGCGACGG AGAGGTCGAT GAGCTGCTTG CCGAGCTGTT GGCCGACGAC GCCGAGGAGG
35581  AAGTCGCGTT TCGCGGCGGT GAGCGGCGCG TGGCCCGGCT CGTCCGAAGG CTGCCCGAGA
35641  CCGACTGCCG AGAGAAAATC GAGCCCGCGG AAGGCCGGCC GTTCCGGCTG GAGATCGATG
```

```
35701 GGTCCGGCGT GCTCGACGAC CTGGTGCTCC GAGCCACGGA GCGGCGCCCT CCTGGCCCGG

35761 GCGAGGTCGA GATCGCCGTC GAGGCGGCGG GGCTCAACTT TCTCGACGTG ATGAGGGCCA

35821 TGGGGATCTA CCCTGGGCCC GGGGACGGTC CGGTTGCGCT GGGCGCCGAG TGCTCCGGCC

35881 GAATTGTCGC GATGGGCGAA GGTGTCGAGA GCCTTCGTAT CGGCCAGGAC GTCGTGGCCG

35941 TCGCGCCCTT CAGTTTCGGC ACCCACGTCA CCATCGACGC CCGGATGGTC GCACCTCGCC

36001 CCGCGGCGCT GACGGCCGCG CAGGCAGCCG CGCTGCCCGT CGCATTCATG ACGGCCTGGT

36061 ACGGTCTCGT CCATCTGGGG AGGCTCCGGG CCGGCGAGCG CGTGCTCATC CACTCGGCGA

36121 CGGGGGGCAC CGGGCTCGCT GCTGTGCAGA TCGCCCGCCA CCTCGGCGCG GAGATATTTG

36181 CGACCGCTGG TACGCCGGAG AAGCGGGCGT GGCTGCGCGA GCAGGGGATC GCGCACGTGA

36241 TGGACTCGCG GTCGCTGGAC TTCGCCGAGC AAGTGCTGGC CGCGACGAAG GGCGAGGGGG

36301 TCGACGTCGT GTTGAACTCG CTGTCTGGCG CCGCGATCGA CGCGAGCCTT GCGACCCTCG

36361 TGCCGGACGG CCGCTTCATC GAGCTCGGCA AGACGGACAT CTATGCAGAT CGCTCGCTGG

36421 GGCTCGCTCA CTTTAGGAAG AGCCTGTCCT ACAGCGCCGT CGATCTTGCG GGTTTGGCCG

36481 TGCGTCGGCC CGAGCGCGTC GCAGCGCTGC TGGCGGAGGT GGTGGACCTG CTCGCACGGG

36541 GAGCGCTGCA GCCGCTTCCG GTAGAGATCT TCCCCCTCTC GCGGGCCGCG GACGCGTTCC

36601 GGAAAATGGC GCAAGCGCAG CATCTCGGGA AGCTCGTGCT CGCGCTGGAG GACCCGGACG

36661 TGCGGATCCG CGTTCCGGGC GAATCCGGCG TCGCCATCCG CGCGGACGGC ACCTACCTCG

36721 TGACCGGCGG TCTGGGTGGG CTCGGTCTGA GCGTGGCTGG ATGGCTGGCC GAGCAGGGGG

36781 CTGGGCATCT GGTGCTGGTG GGCCGCTCCG GTGCGGTGAG CGCGGAGCAG CAGACGGCTG

36841 TCGCCGCGCT CGAGGCGCAC GGCGCGCGTG TCACGGTAGC GAGGGCAGAC GTCGCCGATC

36901 GGGCGCAGAT CGAGCGGATC CTCCGCGAGG TTACCGCGTC GGGGATGCCG CTCCGCGGCG

36961 TCGTTCATGC GGCCGGTATC CTGGACGACG GCTGCTGATG CAGCAAACC CCCGCGCGGT

37021 TCCGCGCGGT CATGGCGCCC AAGGTCCGAG GGGCCTTGCA CCTGCATGCG TTGACACGCG

37081 AAGCGCCGCT CTCCTTCTTC GTGCTGTACG CTTCGGGAGC AGGGCTCTTG GGCTCGCCGG

37141 GCCAGGGCAA CTACGCCGCG GCCAACACGT TCCTCGACGC TCTGGCACAC CACCGGAGGG

37201 CGCAGGGGCT GCCAGCATTG AGCATCGACT GGGGCCTGTT CGCGGACGTG GGTTTGGCCG

37261 CCGGGCAGCA AAATCGCGGC GCACGGCTGG TCACCCGCGG GACGCGGAGC CTCACCCCCG

37321 ACGAAGGGCT GTGGGCGCTC GAGCGTCTGC TCGACGGCGA TCGCACCCAG GCCGGGGTCA

37381 TGCCGTTCGA CGTGCGGCAG TGGGTGGAGT TCTACCCGGC GGCGGCATCT TCGCGGAGGT

37441 TGTCGCGGCT GGTGACGGCA CGGCGCGTGG CTTCCGGTCG GCTCGCCGGG GATCGGGACC

37501 TGCTCGAACG GCTCGCCACC GCCGAGGCGG GCGCGCGGGC AGGAATGCTG CAGGAGGTCG

37561 TGCGCGCGCA GGTCTCGCAG GTGCTGCGCC TCCCCGAAGG CAAGCTCGAC GTGGATGCGC

37621 CGCTCACGAG CCTGGGAATG GACTCGCTGA TGGGGCTAGA GCTGCGCAAC CGCATCGAGG

37681 CCGTGCTCGG CATCACCATG CCGGCGACCC TGCTGTGGAC CTACCCCACG GTGGCAGCGC

37741 TGAGTGCGCA TCTGGCTTCT CATGTCGTCT CTACGGGGGA TGGGGAATCC GCGCGCCCGC

37801 CGGATACAGG GAACGTGGCT CCAATGACCC ACGAAGTCGC TTCGCTCGAC GAAGACGGGT

37861 TGTTCGCGTT GATTGATGAG TCACTCGCGC GTGCGGGAAA GAGGTGATTG CGTGACAGAC

37921 CGAGAAGGCC AGCTCCTGGA GCGCTTGCGT GAGGTTACTC TGGCCCTTCG CAAGACGCTG

37981 AACGAGCGCG ATACCCTGGA GCTCGAGAAG ACCGAGCCGA TCGCCATCGT GGGGATCGGC

38041 TGCCGCTTCC CCGGCGGAGC GGGCACTCCG GAGGCGTTCT GGGAGCTGCT CGACGACGGG
```

```
                      -continued
38101  CGCGACGCGA TCCGGCCGCT CGAGGAGCGC TGGGCGCTCG TAGGTGTCGA CCCAGGCGAC

38161  GACGTACCGC GCTGGGCGGG GCTGCTCACC GAAGCCATCG ACGGCTTCGA CGCCGCGTTC

38221  TTCGGTATCG CCCCCCGGGA GGCACGGTCG CTCGACCCGC AGCATCGCTT GCTGCTGGAG

38281  GTCGCCTGGG AGGGGTTCGA AGACGCCGGC ATCCCGCCTA GGTCCCTCGT CGGGAGCCGC

38341  ACCGGCGTGT TCGTCGGCGT CTGCGCCACG GAGTATCTCC ACGCCGCCGT CGCGCACCAG

38401  CCGCGCGAAG AGCGGGACGC GTACAGCACC ACCGGCAACA TGCTCAGCAT CGCCGCCGGA

38461  CGGCTATCGT ACACGCTGGG GCTGCAGGGA CCTTGCCTGA CCGTCGACAC GGCGTGCTCG

38521  TCATCGCTGG TGGCCATTCA CCTCGCCTGC CGCAGCCTGC GCGCTCGAGA GAGCGATCTC

38581  GCGCTGGCGG GAGGGGTCAA CATGCTTCTC TCCCCCGACA CGATGCGAGC TCTGGCGCGC

38641  ACCCAGGCGC TGTCGCCCAA TGGCCGTTGC AGACCTTCG ACGCGTCGGC CAACGGGTTC

38701  GTCCGTGGGG AGGGCTGCGG TCTGATCGTG CTCAAGCGAT TGAGCGACGC GCGGCGGGAT

38761  GGGGACCGGA TCTGGGCGCT GATCCGAGGA TCGGCCATCA ATCAGGACGG CCGGTCGACG

38821  GGGTTGACGG CGCCCAACGT GCTCGCCCAG GGGGCGCTCT TGCGCGAGGC GCTGCGGAAC

38881  GCCGGCGTCG AGGCCGAGGC CATCGGTTAC ATCGAGACCC ACGGGGCGGC GACCTCGCTG

38941  GGCGACCCCA TCGAGATCGA AGCGCTGCGC ACCGTGGTGG GGCCGGCGCG AGCCGACGGA

39001  GCGCGCTGCG TGCTGGGCGC GGTGAAGACC AACCTCGGCC ACCTGGAGGG CGCTGCCGGC

39061  GTGGCGGGCC TGATCAAGGC TACACTTTCG CTACATCACG AGCGCATCCC GAGGAACCTC

39121  AACTTTCGTA CGCTCAATCC GCGGATCCGG ATCGAGGGGA CCGCGCTCGC GTTGGCGACC

39181  GAACCGGTGC CCTGGCCGCG GACGGGCCGG ACGCGCTTCG CGGGAGTGAG CTCGTTCGGG

39241  ATGAGCGGGA CCAACGCGCA TGTGGTGTTG GAGGAGGCGC CGGCGGTGGA GCCTGAGGCC

39301  GCGGCCCCCG AGCGCGCTGC GGAGCTGTTC GTCCTGTCGG CGAAGAGCGT GGCGGCGCTG

39361  GATGCGCAGG CAGCCCGGCT GCGGGACCAC CTGGAGAAGC ATGTCGAGCT TGGCCTCGGC

39421  GATGTGGCGT TCAGCCTGGC GACGACGCGC AGCGCGATGG AGCACCGGCT GGCGGTGGCC

39481  GCGAGCTCGC GCGAGGCGCT GCGAGGGGCG CTTTCGGCCG CAGCGCAGGG GCATACGCCG

39541  CCGGGAGCCG TGCGTGGGCG GGCCTCCGGC GGCAGCGCGC CGAAGGTGGT CTTCGTGTTT

39601  CCCGGCCAGG GCTCGCAGTG GGTGGGCATG GGCCGAAAGC TCATGGCCGA AGAGCCGGTC

39661  TTCCGGGCGG CGCTGGAGGG TTGCGACCGG GCCATCGAGG CGGAAGCGGG CTGGTCGCTG

39721  CTCGGGGAGC TCTCCGCCGA CGAGGCCGCC TCGCAGCTCG GCGCATCGA CGTGGTTCAG

39781  CCGGTGCTCT TCGCCATGGA AGTAGCGCTT TCTGCGCTGT GGCGGTCGTG GGGAGTGGAG

39841  CCGGAAGCGG TGGTGGGCCA CAGCATGGGC GAGGTGGCGG CGGCGCACGT GGCCGGCGCG

39901  CTGTCGCTCG AGGACGCGGT GGCGATCATC TGCCGGCGCA GCCGGCTGCT GCGGCGGATC

39961  AGCGGTCAGG GCGAGATGGC GCTGGTCGAG CTGTCGCTGG AGGAGGCCGA GGCGGCGCTG

40021  CGTGGCCATG AGGGTCGGCT GAGCGTGGCG GTGAGCAACA GCCCGCGCTC GACCGTGCTC

40081  GCAGGCGAGC CGGCGGCGCT CTCGGAGGTG CTGGCGGCGC TGACGGCCAA GGGGGTGTTC

40141  TGGCGGCAGG TGAAGGTGGA CGTCGCCAGC CATAGCCCGC AGGTCGACCC GCTGCGCGAA

40201  GAGCTGATCG CGGCGCTGGG GGCGATCCGG CCGCGAGCGG CTGCGGTGCC GATGCGCTCG

40261  ACGGTGACGG GCGGGGTGAT CGCGGGTCCG GAGCTCGGTC CGAGCTACTG GCGGACAAT

40321  CTTCGGCAGC CGGTGCGCTT CGCTGCGGCG GCGCAAGCGC TGCTGGAAGG TGGCCCCACG

40381  CTGTTCATCG AGATGAGCCC GCACCCGATC CTGGTGCCGC CCCTGGACGA GATCCAGACG

40441  GCGGTCGAGC AAGGGGGCGC TGCGGTGGGC TCGCTGCGGC GAGGGCAGGA CGAGCGCGCG
```

```
40501 ACGCTGCTGG AGGCGCTGGG GACGCTGTGG GCGTCCGGCT ATCCGGTGAG CTGGGCTCGG
40561 CTGTTCCCCG CGGGCGGCAG GCGGGTTCCG CTGCCGACCT ATCCCTGGCA GCACGAGCGG
40621 TGCTGGATCG AGGTCGAGCC TGACGCCCGC CGCCTCGCCG CAGCCGACCC CACCAAGGAC
40681 TGGTTCTACC GGACGGACTG GCCCGAGGTG CCCCGCGCCG CCCCGAAATC GGAGACAGCT
40741 CATGGGAGCT GGCTGCTGTT GGCCGACAGG GGTGGGGTCG GCGAGGCGGT CGCTGCAGCG
40801 CTGTCGACGC GCGGACTTTC CTGCACCGTG CTTCATGCGT CGGCTGACGC CTCCACCGTC
40861 GCCGAGCAGG TATCCGAAGC TGCCAGTCGC CGAAACGACT GGCAGGGAGT CCTCTACCTG
40921 TGGGGCCTCG ACGCCGTCGT CGATGCTGGG GCATCGGCCG ACGAAGTCAG CGAGGCTACC
40981 CGCCGTGCCA CCGCACCCGT CCTTGGGCTG GTTCGATTCC TGAGCGCTGC GCCCCATCCT
41041 CCTCGCTTCT GGGTGGTGAC CCGCGGGGCA TGCACGGTGG GCGGCGAGCC AGAGGTCTCT
41101 CTTTGCCAAG CGGCGTTGTG GGGCCTCGCG CGCGTCGTGG CGCTGGAGCA TCCCGCTGCC
41161 TGGGGTGGCC TCGTGGACCT GGATCCTCAG AAGAGCCCGA CGGAGATCGA GCCCCTGGTG
41221 GCCGAGCTGC TTTCGCCGGA CGCCGAGGAT CAACTGGCGT TCCGCAGCGG TCGCCGGCAC
41281 GCAGCACGCC TTGTAGCCGC CCCGCCGGAG GGCGACGTCG CACCGATATC GCTGTCCGCG
41341 GAGGGAAGCT ACCTGGTGAC GGGTGGGCTG GGTGGCCTTG GTCTGCTCGT GGCTCGGTGG
41401 CTGGTGGAGC GGGGAGCTCG ACATCTGGTG CTCACCAGCC GGCACGGGCT GCCAGAGCGA
41461 CAGGCGTCGG GCGGAGAGCA GCCGCCGGAG GCCCGCGCGC GCATCGCAGC GGTCGAGGGG
41521 CTGGAAGCGC AGGGCGCGCG GGTGACCGTG GCAGCGGTGG ATGTCGCCGA GGCCGATCCC
41581 ATGACGGCGC TGCTGGCCGC CATCGAGCCC CCGTTGCGCG GGGTGGTGCA CGCCGCCGGC
41641 GTCTTCCCCG TGCGTCCCCT GGCGGAGACG GACGAGGCCC TGCTGGAGTC GGTGCTCCGT
41701 CCCAAGGTGG CCGGGAGCTG GCTGCTGCAC CGGCTGCTGC GCGACCGGCC TCTCGACCTG
41761 TTCGTGCTGT TCTCGTCGGG CGCGGCGGTG TGGGGTGGCA AAGGCCAAGG CGCATACGCC
41821 GCGGCCAATG CGTTCCTCGA CGGGCTCGCG CACCATCGCC GCGCGCACTC CCTGCCGGCG
41881 TTGAGCCTCG CCTGGGGCCT ATGGGCCGAG GGAGGCGTGG TTGATGCAAA GGCTCATGCA
41941 CGTCTGAGCG ACATCGGAGT CCTGCCCATG GCCACGGGGC CGGCCTTGTC GGCGCTGGAG
42001 CGCCTGGTGA ACACCAGCGC TGTCCAGCGT TCGGTCACAC GGATGGACTG GGCGCGCTTC
42061 GCGCCGGTCT ATGCCGCGCG AGGGCGGCGC AACTTGCTTT CGGCTCTGGT CGCGGAGGAC
42121 GAGCGCACTG CGTCTCCCCC GGTGCCGACG GCAAACCGGA TCTGGCGCGG CCTGTCCGTT
42181 GCGGAGAGCC GCTCAGCCCT CTACGAGCTC GTTCGCGGCA TCGTCGCCCG GGTGCTGGGC
42241 TTCTCCGACC CGGGCGCGCT CGACGTCGGC CGAGGCTTCG CCGAGCAGGG GCTCGACTCC
42301 CTGATGGCTC TGGAGATCCG TAACCGCCTT CAGCGCGAGC TGGGCGAACG GCTGTCGGCG
42361 ACTCTGGCCT TCGACCACCC GACGGTGGAG CGGCTGGTGG CGCATCTCCT CACCGACGTG
42421 CTGAAGCTGG AGGACCGGAG CGACACCCGG CACATCCGGT CGGTGGCGGC GGATGACGAC
42481 ATCGCCATCG TCGGTGCCGC CTGCCGGTTC CCGGGCGGGG ATGAGGGCCT GGAGACATAC
42541 TGGCGGCATC TGGCCGAGGG CATGGTGGTC AGCACCGAGG TGCCAGCCGA CCGGTGGCGC
42601 GCGGCGGACT GGTACGACCC CGATCCGGAG GTTCCGGGCC GGACCTATGT GGCCAAGGGG
42661 GCCTTCCTCC GCGATGTGCG CAGCTTGGAT GCGGCGTTCT TCTCCATCTC CCCTCGTGAG
42721 GCGATGAGCC TGGACCCGCA ACAGCGGCTG TTGCTGGAGG TGAGCTGGGA GGCGATCGAG
42781 CGCGCTGGCC AGGACCCGAT GGCGCTGCGC GAGAGCGCCA CGGGCGTGTT CGTGGGCATG
42841 ATCGGGAGCG AGCACGCCGA GCGGGTGCAG GGCCTCGACG ACGACGCGGC GTTGCTGTAC
```

```
42901 GGCACCACCG GCAACCTGCT CAGCGTCGCC GCTGGACGGC TGTCGTTCTT CCTGGGTCTG

42961 CACGGCCCGA CGATGACGGT GGACACCGCG TGCTCGTCGT CGCTGGTGGC GTTGCACCTC

43021 GCCTGCCAGA GCCTGCGATT GGGCGAGTGC GACCAGGCAC TGGCCGGCGG GTCCAGCGTG

43081 CTTTTGTCGC CGCGGTCATT CGTCGCGGCA TCGCGCATGC GTTTGCTTTC GCCAGATGGG

43141 CGGTGCAAGA CGTTCTCGGC CGCTGCAGAC GGCTTTGCGC GGGCCGAGGG CTGCGCCGTG

43201 GTGGTGCTCA AGCGGCTCCG TGACGCGCAG CGCGACCGCG ACCCCATCCT GGCGGTGGTC

43261 CGGAGCACGG CGATCAACCA CGATGGCCCG AGCAGCGGGC TCACGGTGCC CAGCGGTCCT

43321 GCCCAGCAGG CGTTGCTAGG CCAGGCGCTG GCGCAAGCGG GCGTGGCACC GGCCGAGGTC

43381 GATTTCGTGG AGTGCCACGG GACGGGGACA GCGCTGGGTG ACCCGATCGA GGTGCAGGCG

43441 CTGGGCGCGG TGTATGGCCG GGGCCGCCCC GCGGAGCGGC CGCTCTGGCT GGGCGCTGTC

43501 AAGGCCAACC TCGGCCACCT GGAGGCCGCG GCGGGCTTGG CCGGCGTGCT CAAGGTGCTC

43561 TTGGCGCTGG AGCACGAGCA GATTCCGGCT CAACCGGAGC TCGACGAGCT CAACCCGCAC

43621 ATCCCGTGGG CAGAGCTGCC AGTGGCCGTT GTCCGCGCGG CGGTCCCCTG GCCGCGCGGC

43681 GCGCGCCCGC GTCGTGCAGG CGTGAGCGCT TTCGGCCTGA GCGGGACCAA CGCGCATGTG

43741 GTGTTGGAGG AGGCGCCGGC GGTGGAGCCT GAGGCCGCGG CCCCGAGCG CGCTGCGGAG

43801 CTGTTCGTCC TGTCGGCGAA GAGCGTGGCG GCGCTGGATG CGCAGGCAGC CCGGCTGCGG

43861 GATCATCTGG AGAAGCATGT CGAGCTTGGC CTCGGCGATG TGGCGTTCAG CCTGGCGACG

43921 ACGCGCAGCG CGATGGAGCA CCGGCTGGCG GTGGCCGCGA GCTCGCGCGA GGCGCTGCGA

43981 GGGGCGCTTT CGGCCGCAGC GCAGGGGCAT ACGCCGCCGG GAGCCGTGCG TGGGCGGGCC

44041 TCCGGCGGCA GCGCGCCGAA GGTGGTCTTC GTGTTTCCCG GCCAGGGCTC GCAGTGGGTG

44101 GGCATGGGCC GAAAGCTCAT GGCCGAAGAG CCGGTCTTCC GGGCGGCGCT GGAGGGTTGC

44161 GACCGGGCCA TCGAGGCGGA AGCGGGCTGG TCGCTGCTCG GGGAGCTCTC CGCCGACGAG

44221 GCCGCCTCGC AGCTCGGGCG CATCGACGTG GTTCAGCCGG TGCTCTTCGC CGTGGAAGTA

44281 GCGCTTTCAG CGCTGTGGCG GTCGTGGGGA GTGGAGCCGG AAGCGGTGGT GGGCCACAGC

44341 ATGGGCGAGG TTGCGGCGGC GCACGTGGCC GGCGCGCTGT CGCTCGAGGA TGCGGTGGCG

44401 ATCATCTGCC GGCGCAGCCG GCTGCTGCGG CGGATCAGCG GTCAGGGCGA GATGGCGCTG

44461 GTCGAGCTGT CGCTGGAGGA GGCCGAGGCG GCGCTGCGTG GCCATGAGGG TCGGCTGAGC

44521 GTGGCGGTGA GCAACAGCCC GCGCTCGACC GTGCTCGCAG GCGAGCCGGC GGCGCTCTCG

44581 GAGGTGCTGG CGGCGCTGAC GGCCAAGGGG GTGTTCTGGC GGCAGGTGAA GGTGGACGTC

44641 GCCAGCCATA GCCCGCAGGT CGACCCGCTG CGCGAAGAGC TGGTCGCGGC GCTGGGAGCG

44701 ATCCGGCCGC GAGCGGCTGC GGTGCCGATG CGCTCGACGG TGACGGGCGG GGTGATTGCG

44761 GGTCCGGAGC TCGGTGCGAG CTACTGGGCG GACAATCTTC GGCAGCCGGT GCGCTTCGCT

44821 GCGGCGGCGC AAGCGCTGCT GGAAGGTGGC CCCACGCTGT CATCGAGAT GAGCCCGCAC

44881 CCGATCCTGG TGCCGCCTCT GGACGAGATC CAGACGGCGG TCGAGCAAGG GGGCGCTGCG

44941 GTGGGCTCGC TGCGGCGAGG GCAGGACGAG CGCGCGACGC TGCTGGAGGC GCTGGGGACG

45001 CTGTGGGCGT CCGGCTATCC GGTGAGCTGG GCTCGGCTGT TCCCCGCGGG CGGCAGGCGG

45061 GTTCCGCTGC CGACCTATCC CTGGCAGCAC GAGCGGTACT GGATCGAGGA CAGCGTGCAT

45121 GGGTCGAAGC CCTCGCTGCG GCTTCGGCAG CTTCATAACG GCGCCACGGA CCATCCGCTG

45181 CTCGGGGCTC CATTGCTCGT CTCGGCGCGA CCCGGAGCTC ACTTGTGGGA GCAAGCGCTG

45241 AGCGACGAGA GGCTATCCTA TCTTTCGGAA CATAGGGTCC ATGGCGAAGC CGTGTTGCCC
```

-continued

```
45301 AGCGCGGCGT ATGTAGAGAT GGCGCTCGCC GCCGGCGTAG ATCTCTATGG CGCGGCGACG
45361 CTGGTGCTGG AGCAGCTGGC GCTCGAGCGA GCCCTCGCCG TGCCTTCCGA AGGCGGACGC
45421 ATCGTGCAAG TGGCCCTCAG CGAAGAAGGG CCCGGTCGGG CCTCATTCCA GGTATCGAGC
45481 CGTGAGGAGG CAGGTAGAAG CTGGGTTCGG CACGCCACGG GGCACGTGTG TAGCGACCAG
45541 AGCTCAGCAG TGGGAGCGTT GAAGGAAGCT CCGTGGGAGA TTCAACAGCG ATGTCCGAGC
45601 GTCCTGTCGT CGGAGGCGCT CTATCCGCTG CTCAACGAGC ACGCCCTCGA CTATGGCCCC
45661 TGCTTCCAGG GTGTGGAGCA GGTGTGGCTC GGCACGGGGG AGGTGCTCGG CCGGGTACGC
45721 TTGCCAGAAG ACATGGCATC CTCAAGTGGC GCCTATCGGA TTCATCCCGC CTTGTTGGAT
45781 GCATGTTTTC AAGTGCTGAC CGCGCTGCTC ACCACGCCGG AATCCATCGA GATTCGGAGG
45841 CGGCTGACGG ATCTCCACGA ACCGGATCTC CCGCGGTCCA GGGCTCCGGT GAATCAAGCG
45901 GTGAGTGACA CCTGGCTGTG GGACGCCGCG CTGGACGGTG ACGGCGCCA GAGCGCGAGC
45961 GTGCCCGTCG ACCTGGTGCT CGGCAGCTTC CACGCGAAGT GGGAGGTCAT GGATCGCCTC
46021 GCGCAGACGT ACATCATCCG CACTCTCCGC ACATGGAACG TCTTCTGCGC TGCTGGAGAG
46081 CGTCACACGA TAGACGAGTT GCTCGTCAGG CTCCAAATCT CTGCTGTCTA CAGGAAGGTC
46141 ATCAAGCGAT GGATGGATCA CCTTGTCGCG ATCGGCGTCC TTGTAGGGGA CGGAGAGCAT
46201 CTTGTGAGCT CTCAGCCGCT GCCGGAGCAT GATTGGGCGG CGGTGCTCGA GGAGGCCGCG
46261 ACGGTGTTCG CCGACCTCCC AGTCCTACTT GAGTGGTGCA AGTTTGCCGG GGAACGGCTC
46321 GCGGACGTGT TGACCGGGAA GACGCTGGCG CTCGAGATCC TCTTCCCTGG CGGCTCGTTC
46381 GATATGGCGG AGCGAATCTA TCAAGATTCG CCCATCGCCC GTTACTCGAA CGGCATCGTG
46441 CGCGGTGTCG TCGAGTCGGC GGCGCGGGTG GTAGCACCGT CGGGAACGTT CAGCATCTTG
46501 GAGATCGGAG CAGGGACGGG CGCGACCACC GCCGCCGTCC TCCCGGTGTT GCTGCCTGAC
46561 CGGACAGAAT ACCATTTCAC CGATGTTTCT CCGCTCTTCC TTGCTCGTGC GGAGCAAAGA
46621 TTTCGAGATC ATCCATTCCT GAAGTATGGT ATTCTGGATA TCGACCAGGA GCCAGCTGGC
46681 CAGGGATACG CACATCAGAA GTTCGACGTC ATCGTCGCGG CCAACGTCAT CCATGCGACC
46741 CGCGATATAA GAGCCACGGC GAAGCGTCTC CTGTCGTTGC TCGCGCCCGG AGGCCTTCTG
46801 GTGCTGGTCG AGGGCACAGG GCATCCGATC TGGTTCGATA TCACCACGGG ATTGATCGAG
46861 GGGTGGCAGA AGTACGAAGA TGATCTTCGT ACCGACCATC CGCTCCTGCC TGCTCGGACC
46921 TGGTGTGACG TCCTGCGCCG GGTAGGCTTT GCGGATGCCG TGAGTCTGCC AGGCGACGGA
46981 TCTCCGGCGG GGATCCTCGG ACAGCACGTG ATCCTCTCGC GCGCTCCGGG CATAGCAGGA
47041 GCCGCTTGTG ACAGCTCCGG TGAGTCGGCG ACCGAATCGC CGGCCGCGCG TGCAGTACGG
47101 CAGGAATGGG CCGATGGCTC CGCTGACGGC GTCCATCGGA TGGCGTTGGA GAGAATGTAC
47161 TTCCACCGCC GGCCGGGCCG GCAGGTTTGG GTCCACGGTC GATTGCGTAC CGGTGGAGGC
47221 GCGTTCACGA AGGCGCTCAC TGGAGATCTG CTCCTGTTCG AAGAGACCGG GCAGGTCGTG
47281 GCAGAGGTTC AGGGGCTCCG CCTGCCGCAG CTCGAGGCTT CTGCTTTCGC GCCGCGGGAC
47341 CCGCGGGAAG AGTGGTTGTA CGCGTTGGAA TGGCAGCGCA AAGACCCTAT ACCAGAGGCT
47401 CCGGCAGCCG CGTCTTCTTC CACCGCGGGG GCTTGGCTCG TGCTGATGGA CCAGGGCGGG
47461 ACAGGCGCTG CGCTCGTATC GCTGCTGGAA GGGCGAGGCG AGGCGTGCGT GCGCGTCGTC
47521 GCGGGTACGG CATACGCCTG CCTCGCGCCG GGGCTGTATC AAGTCGATCC GGCGCAGCCA
47581 GATGGCTTTC ATACCCTGCT CCGCGATGCA TTCGGCGAGG ACCGGATGTG CCGCGCGGTA
47641 GTGCATATGT GGAGCCTTGA TGCGAAGGCA GCAGGGGAGA GGACGACAGC GGAGTCGCTT
```

-continued

```
47701 CAGGCCGATC AACTCCTGGG GAGCCTGAGC GCGCTTTCTC TGGTGCAGGC GCTGGTGCGC
47761 CGGAGGTGGC GCAACATGCC GCGACTTTGG CTCTTGACCC GCGCCGTGCA TGCGGTGGGC
47821 GCGGAGGACG CAGCGGCCTC GGTGGCGCAG GCGCCGGTGT GGGGCCTCGG TCGGACGCTC
47881 GCGCTCGAGC ATCCAGAGCT GCGGTGCACG CTCGTGGACG TGAACCCGGC GCCGTCTCCA
47941 GAGGACGCAG CTGCACTCGC GGTGGAGCTC GGGGCGAGCG ACAGAGAGGA CCAGATCGCA
48001 TTGCGCTCGA ATGGCCGCTA CGTGGCGCGC CTCGTGCGGA GCTCCTTTTC CGGCAAGCCT
48061 GCTACGGATT GCGGCATCCG GGCGGACGGC AGTTATGTGA TCACCGATGG CATGGGGAGA
48121 GTGGGGCTCT CGGTCGCGCA ATGGATGGTG ATGCAGGGGG CCCGCCATGT GGTGCTCGTG
48181 GATCGCGGCG GCGCTTCCGA CGCCTCCCGG GATGCCCTCC GGTCCATGGC CGAGGCTGGC
48241 GCAGAGGTGC AGATCGTGGA GGCCGACGTG GCTCGGCGCG TCGATGTCGC TCGGCTTCTC
48301 TCGAAGATCG AACCGTCGAT GCCGCCGCTT CGGGGGATCG TGTACGTGGA CGGGACCTTC
48361 CAGGGCGACT CCTCGATGCT GGAGCTGGAT GCCCATCGCT TCAAGGAGTG GATGTATCCC
48421 AAGGTGCTCG GAGCGTGGAA CCTGCACGCG CTGACCAGGG ATAGATCGCT GGACTTCTTC
48481 GTCCTGTACT CCTCGGGCAC CTCGCTTCTG GGCTTGCCCG GACAGGGGAG CCGCGCCGCC
48541 GGTGACGCCT TCTTGGACGC CATCGCGCAT CACCGGTGTA GGCTGGGCCT CACAGCGATG
48601 AGCATCAACT GGGGATTGCT CTCCGAAGCA TCATCGCCGG CGACCCCGAA CGACGGCGGC
48661 GCACGGCTCC AATACCGGGG GATGGAAGGT CTCACGCTGG AGCAGGGAGC GGAGGCGCTC
48721 GGGCGCTTGC TCGCACAACC CAGGGCGCAG GTAGGGGTAA TGCGGCTGAA TCTGCGCCAG
48781 TGGCTGGAGT CTATCCCAA CGCGGCCCGA CTGGCGCTGT GGGCGGAGTT GCTGAAGGAG
48841 CGTGACCGCA CCGACCGGAG CGCGTCGAAC GCATCGAACC TGCGCGAGGC GCTGCAGAGC
48901 GCCAGGCCCG AAGATCGTCA GTTGGTTCTG GAGAAGCACT TGAGCGAGCT GTTGGGGCGG
48961 GGGCTGCGCC TTCCGCCGGA GAGGATCGAG CGGCACGTGC CGTTCAGCAA TCTCGGCATG
49021 GACTCGTTGA TAGGCCTGGA GCTCCGCAAC CGCATCGAGG CCGCGCTCGG CATCACCGTG
49081 CCGGCGACCC TGCTATGGAC TTACCCTACC GTAGCAGCTC TGAGCGGGAA CCTGCTAGAT
49141 ATTCTGTTCC CGAATGCCGG CGCGACTCAC GCTCCGGCCA CCGAGCGGGA GAAGAGCTTC
49201 GAGAACGATG CCGCAGATCT CGAGGCTCTG CGGGGTATGA CGGACGAGCA GAAGGACGCG
49261 TTGCTCGCCG AAAAGCTGGC GCAGCTCGCG CAGATCGTTG GTGAGTAAGG GACTGAGGGA
49321 GTATGGCGAC CACGAATGCC GGGAAGCTTG AGCATGCCCT TCTGCTCATG GACAAGCTTG
49381 CGAAAAAGAA CGCGTCTTTG GAGCAAGAGC GGACCGAGCC GATCGCCATC ATAGGTATTG
49441 GCTGCCGCTT CCCCGGCGGA GCGGACACTC CGGAGGCATT CTGGGAGCTG CTCGACTCGG
49501 GCCGAGACGC GGTCCAGCCG CTCGACCGGC GCTGGGCGCT GGTCGGCGTC CATCCCAGCG
49561 AGGAGGTGCC GCGCTGGGCC GGACTGCTCA CCGAGGCGGT GGACGGCTTC GACGCCGCGT
49621 TCTTTGGCAC CTCGCCTCGG GAGGCGCGGT CGCTCGATCC TCAGCAACGC CTGCTGCTGG
49681 AGGTCACCTG GGAAGGGCTC GAGGACGCCG GCATCGCACC CCAGTCCCTC GACGGCAGCC
49741 GCACCGGGGT ATTCCTGGGC GCATGCAGCA GCGACTACTC GCATACCGTT GCGCAACAGC
49801 GGCGCGAGGA GCAGGACGCG TACGACATCA CCGGCAATAC GCTCAGCGTC GCCGCCGGAC
49861 GGTTGTCTTA TACGCTAGGG CTGCAGGGAC CCTGCCTGAC CGTCGACACG GCCTGCTCGT
49921 CGTCGCTCGT GGCCATCCAC CTTGCCTGCC GCAGCCTGCG CGCTCGCGAG AGCGATCTCG
49981 CGCTGGCGGG GGGCGTCAAC ATGCTCCTTT CGTCCAAGAC GATGATAATG CTGGGCGCA
50041 TCCAGGCGCT GTCGCCCGAT GGCCACTGCC GGACATTCGA CGCCTCGGCC AACGGGTTCG
```

-continued

```
50101  TCCGTGGGGA GGGCTGCGGT ATGGTCGTGC TCAAACGGCT CTCCGACGCC CAGCGACATG
50161  GCGATCGGAT CTGGGCTCTG ATCCGGGGTT CGGCCATGAA TCAGGATGGC CGGTCGACAG
50221  GGTTGATGGC ACCCAATGTG CTCGCTCAGG AGGCGCTCTT ACGCCAGGCG CTGCAGAGCG
50281  CTCGCGTCGA CGCCGGGGCC ATCGATTATG TCGAGACCCA CGGAACGGGG ACCTCGCTCG
50341  GCGACCCGAT CGAGGTCGAT GCGCTGCGTG CCGTGATGGG GCCGGCGCGG GCCGATGGGA
50401  GCCGCTGCGT GCTGGGCGCA GTGAAGACCA ACCTCGGCCA CCTGGAGGGC GCTGCAGGCG
50461  TGGCGGGTTT GATCAAGGCG GCGCTGGCTC TGCACCACGA ATCGATCCCG CGAAACCTCC
50521  ATTTTCACAC GCTCAATCCG CGGATCCGGA TCGAGGGGAC CGCGCTCGCG CTGGCGACGG
50581  AGCCGGTGCC GTGGCCGCGG GCGGGCCGAC CGCGCTTCGC GGGGGTGAGC GCGTTCGGCC
50641  TCAGCGGCAC CAACGTCCAT GTCGTGCTGG AGGAGGCGCC GGCCACGGTG CTCGCACCGG
50701  CGACGCCGGG GCGCTCAGCA GAGCTTTTGG TGCTGTCGGC GAAGAGCACC GCCGCGCTGG
50761  ACGCACAGGC GGCGCGGCTC TCAGCGCACA TCGCCGCGTA CCCGGAGCAG GGCCTCGGAG
50821  ACGTCGCGTT CAGCCTGGTA GCGACGCGGA GCCCGATGGA GCACCGGCTC GCGGTGGCGG
50881  CGACCTCGCG CGAGGCGCTG CGAAGCGCGC TGGAAGCTGC GGCGCAGGGG CAGACCCCGG
50941  CAGGCGCGGC GCGCGGCAGG GCCGCTTCCT CGCCCGGCAA GCTCGCCTTC CTGTTCGCCG
51001  GGCAGGGCGC GCAGGTGCCG GGCATGGGCC GTGGGTTGTG GGAGGCGTGG CCGGCGTTCC
51061  GCGAGACCTT CGACCGGTGC GTCACGCTCT TCGACCGGGA GCTCCATCAG CCGCTCTGCG
51121  AGGTGATGTG GGCCGAGCCG GGCAGCAGCA GGTCGTCGTT GCTGGACCAG ACGGCATTCA
51181  CCCAGCCGGC GCTCTTTGCG CTGGAGTACG CGCTGGCCGC GCTCTTCCGG TCGTGGGGCG
51241  TGGAGCCGGA GCTCATCGCT GGCCATAGCC TCGGCGAGCT GGTGGCCGCC TGCGTGGCGG
51301  GTGTGTTCTC CCTCGAGGAC GCCGTGCGCT TGGTGGTCGC GCGCGGCCGG TTGATGCAGG
51361  CGCTGCCGGC CGGCGGTGCG ATGGTATCGA TCGCCGCGCC GGAGGCCGAC GTGGCTGCCG
51421  CGGTGGCGCC GCACGCAGCG TCGGTGTCGA TCGCGGCAGT CAATGGGCCG GAGCAGGTGG
51481  TGATCGCGGG CGCCGAGAAA TTCGTGCAGC AGATCGCGGC GGCGTTCGCG GCGCGGGGGG
51541  CGCGAACCAA ACCGCTGCAT GTTTCGCACG CGTTCCACTC GCCGCTCATG GATCCGATGC
51601  TGGAGGCGTT CCGGCGGGTG ACCGAGTCGG TGACGTATCG GCGGCCTTCG ATGGCGCTGG
51661  TGAGCAACCT GAGCGGGAAG CCCTGCACGG ATGAGGTGTG CGCGCCGGGT TACTGGGTGC
51721  GTCACGCGCG AGAGGCGGTG CGCTTCGCGG ACGGCGTGAA GGCGCTGCAC GCGGCCGGTG
51781  CGGGCATCTT CGTCGAGGTG GGCCCGAAGC CGGCGCTGCT CGGCCTTTTG CCGGCCTGCC
51841  TGCCGGATGC CAGGCCGGTG CTGCTCCCAG CGTCGCGCGC CGGGCGTGAC GAGGCTGCGA
51901  GCGCGCTGGA GGCGCTGGGT GGGTTCTGGG TCGTCGGTGG ATCGGTCACC TGGTCGGGTG
51961  TCTTCCCTTC GGGCGGACGG CGGGTACCGC TGCCAACCTA TCCCTGGCAG CGCGAGCGTT
52021  ACTGGATCGA AGCGCCGGTC GATGGTGAGG CGGACGGCAT CGGCCGTGCT CAGGCGGGGG
52081  ACCACCCCCT TCTGGGTGAA GCCTTTTCCG TGTCGACCCA TGCCGGTCTG CGCCTGTGGG
52141  AGACGACGCT GGACCGAAAG CGGCTGCCGT GGCTCGGCGA GCACCGGGCG CAGGGGGAGG
52201  TCGTGTTTCC TGGCGCCGGG TACCTGGAGA TGGCGCTGTC GTCGGGGGCC GAGATCTTGG
52261  GCGATGGACC GATCCAGGTC ACGGATGTGG TGCTCATCGA GACGCTGACC TTCGCGGGCG
52321  ATACGGCGGT ACCGGTCCAG GTGGTGACGA CCGAGGAGCG ACCGGGACGG CTGCGGTTCC
52381  AGGTAGCGAG TCGGGAGCCG GGGGCACGTC GCGCGTCCTT CCGGATCCAC GCCCGCGGCC
52441  TGCTGCGCCG GGTCGGGCGC GCCGAGACCC CGGCGAGGTT GAACCTCGCC GCCCTGCGCG
```

```
52501 CCCGGCTTCA TGCCGCCGTG CCCGCTGCGG CTATCTATGG GGCGCTCGCC GAGATGGGGC
52561 TTCAATACGG CCCGGCGTTG CGGGGGCTCG CCGAGCTGTG GCGGGGTGAG GGCGAGGCGC
52621 TGGGCAGAGT GAGACTGCCT GAGTCCGCCG GCTCCGCGAC AGCCTACCAG CTGCATCCGG
52681 TGCTGCTGGA CGCGTGCGTC CAAATGATTG TTGGCGCGTT CGCCGATCGC GATGAGGCGA
52741 CGCCGTGGGC GCCGGTGGAG GTGGGCTCGG TGCGGCTGTT CCAGCGGTCT CCTGGGGAGC
52801 TATGGTGCCA TGCGCGCGTC GTGAGCGATG GTCAACAGGC CCCCAGCCGG TGGAGCGCCG
52861 ACTTTGAGTT GATGGACGGT ACGGGCGCGG TGGTCGCCGA GATCTCCCGG CTGGTGGTGG
52921 AGCGGCTTGC GAGCGGTGTA CGCCGGCGCG ACGCAGACGA CTGGTTCCTG GAGCTGGATT
52981 GGGAGCCCGC GGCGCTCGAG GGGCCCAAGA TCACAGCCGG CCGGTGGCTG CTGCTCGGCG
53041 AGGGTGGTGG GCTCGGGCGC TCGTTGTGCT CAGCGCTGAA GGCCGCCGGC CATGTCGTCG
53101 TCCACGCCGC GGGGGACGAC ACGAGCGCTG CAGGAATGCG CGCGCTCCTG GCCAACGCGT
53161 TCGACGGCCA GGCCCCGACG GCCGTGGTGC ACCTCAGCAG CCTCGACGGG GGCGGCCAGC
53221 TCGACCCGGG GCTCGGGGCG CAGGGCGCGC TCGACGCGCC CCGGAGCCCA GATGTCGATG
53281 CCGATGCCCT CGAGTCGGCG CTGATGCGTG GTTGCGACAG CGTGCTCTCC CTGGTGCAAG
53341 CGCTGGTCGG CATGGACCTC CGAAATGCGC CGCGGCTGTG GCTTTTGACC CGCGGGGCTC
53401 AGGCGGCCGC CGCCGGCGAT GTCTCCGTGG TGCAAGCGCC GCTGTTGGGG CTGGGCCGCA
53461 CCATCGCCTT GGAGCACGCC GAGCTGCGCT GTATCAGCGT CGACCTCGAT CCAGCCCAGC
53521 CTGAAGGGGA AGCCGATGCT TTGCTGGCCG AGCTACTTGC AGATGATGCC GAGGAGGAGG
53581 TCGCGCTGCG CGGTGGCGAG CGGTTTGTTG CGCGGCTCGT CCACCGGCTG CCCGAGGCTC
53641 AACGCCGGGA GAAGATCGCG CCCGCCGGTG ACAGGCCGTT CCGGCTAGAG ATCGATGAAC
53701 CCGGCGTGCT GGACCAACTG GTGCTCCGGG CCACGGGGCG GCGCGCTCCT GGTCCGGGCG
53761 AGGTCGAGAT CGCCGTCGAA GCGGCGGGGC TCGACTCCAT CGACATCCAG CTGGCGGTGG
53821 GCGTTGCTCC CAATGACCTG CCTGGAGGAG AAATCGAGCC GTCGGTGCTC GGAAGCGAGT
53881 GCGCCGGGCG CATCGTCGCT GTGGGCGAGG GCGTGAACGG CCTTGTGGTG GGCCAGCCGG
53941 TGATCGCCCT TGCGGCGGGA GTATTTGCTA CCCATGTCAC CACGTCGGCC ACGCTGGTGT
54001 TGCCTCGGCC TCTGGGGCTC TCGGCGACCG AGGCGGCCGC GATGCCCCTC GCGTATTTGA
54061 CGGCCTGGTA CGCCCTCGAC AAGGTCGCCC ACCTGCAGGC GGGGGAGCGG GTGCTGATCC
54121 GTGCGGAGGC CGGTGGTATC GGTCTTTGCG CGGTGCGATG GGCGCAGCGC GTGGGCGCCG
54181 AGGTGTATGC GACCGCCGAC ACGCCCGAGA AACGTGCCTA CCTGGAGTCG CTGGGCGTGC
54241 GGTACGTGAG CGATTCCCGC TCGGGCCGGT TCGCCGCAGA CGTGCATGCA TGGACGGACG
54301 GCGAGGGTGT GGACGTCGTG CTCGACTCGC TTTCGGGCGA GCACATCGAC AAGAGCCTCA
54361 TGGTCCTGCG CGCCTGTGGC CGCCTTGTGA AGCTGGGCAG GCGCGACGAC TGCGCCGACA
54421 CGCAGCCTGG GCTGCCGCCG CTCCTACGGA ATTTTTCCTT CTCGCAGGTG GACTTGCGGG
54481 GAATGATGCT CGATCAACCG GCGAGGATCC GTGCGCTCCT CGACGAGCTG TTCGGGTTGG
54541 TCGCAGCCGG TGCCATCAGC CCACTGGGGT CGGGGTTGCG CGTTGGCGGA TCCCTCACGC
54601 CACCGCCGGT CGAGACCTTC CCGATCTCTC GCGCAGCCGA GGCATTCCGG AGGATGGCGC
54661 AAGGACAGCA TCTCGGGAAG CTCGTGCTCA CGCTGGACGA CCCGGAGGTG CGGATCCGCG
54721 CTCCGGCCGA ATCCAGCGTC GCCGTCCGCG CGGACGGCAC CTACCTTGTG ACCGGCGGTC
54781 TGGGTGGGCT CGGTCTGCGC GTGGCCGGAT GGCTGGCCGA GCGGGGCGCG GGGCAACTGG
54841 TGCTGGTGGG CCGCTCCGGT GCGGCGAGCG CAGAGCAGCG AGCCGCCGTG GCGGCGCTAG
```

```
54901 AGGCCCACGG CGCGCGCGTC ACGGTGGCGA AAGCGGATGT CGCCGATCGG TCACAGATCG
54961 AGCGGGTCCT CCGCGAGGTT ACCGCGTCGG GGATGCCGCT GCGGGGTGTC GTGCATGCGG
55021 CAGGTCTTGT GGATGACGGG CTGCTGATGC AGCAGACTCC GGCGCGGCTC CGCACGGTGA
55081 TGGGACCTAA GGTCCAGGGA GCCTTGCACT TGCACACGCT GACACGCGAA GCGCCTCTTT
55141 CCTTCTTCGT GCTGTACGCT TCTGCAGCTG GGCTGTTCGG CTCGCCAGGC CAGGGCAACT
55201 ATGCCGCAGC CAACGCGTTC CTCGACGCCC TTTCGCATCA CCGCAGGGCG CACGGCCTGC
55261 CGGCGCTGAG CATCGACTGG GGCATGTTCA CGGAGGTGGG GATGGCCGTT GCGCAAGAAA
55321 ACCGTGGCGC GCGGCTGATC TCTCGCGGGA TGCGGGGCAT CACCCCCGAT GAGGGTCTGT
55381 CAGCTCTGGC GCGCTTGCTC GAGGGTGATC GCGTGCAGAC GGGGGTGATA CCGATCACTC
55441 CGCGGCAGTG GGTGGAGTTC TACCCGGCAA CAGCGGCCTC ACGGAGGTTG TCGCGGCTGG
55501 TGACCACGCA GCGCGCGGTT GCTGATCGGA CCGCCGGGGA TCGGGACCTG CTCGAACAGC
55561 TTGCCTCGGC TGAGCCGAGC GCGCGGGCGG GGCTGCTGCA GGACGTCGTG CGCGTGCAGG
55621 TCTCGCATGT GCTGCGTCTC CCTGAAGACA AGATCGAGGT GGATGCCCCG CTCTCGAGCA
55681 TGGGCATGGA CTCGCTGATG AGCCTGGAGC TGCGCAACCG CATCGAGGCT GCGCTGGGCG
55741 TCGCCGCGCC TGCAGCCTTG GGGTGGACGT ACCCAACGGT AGCAGCGATA ACGCGCTGGC
55801 TGCTCGACGA CGCCCTCGCC GTCCGGCTTG GCGGCGGGTC GGACACGGAC GAATCGACGG
55861 CAAGCGCCGG ATCGTTCGTC CACGTCCTCC GCTTTCGTCC TGTCGTCAAG CCGCGGGCTC
55921 GTCTCTTCTG TTTTCACGGT TCTGGCGGCT CGCCCGAGGG CTTCCGTTCC TGGTCGGAGA
55981 AGTCTGAGTG GAGCGATCTG GAAATCGTGG CCATGTGGCA CGATCGCAGC CTCGCCTCCG
56041 AGGACGCGCC TGGTAAGAAG TACGTCCAAG AGGCGGCCTC GCTGATTCAG CACTATGCAG
56101 ACGCACCGTT TGCGTTAGTA GGGTTCAGCC TGGGTGTCCG GTTCGTCATG GGGACAGCCG
56161 TGGAGCTCGC TAGTCGTTCC GGCGCACCGG CTCCGCTGGC CGTTTTTGCG TTGGGCGGCA
56221 GCTTGATCTC TTCTTCAGAG ATCACCCCGG AGATGGAGAC CGATATAATA GCCAAGCTCT
56281 TCTTCCGAAA TGCCGCGGGT TTCGTGCGAT CCACCCAACA AGTTCAGGCC GATGCTCGCG
56341 CAGACAAGGT CATCACAGAC ACCATGGTGG CTCCGGCCCC CGGGGACTCG AAGGAGCCGC
56401 CCTCGAAGAT CGCCGGTCCCT ATCGTCGCCA TCGCCGGCTC GGACGATGTG ATCGTGCCTC
56461 CAAGCGACGT TCAGGATCTA CAATCTCGCA CCACGGAGCG CTTCTATATG CATCTCCTTC
56521 CCGGAGATCA CGAGTTTCTC GTCGATCGAG GGCGCGAGAT CATGCACATC GTCGACTCGC
56581 ATCTCAATCC GCTGCTCGCC GCGAGGACGA CGTCGTCAGG CCCCGCGTTC GAGGCAAAAT
56641 GATGGCAGCC TCCCTCGGGC GCGCGAGATG GTTGGGAGCA GCGTGGGTGC TGGTGGCCGG
56701 CGGCAGGCAG CGGAGGCTCA TGAGCCTTCC TGGAAGTTTG CAGCATAGGA GATTTTATGA
56761 CACAGGAGCA AGCGAATCAG AGTGAGACGA AGCCTGCTTT CGACTTCAAG CCGTTCGCGC
56821 CTGGGTACGC GGAGGACCCG TTTCCCGCGA TCGAGCGCCT GAGAGAGGCA ACCCCCATCT
56881 TCTACTGGGA TGAAGGCCGC TCCTGGGTCC TCACCCGATA CCACGACGTG TCGGCGGTGT
56941 TCCGCGACGA ACGCTTCGCG GTCAGTCGAG AAGAATGGGA ATCGAGCGCG GAGTACTCGT
57001 CGGCCATTCC CGAGCTCAGC GATATGAAGA AGTACGGATT GTTCGGGCTG CCGCCGGAGG
57061 ATCACGCTCG GGTCCGCAAG CTCGTCAACC CATCGTTTAC GTCACGCGCG ATCGACCTGC
57121 TGCGCGCCGA AATACAGCGC ACCGTCGACC AGCTGCTCGA TGCTCGCTCC GGACAAGAGG
57181 AGTTCGACGT TGTGCGGGAT TACGCGGAGG GAATCCCGAT GCGTGCGATC AGCGCTCTGT
57241 TGAAGGTTCC GGCCGAGTGT GACGAGAAGT TCCGTCGCTT CGGCTCGGCG ACTGCGCGCG
```

```
-continued
57301 CGCTCGGCGT GGGTTTGGTG CCCCGGGTCG ATGAGGAGAC CAAGACCCTG GTCGCGTCCG
57361 TCACCGAGGG GCTCGCGCTG CTCCATGGCG TCCTCGATGA GCGGCGCAGG AACCCGCTCG
57421 AAAATGACGT CTTGACGATG CTGCTTCAGG CCGAGGCCGA CGGCAGCAGG CTGAGCACGA
57481 AGGAGCTGGT CGCGCTCGTG GGTGCGATTA TCGCTGCTGG CACCGATACC ACGATCTACC
57541 TTATCGCGTT CGCTGTGCTC AACCTGCTGC GGTCGCCCGA GGCGCTCGAG CTGGTGAAGG
57601 CCGAGCCCGG GCTCATGAGG AACGCGCTCG ATGAGGTGCT CCGCTTCGAC AATATCCTCA
57661 GAATAGGAAC TGTGCGTTTC GCCAGGCAGG ACCTGGAGTA CTGCGGGGCA TCGATCAAGA
57721 AAGGGAGAT GGTCTTTCTC CTGATCCCGA GCGCCCTGAG AGATGGGACT GTATTCTCCA
57781 GGCCAGACGT GTTTGATGTG CGACGGGACA CGAGCGCGAG CCTCGCGTAC GGTAGAGGCC
57841 CCCATGTCTG CCCCGGGGTG TCCCTTGCTC GCCTCGAGGC GGAGATCGCC GTGGGCACCA
57901 TCTTCCGTAG GTTCCCCGAG ATGAAGCTGA AGAAACTCC CGTGTTTGGA TACCACCCCG
57961 CGTTCCGGAA CATCGAATCA CTCAACGTCA TCTTGAAGCC CTCCAAAGCT GGATAACTCG
58021 CGGGGGCATC GCTTCCCGAA CCTCATTCTT TCATGATGCA ACTCGCGCGC GGGTGCTGTC
58081 TGCCGCGGGT GCGATTCGAT CCAGCGGACA AGCCCATTGT CAGCGCGCGA AGATCGAATC
58141 CACGGCCCGG AGAAGAGCCC GATGGCGAGC CCGTCCGGGT AACGTCGGAA GAAGTGCCGG
58201 GCGCCGCCCT GGGAGCGCAA AGCTCGCTCG CTCGCGCTCA GCGCGCCGCT TGCCATGTCC
58261 GGCCCTGCAC CCGCACCGAG GAGCCACCCG CCCTGATGCA CGGCCTCACC GAGCGGCAGG
58321 TTCTGCTCTC GCTCGTCGCC CTCGCGCTCG TCCTCCTGAC CGCGCGCGCC TTCGGCGAGC
58381 TCGCGCGGCG GCTGCGCCAG CCCGAGGTGC TCGGCGAGCT CTTCGGCGGC GTGGTGCTGG
58441 GCCCGTCCGT CGTCGGCGCG CTCGCTCCTG GGTTCCATCG AGTCCTCTTC CAGGATCCGG
58501 CGGTCGGGGG CGTGCTCTCC GGCATCTCCT GGATAGGCGC GCTCGTCCTG CTGCTCATGG
58561 CGGGTATCGA GGTCGATGTG AGCATTCTAC GCAAGGAGGC GCGCCCCGGG GCGCTCTCGG
58621 CGCTCGGCGC GATCGCGCCC CCGCTGCGCA CGCCGGGCCC GCTGGTGCAG CGCATGCAGG
58681 GCACGTTGAC GTGGGATCTC GACGTCTCGC CGCGACGCTC TGCGCAAGCC TGAGCCTCGG
58741 CGCCTGCTCG TACACCTCGC CGGTGCTCGC TCCGCCCGCG GACATCCGGC CGCCCCCCGC
58801 GGCCCAGCTC GAGCCGGACT CGCCGGATGA CGAGGCCGAC GAGGCGCTCC GCCCGTTCCG
58861 CGACGCGATC GCCGCGTACT CGGAGGCCGT TCGGTGGGCG GAGGCGGCGC AGCGGCCGCG
58921 GCTGGAGAGC CTCGTGCGGC TCGCGATCGT GCGGCTGGGC AAGGCGCTCG ACAAGGCACC
58981 TTTCGCGCAC ACGACGGCCG GCGTCTCCCA GATCGCCGGC AGACTTCCCC AGAAAAACGAA
59041 TGCGGTCTGG TTCGATGTCG CCGCCCGGTA CGCGAGCTTC CGCGCGGCGA CGGAGCACGC
59101 GCTCCGCGAC GCGGCGTCGG CCACGGAGGC GCTCGCGGCC GGCCCGTACC GCGGATCGAG
59161 CAGCGTGTCC GCTGCCGTAG GGGAGTTTCG GGGGGAGGCG GCGCGCCTTC ACCCCGCGGA
59221 CCGCGTACCC GCGTCCGACC AGCAGATCCT GACCGCGCTG CGCGCAGCCG AGCGGGCGCT
59281 CATCGCGCTC TACACCGCGT TCGCCCGTGA GGAGTGAGCC TCTCTCGGGC GCAGCCGAGC
59341 GGCGGCGTGC CGGTTGTTCC CTCTTCGCAA CCATGACCGG AGCCGCGCCC GGTCCGCGCA
59401 GCGGCTAGCG CGCGTCGAGG CAGAGAGCGC TGGAGCGACA GGCGACGACC CGCCCGAGGG
59461 TGTCGAACGG ATTGCCGCAG CCCTCATTGC GGATCCCCTC CAGACACTCG TTCAGCGCCT
59521 TGGCGTCGAT GCCGCCTGGG CACTCGCCGA AGGTCAGCTC GTCGCGCCAG TCGGATCGGA
59581 TCTTGTTCGA GCACGCATCC TTGCTCGAAT ACTCCCGGTC TTGTCCGATG TTGTTGCACC
59641 GCGCCTCGCG GTCGCACCGC GCCGCCACGA TGCTATCGAC GGCGCTGCCG ACTGGCACCG
```

```
-continued
59701   GCGCCTCGCC TTGCGCGCCA CCCGGGGTTT GCGCCTCCCC GCCTGACCGC TTTTCGCCGC
59761   CGCACGCCGC CGCGAGCAGG CTCATTCCCG ACATCGAGAT CAGGCCCACG ACCAGTTTCC
59821   CAGCAATCTT TTGCATGGCT TCCCCTCCCT CACGACACGT CACATCAGAG ATTCTCCGCT
59881   CGGCTCGTCG GTTCGACAGC CGGCGACGGC CACGAGCAGA ACCGTCCCCG ACCAGAACAG
59941   CCGCATGCGG GTTTCTCGCA GCATGCCACG ACATCCTTGC GACTAGCGTG CCTCCGCTCG
60001   TGCCGAGATC GGCTGTCCTG TGCGACGGCA ATGTCCTGCG ATCGGCCGGG CAGGATCGAC
60061   CGACACGGGC GCCGGGCTGG AGGTGCCGCC ACGGGCTCGA AATGCGCTGT GGCAGGCGCC
60121   TCCATGCCCG CTGCCGGGAA CGCAGCGCCC GGCCAGCCTC GGGGCGACGC TGCGAACGGG
60181   AGATGCTCCC GGAGAGGCGC CGGGCACAGC CGAGCGCCGT CACCACCGTG CGCACTCGTG
60241   AGCGCTAGCT CCTCGGCATA GAAGAGACCG TCACTCCCGG TCCGTGTAGG CGATCGTGCT
60301   GATCAGCGCG TCCTCCGCCT GACGCGAGTC GAGCCGGGTA TGCTGCACGA CGATGGGCAC
60361   GTCCGATTCG ATCACGCTGG CATAGTCCGT ATCGCGCGGG ATCGGCTCGG GGTCGGTCAG
60421   ATCGTTGAAC CGGACGTGCC GGGTGCGCCT CGCTGGAACG GTCACCCGGT ACGGCCCGGC
60481   GGGGTCGCGG TCGCTGAAGT AGACGGTGAT GGCGACCTGC GCGTCCCGGT CCGACGCATT
60541   CAACAGGCAG GCCGTCTCAT GGCTCGTCAT CTGCGGCTCA GGTCCGTTGC TCCGGCCTGG
60601   GATGTAGCCC TCTGCGATTG CCCAGCGCGT CCGCCCGATC GGCTTGTCCA TGTGTCCTCC
60661   CTCCTGGCTC CTCTTTGGCA GCCTCCCTCT GCTGTCCAGG TGCGACGGCC TCTTCGCTCG
60721   ACGCGCTCGG GGCTCCATGG CTGAGAATCC TCGCCGAGCG CTCCTTGCCG ACCGGCGCGC
60781   TGAGCGCCGA CGGGCCTTGA AGCACGCGA CCGGACACGG GATGCCGGCG CGACGAGGCC
60841   GCCCCGCGTC TGATCCCGAT CGTGGCATCA CGACGTCCGC CGACGCCTCG GCAGGCCGGC
60901   GTGAGCGCTG CGCGGTCATG GTCGTCCTCG CGTCACCGCC ACCCGCCGAT TCACATCCCA
60961   CCGCGGCACG ACGCTTGCTC AAACCGCGAC GACACGGCCG GGCGGCTGTG GTACCGGCCA
61021   GCCCGGACGC GAGGCCCGAG AGGGACAGTG GGTCCGCCGT GAAGCAGAGA GGCGATCGAG
61081   GTGGTGAGAT GAAACACGTT GACACGGGCC GACGAGTCGG CCGCCGGATA GGGCTCACGC
61141   TCGGTCTCCT CGCGAGCATG GCGCTCGCCG GCTGCGGCGG CCCGAGCGAG AAGACCGTGC
61201   AGGGCACGCG GCTCGCGCCC GGCGCCGATG CGCACGTCAC CGCCGACGTC GACGCCGACG
61261   CCGCGACCAC GCGGCTGGCG GTGGACGTCG TTCACCTCTC GCCGCCCGAG CGGATCGAGG
61321   CCGGCAGCGA GCGGTTCGTC GTCTGGCAGC GTCCGAACTC CGAGTCCCCG TGGCTACGGG
61381   TCGGAGTGCT CGACTACAAC GCTGCCAGCC GAAGAGGCAA GCTGGCCGAG ACGACCGTGC
61441   CGCATGCCAA CTTCGAGCTG CTCATCACCG TCGAGAAGCA GAGCAGCCCT CAGTCGCCAT
61501   CGTCTGCCGC CGTCATCGGG CCGACGTCCG TCGGGTAACA TCGCGCTATC AGCAGCGCTG
61561   AGCCCGCCAG CATGCCCCAG AGCCCTGCCT CGATCGCTTT CCCCATCATC CGTGCGCACT
61621   CCTCCAGCGA CGGCCGCGTC AAAGCAACCG CCGTGCCGGC GCGGCTCTAC GTGCGCGACA
61681   GGAGAGCGTC CTAGCGCGGC CTGCGCATCG CTGGAAGGAT CGGCGGAGCA TGGAGAAAGA
61741   ATCGAGGATC GCGATCTACG GCGCCGTCGC CGCCAACGTG GCGATCGCGG CGGTCAAGTT
61801   CATCGCCGCC GCCGTGACCG GCAGCTCTGC GATGCTCTCC GAGGGCGTGC ACTCCCTCGT
61861   CGATACCGCA GACGGGCTCC TCCTCCTGCT CGGCAAGCAC CGGAGCGCCC GCCCGCCCGA
61921   CGCCGAGCAT CCGTTCGGCC ACGGCAAGGA GCTCTATTTC TGGACGCTGA TCGTCGCCAT
61981   CATGATCTTC GCCGCGGGCG GCGGCGTCTC GATCTACGAA GGGATCTTGC ACCTCTTGCA
62041   CCCGCGCTCG ATCGAGGATC CGACGTGGAA CTACGTTGTC CTCGGCGCAG CGGCCGTCTT
```

```
62101  CGAGGGGACG TCGCTCGCCA TCTCGATCCA CGAGTTCAAG AAGAAAGACG GACAGGGCTA
62161  CGTCGCGGCG ATGCGGTCCA GCAAGGACCC GACGACGTTC ACGATCGTCC TGGAGGATTC
62221  CGCGGCGCTC GCCGGGCTCG CCATCGCCTT CCTCGGCGTC TGGCTTGGGC ACCGCCTGGG
62281  AAACCCCTAC CTCGACGGCG CGGCGTCGAT CGGCATCGGC CTCGTGCTCG CCGCGGTCGC
62341  GGTCTTCCTC GCCAGCCAGA GCCGTGGACT CCTCGTAGGG GAGAGCGCGG ACAGGGAGCT
62401  CCTCGCCGCG ATCCGCGCGC TCGCCAGCGC AGATCCTGGC GTGTCGGCGG TGGGGCGGCC
62461  CCTGACGATG CACTTCGGTC CGCACGAAGT CCTGGTCGTG CTGCGCATCG AGTTCGACGC
62521  CGCGCTCACG GCGTCCGGGG TCGCGGAGGC GATCGAGCGA ATCGAGACAC GGATACGGAG
62581  CGAGCGACCC GACGTGAAGC ACATCTACGT CGAGGCCAGG TCGCTCCACC AGCGCGCGAG
62641  GGCGTGACGC GCCGTGGAGA GACCGCTCGC GGCCTCCGCC ATCCTCCGCG GCGCCCGGGC
62701  TCGGGTAGCC CTCGCAGCAG GGCGCGCCTG GCGGGCAAAC CGTGAAGACG TCGTCCTTCG
62761  ACGCGAGGTA CGCTGGTTGC AAGTTGTCAC GCCGTATCGC GAGGTCCGGC AGCGCCGGAG
62821  CCCGGGCGGT CCGGGCGCAC GAAGGCCCGG CGAGCGCGGG CTTCGAGGGG GCGACGTCAT
62881  GAGGAAGGGC AGGGCGCATG GGGCGATGCT CGGCGGGCGA GAGGACGGCT GGCGTCGCGG
62941  CCTCCCCGGC GCCGGCGCGC TTCGCGCCGC GCTCCAGCGC GGTCGCTCGC GCGATCTCGC
63001  CCGGCGCCGG CTCATCGCCG CCGTGTCCCT CACCGGCGGC GCCAGCATGG CGGTCGTCTC
63061  GCTGTTCCAG CTCGGGATCA TCGAGCACCT GCCCGATCCT CCGCTTCCAG GGTTCGATTC
63121  GGCCAAGGTG ACGAGCTCCG ATATCGCGTT CGGGCTCACG ATGCCGGACG CGCCGCTCGC
63181  GCTCACCAGC TTCGCGTCCA ACCTGGCGCT GGCTGGCTGG GGAGGCGCCG AGCGCGCCAG
63241  GAACACCCCC TGGATCCCCG TCGCCGTGGC GGCCAAGGCG GCCGTCGAGG CGGCCGTGTC
63301  CGGATGGCTC CTCGTCCAGA TGCGACGGCG GGAGAGGGCC TGGTGCGCGT ACTGCCTGGT
63361  CGCCATGGCG GCCAACATGG CCGTGTTCGC GCTCTCGCTC CCGGAAGGGT GGGCGGCGCT
63421  GAGGAAGGCG CGAGCGCGCT CGTGACAGGG CCGTGCGGGC GCCGCGGCCA TCGGAGGCCG
63481  GCGTGCACCC GCTCCGTCAC GCCCCGGCCC GCGCCGCGGT GAGCTGCCGC GGACAGGGCG
63541  CGTACCGTGG ACCCCGCACG CGCCGCGTCG ACGGACATCC CCGGCGGCTC GCGCGGCGCG
63601  GCCGGCGCAA CTCCGGCCCG CCGCCGGGCA TCGACATCTC CCGCGAGCAA GGGCACTCCG
63661  CTCCTGCCCG CGTCCGCGAA CGATGGCTGC GCTGTTTCCA CCCTGGAGCA ACTCCGTTTA
63721  CCGCGTGGCG CTCGTCGGGC TCATCGCCTC GGCGGGCGGC GCCATCCTCG CGCTCATGAT
63781  CTACGTCCGC ACGCCGTGGA AGCGATACCA GTTCGAGCCC GTCGATCAGC CGGTGCAGTT
63841  CGATCACCGC CATCACGTGC AGGACGATGG CATCGATTGC GTCTACTGCC ACACCACGGT
63901  GACCCGCTCG CCGACGGCGG GGATGCCGCC GACGGCCACG TGCATGGGGT GCCACAGCCA
63961  GATCTGGAAT CAGAGCGTCA TGCTCGAGCC CGTGCGGCGG AGCTGGTTCT CCGGCATGCC
64021  GATCCCGTGG AACCGGGTGA ACTCCGTGCC CGACTTCGTT TATTTCAACC ACGCGATTCA
64081  CGTGAACAAG GGCGTGGGCT GCGTGAGCTG CCACGGGCGC GTGGACGAGA TGGCGGCCGT
64141  CTACAAGGTG GCGCCGATGA CGATGGGCTG GTGCCTGGAG TGCCATCGCC TGCCGGAGCC
64201  GCACCTGCGC CCGCTCTCCG CGATCACCGA CATGCGCTGG GACCCGGGGG AACGGAGGGA
64261  CGAGCTCGGG GCGAAGCTCG CGAAGGAGTA CGGGGTCCGG CGGCTCACGC ACTGCACAGC
64321  GTGCCATCGA TGAACGATGA ACAGGGGATC TCCGTGAAAG ACGCAGATGA GATGAAGGAA
64381  TGGTGGCTAG AAGCGCTCGG GCCGGCGGGA GAGCGCGCGT CCTACAGGCT GCTGGCGCCG
64441  CTCATCGAGA GCCCGGAGCT CCGCGCGCTC GCCGCGGGCG AACCGCCCCG GGGCGTGGAC
```

```
-continued
64501  GAGCCGGCGG GCGTCAGCCG CCGCGCGCTG CTCAAGCTGC TCGGCGCGAG CATGGCGCTC
64561  GCCGGCGTCG CGGGCTGCAC CCCGCATGAG CCCGAGAAGA TCCTGCCGTA CAACGAGACC
64621  CCGCCCGGCG TCGTGCCGGG TCTCTCCCAG TCCTACGCGA CGAGCATGGT GCTCGACGGG
64681  TATGCCATGG GCCTCCTCGC CAAGAGCTAC GCGGGGCGGC CCATCAAGAT CGAGGGCAAC
64741  CCCGCGCACC CGGCGAGCCT CGGCGCGACC GGCGTCCACG AGCAGGCCTC GATCCTCTCG
64801  CTGTACGACC CGTACCGCGC GCGCGCGCCG ACGCGCGGCG GCCAGGTCGC GTCGTGGGAG
64861  GCGCTCTCCG CGCGCTTCGG CGGCGACCGC GAGGACGGCG GCGCTGGCCT CCGCTTCGTC
64921  CTCCAGCCCA CGAGCTCGCC CCTCATCGCC GCGCTGATCG AGCGCGTCCG GCGCAGGTTC
64981  CCCGGCGCGC GGTTCACCTT CTGGTCGCCG GTCCACGCCG AGCAAGCGCT CGAAGGCGCG
65041  CGGGCGGCGC TCGGCCTCAG GCTCTTGCCT CAGCTCGACT TCGACCAGGC CGAGGTGATC
65101  CTCGCCCTGG ACGCGGACTT CCTCGCGGAC ATGCCGTTCA GCGTGCGCTA TGCGCGCGAC
65161  TTCGCCGCGC GCCGCCGACC CGCGAGCCCG GCGGCGGCCA TGAACCGCCT CTACGTCGCG
65221  GAGGCGATGT TCACGCCCAC GGGGACGCTC GCCGACCACC GGCTCCGCGT GCGGCCCGCC
65281  GAGGTCGCGC GCGTCGCGGC CGGCGTCGCG GCGGAGCTCG TGCACGGCCT CGGCCTGCGC
65341  CCGCGCGGGA TCACGGACGC CGACGCCGCC GCGCTGCGCG CGCTCCGCCC CCCGGACGGC
65401  GAGGGGCACG GCGCCTTCGT CCGGGCGCTC GCGCGCGATC TCGCGCGCGC GGGGGGCGCC
65461  GGCGTCGCCG TCGTCGGCGA CGGCCAGCCG CCCATCGTCC ACGCCCTCGG GCACGTCATC
65521  AACGCCGCGC TCCGCAGCCG GGCGGCCTGG ATGGTCGATC CTGTGCTGAT CGACGCGGGC
65581  CCCTCCACGC AGGGCTTCTC CGAGCTCGTC GGCGAGCTCG GGCGCGGCGC GGTCGACACC
65641  TGATCCTCCT CGACGTGAAC CCCGTGTACG CCGCGCGGGC CGACGTCGAT TTCGCGGGCC
65701  TCCTCGCGCG CGTGCCCACG AGCTTGAAGG CCGGGCTCTA CGACGACGAG ACCGCCCGCG
65761  CTTGCACGTG GTTCGTGCCG ACCCGGCATT ACCTCGAGTC GTGGGGGGAC GCGCGGGCGT
65821  ACGACGGGAC GGTCTCGTTC GTGCAACCCC TCGTCCGGCC GCTGTTCGAC GGCCGGGCGG
65881  TGCCCGAGCT GCTCGCCGTC TTCGCGGGGG ACGAGCGCCC GGATCCCCGG CTGCTGCTGC
65941  GCGAGCACTG GCGCGGCGCG CGCGGAGAGG CGGATTTCGA GGCCTTCTGG GGCGAGGCAT
66001  TGAAGCGCGG CTTCCTCCCT GACAGCGCCC GGCCGAGGCA GACACCGGAT CTCGCGCCGG
66061  CCGACCTCGC CAAGGAGCTC GCGCGGCTCG CCGCCGCGCC GCGGCCGGCC GGCGGCGCGC
66121  TCGACGTGGC GTTCCTCAGG TCGCCGTCGG TCCACGACGG CAGGTTCGCC AACAACCCCT
66181  GGCTGCAAGA GCTCCCGCGG CCGATCACCA GGCTCACCTG GGGCAACGCC GCCATGATGA
66241  GCGCGGCGAC CGCGGCGCGG CTCGGCGTCG AGCGCGGCGA TGTCGTCGAG CTCGCGCTGC
66301  GCGGCCGTAC GATCGAGATC CCGGCCGTCG TCGTCCGCGG CACGCCGAC GACGTGATCA
66361  GCGTCGACCT CGGCTACGGG CGCGACGCCG GCGAGGAGGT CGCGCGCGGG GTGGGCGTGT
66421  CGGCGTATCG GATCCGCCCG TCCGACGCGC GGTGGTTCGC GGGGGGCCTC TCCGTGAGGA
66481  AGACCGGCGC CACGGCCGCG CTCGCGCTGG CTCAGATCGA GCTGTCCCAG CACGACCGTC
66541  CCATCGCGCT CCGGAGGACG CTGCCGCAGT ACCGTGAACA GCCCGGTTTC GCGGAGGAGC
66601  ACAAGGGGCC GGTCCGCTCG ATCCTGCCGG AGGTCGAGTA CACCGGCGCG CAATGGGCGA
66661  TGTCCATCGA CATGTCGATC TGCACCGGGT GCTCCTCGTG CGTCGTGGCC TGTCAGGCCG
66721  AGAACAACGT CCTCGTCGTC GGCAAGGAGG AGGTGATGCA CGGCCGCGAG ATGCAGTGGT
66781  TGCGGATCGA TCAGTACTTC GAGGGTGGAG GCGACGAGGT GAGCGTCGTC AACCAGCCGA
66841  TGCTCTGCCA GCACTGCGAG AAGGCGCCGT GCGAGTACGT CTGTCCGGTG AACGCGACGG
```

```
66901  TCCACAGCCC CGATGGCCTC AACGAGATGA TCTACAACCG ATGCATCGGG ACGCGCTTTT
66961  GCTCCAACAA CTGTCCGTAC AAGATCCGGC GGTTCAATTT CTTCGACTAC AATGCCCACG
67021  TCCCGTACAA CGCCGGCCTC CGCAGGCTCC AGCGCAACCC GGACGTCACC GTCCGCGCCC
67081  GCGGCGTCAT GGAGAAATGC ACGTACTGCG TGCAGCGGAT CCGAGAGGCG GACATCCGCG
67141  CGCAGATCGA GCGGCGGCCG CTCCGGCCGG GCGAGGTGGT CACCGCCTGC CAGCAGGCCT
67201  GTCCGACCGG CGCGATCCAG TTCGGGTCGC TGGATCACGC GGATACAAAG ATGGTCGCGT
67261  GGCGCAGGGA GCCGCGCGCG TACGCCGTGC TCCACGACCT CGGCACCCGG CCGCGGACGG
67321  AGTACCTCGC CAAGATCGAG AACCCGAACC CGGGGCTCGG GGCGGAGGGC GCCGAGAGGC
67381  GACCCGGAGC CCCGAGCGTC AAACCCGCGC TCGGGCGGA GGGCGCCGAG AGGCGACCCG
67441  GAGCCCCGAG CGTCAAACCG GAGATTGAAT GAGCCATGGC GGGCCCGCTC ATCCTGGACG
67501  CACCGACCGA CGATCAGCTG TCGAAGCAGC TCCTCGAGCC GGTATGGAAG CCGCGCTCCC
67561  GGCTCGGCTG GATGCTCGCG TTCGGGCTCG CGCTCGGCGG CACGGGCCTG CTCTTCCTCG
67621  CGATCACCTA CACCGTCCTC ACCGGGATCG GCGTGTGGGG CAACAACATC CCGGTCGCCT
67681  GGGCCTTCGC GATCACCAAC TTCGTCTGGT GGATCGGGAT CGGCCACGCC GGGACGTTCA
67741  TCTCCGCGAT CCTCCTCCTG CTCGAGCAGA AGTGGCGGAC GAGCATCAAC CGCTTCGCCG
67801  AGGCGATGAC GCTCTTCGCG GTCGTCCAGG CCGGCCTCTT TCCGGTCCTC CACCTCGGCC
67861  GCCCCTGGTT CGCCTACTGG ATCTTCCCGT ACCCCGCGAC GATGCAGGTG TGGCCGCAGT
67921  TCCGGAGCGC GCTGCCGTGG GACGCCGCCG CGATCGCGAC CTACTTCACG GTGTCGCTCC
67981  TGTTCTGGTA CATGGGCCTC GTCCCGGATC TGGCGGCGCT GCGCGACCAC GCCCCGGGCC
68041  GCGTCCGGCG GGTGATCTAC GGGCTCATGT CGTTCGGCTG GCACGGCGCG GCCGACCACT
68101  TCCGGCATTA CCGGGTGCTG TACGGGCTGC TCGCGGGGCT CGCGACGCCC CTCGTCGTCT
68161  CGGTGCACTC GATCGTGAGC AGCGATTTCG CGATCGCCCT GGTGCCCGGC TGGCACTCGA
68221  CGCTCTTTCC GCCGTTCTTC GTCGCGGGCG CGATCTTCTC CGGGTTCGCG ATGGTGCTCA
68281  CGCTGCTCAT CCCGGTGCGG CGGATCTACG GGCTCCATAA CGTCGTGACC GCGCGCCACC
68341  TCGACGATCT CGCGAAGATG ACGCTCGTGA CCGGCTGGAT CGTCATCCTC TCGTACATCA
68401  TCGAGAACTT CCTCGCCTGG TACAGCGGCT CGGCGTACGA GATGCATCAG TTTTTCCAGA
68461  CGCGCCTGCA CGGCCCGAAC AGCGCCGCCT ACTGGGCCCA GCACGTCTGC AACGTGCTCG
68521  TCATCCAGCT CCTCTGGAGC GAGCGGATCC GGACGAGCCC CGTCGCGCTC TGGCTCATCT
68581  CCCTCCTGGT CAACGTCGGG ATGTGGAGCG AGCGGTTCAC GCTCATCGTG ATGTCGCTCG
68641  AGCAAGAGTT CCTCCCGTCC AAGTGGCACG GCTACAGCCC GACGTGGGTG GACTGGAGCC
68701  TCTTCATCGG GTCAGGCGGC TTCTTCATGC TCCTGTTCCT GAGCTTTTTG CGCGTCTTTC
68761  CGTTCATCCC CGTCGCGGAG GTCAAGGAGC TCAACCATGA AGAGCTGGAG AAGGCTCGGG
68821  GCGAGGGGGG CCGCTGATGA AGACCGGAAT GCTCGGCGAG TTCGATGACC CGGAGGCGAT
68881  GCTCCATGCG ATCCGAGAGC TCAGGCGGCG CGGCTACCGC CGGGTGGAAG CGTTCACGCC
68941  CTATCCGGTG AAGGGGCTCG ACGAGGCGCT CGGCCTCCCG CGCTCGAACC TCAACCGGAT
69001  GGTGCTGCCC TTCGCGATCC TGGGGGTCGT GGGCGGCTAC TTCGTCCAGT GGTTCTGCAA
69061  CGCTTTCCAC TATCCGCTGA ACGTGGGCGG GCGCCCGCTG AACTCGGCGC CGGCGTTCAT
69121  CCCGATCACG TTCGAGATGG GGGTGCTCTC CACCTCGATC TTCGGCGTGC TCATCGGCTT
69181  TTACCTGACG AGGCTGCCGA GGCTCTACCT CCCGCTCTTC GACGCCCCGG GCTTCGAGCG
69241  CGTCACGCTG GATCGGTTTC TGGTCGGGCT CGACGACACG GAACCTTCCT TCTCGAGCGC
```

```
69301  CCAGGCGGAG CGCGACCTCC TCGCGCTCGG CGCCCGGCGC GTCGTCGTCG CGAGGAGGCG
69361  CGAGGAGCCA TGAGGGCCGG CGCCCCGGCT CGCCCTCTCG GGCGCGCGCT CGCGCCGTTC
69421  GCCCTCGTCC TGCTCGCCGG GTGCCGCGAG AAGGTGCTGC CCGAGCCGGA CTTCGAGCGG
69481  ATGATCCGCC AGGAGAAATA CGGACTCTGG GAGCCGTGCG AGCACTTCGA CGACGGCCGC
69541  GCGATGCAGC ACCCGCCCGA GGGGACCGTC GCGCGCGGGC GCGTCACCGG GCCGCCCGGC
69601  TATCTCCAGG GCGTCCTCGA CGGGGCGTAC GTCACGGAGG TGCCGCTCTT GCTCACGGTC
69661  GAGCTCGTGC AGCGCGGCCG GCAGCGCTTC GAGACCTTCT GCGCGCCGTG CCACGGGATC
69721  CTCGGCGACG GCAGCTCGCG CGTGGCGACG AACATGACGC TGCCCCGCC CCCGTCGCTC
69781  ATCGGACCCG AGGCGCGGAG CTTCCCGCCG GGCAGGATCT ACCAGGTCAT CATCGAGGGC
69841  TACGGCCTGA TGCCGCGCTA CTCGGACGAT CTGCCCGACA TCGAAGAGCG CTGGGCCGTG
69901  GTCGCCTACG TGAAGGCGCT TCAGCTGAGC CGCGGAGTGG CCGCGGGCGC CCTCCCGCCA
69961  GCGCTCCGCG GCCGGGCAGA GCAGGAGCTG CGATGAACAG GGATGCCATC GAGTACAAGG
70021  GCGGCGCGAC GATCGCGGCC TCGCTCGCGA TCGCGGCGCT CGGCGCGGTC GCCGCGATCG
70081  TCGGCGGCTT CGTCGATCTC CGCCGGTTCT TCTTCTCGTA CCTCGCCGCG TGGTCGTTCG
70141  CGGTGTTTCT GTCCGTGGGC GCGCTCGTCA CGCTCCTCAC CTGCAACGCC ATGCGCGCGG
70201  GCTGGCCCAC GGCGGTGCGC CGCCTCCTCG AGACGATGGT GGCGCCGCTG CCTCTGCTCG
70261  CGGCGCTCTC CGCGCCGATC CTGGTCGGCC TGGACACGCT GTATCCGTGG ATGCACCCCG
70321  AGCGGATCGC CGGCGAGCAC GCGCGGCGCA TCCTCGAGCA CAGGGCGCCC TACTTCAATC
70381  CAGGCTTCTT CGTCGTGCGC TCGGCGATCT ACTTCGCGAT CTGGATCGCC GTCGCCCTCG
70441  TGCTCCGCCG GCGATCGTTC GCGCAGGACC GTGAGCCGAG GGCCGACGTC AAGGACGCGA
70501  TGTATGGCCT GAGCGGCGCC ATGCTGCCGG TCGTGGCGAT CACGATCGTC TTCTCGTCGT
70561  TCGACTGGCT CATGTCCCTC GACGCGACCT GGTACTCGAC GATGTTCCCG GTCTACGTGT
70621  TCGCGAGCGC CTTCGTGACC GCCGTCGGCG CGCTCACGGT CCTCTCGTAT GCCGCGCAGA
70681  CGTCCGGCTA CCTCGCGAGG CTGAACGACT CGCACTATTA CGCGCTCGGG CGGCTGCTCC
70741  TCGCGTTCAC GATATTCTGG GCCTATGCGG CCTATTTCCA GTTCATGTTG ATCTGGATCG
70801  CGAACAAGCC CGATGAGGTC GCCTTCTTCC TCGACCGCTG GGAAGGGCCC TGGCGGCCGA
70861  CCTCCGTGCT CGTCGTCCTC ACGCGGTTCG TCGTCCCGTT CCTGATCCTG ATGTCGTACG
70921  CGATCAAGCG GCGCCCGCGC CAGCTCTCGT GGATGGCGCT CTGGGTCGTC GTCTCCGGCT
70981  ACATCGACTT TCACTGGCTC GTGGTGCCGG CGACAGGGCC CCACGGGTTC GCCTATCACT
71041  GGCTCGACCT CGCGACCCTG TGCGTCGTGG GCGGCCTCTC GACCGCGTTC GCCGCGTGGC
71101  GGCTGCGAGG GCGGCCGGTG GTCCCGGTCC ACGACCCGCG GCTCGAAGAG GCCTTTGCGT
71161  ACCGGAGCAT ATGATGTTCC GTTTCCGTCA CAGCGAGGTT CGCCAGGAGG AGGACACGCT
71221  CCCCTGGGGG CGCGTGATCC TCGCGTTCGC CGTCGTGCTC GCGATCGGCG GCGCGCTGAC
71281  GCTCTGGGCC TGGCTCGCGA TGCGGGCCCG CGAGGCGGAT CTGCGGCCCT CCCTCGCGTT
71341  CCCCGAGAAG GATCTCGGGC CGCGGCGCGA GGTCGGCATG GTCCAGCAGT CGCTGTTCGA
71401  CGAGGCGCGC CTGGGCCAGC AGCTCGTCGA CGCGCAGCGC GCGGAGCTCC GCCGCTTCGG
71461  CGTCGTCGAT CGGGAGAGGG GCATCGTGAG CATCCCGATC GACGACGCGA TCGAGCTCAT
71521  GGTGGCGGGG GGCGCGCGAT GAGCCGGGCC GTCGCCGTGG CCCTCCTGCT GGCAGCCGGC
71581  CTCGTGTCGC GCCCGGGCGC CGCGTCCGAG CCCGAGCGCG CGCGCCCCGC GCTGGGCCCG
71641  TCCGCGGCCG ACGCCGCGCC GGCGAGCGAC GGCTCCGGCG CGGAGGAGCC GCCCGAAGGC
```

```
                                             -continued
71701    GCCTTCCTGG AGCCCACGCG CGGGGTGGAC ATCGAGGAGC GCCTCGGCCG CCCGGTGGAC

71761    CGCGAGCTCG CCTTCACCGA CATGGACGGG CGGCGGGTGC GCCTCGGCGA CTACTTCGCC

71821    GACGGCAAGC CCCTCCTCCT CGTCCTCGCG TACTACCGGT GTCCCGCGCT GTGCGGCCTC

71881    GTGCTGCGCG GCGCCGTCGA GGGGCTGAAG CTCCTCCCGT ACCGGCTCGG CGAGCAGTTC

71941    CACGCGCTCA CGGTCAGCTT CGACCCGCGC GAGCGCCCGG CGGCCGCDD
```

EXAMPLE 2

Construction of a *Myxococcus xanthus* Expression Vector

The DNA providing the integration and attachment function of phage Mx8 was inserted into commercially available pACYC184 (New England Biolabs). An ~2360 bp MfeI-SmaI from plasmid pPLH343, described in Salmi et al., February 1998, J. Bact. 180(3): 614-621, was isolated and ligated to the large EcoRI-XmnI restriction fragment of plasmid pACYC184. The circular DNA thus formed was ~6 kb in size and called plasmid pKOS35-77.

Plasmid pKOS35-77 serves as a convenient plasmid for expressing recombinant PKS genes of the invention under the control of the epothilone PKS gene promoter. In one illustrative embodiment, the entire epothilone PKS gene with its homologous promoter is inserted in one or more fragments into the plasmid to yield an expression vector of the invention.

The present invention also provides expression vectors in which the recombinant PKS genes of the invention are under the control of a *Myxococcus xanthus* promoter. To construct an illustrative vector, the promoter of the pilA gene of *M. xanthus* was isolated as a PCR amplification product. Plasmid pSWU357, which comprises the pilA gene promoter and is described in Wu and Kaiser, December 1997, J. Bact. 179 (24):7748-7758, was mixed with PCR primers Seq1 and Mxpil1 primers:

```
                                                 (SEQ ID NO: 3)
Seq1:     5'-AGCGGATAACAATTTCACACAGGAAACAGC-3';
and (SEQ ID NO: 4)
Mxpil1:   5'-TTAATTAAGAGAAGGTTGCAACGGGGGGC-3',
``` and amplified using standard PCR conditions to yield an ~800 bp fragment. This fragment was cleaved with restriction enzyme KpnI and ligated to the large KpnI-EcoRV restriction fragment of commercially available plasmid pLitmus 28 (New England Biolabs). The resulting circular DNA was designated plasmid pKOS35-71B.

The promoter of the pilA gene from plasmid pKOS35-71B was isolated as an ~800 bp EcoRV-SnaBI restriction fragment and ligated with the large MscI restriction fragment of plasmid pKOS35-77 to yield a circular DNA ~6.8 kb in size. Because the ~800 bp fragment could be inserted in either one of two orientations, the ligation produced two plasmids of the same size, which were designated as plasmids pKOS35-82.1 and pKOS35-82.2. Restriction site and function maps of these plasmids are presented in FIG. 3.

Plasmids pKOS35-82.1 and pKOS35-82.2 serve as convenient starting materials for the vectors of the invention in which a recombinant PKS gene is placed under the control of the *Myxococcus xanthus* pilA gene promoter. These plasmids comprise a single PacI restriction enzyme recognition sequence placed immediately downstream of the transcription start site of the promoter. In one illustrative embodiment, the entire epothilone PKS gene without its homologous promoter is inserted in one or more fragments into the plasmids at the PacI site to yield expression vectors of the invention.

The sequence of the pilA promoter in these plasmids is shown below (SEQ ID NO: 5).

```
CGACGCAGGTGAAGCTGCTTCGTGTGCTCCAGGAGCGGAAGGTGAAGCCG

GTCGGCAGCGCCGCGGAGATTCCCTTCCAGGCGCGTGTCATCGCGGCAAC

GAACCGGCGGCTCGAAGCCGAAGTAAAGGCCGGACGCTTTCGTGAGGACC

TCTTCTACCGGCTCAACGTCATCACGTTGGAGCTGCCTCCACTGCGCGAG

CGTTCCGGCGACGTGTCGTTGCTGGCGAACTACTTCCTGTCCAGACTGTC

GGAGGAGTTGGGGCGACCCGGTCTGCGTTTCTCCCCCGAGACACTGGGGC

TATTGGAGCGCTATCCCTTCCCAGGCAACGTGCGGCAGCTGCAGAACATG

GTGGAGCGGGCCGCGACCCTGTCGGATTCAGACCTCCTGGGGCCCTCCAC

GCTTCCACCCGCAGTGCGGGGCGATACAGACCCCGCCGTGCGTCCCGTGG

AGGGCAGTGAGCCAGGGCTGCTGGCGGGCTTCAACCTGGAGCGGCATCTC

GACGACAGCGAGCGGCGCTATCTCGTCGCGGCGATGAAGCAGGCCGGGGG

CGTGAAGACCCGTGCTGCGGAGTTGCTGGGCCTTTCGTTCCGTTCATTCC

GCTACCGGTTGGCCAAGCATGGGCTGACGGATGACTTGGAGCCCGGGAGC

GCTTCGGATGCGTAGGCTGATCGACAGTTATCGTCAGCGTCACTGCCGAA

TTTTGTCAGCCCTGGACCCATCCTCGCCGAGGGGATTGTTCCAAGCCTTG

AGAATTGGGGGGCTTGGAGTGCGCACCTGGGTTGGCATGCGTAGTGCTAA

TCCCATCCGCGGGCGCAGTGCCCCCCGTTGCAACCTTCTCTTAATTAA
```

To make the recombinant *Myxococcus xanthus* host cells of the invention, *M. xanthus* cells are grown in CYE media (Campos and Zusman, 1975, Regulation of development in *Myxococcus xanthus*: effect of 3':5'-cyclic AMP, ADP, and nutrition, Proc. Natl. Acad. Sci. USA 72: 518-522) to a Klett of 100 at 30° C. at 300 rpm. The remainder of the protocol is conducted at 25° C. unless otherwise indicated. The cells are then pelleted by centrifugation (8000 rpm for 10 min. in an SS34 or SA600 rotor) and resuspended in deionized water. The cells are again pelleted and resuspended in ¹⁄₁₀₀th of the original volume.

DNA (one to two µL) is electroporated into the cells in a 0.1 cm cuvette at room temperature at 400 ohm, 25 µFD, 0.65 V with a time constant in the range of 8.8-9.4. The DNA should be free of salts and so should be resuspended in distilled and deionized water or dialyzed on a 0.025 µm Type VS membrane (Millipore). For low efficiency electroporations, spot dialyze the DNA, and allow outgrowth in CYE. Immediately after electroporation, add 1 mL of CYE, and pool the cells in the cuvette with an additional 1.5 mL of CYE previously added to a 50 mL Erlenmeyer flask (total volume 2.5 ml). Allow the cells to grow for four to eight hours (or overnight) at 30 to 32° C. at 300 rpm to allow for expression of the selectable marker. Then, plate the cells in CYE soft agar on plates with selection. If kanamycin is the selectable marker, then typical yields are $10^3$ to $10^5$ per µg of DNA. If streptomycin is the selectable marker, then it must be included in the top agar, because it binds agar.

With this procedure, the recombinant DNA expression vectors of the invention are electroporated into *Myxococcus* host cells that express recombinant PKSs of the invention and produce the epothilone, epothilone derivatives, and other novel polyketides encoded thereby.

EXAMPLE 3

Construction of a Bacterial Artificial Chromosome (BAC) for Expression of Epothilone in *Myxococcus xanthus*

To express the epothilone PKS and modification enzyme genes in a heterologous host to produce epothilones by fermentation, *Myxococcus xanthus*, which is closely related to *Sorangium cellulosum* and for which a number of cloning vectors are available, can also be employed in accordance with the methods of the invention. Because both M xanthus and *S. cellulosum* are myxobacteria, it is expected that they share common elements of gene expression, translational control, and post translational modification (if any), thereby enhancing the likelihood that the epo genes from *S. cellulosum* can be expressed to produce epothilone in *M. xanthus*. Secondly, *M. xanthus* has been developed for gene cloning and expression. DNA can be introduced by electroporation, and a number of vectors and genetic markers are available for the introduction of foreign DNA, including those that permit its stable insertion into the chromosome. Finally, *M. xanthus* can be grown with relative ease in complex media in fermentors and can be subjected to manipulations to increase gene expression, if required.

To introduce the epothilone gene cluster into *Myxococcus xanthus*, one can build the epothilone cluster into the chromosome by using cosmids of the invention and homologous recombination to assemble the complete gene cluster. Alternatively, the complete epothilone gene cluster can be cloned on a bacterial artificial chromosome (BAC) and then moved into *M. xanthus* for integration into the chromosome.

Figure 4:
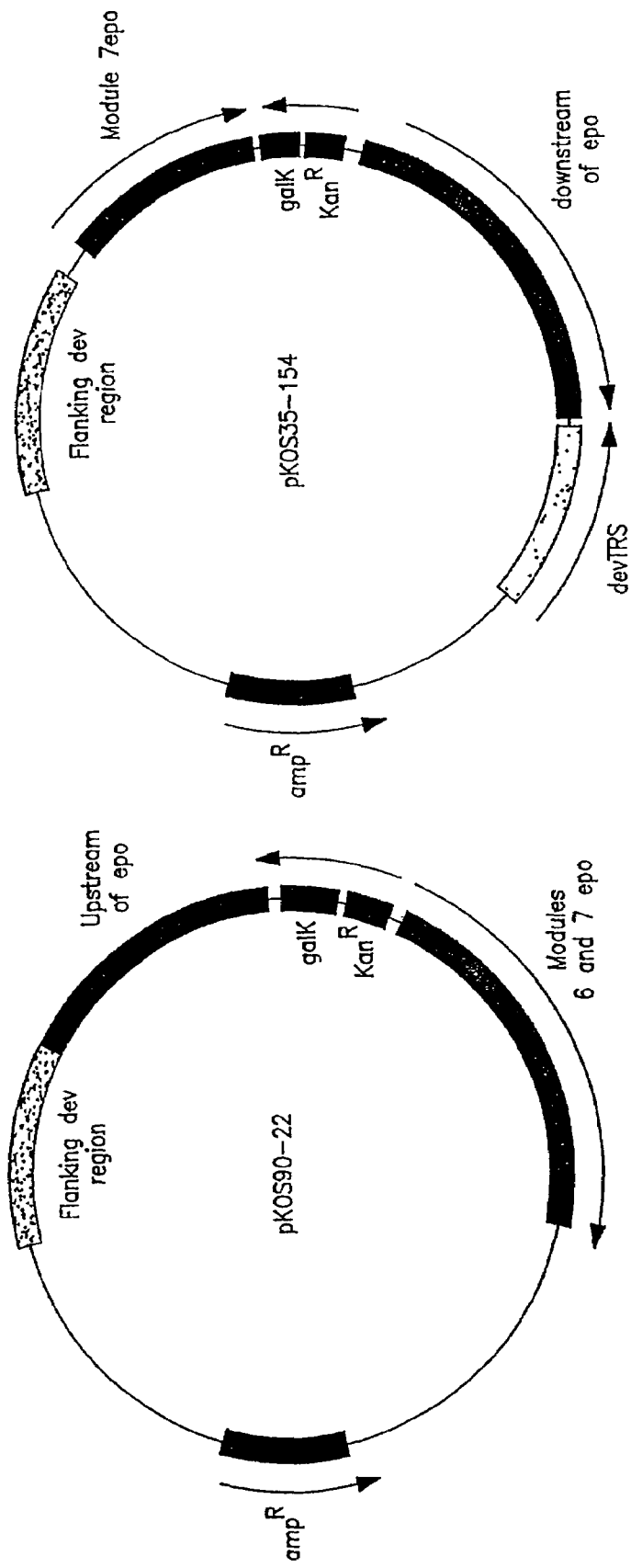
FIG. 4 shows restriction site and function maps of plasmids pKOS35-154 and pKOS90-22.
Figure 5:
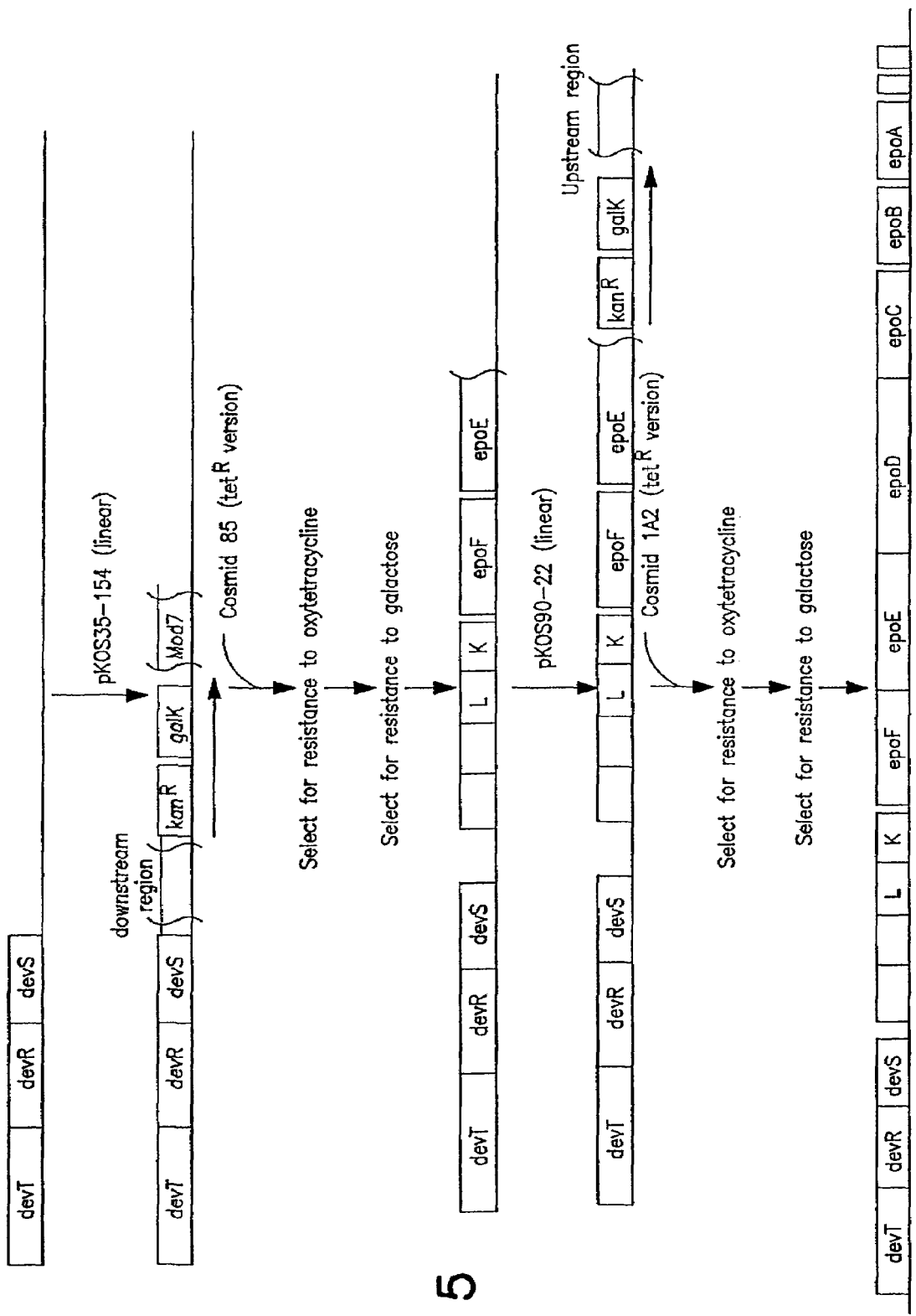
FIG. 5 shows a schematic of a protocol for introducing the epothilone PKS and modification enzyme genes into the chromosome of a *Myxococcus xanthus* host cell as described in Example 3.
Figure 6:
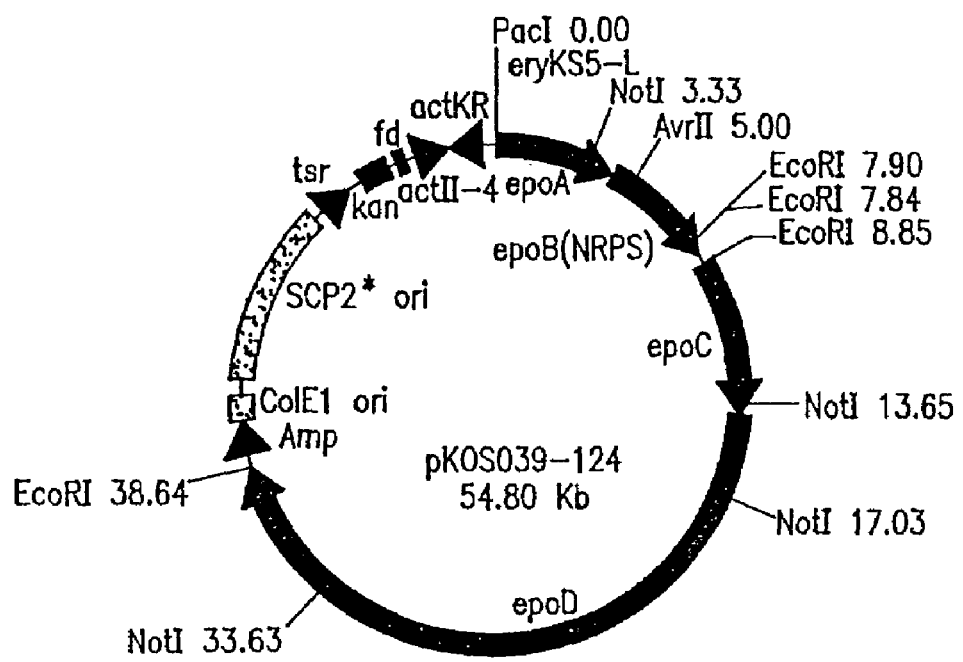
FIG. 6 shows restriction site and function maps of plasmids pKOS039-124 and pKOS039-124R.
Figure 6:
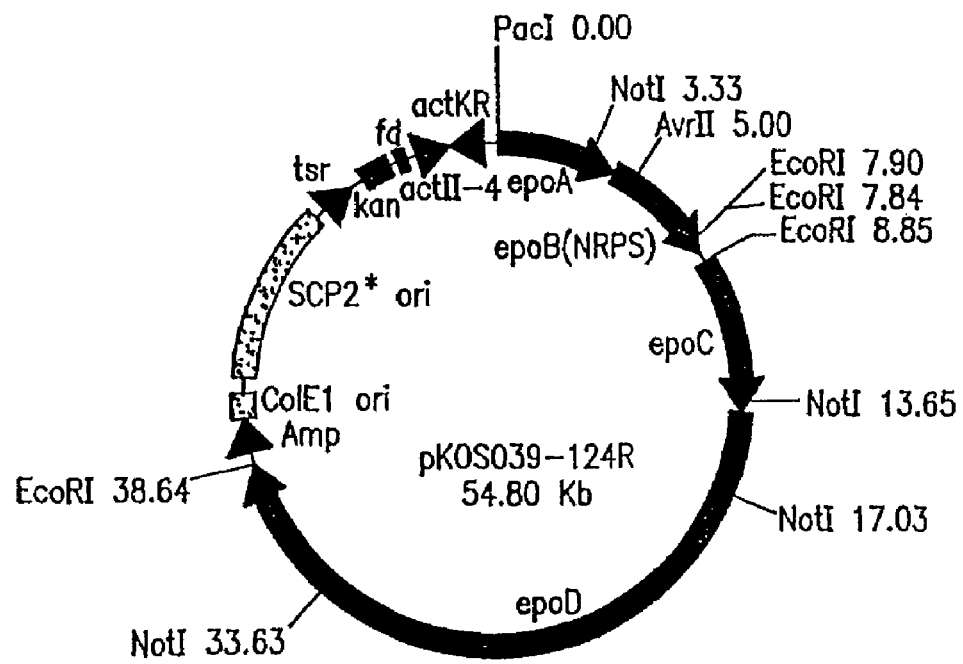
Figure 7:
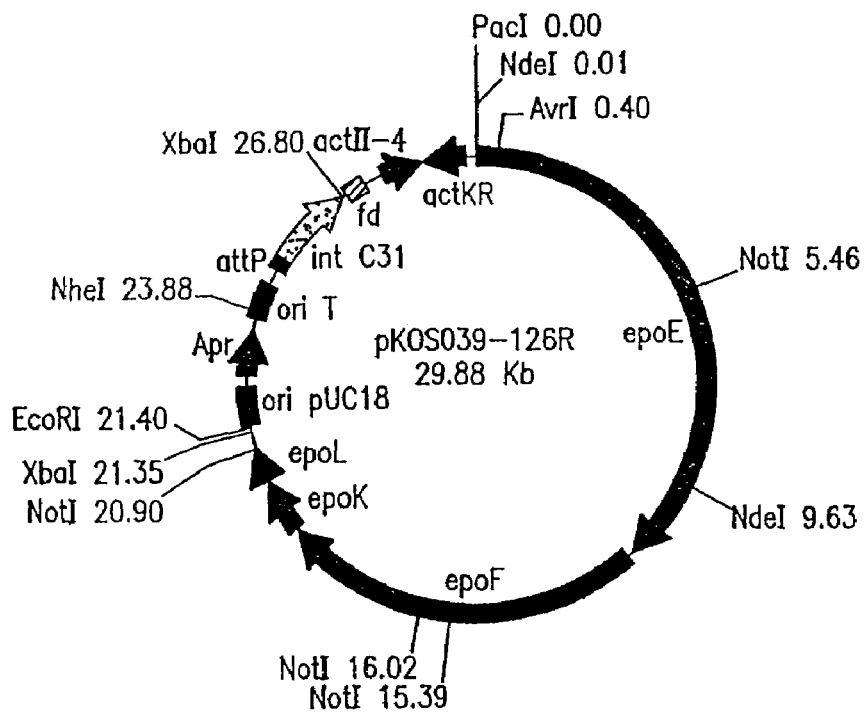
FIG. 7 shows a restriction site and function map of plasmid pKOS039-126R.

To assemble the gene cluster from cosmids pKOS35-70.1A2, and pKOS35-79.85, small regions of homology from these cosmids have to be introduced into *Myxococcus xanthus* to provide recombination sites for larger pieces of the gene cluster. As shown in FIG. 4, plasmids pKOS35-154 and pKOS90-22 are created to introduce these recombination sites. The strategy for assembling the epothilone gene cluster in the *M. xanthus* chromosome is shown in FIG. 5. Initially, a neutral site in the bacterial chromosome is chosen that does not disrupt any genes or transcriptional units. One such region is downstream of the devS gene, which has been shown not to affect the growth or development of *M xanthus*. The first plasmid, pKOS35-154, is linearized with DraI and electroporated into *M. xanthus*. This plasmid contains two regions of the dev locus flanking two fragments of the epothilone gene cluster. Inserted in between the epo gene regions are the kanamycin resistance marker and the galK gene. Kanamycin resistance arises in colonies if the DNA recombines into the dev region by a double recombination using the dev sequence as regions of homology. This strain, K35-159, contains small regions of the epothilone gene cluster that will allow for recombination of pKOS35-79.85. Because the resistance markers on pKOS35-79.85 are the same as that for K35-159, a tetracycline transposon was transposed into the cosmid, and cosmids that contain the transposon inserted into the kanamycin marker were selected. This cosmid, pKOS90-23, was electroporated into K35-159, and oxytetracycline resistant colonies were selected to create strain K35-174. To remove the unwanted regions from the cosmid and leave only the epothilone genes, cells were plated on CYE plates containing 1% galactose. The presence of the galK gene makes the cells sensitive to 1% galactose. Galactose resistant colonies of K35-174 represent cells that have lost the galK marker by recombination or by a mutation in the galK gene. If the recombination event occurs, then the galactose resistant strain is sensitive to kanamycin and oxytetracycline. Strains sensitive to both antibiotics are verified by Southern blot analysis. The correct strain is identified and designated K35-175 and contains the epothilone gene cluster from module 7 through two open reading frames past the epoL gene.

To introduce modules 1 through module 7, the above process is repeated once more. The plasmid pKOS90-22 is linearized with DraI and electroporated into K35-175 to create K35-180. This strain is electroporated with the tetracycline resistant version of pKOS35-70.1A2, pKOS90-38, and colonies resistant to oxytetracycline are selected. This creates strain K35-185. Recombinants that now have the whole epothilone gene cluster are selected by resistance to 1% galactose. This results in strain K35-188. This strain contains all the epothilone genes as well as all potential promoters. This strain is fermented and tested for the production of epothilones A and B.

To clone the whole gene cluster as one fragment, a bacterial artificial chromosome (BAC) library is constructed. First, SMP44 cells are embedded in agarose and lysed according to the BIO-RAD genomic DNA plug kit. DNA plugs are partially digested with restriction enzyme, such as Sau3AI or HindIII, and electrophoresed on a FIGE or CHEF gel. DNA fragments are isolated by electroeluting the DNA from the agarose or using gelase to degrade the agarose. The method of choice to isolate the fragments is electroelution, as described in Strong et al., 1997, Nucleic Acids Res. 19: 3959-3961, incorporated herein by reference. The DNA is ligated into the BAC (pBeloBACII) cleaved with the appropriate enzyme. A map of pBeloBACII is shown below.

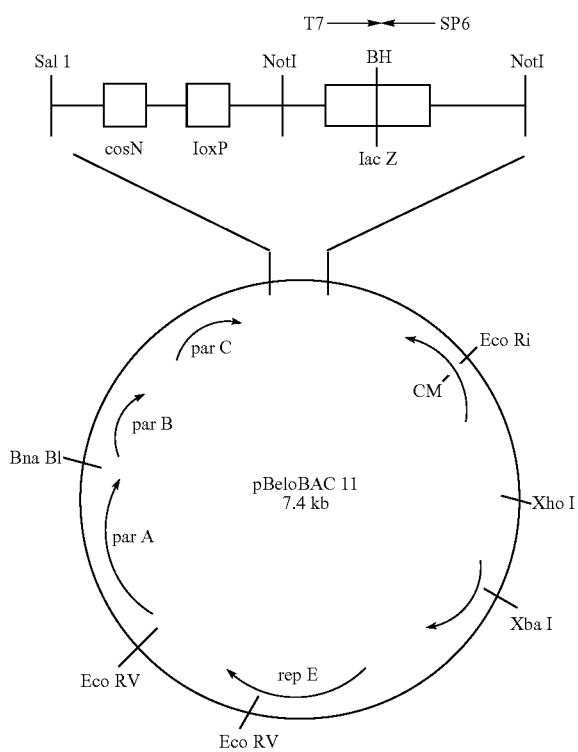

The DNA is electroporated into DH10B cells by the method of Sheng et al., 1995, Nucleic Acids Res. 23: 1990-1996, incorporated herein by reference, to create an *S. cellulosum* genomic library. Colonies are screened using a probe from the NRPS region of the epothilone cluster. Positive clones are picked and DNA is isolated for restriction analysis to confirm the presence of the complete gene cluster. This positive clone is designated pKOS35-178.

To create a strain that can be used to introduce pKOS35-178, a plasmid, pKOS35-164, is constructed that contains regions of homology that are upstream and downstream of the epothilone gene cluster flanked by the dev locus and containing the kanamycin resistance galK cassette, analogous to plasmids pKOS90-22 and pKOS35-154. This plasmid is linearized with DraI and electroporated into *M. xanthus*, in accordance with the method of Kafeshi et al., 1995, Mol. Microbiol. 15: 483-494, to create K35-183. The plasmid pKOS35-178 can be introduced into K35-183 by electroporation or by transduction with bacteriophage P1 and chloramphenicol resistant colonies are selected. Alternatively, a version of pKOS35-178 that contains the origin of conjugative transfer from pRP4 can be constructed for transfer of DNA from *E. coli* to K35-183. This plasmid is made by first constructing a transposon containing the oriT region from RP4 and the tetracycline resistance maker from pACYC184 and then transposing the transposon in vitro or in vivo onto pKOS35-178. This plasmid is transformed into S17-1 and conjugated into *M. xanthus*. This strain, K35-190, is grown in the presence of 1% galactose to select for the second recombination event. This strain contains all the epothilone genes as well as all potential promoters. This strain will be fermented and tested for the production of epothilones A and B.

Besides integrating pKOS35-178 into the dev locus, it can also be integrated into a phage attachment site using integration functions from myxophages Mx8 or Mx9. A transposon is constructed that contains the integration genes and att site from either Mx8 or Mx9 along with the tetracycline gene from pACYC184. Alternative versions of this transposon may have only the attachment site. In this version, the integration genes are then supplied in trans by coelectroporation of a plasmid containing the integrase gene or having the integrase protein expressed in the electroporated strain from any constitutive promoter, such as the mgl promoter (see Magrini et al., July 1999, J. Bact. 181(13): 4062-4070, incorporated herein by reference). Once the transposon is constructed, it is transposed onto pKOS35-178 to create pKOS35-191. This plasmid is introduced into *Myxococcus xanthus* as described above. This strain contains all the epothilone genes as well as all potential promoters. This strain is fermented and tested for the production of epothilones A and B.

Once the epothilone genes have been established in a strain of *Myxococcus xanthus*, manipulation of any part of the gene cluster, such as changing promoters or swapping modules, can be performed using the kanamycin resistance and galK cassette.

Cultures of *Myxococcus xanthus* containing the epo genes are grown in a number of media and examined for production of epothilones. If the levels of production of epothilones (in particular B or D) are too low to permit large scale fermentation, the *M. xanthus*-producing clones are subjected to media development and strain improvement, as described below for enhancing production in *Streptomyces*.

EXAMPLE 4

Construction of a *Streptomyces* Expression Vector

The present invention provides recombinant expression vectors for the heterologous expression of modular polyketide synthase genes in *Streptomyces* hosts. These vectors include expression vectors that employ the actI promoter that is regulated by the gene actII ORF4 to allow regulated expression at high levels when growing cells enter stationary phase. Among the vectors available are plasmids pRM1 and pRM5, and derivatives thereof such as pCK7, which are stable, low copy plasmids that carry the marker for thiostrepton resistance in actinomycetes. Such plasmids can accommodate large inserts of cloned DNA and have been used for the expression of the DEBS PKS in *S. coelicolor* and *S. lividans*, the picromycin PKS genes in *S. lividans*, and the oleandomycin PKS genes in *S. lividans*. See U.S. Pat. No. 5,712,146. Those of skill in the art recognize that *S. lividans* does not make the tRNA that recognizes the TTA codon for leucine until late-stage growth and that if production of a protein is desired earlier, then appropriate codon modifications can be made.

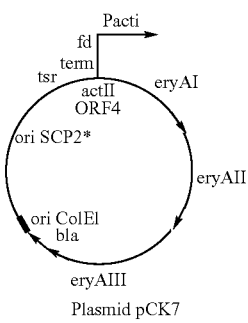

Plasmid pCK7

Another vector is a derivative of plasmid pSET152 and comprises the actII ORF4-PactI expression system but carries the selectable marker for apramycin resistance. These vectors contain the attP site and integrase gene of the actinophage phiC31 and do not replicate autonomously in *Streptomyces* hosts but integrate by site specific recombination into the chromosome at the attachment site for phiC31 after introduction into the cell. Derivatives of pCK7 and pSET152 have been used together for the heterologous production of a polyketide, with different PKS genes expressed from each plasmid. See U.S. patent application Ser. No. 60/129,731, filed 16 Apr. 1999, incorporated herein by reference.

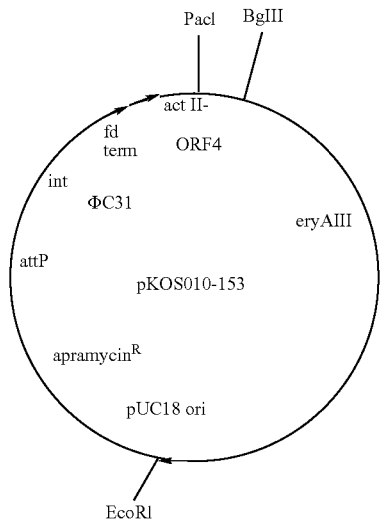

Plasmid pKOS010-153, a pSET152 Derivative

The need to develop expression vectors for the epothilone PKS that function in *Streptomyces* is significant. The epothilone compounds are currently produced in the slow growing, genetically intractable host *Sorangium cellulosum* or are made synthetically. The streptomycetes, bacteria that produce more than 70% of all known antibiotics and important complex polyketides, are excellent hosts for production of epothilones and epothilone derivatives. *S. lividans* and *S. coelicolor* have been developed for the expression of heterologous PKS systems. These organisms can stably maintain cloned heterologous PKS genes, express them at high levels under controlled conditions, and modify the corresponding PKS proteins (e.g. phosphopantetheinylation) so that they are capable of production of the polyketide they encode. Furthermore, these hosts contain the necessary pathways to produce the substrates required for polyketide synthesis, e.g. malonyl CoA and methylmalonyl CoA. A wide variety of cloning and expression vectors are available for these hosts, as are methods for the introduction and stable maintenance of large segments of foreign DNA. Relative to the slow growing *Sorangium* host, *S. lividans* and *S. coelicolor* grow well on a number of media and have been adapted for high level production of polyketides in fermentors. A number of approaches are available for yield improvements, including rational approaches to increase expression rates, increase precursor supply, etc. Empirical methods to increase the titers of the polyketides, long since proven effective for numerous other polyketides produced in streptomycetes, can also be employed for the epothilone and epothilone derivative producing host cells of the invention.

To produce epothilones by fermentation in a heterologous *Streptomyces* host, the epothilone PKS (including the NRPS module) genes are cloned in two segments in derivatives of pCK7 (loading domain through module 6) and pKOS010-153 (modules 7 through 9). The two plasmids are introduced into *S. lividans* employing selection for thiostrepton and apramycin resistance. In this arrangement, the pCK7 derivative replicates autonomously whereas the pKOS010-153 derivative is integrated in the chromosome. In both vectors, expression of the epothilone genes is from the actI promoter resident within the plasmid.

To facilitate the cloning, the two epothilone PKS encoding segments (one for the loading domain through module six and one for modules seven through nine) were cloned as translational fusions with the N-terminal segment of the KS domain of module 5 of the ery PKS. High level expression has been demonstrated from this promoter employing KS5 as the first translated sequence, see Jacobsen et al., 1998, Biochemistry 37: 4928-4934, incorporated herein by reference. A convenient BsaBI site is contained within the DNA segment encoding the amino acid sequence EPIAV that is highly conserved in many KS domains including the KS-encoding regions of epoA and of module 7 in epoE.

The expression vector for the loading domain and modules one through six of the epothilone PKS was designated pKOS039-124, and the expression vector for modules seven through nine was designated pKOS039-126. Those of skill in the art will recognize that other vectors and vector components can be used to make equivalent vectors. Because preferred expression vectors of the invention, described below and derived from pKOS039-124 and pKOS039-126, have been deposited under the terms of the Budapest Treaty, only a summary of the construction of plasmids pKOS039-124 and pKOS039-126 is provided below.

The eryKS5 linker coding sequences were cloned as an ~0.4 kb PacI-BglII restriction fragment from plasmid pKOS10-153 into pKOS039-98 to construct plasmid pKOS039-117. The coding sequences for the eryKS5 linker were linked to those for the epothilone loading domain by inserting the ~8.7 kb EcoRI-XbaI restriction fragment from cosmid pKOS35-70.1A2 into EcoRI-XbaI digested plasmid pLItmus28. The ~3.4 kb of BsaBI-NotI and ~3.7 kb NotI-HindIII restriction fragments from the resulting plasmid were inserted into BsaBI-HindIII digested plasmid pKOS039-117 to construct plasmid pKOS039-120. The ~7 kb PacI-XbaI restriction fragment of plasmid pKOS039-120 was inserted into plasmid pKAO18' to construct plasmid pKOS039-123. The final pKOS039-124 expression vector was constructed by ligating the ~34 kb XbaI-AvrII restriction fragment of cosmid pKOS35-70.1A2 with the ~21.1 kb AvrII-XbaI restriction fragment of pKOS039-123.

The plasmid pKOS039-126 expression vector was constructed as follows. First the coding sequences for module 7 were linked from cosmids pKOS35-70.4 and pKOS35-79.85 by cloning the ~6.9 kb BglII-NotI restriction fragment of pKOS35-70.4 and the ~5.9 kb NotI-HindIII restriction fragment of pKOS35-79.85 into BglII-HindIII digested plasmid pLitmus28 to construct plasmid pKOS039-119. The ~12 kb NdeI-NheI restriction fragment of cosmid pKOS35-79.85 was cloned into NdeI-XbaI digested plasmid pKOS039-119 to construct plasmid pKOS039-122.

To fuse the eryKS5 linker coding sequences with the coding sequences for module 7, the ~1 kb BsaBI-BglII restriction fragment derived from cosmid pKOS35-70.4 was cloned into BsaBI-BclI digested plasmid pKOS039-117 to construct plasmid pKOS039-121. The ~21.5 kb AvrII restriction fragment from plasmid pKOS039-122 was cloned into AvrII-XbaI digested plasmid pKOS039-121 to construct plasmid pKOS039-125. The ~21.8 kb PacI-EcoRI restriction fragment of plasmid pKOS039-125 was ligated with the ~9 kb PacI-EcoRI restriction fragment of plasmid pKOS039-44 to construct pKOS039-126.

Plasmids pKOS039-124 and pKOS126 were introduced into S. lividans K4-114 sequentially employing selection for the corresponding drug resistance marker. Because plasmid pKOS039-126 does not replicate autonomously in streptomycetes, the selection is for cells in which the plasmid has integrated in the chromosome by site-specific recombination at the attB site of phiC31. Because the plasmid stably integrates, continued selection for apramycin resistance is not required. Selection can be maintained if desired. The presence of thiostrepton in the medium is maintained to ensure continued selection for plasmid pKOS039-124. Plasmids pKOS039-124 and pKOS039-126 were transformed into Streptomyces lividans K4-114, and transformants containing the plasmids were cultured and tested for production of epothilones. Initial tests did not indicate the presence of an epothilone.

To improve production of epothilones from these vectors, the eryKS5 linker sequences were replaced by epothilone PKS gene coding sequences, and the vectors were introduced into Streptomyces coelicolor CH999. To amplify by PCR coding sequences from the epoA gene coding sequence, two oligonucleotides primers were used:

N39-73,
(SEQ ID NO: 6)
5'-GCTTAATTAAGGAGGACACATATGCCCGTCGTGGCGGATCGTC

C-3';
and

N39-74,
(SEQ ID NO: 7)
5'-GCGGATCCTCGAATCACCGCCAATATC-3'.

The template DNA was derived from cosmid pKOS35-70.8A3. The ~0.8 kb PCR product was digested with restriction enzymes PacI and BamHI and then ligated with the ~2.4 kb BamHI-NotI and the ~6.4 kb PacI-NotI restriction fragments of plasmid pKOS039-120 to construct plasmid pKOS039-136. To make the expression vector for the epoA, epoB, epoC, and epoD genes, the ~5 kb PacI-AvrII restriction fragment of plasmid pKOSO39-136 was ligated with the ~50 kb PacI-AvrII restriction fragment of plasmid pKOS039-124 to construct the expression plasmid pKOS039-124R. Plasmid pKOS039-124R has been deposited with the ATCC under the terms of the Budapest Treaty and is available under accession number PTA-926.

To amplify by PCR sequences from the epoE gene coding sequence, two oligonucleotide primers were used:

N39-67A,
(SEQ ID NO: 8)
5'-GCTTAATTAAGGAGGACACATATGACCGACCGAGAAGGCCAGCTC-

CTGGA-3',
and

N39-68,
(SEQ ID NO: 9)
5'-GGACCTAGGCGGGATGCCGGCGTCT-3'.

The template DNA was derived from cosmid pKOS35-70.1A2. The ~0.4 kb amplification product was digested with restriction enzymes PacI and AvrII and ligated with either the ~29.5 kb PacI-AvrII restriction fragment of plasmid pKOS039-126 or the ~23.8 kb PacI-AvrII restriction fragment of plasmid pKOS039-125 to construct plasmid pKOS039-126R or plasmid pKOS039-125R, respectively. Plasmid pKOS039-126R was deposited with the ATCC under the terms of the Budapest Treaty and is available under accession number PTA-927.

Figure 8:
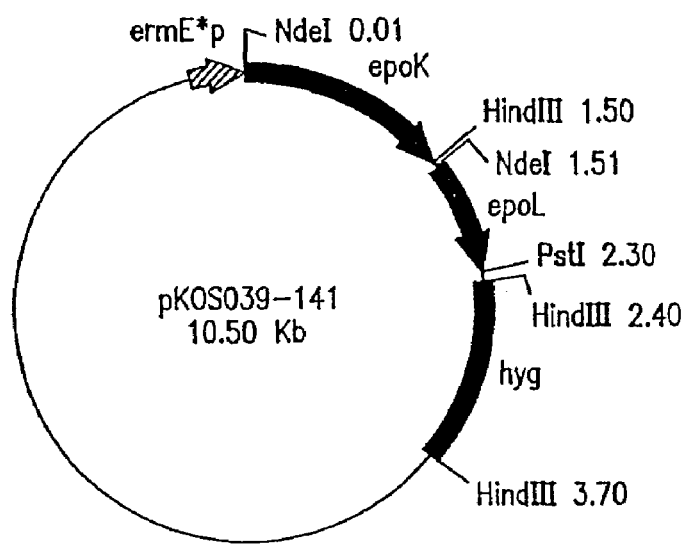
FIG. 8 shows a restriction site and function map of plasmid pKOS039-141.

The plasmid pair pKOS039-124R and pKOS039-126R (as well as the plasmid pair pKOS039-124 and pKOS039-126) contain the full complement of epoA, epoB, epoC, epoD, epoE, epoF, epoK, and epoL genes. The latter two genes are present on plasmid pKOS039-126R (as well as plasmid pKOS039-126); however, to ensure that these genes were expressed at high levels, another expression vector of the invention, plasmid pKOS039-141 (FIG. 8), was constructed in which the epoK and epoL genes were placed under the control of the ermE* promoter.

The epoK gene sequences were amplified by PCR using the oligonucleotide primers:

N39-69,
(SEQ ID NO: 10)
5'-AGGCATGCATATGACCCAGGAGCAAGCGAATCAGAGTG-3';
and

N39-70,
(SEQ ID NO: 11)
5'-CCAAGCTTTATCCAGCTTTGGAGGGCTTCAAG-3'.

The epoL gene sequences were amplified by PCR using the oligonucleotide primers:

N39-71A,
(SEQ ID NO: 3)
5'-GTAAGCTTAGGAGGACACATATGATGCAACTCGCGCGCGGGTG-3';
and

N39-72,
(SEQ ID NO: 13)
5'-GCCTGCAGGCTCAGGCTTGCGCAGAGCGT-3'.

The template DNA for the amplifications was derived from cosmid pKOS35-79.85. The PCR products were subcloned into PCR-script for sequence analysis. Then, the epoK and epoL genes were isolated from the clones as NdeI-HindIII and HindIII-EcoRI restriction fragments, respectively, and ligated with the ~6 kb NdeI-EcoRI restriction fragment of plasmid pKOS039-134B, which contains the ermE* promoter, to construct plasmid pKOS039-140. The ~2.4 kb NheI-PstI restriction fragment of plasmid pKOS039-140 was cloned into XbaI-PstI digested plasmid pSAM-Hyg, a plasmid pSAM2 derivative containing a hygromycin resistance conferring gene, to construct plasmid pKOS039-141.

Figure 9:
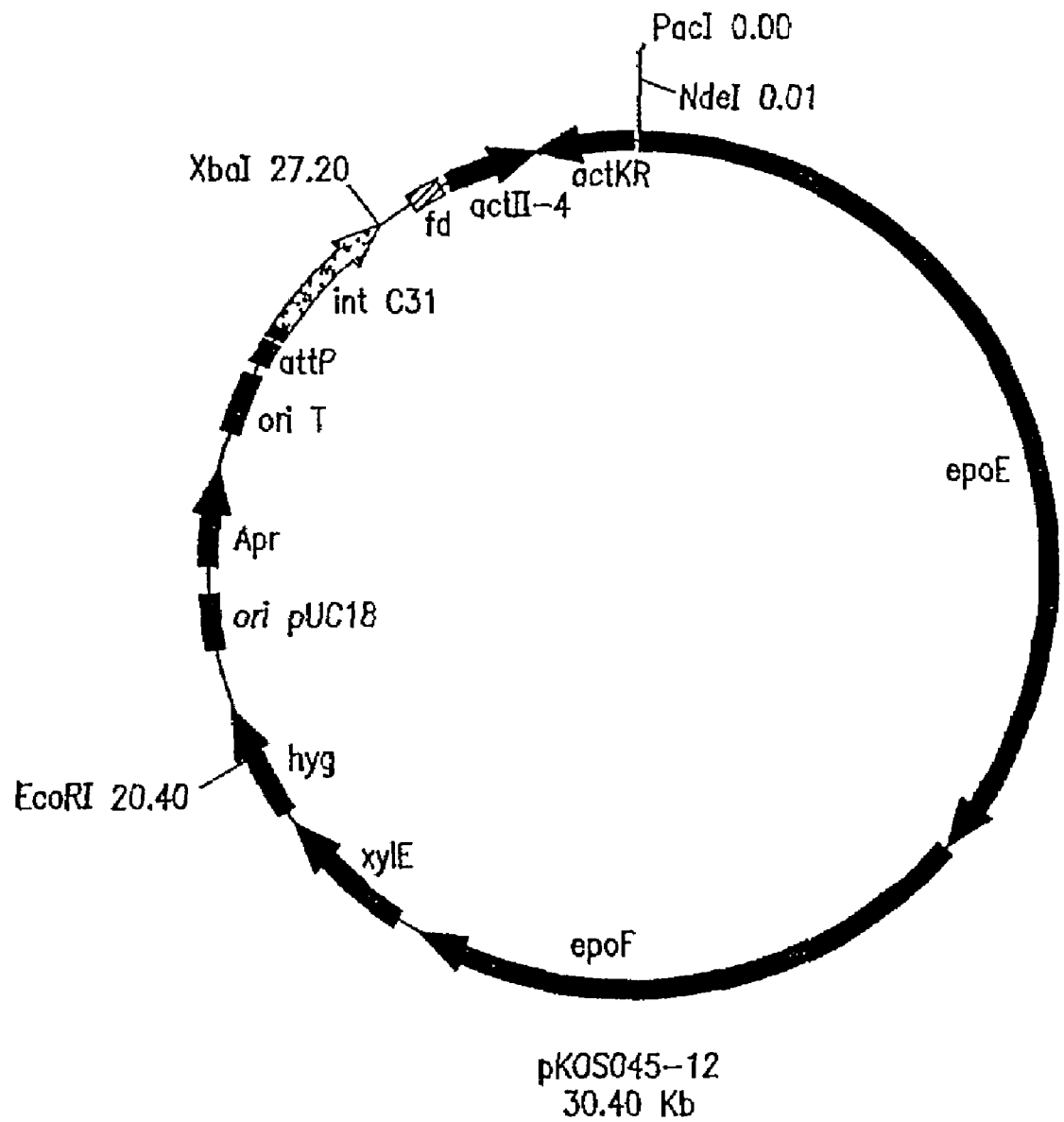
FIG. 9 shows a restriction site and function map of plasmid pKOSO45-12.

Another variant of plasmid pKOS039-126R was constructed to provide the epoE and epoF genes on an expression vector without the epoK and epoL genes. This plasmid, pKOSO45-12 (FIG. 9), was constructed as follows. Plasmid pXH106 (described in J. Bact., 1991, 173: 5573-5577, incorporated herein by reference) was digested with restriction enzymes StuI and BamHI, and the ~2.8 kb restriction fragment containing the xylE and hygromycin resistance conferring genes was isolated and cloned into EcoRV-BglII digested plasmid pLitmus28. The ~2.8 kb NcoI-AvrII restriction fragment of the resulting plasmid was ligated to the ~18 kb PacI-BspHI restriction fragment of plasmid pKOS039-125R and the ~9 kb SpeI-PacI restriction fragment of plasmid pKOS039-42 to construct plasmid pKOSO45-12.

To construct an expression vector that comprised only the epoL gene, plasmid pKOS039-141 was partially digested with restriction enzyme NdeI, the ~9 kb NdeI restriction fragment was isolated, and the fragment then circularized by ligation to yield plasmid pKOS039-150.

The various expression vectors described above were then transformed into *Streptomyces coelicolor* CH$_{999}$ and *S. lividans* K4-114 in a variety of combinations, the transformed host cells fermented on plates and in liquid culture (R5 medium, which is identical to R2YE medium without agar). Typical fermentation conditions follow. First, a seed culture of about 5 mL containing 50 μg/L thiostrepton was inoculated and grown at 30° C. for two days. Then, about 1 to 2 mL of the seed culture was used to inoculate a production culture of about 50 mL containing 50 μg/L thiostrepton and 1 mM cysteine, and the production culture was grown at 30° C. for 5 days. Also, the seed culture was used to prepare plates of cells (the plates contained the same media as the production culture with 10 mM propionate), which were grown at 30° C. for nine days.

Certain of the *Streptomyces coelicolor* cultures and culture broths were analyzed for production of epothilones. The liquid cultures were extracted with three times with equal volumes of ethyl acetate, the organic extracts combined and evaporated, and the residue dissolved in acetonitrile for LC/MS analysis. The agar plate media was chopped and extracted twice with equal volumes of acetone, and the acetone extracts were combined and evaporated to an aqueous slurry, which was extracted three times with equal volumes of ethyl acetate. The organic extracts were combined and evaporated, and the residue dissolved in acetonitrile for LC/MS analysis.

Production of epothilones was assessed using LC-mass spectrometry. The output flow from the UV detector of an analytical HPLC was split equally between a Perkin-Elmer/Sciex API100LC mass spectrometer and an Alltech 500 evaporative light scattering detector. Samples were injected onto a 4.6×150 mm reversed phase HPLC column (MetaChem 5 m ODS-3 Inertsil) equilibrated in water with a flow rate of 1.0 mL/min. UV detection was set at 250 nm. Sample components were separated using H$_2$O for 1 minute, then a linear gradient from 0 to 100% acetonitrile over 10 minutes. Under these conditions, epothilone A elutes at 10.2 minutes and epothilone B elutes at 10.5 minutes. The identity of these compounds was confirmed by the mass spectra obtained using an atmospheric chemical ionization source with orifice and ring voltages set at 75 V and 300 V, respectively, and a mass resolution of 0.1 amu. Under these conditions, epothilone A shows [M+H] at 494.4 amu, with observed fragments at 476.4, 318.3, and 306.4 amu. Epothilone B shows [M+H] at 508.4 amu, with observed fragments at 490.4, 320.3, and 302.4 amu.

Transformants containing the vector pairs pKOS039-124R and pKOS039-126R or pKOS039-124 and pKOS039-126R produced detectable amounts of epothilones A and B. Transformants containing these plasmid pairs and the additional plasmid pKOS039-141 produced similar amounts of epothilones A and B, indicating that the additional copies of the epoK and epoL genes were not required for production under the test conditions employed. Thus, these transformants produced epothilones A and B when recombinant epoA, epoB, epoC, epoD, epoE, epoF, epoK, and epoL genes were present. In some cultures, it was observed that the absence of propionate increased the proportion of epothilone B to epothilone A.

Transformants containing the plasmid pair pKOS039-124R and pKOSO45-12 produced epothilones C and D, as did transformants containing this plasmid pair and the additional plasmid pKOS039-150. These results showed that the epoL gene was not required under the test conditions employed to form the C-12-C-13 double bond. These results indicate that either the epothilone PKS gene alone is able to form the double bond or that *Streptomyces coelicolor* expresses a gene product able to convert epothilones G and H to epothilones C and D. Thus, these transformants produced epothilones C and D when recombinant epoA, epoB, epoC, epoD, epoE, and epoF genes were present.

The heterologous expression of the epothilone PKS described herein is believed to represent the recombinant expression of the largest proteins and active enzyme complex that have ever been expressed in a recombinant host cell. The epothilone producing *Streptomyces coelicolor* transformants exhibited growth characteristics indicating that either the epothilone PKS genes, or their products, or the epothilones inhibited cell growth or were somewhat toxic to the cells. Any such inhibition or toxicity could be due to accumulation of the epothilones in the cell, and it is believed that the native *Sorangium* producer cells may contain transporter proteins that in effect pump epothilones out of the cell. Such transporter genes are believed to be included among the ORFs located downstream of the epoK gene and described above. Thus, the present invention provides *Streptomyces* and other host cells that include recombinant genes that encode the products of one or more, including all, of the ORFs in this region.

For example, each ORF can be cloned behind the ermE* promoter, see Stassi et al., 1998, Appl. Microbiol. Biotechnol. 49: 725-731, incorporated herein by reference, in a pSAM2-based plasmid that can integrate into the chromosome of *Streptomyces coelicolor* and *S. lividans* at a site distinct from attB of phage phiC31, see Smokvina et al., 1990, Gene 94: 53-59, incorporated herein by reference. A pSAM2-based vector carrying the gene for hygromycin resistance is modified to carry the ermE* promoter along with additional cloning sites. Each ORF downstream is PCR cloned into the vector which is then introduced into the host cell (also containing pKOS039-124R and pKOS039-126Ror other expression vectors of the invention) employing hygromycin selection. Clones carrying each individual gene downstream from epoK are analyzed for increased production of epothilones.

Additional fermentation and strain improvement efforts can be conducted as illustrated by the following. The levels of expression of the PKS genes in the various constructs can be measured by assaying the levels of the corresponding mRNAs (by quantitative RT PCR) relative to the levels of another heterologous PKS mRNA (e.g. picromycin) produced from genes cloned in similar expression vectors in the same host. If one of the epothilone transcripts is underproduced, experiments to enhance its production by cloning the corresponding DNA segment in a different expression vector are conducted for example, multiple copies of any one or more of the epothilone PKS genes can be introduced into a cell if one or more gene products are rate limiting for biosynthesis. If the basis for low level production is not related to low level PKS gene expression (at the RNA level), an empirical mutagenesis and screening approach that is the backbone of yield improvement of every commercially important fermentation product is undertaken. Spores are subjected to V, X-ray or chemical mutagens, and individual survivors are plated and picked and tested for the level of compound produced in small scale fermentations. Although this process can be automated, one can examine several thousand isolates for quantifiable epothilone production using the susceptible fungus Mucor hiemalis as a test organism.

Another method to increase the yield of epothilones produced is to change the $KS^Y$ domain of the loading domain of the epothilone PKS to a $KS^Q$ domain. Such altered loading domains can be constructed in any of a variety of ways, but one illustrative method follows. Plasmid pKOS39-124R of the invention can be conveniently used as a starting material. To amplify DNA fragments useful in the construction, four oligonucleotide primers are employed:

```
                                           (SEQ ID NO: 14)
  N39-83:  5'-CCGGTATCCACCGCGACACACGGC-3', (SEQ ID NO: 15)
  N39-84:  5'-GCCAGTCGTCCTCGCTCGTGGCCGTTC-3',
``` and N39-73 and N39-74, which have been described above. The PCR fragment generated with N37-73 and N39-83 and the PCR fragment generated with N39-74 and N39-84 are treated with restriction enzymes PacI and BamHI, respectively, and ligated with the ~3.1 kb PacI-BamHI fragment of plasmid pKOS39-120 to construct plasmid pKOS039-148. The ~0.8 kb PacI-BamHI restriction fragment of plasmid pKOS039-148 (comprising the two PCR amplification products) is ligated with the ~2.4 kb BamHI-NotI restriction fragment and the ~6.4 kb PacI-NotI restriction fragment of plasmid pKOS39-120 to construct pKOS39-136Q. The ~5 kb PacI-AvrII restriction fragment of plasmid pKOS039-136Q is ligated to the ~50 kb PacI-AvrII restriction fragment of plasmid pKOS039-124 to construct plasmid pKOS39-124Q. Plasmids pKOS039-124Q and pKOS039-126R are then transformed into Streptomyces coelicolor CH999 for epothilone production.

The epoA through epoF, optionally with epoK or with epoK plus epoL, genes cloned and expressed are sufficient for the synthesis of epothilone compounds, and the distribution of the C-12H to C-12 methyl congeners appears to be similar to that seen in the natural host (A:B:2:1). This ratio reflects that the AT domain of module 4 more closely resembles that of the malonyl rather than methylmalonyl specifying AT consensus domains. Thus, epothilones D and B are produced at lower quantities than their C-12 unmethylated counterparts C and A. The invention provides PKS genes that produce epothilone D and/or B exclusively. Specifically, methylmalonyl CoA specifying AT domains from a number of sources (e.g. the narbonolide PKS, the rapamycin PKS, and others listed above) can be used to replace the naturally occurring at domain in module 4. The exchange is performed by direct cloning of the incoming DNA into the appropriate site in the epothilone PKS encoding DNA segment or by gene replacement through homologous recombination.

For gene replacement through homologous recombination, the donor sequence to be exchanged is placed in a delivery vector between segments of at least 1 kb in length that flank the AT domain of epo module 4 encoding DNA. Crossovers in the homologous regions result in the exchange of the epo AT4 domain with that on the delivery vector. Because pKOS039-124 and pKOS039-124R contain AT4 coding sequences, they can be used as the host DNA for replacement. The adjacent DNA segments are cloned in one of a number of E. coli plasmids that are temperature sensitive for replication. The heterologous AT domains can be cloned in these plasmids in the correct orientation between the homologous regions as cassettes enabling the ability to perform several AT exchanges simultaneously. The reconstructed plasmid (pKOS039-124* or pKOS039-124R*) is tested for ability to direct the synthesis of epothilone B and/or by introducing it along with pKOS039-126 or pKOS039-126R in Streptomyces coelicolor and/or S. lividans.

Because the titers of the polyketide can vary from strain to strain carrying the different gene replacements, the invention provides a number of heterologous methylmalonyl CoA specifying AT domains to ensure that production of epothilone D at titers equivalent to that of the C and D mixture produced in the Streptomyces coelicolor host described above. In addition, larger segments of the donor genes can be used for the replacements, including, in addition to the AT domain, adjacent upstream and downstream sequences that correspond to an entire module. If an entire module is used for the replacement, the KS, methylmalonyl AT, DH, KR, ACP— encoding DNA segment can be obtained from for example and without limitation the DNA encoding the tenth module of the rapamycin PKS, or the first or fifth modules of the FK-520 PKS.

EXAMPLE 5

Heterologous Expression of EpoK and Conversion of Epothilone D to Epothilone B

This Example describes the construction of E. coli expression vectors for epoK. The epoK gene product was expressed in E. coli as a fusion protein with a polyhistidine tag (his tag). The fusion protein was purified and used to convert epothilone D to epothilone B.

Plasmids were constructed to encode fusion proteins composed of six histidine residues fused to either the amino or carboxy terminus of EpoK. The following oligos were used to construct the plasmids:

```
55-101.a1:
                                           (SEQ ID NO: 16)
5'-AAAAACATATGCACCACCACCACCACCACATGACACAGGAGCAAGCG

AAT-CAGAGTGAG-3', 55-101.b:
                                           (SEQ ID NO: 17)
5'-AAAAAGGATCCTTAATCCAGCTTTGGAGGGCTT-3', 55-101.c:
                                           (SEQ ID NO: 18)
5'-AAAAACATATGACACAGGAGCAAGCGAAT-3',
and 55-101.d:
                                           (SEQ ID NO: 19)
5'-AAAAAGGATCCTTAGTGGTGGTGGTGGTGGTGTCCAGCTTTGGAGGG

CTTC-AAGATGAC-3'.
```

The plasmid encoding the amino terminal his tag fusion protein, pKOS55-121, was constructed using primers 55-101.a-1 and 55-101.b, and the one encoding the carboxy terminal his tag, pKOS55-129, was constructed using primers 55-101.c and 55-101.d in PCR reactions containing pKOS35-83.5 as the template DNA. Plasmid pKOS35-83.5 contains the ~5 kb NotI fragment comprising the epoK gene ligated into pBluescriptSKII+ (Stratagene). The PCR products were cleaved with restriction enzymes BamHI and NdeI and ligated into the BamHI and NdeI sites of pET22b (Invitrogen). Both plasmids were sequenced to verify that no mutations were introduced during the PCR amplification. Protein gels were run as known in the art.

Purification of EpoK was performed as follows. Plasmids pKOS55-121 and pKOS55-129 were transformed into BL21 (DE3) containing the groELS expressing plasmid pREP4-groELS (Caspers et al., 1994, Cellular and Molecular Biology 40(5): 635-644). The strains were inoculated into 250 mL of M9 medium supplemented with 2 mM MgSO4, 1% glucose, 20 mg thiamin, 5 mg $FeCl_2$, 4 mg $CaCl_2$ and 50 mg levulinic acid. The cultures were grown to an $OD_{600}$ between 0.4 and 0.6, at which point IPTG was added to 1 mM, and the cultures were allowed to grow for an additional two hours. The cells were harvested and frozen at −80° C. The frozen cells were resuspended in 10 ml of buffer 1 (5 mM imidazole, 500 mM NaCl, and 45 mM Tris pH 7.6) and were lysed by sonicating three times for 15 seconds each on setting 8. The cellular debris was pelleted by spinning in an SS-34 rotor at 16,000 rpm for 30 minutes. The supernatant was removed and spun again at 16,000 rpm for 30 minutes. The supernatant was loaded onto a 5 mL nickel column (Novagen), after which the column was washed with 50 mL of buffer 1 (Novagen). EpoK was eluted with a gradient from 5 mM to 1M imidazole. Fractions containing EpoK were pooled and dialyzed twice against 1 L of dialysis buffer (45 mM Tris pH7.6, 0.2 mM DTT, 0.1 mM EDTA, and 20% glycerol). Aliquots were frozen in liquid nitrogen and stored at −80° C. The protein preparations were greater than 90% pure.

The EpoK assay was performed as follows (See Betlach et al., *Biochem* (1998) 37:14937, incorporated herein by reference). Briefly, reactions consisted of 50 mM Tris (pH7.5), 21 µM spinach ferredoxin, 0.132 units of spinach ferredoxin:$NADP^+$ oxidoreductase, 0.8 units of glucose-6-phosphate dehydrogenase, 1.4 mM NADP, and 7.1 mM glucose-6-phosphate, 100 µM or 200 µM epothilone D (a generous gift of S. Danishefsky), and 1.7 µM amino terminal his tagged EpoK or 1.6 µM carboxy terminal his tagged EpoK in a 100 µL volume. The reactions were incubated at 30° C. for 67 minutes and stopped by heating at 90° C. for 2 minutes. The insoluble material was removed by centrifugation, and 50 µL of the supernatant were analyzed by LC/MS. HPLC conditions: Metachem 5 A ODS-3 Inertsil (4.6×150 mm); 80% $H_2O$ for 1 min, then to 100% MeCN over 10 min at 1 mL/min, with UV ($\lambda_{max}$=250 nm), ELSD, and MS detection. Under these conditions, epothilone D eluted at 11.6 min and epothilone B at 9.3 min. the LC/MS spectra were obtained using an atmosphere pressure chemical ionization source with orifice and ring voltages set at 20 V and 250 V, respectively, at a mass resolution of 1 amu. Under these conditions, epothilone E shows an [M+H] at m/z 493, with observed fragments at 405 and 304. Epothilone B shows an [M+H] at m/z 509, with observed fragments at 491 and 320.

The reactions containing EpoK and epothilone D contained a compound absent in the control that displayed the same retention time, molecular weight, and mass fragmentation pattern as pure epothilone B. With an epothilone D concentration of 100 µM, the amino and the carboxy terminal his tagged EpoK was able to convert 82% and 58% to epothilone B, respectively. In the presence of 200 µM, conversion was 44% and 21%, respectively. These results demonstrate that EpoK can convert epothilone D to epothilone B.

EXAMPLE 6

Modified Epothilones from Chemobiosynthesis

This Example describes a series of thioesters provided by the invention for production of epothilone derivatives via chemobiosynthesis. The DNA sequence of the biosynthetic gene cluster for epothilone from *Sorangium cellulosum* indicates that priming of the PKS involves a mixture of polyketide and amino acid components. Priming involves loading of the PKS-like portion of the loading domain with malonyl CoA followed by decarboxylation and loading of the module one NRPS with cysteine, then condensation to form enzyme-bound N-acetylcysteine. Cyclization to form a thiazoline is followed by oxidation to form enzyme bound 2-methylthiazole-4-carboxylate, the product of the loading domain and NRPS. Subsequent condensation with methylmalonyl CoA by the ketosynthase of module 2 provides the substrate for module, as shown in the following diagram.

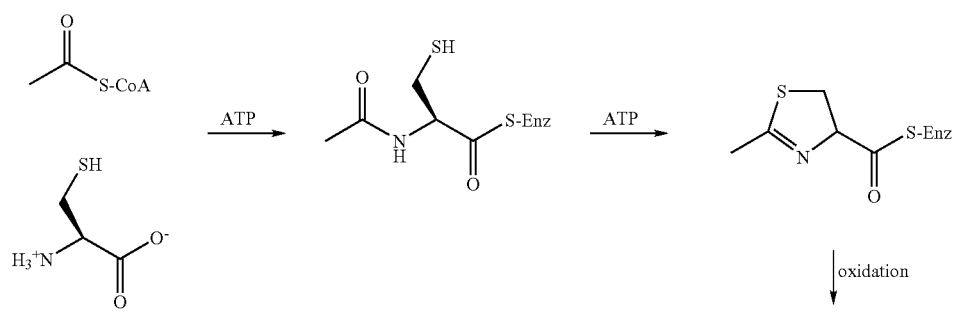

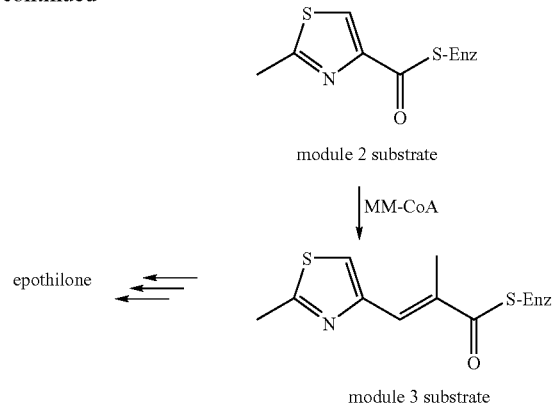

module 2 substrate

MM-CoA epothilone module 3 substrate

The present invention provides methods and reagents for chemobiosynthesis to produce epothilone derivatives in a manner similar to that described to make 6-dEB and erythromycin analogs in PCT Pat. Pub. Nos. 99/03986 and 97/02358. Two types of feeding substrates are provided: analogs of the NRPS product, and analogs of the module 3 substrate. The module 2 substrates are used with PKS enzymes with a mutated NRPS-like domain, and the module 3 substrates are used with PKS enzymes with a mutated KS domain in module 2.

The following illustrate module 2 substrates (as N-acetyl cysteamine thioesters) for use as substrates for epothilone PKS with modified inactivated NRPS:

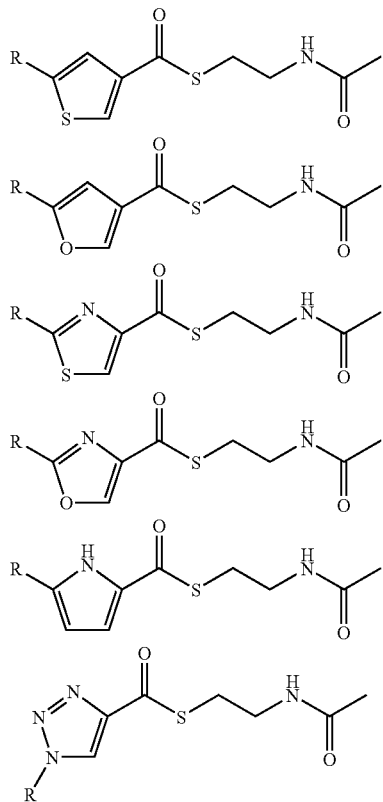

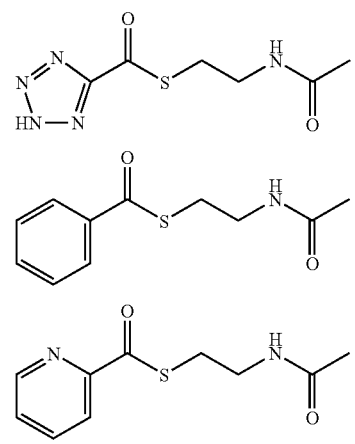

The module 2 substrates are prepared by activation of the corresponding carboxylic acid and treatment with N-acetyl-cysteamine. Activation methods include formation of the acid chloride, formation of a mixed anhydride, or reaction with a condensing reagent such as a carbodiimide.

Exemplary module 3 substrates, also as NAc thioesters for use as substrates for epothilone PKS with KS2 knockout are:

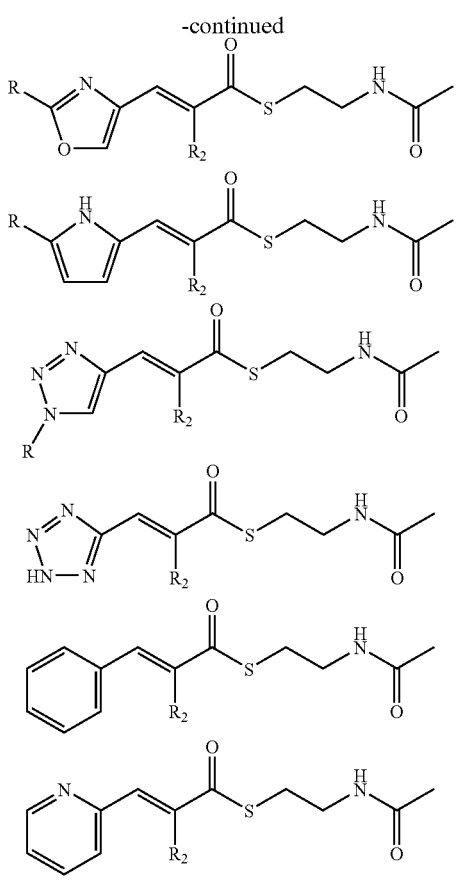

These compounds are prepared in a three-step process. First, the appropriate aldehyde is treated with a Wittig reagent or equivalent to form the substituted acrylic ester. The ester is saponified to the acid, which is then activated and treated with N-acetylcysteamine.

Illustrative reaction schemes for making module 2 and module 3 substrates follow. Additional compounds suitable for making starting materials for polyketide synthesis by the epothilone PKS are shown in FIG. 2 as carboxylic acids (or aldehydes that can be converted to carboxylic acids) that are converted to the N-acylcysteamides for supplying to the host cells of the invention.

A. Thiophene-3-carboxylate N-acetylcysteamine thioester

A solution of thiophene-3-carboxylic acid (128 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added, and the reaction was allowed to proceed for 12 hours. The mixture was poured into water and extracted three times with equal volumes of ethyl acetate. The organic extracts were combined, washed sequentially with water, 1 N HCl, sat. CuSO$_4$, and brine, then dried over MgSO$_4$, filtered, and concentrated under vacuum. Chromatography on SiO$_2$ using ether followed by ethyl acetate provided pure product, which crystallized upon standing.

B. Furan-3-carboxylate N-acetylcysteamine thioester

A solution of furan-3-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. CuSO$_4$, and brine, then dried over MgSO$_4$, filtered, and concentrated under vacuum. Chromatography on SiO$_2$ using, ether followed by ethyl acetate provided pure product, which crystallized upon standing.

C. Pyrrole-2-carboxylate N-acetylcysteamine thioester

A solution of pyrrole-2-carboxylic acid (112 mg) in 2 mL of dry tetrahydrofuran under inert atmosphere was treated with triethylamine (0.25 mL) and diphenylphosphoryl azide (0.50 mL). After 1 hour, N-acetylcysteamine (0.25 mL) was added and the reaction was allowed to proceed for 12 hours. The mixture was poured into water and extracted three times with equal volumes of ethyl acetate. The organic extracts were combined, washed sequentially with water, 1 N HCl, sat. CuSO$_4$, and brine, then dried over MgSO$_4$, filtered, and concentrated under vacuum. Chromatography on SiO$_2$ using ether followed by ethyl acetate provided pure product, which crystallized upon standing.

D. 2-Methyl-3-(3-thienyl) acrylate N-acetylcysteamine thioester (1) Ethyl 2-methyl-3-(3-thienyl)acrylate: A mixture of thiophene-3-carboxaldehyde (1.12 g) and (carbethoxyethylidene)triphenylphosphorane (4.3 g) in dry tetrahydrofuran (20 mL) was heated at reflux for 16 hours. The mixture was cooled to ambient temperature and concentrated to dryness under vacuum. The solid residue was suspended in 1:1 ether/hexane and filtered to remove triphenylphosphine oxide. The filtrate was filtered through a pad of SiO$_2$ using 1:1 ether/hexane to provide the product (1.78 g, 91%) as a pale yellow oil.

(2) 2-Methyl-3-(3-thienyl)acrylic acid: The ester from (1) was dissolved in a mixture of methanol (5 mL) and 8 N KOH (5 mL) and heated at reflux for 30 minutes. The mixture was cooled to ambient temperature, diluted with water, and washed twice with ether. The aqueous phase was acidified using 1N HCl then extracted 3 times with equal volumes of ether. The organic extracts were combined, dried with MgSO$_4$, filtered, and concentrated to dryness under vacuum. Crystallization from 2:1 hexane/ether provided the product as colorless needles.

(3) 2-Methyl-3-(3-thienyl)acrylate N-acetylcysteamine thioester: A solution of 2-Methyl-3-(3-thienyl)acrylic acid (168 mg) in 2 mL of dry tetrahydrofuran under inert atmosphere was treated with triethylamine (0.56 mL) and diphenylphosphoryl azide (0.45 mL). After 15 minutes, N-acetylcysteamine (0.15 mL) is added and the reaction is allowed to proceed for 4 hours. The mixture is poured into water and extracted three times with equal volumes of ethyl acetate. The organic extracts are combined, washed sequentially with water, 1 N HCl, sat. CuSO$_4$, and brine, then dried over MgSO$_4$, filtered, and concentrated under vacuum. Chromatography on SiO$_2$ using ethyl acetate provided pure product, which crystallized upon standing.

The above compounds are supplied to cultures of host cells containing a recombinant epothilone PKS of the invention in which either the NRPS or the KS domain of module 2 as appropriate has been inactivated by mutation to prepare the corresponding epothilone derivative of the invention.

EXAMPLE 7

Producing Epothilones and Epothilone Derivatives in *Sorangium cellulosum* SMP44

The present invention provides a variety of recombinant *Sorangium cellulosum* host cells that produce less complex mixtures of epothilones than the naturally occurring epothilone producers as well as host cells that produce epothilone derivatives. This Example illustrates the construction of such strains by describing how to make a strain that produce only epothilones C and D without epothilones A and B. To construct this strain, an inactivating mutation is made in epoK. Using plasmid pKOS35-83.5, which contains a NotI fragment harboring the epoK gene, the kanamycin and bleomycin resistance markers from Tn5 are ligated into the ScaI site of the epoK gene to construct pKOS90-55. The orientation of the resistance markers is such that transcription initiated at the kanamycin promoter drives expression of genes immediately downstream of epoK. In other words, the mutation should be nonpolar. Next, the origin of conjugative transfer, oriT, from RP4 is ligated into pKOS90-55 to create pKOS90-63. This plasmid can be introduced into S17-1 and conjugated into SMP44. The transconjugants are selected on phleomycin plates as previously described. Alternatively, electroporation of the plasmid can be achieved using conditions described above for *Myxococcus xanthus*.

Because there are three generalized transducing phages for *Myxococcus xanthus*, one can transfer DNA from *M. xanthus* to SMP44. First, the epoK mutation is constructed in *M. xanthus* by linearizing plasmid pKOS90-55 and electroporating into *M. xanthus*. Kanamycin resistant colonies are selected and have a gene replacement of epoK. This strain is infected with Mx9, Mx8, Mx4 ts18 hft hrm phages to make phage lysates. These lysates are then individually infected into SMP44 and phleomycin resistant colonies are selected. Once the strain is constructed, standard fermentation procedures, as described below, are employed to produce epothilones C and D.

Prepare a fresh plate of *Sorangium* host cells (dispersed) on S42 medium. S42 medium contains tryptone, 0.5 g/L; $MgSO_4$, 1.5 g/L; HEPES, 12 g/L; agar, 12 g/L, with deionized water. The pH of S42 medium is set to 7.4 with KOH. To prepare S42 medium, after autoclaving at 121° C. for at least 30 minutes, add the following ingredients (per liter): $CaCl_2$, 1 g; $K_2HPO_4$, 0.06 g; Fe Citrate, 0.008 g; Glucose, 3.5 g; Ammonium sulfate, 0.5 g; Spent liquid medium, 35 mL; and 200 micrograms/mL of kanamycin is added to prevent contamination. Incubate the culture at 32° C. for 4-7 days, or until orange sorangia appear on the surface.

To prepare a seed culture for inoculating agar plates/bioreactor, the following protocol is followed. Scrape off a patch of orange *Sorangium* cells from the agar (about 5 mm) and transfer to a 250 ml baffle flask with 38 mm silicone foam closures containing 50 ml of Soymeal Medium containing potato starch, 8 g; defatted soybean meal, 2 g; yeast extract, 2 g; Iron (III) sodium salt EDTA, 0.008 g; $MgSO_4.7H_2O$, 1 g; $CaCl_2.2H_2O$, 1 g; glucose, 2 g; HEPES buffer, 11.5 g. Use deionized water, and adjust pH to 7.4 with 10% KOH. Add 2-3 drops of antifoam B to prevent foaming. Incubate in a coffin shaker for 4-5 days at 30° C. and 250 RPM. The culture should appear an orange color. This seed culture can be sub-cultured repeatedly for scale-up to inoculate in the desired volume of production medium.

The same preparation can be used with Medium 1 containing (per liter) $CaCl_2.2H_2O$, 1 g; yeast extract, 2 g; Soytone, 2 g; FeEDTA, 0.008 g; $Mg SO_4.7H_2O$, 1 g; HEPES, 11.5 g. Adjust pH to 7.4 with 10% KOH, and autoclave at 121° C. for 30 minutes. Add 8 ml of 40% glucose after sterilization. Instead of a baffle flask, use a 250 ml coiled spring flask with a foil cover. Include 2-3 drops of antifoam B, and incubate in a coffin shaker for 7 days at 37° C. and 250 RPM. Subculture the entire 50 mL into 500 mL of fresh medium in a baffled narrow necked Fembach flask with a 38 mm silicone foam closure. Include 0.5 ml of antifoam to the culture. Incubate under the same conditions for 2-3 days. Use at least a 10% inoculum for a bioreactor fermentation.

To culture on solid media, the following protocol is used. Prepare agar plates containing (per liter of CNS medium) $KNO_3$, 0.5 g; $Na_2BPO_4$, 0.25 g; $MgSO_4.7H_2O$, 1 g; $FeCl_2$, 0.01 g; HEPES, 2.4 g; Agar, 15 g; and sterile Whatman filter paper. While the agar is not completely solidified, place a sterile disk of filter paper on the surface. When the plate is dry, add just enough of the seed culture to coat the surface evenly (about 1 mL). Spread evenly with a sterile loop or an applicator, and place in a 32° C. incubator for 7 days. Harvest plates.

For production in a 5 L bioreactor, the following protocol is used. The fermentation can be conducted in a B. Braun Biostat MD-15 L bioreactor. Prepare 4 L of production medium (same as the soymeal medium for the seed culture without HEPES buffer). Add 2% (volume to volume) XAD-16 absorption resin, unwashed and untreated, e.g. add 1 mL of XAD per 50 mL of production medium. Use 2.5 N $H_2SO_4$ for the acid bottle, 10% KOH for the base bottle, and 50% antifoam B for the antifoam bottle. For the sample port, be sure that the tubing that will come into contact with the culture broth has a small opening to allow the XAD to pass through into the vial for collecting daily samples. Stir the mixture completely before autoclaving to evenly distribute the components. Calibrate the pH probe and test dissolved oxygen probe to ensure proper functioning. Use a small antifoam probe, ~3 inches in length. For the bottles, use tubing that can be sterile welded, but use silicone tubing for the sample port. Make sure all fittings are secure and the tubings are clamped off, not too tightly, with C-clamps. Do not clamp the tubing to the exhaust condenser. Attach 0.2 µm filter disks to any open tubing that is in contact with the air. Use larger ACRO 50 filter disks for larger tubing, such as the exhaust condenser and the air inlet tubing. Prepare a sterile empty bottle for the inoculum. Autoclave at 121° C. with a sterilization time of 90 minutes. Once the reactor has been taken out of the autoclave, connect the tubing to the acid, base, and antifoam bottles through their respective pump heads. Release the clamps to these bottles, making sure the tubing has not been welded shut. Attach the temperature probe to the control unit. Allow the reactor to cool, while sparging with air through the air inlet at a low air flow rate.

After ensuring the pumps are working and there is no problem with flow rate or clogging, connect the hoses from the water bath to the water jacket and to the exhaust condenser. Make sure the waterjacket is nearly full. Set the temperature to 32° C. Connect pH, D.O., and antifoam probes to the main control unit. Test the antifoam probe for proper functioning. Adjust the set point of the culture to 7.4. Set the agitation to 400 RPM. Calibrate the D.O. probe using air and nitrogen gas. Adjust the airflow using the rate at which the fermentation will operate, e.g. 1 LPM (liter per minute). To control the dissolved oxygen level, adjust the parameters under the cascade setting so that agitation will compensate for lower levels of air to maintain a D.O. value of 50%. Set the minimum and maximum agitation to 400 and 1000 RPM respectively, based on the settings of the control unit. Adjust the settings, if necessary.

Check the seed culture for any contamination before inoculating the fermenter. The *Sorangium cellulosum* cells are rod shaped like a pill, with 2 large distinct circular vacuoles at opposite ends of the cell. Length is approximately 5 times that of the width of the cell. Use a 10% inoculum (minimum) volume, e.g. 400 mL into 4 L of production medium. Take an initial sample from the vessel and check against the bench pH. If the difference between the fermenter pH and the bench pH is off by $\geq 0.1$ units, do a 1 point recalibration. Adjust the deadband to 0.1. Take daily 25 mL samples noting fermenter pH, bench pH, temperature, D.O., airflow, agitation, acid, base, and antifoam levels. Adjust pH if necessary. Allow the fermenter to run for seven days before harvesting.

Extraction and analysis of compounds is performed substantially as described above in Example 4. In brief, fermentation culture is extracted twice with ethyl acetate, and the ethyl acetate extract is concentrated to dryness and dissolved/suspended in ~500 µL of MeCN—H$_2$O (1:1). The sample is loaded onto a 0.5 mL Bakerbond ODS SPE cartridge pre-equilibrated with MeCN—H$_2$O (1:1). The cartridge is washed with 1 mL of the same solvent, followed by 2 mL of MeCN. The MeCN eluent is concentrated to dryness, and the residue is dissolved in 200 µL of MeCN. Samples (50 µL) are analyzed by HPLC/MS on a system comprised of a Beckman System Gold HPLC and PE Sciex API100LC single quadrapole MS-based detector equipped with an atmospheric pressure chemical ionization source. Ring and orifice voltages are set to 75V and 300V, respectively, and a dual range mass scan from m/z 290-330 and 450-550 is used. HPLC conditions: Metachem 5µ ODS-3 Inertsil (4.6×150 mm); 100% H$_2$O for 1 min, then to 100% MeCN over 10 min a 1 mL/min. Epothilone A elutes at 0.2 min under these conditions and gives characteristic ions at m/z 494 (M+H), 476 (M+H—H$_2$O), 318, and 306.

EXAMPLE 8

Epothilone Derivatives as Anti-Cancer Agents

The novel epothilone derivatives shown below by Formula (1) set forth above are potent anti-cancer agents and can be used for the treatment of patients with various forms of cancer, including but not limited to breast, ovarian, and lung cancers.

The epothilone structure-activity relationships based on tubulin binding assay are (see Nicolaou et al., 1997, Angew. Chem. Int. Ed. Engl. 36: 2097-2103, incorporated herein by reference) are illustrated by the diagram below.

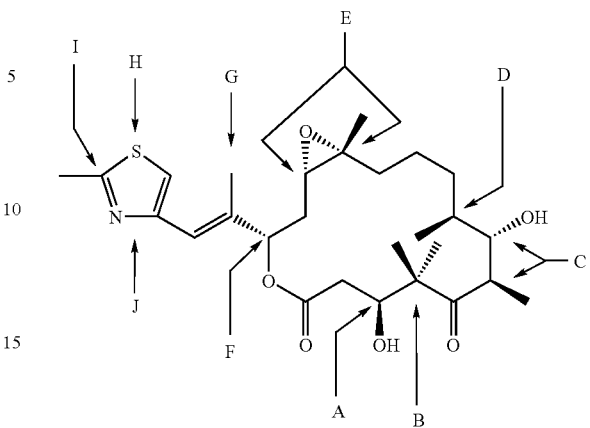

A) (3S) configuration important; B) 4,4-ethano group not tolerated; C) (6R,7S) configuration crucial; D) (8S) configuration important, 8,8-dimethyl group not tolerated; E) epoxide not essential for tubulin polymerization activity, but may be important for cytotoxicity; epoxide configuration may be important; R group important; both olefin geometries tolerated; F) (15S) configuration important; G) bulkier group reduces activity; H) oxygen substitution tolerated; I) substitution important; J) heterocycle important.

Thus, this SAR indicates that modification of the C1-C8 segment of the molecule can have strong effects on activity, whereas the remainder of the molecule is relatively tolerant to change. Variation of substituent stereochemistry with the C1-C8 segment, or removal of the functionality, can lead to significant loss of activity. Epothilone derivative compounds A-H differ from epothilone by modifications in the less sensitive portion of the molecule and so possess good biological activity and offer better pharmacokinetic characteristics, having improved lipophilic and steric profiles.

These novel derivatives can be prepared by altering the genes involved in the biosynthesis of epothilone optionally followed by chemical modification. The 9-hydroxy-epothilone derivatives prepared by genetic engineering can be used to generate the carbonate derivatives (compound D) by treatment with triphosgene or 1,1' carbonyldiimidazole in the presence of a base. In a similar manner, the 9,11-dihydroxy-epothilone derivative, upon proper protection of the C-7 hydroxyl group if it is present, yields the carbonate derivatives (compound F). Selective oximation of the 9 oxo-epothilone derivatives with hydroxylamine followed by reduction (Raney nickel in the presence of hydrogen or sodium cyanoborohydride) yield the 9-amino analogs. Reacting these 9-amino derivatives with p-nitrophenyl chloroformate in the presence of base and subsequently reacting with sodium hydride will produce the carbamate derivatives (compound E). Similarly, the carbamate compound G, upon proper protection of the C7 hydroxyl group if it is present, can be prepared form the 9-amino-11 hydroxy-epothilone derivatives.

Illustrative syntheses are provided below.

Part A. Epothilone D-7,9-cyclic carbonate

To a round bottom flask, a solution of 254 mg epothilone D in 5 mL of methylene chloride is added. It is cooled by an ice bath, and 0.3 mL of triethyl amine is then added. To this solution, 104 mg of triphosgene is added. The ice bath is removed, and the mixture is stirred under nitrogen for 5 hours. The solution is diluted with 20 mL of methylene chloride and washed with dilute sodium bicarbonate solution. The organic solution is dried over magnesium sulfate and filtered. Upon evaporation to dryness, the epothilone D-7,9-cyclic carbonate is isolated.

Part B. Epothilone D-7,9-cyclic carbamate (i) 9-amino-epothilone D

To a rounded bottom flask, a solution of 252 mg 9-oxo-epothilone D in 5 mL of methanol is added. Upon the addition of 0.5 mL 50% hydroxylamine in water and 0.1 mL acetic acid, the mixture is stirred at room temperature overnight. The solvent is then removed under reduced pressure to yield the 9-oxime-epothilone D. To a solution of this 9 oxime compound in 5 mL of tetrahydrofuran (THF) at ice bath is added 0.25 mL 1M solution of cyanoborohydride in THF. After the mixture is allowed to react for 1 hour, the ice bath is removed, and the solution is allowed to warm slowly to room temperature. One mL of acetic acid is added, and the solvent is then removed under reduced pressure. The residue is dissolved in 30 mL of methylene chloride and washed with saturated sodium chloride solution. The organic layer is separated and dried over magnesium sulfate and filtered. Upon evaporation of the solvent yields the 9-amino-epothilone D.

(ii) Epothilone D-7,9-cyclic carbamate

To a solution of 250 mg of 9-amino-epothilone D in 5 mL of methylene is added 110 mg of 4-nitrophenyl chloroformate followed by the addition of 1 mL of triethylamine. The solution is stirred at room temperature for 16 hours. It is diluted with 25 mL of methylene chloride. The solution is washed with saturated sodium chloride and the organic layer is separated and dried over magnesium sulfate. After filtration, the solution is evaporated to dryness at reduced pressure. The residue is dissolved in 10 mL of dry THF. Sodium hydride, 40 mg (60% dispersion in mineral oil), is added to the solution in an ice bath. The ice bath is removed, and the mixture is stirred for 16 hours. One-half mL of acetic acid is added, and the solution is evaporated to dryness under reduced pressure. The residue is re-dissolved in 50 mL methylene chloride and washed with saturated sodium chloride solution. The organic layer is dried over magnesium sulfate and the solution is filtered and the organic solvent is evaporated to dryness under reduced pressure. Upon purification on silica gel column, the epothilone D-7,9-carbamate is isolated.

The invention having now been described by way of written description and examples, those of skill in the art will recognize that the invention can be practiced in a variety of embodiments and that the foregoing description and examples are for purposes of illustration and not limitation of the following claims.

The invention claimed is:

1. A recombinant *Sorangium cellulosum* host cell that contains at least one mutated gene for an epothilone PKS protein or epothilone modification enzyme, wherein said mutated gene is inserted in whole or in part into the genomic DNA of said cell by homologous recombination with a recombinant vector comprising all or a part of a mutated epothilone epoK gene, wherein said recombinant host cell produces more epothilone C than epothilone A and/or more epothilone D than epothilone B.

2. A recombinant *Sorangium cellulosum* host cell that contains a mutated epoK gene that does not produce an enzymatically active epoK gene product, wherein said cell produces more epothilone C than epothilone A and/or more epothilone D than epothilone B.

3. The cell of claim 2, wherein said mutated epoK gene comprises an insertion and/or deletion relative to an unmutated epoK gene.

4. The cell of claim 2, wherein said host cell either
   (i) makes more epothilone C than epothilone A, B or D due to a mutation in the nucleotide sequence encoding epoD altering the extender module 4 acyltransferase ("AT") domain to provide specificity for malonyl CoA or
   (ii) makes more epothilone D than epothilone A, B or C due to a mutation in the nucleotide sequence encoding epoD altering the module 4 AT domain to provide specificity for methylmalonyl CoA.

5. An isolated or recombinant host cell that contains a nucleic acid that codes for expression of *Sorangium cellulosum* epothilone polyketide synthase ("PKS"), wherein said PKS contains an altered epoD extender module 4 acyltransferase ("AT") domain, whereby said acyltransferase domain has specificity for either malonyl CoA or for methylmalonyl CoA, but does not contain an enzymatically active product of a *Sorangium cellulosum* epoK gene.

6. The cell of claim 5, wherein said altered AT domain coding sequence has specificity for malonyl CoA and results in increased production of epothilone C and decreased production of epothilone D as compared to cells containing an unaltered AT domain coding sequence.

7. The cell of claim 5, wherein said altered AT domain coding has specificity for methylmalonyl CoA and results in increased production of epothilone D and decreased production of epothilone C as compared to cells containing an unaltered AT domain coding sequence.

8. A recombinant *Streptomyces* or *Myxococcus* host cell that expresses *Sorangium cellulosum* epothilone polyketide synthase ("PKS") genes, said genes including an epoD gene that comprises an altered extender module 4 acyltransferase ("AT") domain coding sequence, whereby said acyltransferase domain has specificity for either malonyl CoA or for methylmalonyl CoA, and the cell does not express an enzymatically active *Sorangium cellulosum* epoK gene product, wherein said *Strentomyces* or *Myxococcus* host cell optionally comprises one or more of said epothilone PKS genes, either integrated into its chromosomal DNA or comprised by an extrachromosomal expression vector, wherein said recombinant *Streptomyces* or *Myxococcus* host cell produces more epothilone C than epothilone A and/or more epothilone D than epothilone B.

9. The cell of claim 8, wherein said altered AT domain coding sequence has specificity for malonyl CoA and results in increased production of epothilone C and decreased production of epothilone D as compared to cells containing an unaltered AT domain coding sequence.

10. The cell of claim 8, wherein said altered AT domain coding has specificity for methylmalonyl CoA and results in increased production of epothilone D and decreased production of epothilone C as compared to cells containing an unaltered AT domain coding sequence.

* * * * *

UNITED STATES PATENT AND TRADEMARK OFFICE
CERTIFICATE OF CORRECTION

PATENT NO. : 7,732,186 B2  Page 1 of 1
APPLICATION NO. : 11/932927
DATED : June 8, 2010
INVENTOR(S) : Bryan Julien et al.

It is certified that error appears in the above-identified patent and that said Letters Patent is hereby corrected as shown below:

Title page, column 1, item [75] Inventor: Leonard Katz, delete "Hayward," and insert -- Oakland, --, therefor; and Claim 8, column 217, line 12, delete "*Strentomyces*" and insert -- *Streptomyces* --, therefor.

Signed and Sealed this

Seventh Day of December, 2010

David J. Kappos
*Director of the United States Patent and Trademark Office*

SEQUENCE LISTING

```
<160> NUMBER OF SEQ ID NOS: 34

<210> SEQ ID NO 1
<211> LENGTH: 25
<212> TYPE: PRT
<213> ORGANISM: Artificial
<220> FEATURE:
<223> OTHER INFORMATION: Synthetic Construct

<400> SEQUENCE: 1

Gln Thr Ala Phe Thr Gln Pro Ala Leu Phe Thr Phe Glu Tyr Ala Leu
1               5                   10                  15

Ala Ala Leu Trp Gly His Ser Ile Gly
            20                  25

<210> SEQ ID NO 2
<211> LENGTH: 71989
<212> TYPE: DNA
<213> ORGANISM: Artificial
<220> FEATURE:
<223> OTHER INFORMATION: Synthetic Construct

<400> SEQUENCE: 2
tcgtgcgcgg gcacgtcgag gcgtttgccg acttcggcgg cgtcccgcgc gtgctgctct        60
acgacaacct caagaacgcc gtcgtcgagc gccacggcga cgcgatccgg ttccacccca       120
cgctgctggc tctgtcggcg gattaccgct tcgagccgcg ccccgtcgcc gtcgcccgcg       180
gcaacgagaa gggccgcgtc gagcgcgcca tccgctacgt ccgcgagggc ttcttcgagg       240
cccgggccta cgccgacctc ggagacctca accgccaagc gaccgagtgg accagctccg       300
cggcgctcga tcgctcctgg gtcgaggacc gcgcccgcac cgtgcgtcag gccttcgacg       360
acgagcgcag cgtgctgctg cgacaccctg acacaccgtt tccggaccac gagcgcgtcg       420
aggtcgaggt cggaaagacc ccctacgcgc gcttcgatct caacgactac tcggtccccc       480
acgaccggac gcgccgcacg ctggtcgtcc tcgccgacct cagtcaggta cgcatcgccg       540
```

-continued

```
acggcaacca gatcgtcgcg acccacgtcc gttcgtggga ccgcggccag cagatcgagc    600
agcccgagca cctccagcgc ctggtcgacg agaagcgccg cgcccgcgag caccgcggcc    660
ttgatcgcct cgcgcgcgcc gcccgcagca gccaggcatt cctgcgcatc gtcgccgagc    720
gcggcgataa cgtcggcagc gcgatcgccc ggcttctgca actgctcgac gccgtgggcg    780
ccgccgagct cgaagaggcc ctggtcgagg tgcttgagcg cgacaccatc cacatcggtg    840
ccgtccgcca ggtgatcgac cgccgccgct ccgagcgcca cctgccgcct ccagtctcaa    900
tccccgtcac ccgcggcgag cacgccgccc tcgtcgtcac gccgcattcc ctcaccacct    960
acgacgccct gaagaaggac ccgacgccat gaccgacctg acgcccaccg agaccaaaga    1020
ccggctcaag agcctcggcc tcttcggcct gctcgcctgc tgggagcagc tcgccgacaa    1080
gccctggctt cgcgaggtgc tcgccatcga ggagcgcgag cgccacaagc gcagcctcga    1140
acgccgcctg aagaactccc gcgtcgccgc cttcaagccc atgaccgact cgactcgtc    1200
ctggcccaag aagatcgacc gcgaggccgt cgacgacctc tacgatagcc gctacgcgga    1260
cctgctcttc gaggtcgtca cccgtcgcta cgacgcgcag aagccgctct tgctcagcac    1320
gaacaaggca ttcgccgact ggggccaggt cttcccgcac gccgcgtgcg tcgtcacgct    1380
cgtcgaccgg ctcgtgcacc gcgccgaggt gatcgagatc gaggccgaga gctaccggct    1440
gaaggaagcc aaggagctca cgccacccg caccaagcag cgccgcacca agaagcactg    1500
agcggcattt tcaccggtga acttcaccga aatcccgcgt gttgccgaga tcatctacag    1560
gcggatcgag accgtgctca cggcgtggac gacatggcgc ggaaacgtcg tcgtaactgc    1620
ccagcaatgt catgggaatg gcccccttgag gggctggccg gggtcgacga tatcgcgcga    1680
tctccccgtc aattcccgag cgtaaaagaa aaatttgtca tagatcgtaa gctgtgctag    1740
tgatctgcct tacgttacgt cttccgcacc tcgagcgaat tctctcggat aactttcaag    1800
ttttctgagg gggcttggtc tctggttcct caggaagcct gatcgggacg agctaattcc    1860
catccatttt tttgagactc tgctcaaagg gattagaccg agtgagacag ttcttttgca    1920
gtgagcgaag aacctggggc tcgaccggag gacgatcgac gtccgcgagc gggtcagccg    1980
ctgaggatgt gcccgtcgtg gcggatcgtc ccatcgagcg cgcagccgaa gatccgattg    2040
cgatcgtcgg agcgggctgc cgtctgcccg gtggcgtgat cgatctgagc gggttctgga    2100
cgctcctcga gggctcgcgc gacaccgtcg ggcaagtccc cgccgaacgc tgggatgcag    2160
cagcgtggtt tgatcccgac ctcgatgccc cggggaagac gcccgttacg cgcgcatctt    2220
tcctgagcga cgtagcctgc ttcgacgcct ccttcttcgg catctcgcct cgcgaagcgc    2280
tgcggatgga ccctgcacat cgactcttgc tggaggtgtg ctgggaggcg ctggagaacg    2340
ccgcgatcgc tccatcggcg ctcgtcggta cggaaacggg agtgttcatc gggatcggcc    2400
cgtccgaata tgaggccgcg ctgccgcgag cgacggcgtc cgcagagatc gacgctcatg    2460
gcgggctggg gacgatgccc agcgtcggag cgggccgaat ctcgtatgtc ctcgggctgc    2520
gagggccgtg tgtcgcggtg gatacggcct attcgtcctc gctcgtggcc gttcatctgg    2580
cctgtcagag cttgcgctcc ggggaatgct ccacggccct ggctggtggg gtatcgctga    2640
tgttgtcgcc gagcaccctc gtgtggctct cgaagacccg cgcgctggcc acggacggtc    2700
gctgcaaggc gttttcggcg gaggccgatg ggttcggacg aggcgaaggg tgcgccgtcg    2760
tggtcctcaa gcggctcagt ggagcccgcg cggacggcga ccggatattg gcggtgattc    2820
gaggatccgc gatcaatcac gacggagcga gcagcggtct gaccgtgccg aacgggagct    2880
```

```
cccaagaaat cgtgctgaaa cgggccctgg cggacgcagg ctgcgccgcg tcttcggtgg    2940
gttatgtcga ggcacacggc acgggcacga cgcttggtga ccccatcgaa atccaagctc    3000
tgaatgcggt atacggcctc gggcgagacg tcgccacgcc gctgctgatc gggtcggtga    3060
agaccaacct tggccatcct gagtatgcgt cggggatcac tgggctgctg aaggtcgtct    3120
tgtcccttca gcacgggcag attcctgcgc acctccacgc gcaggcgctg aaccccggga    3180
tctcatgggg tgatcttcgg ctgaccgtca cgcgcgcccg gacaccgtgg ccggactgga    3240
atacgccgcg acgggcgggg gtgagctcgt tcggcatgag cgggaccaac gcgcacgtgg    3300
tgctggaaga ggcgccggcg gcgacgtgca caccgccggc gccggagcgg ccggcagagc    3360
tgctggtgct gtcggcaagg accgcggcag ccttggatgc acacgcggcg cggctgcgcg    3420
accatctgga gacctaccct tcgcagtgtc tgggcgatgt ggcgttcagt ctggcgacga    3480
cgcgcagcgc gatggagcac cggctcgcgg tggcggcgac gtcgagcgag gggctgcggg    3540
cagccctgga cgctgcggcg cagggacaga cgccgcccgg tgtggtgcgc ggtatcgccg    3600
attcctcacg cggcaagctc gcctttctct tcaccggaca gggggcgcag acgctgggca    3660
tgggccgtgg gctgtatgat gtatggcccg cgttccgcga ggcgttcgac ctgtgcgtga    3720
ggctgttcaa ccaggagctc gaccggccgc tccgcgaggt gatgtgggcc gaaccggcca    3780
gcgtcgacgc cgcgctgctc gaccagacag ccttttaccca gccggcgctg ttcaccttcg    3840
agtatgcgct cgccgcgctg tggcggtcgt ggggcgtaga gccggagttg gtcgctggcc    3900
atagcatcgg tgagctggtg gctgcctgcg tggcgggcgt gttctcgctt gaggacgcgg    3960
tgttcctggt ggctgcgcgc gggcgcctga tgcaggcgct gccggccggc ggggcgatgg    4020
tgtcgatcgc ggcgccggag gccgatgtgg ctgctgcggt ggcgccgcac gcagcgtcgg    4080
tgtcgatcgc cgcggtcaac ggtccggacc aggtggtcat cgcgggcgcc gggcaacccg    4140
tgcatgcgat cgcggcggcg atggccgcgc gcggggcgcg aaccaaggcg ctccacgtct    4200
cgcatgcgtt ccactcaccg ctcatggccc cgatgctgga ggcgttcggg cgtgtggccg    4260
agtcggtgag ctaccggcgg ccgtcgatcg tcctggtcag caatctgagc gggaaggctg    4320
gcacagacga ggtgagctcg ccgggctatt gggtgcgcca cgcgcgagag gtggtgcgct    4380
tcgcggatgg agtgaaggcg ctgcacgcgg ccggtgcggg caccttcgtc gaggtcggtc    4440
cgaaatcgac gctgctcggc ctggtgcctg cctgcctgcc ggacgccggg ccggcgctgc    4500
tcgcatcgtc gcgcgctggg cgtgacgagc cagcgaccgt gctcgaggcg ctcggcgggc    4560
tctgggccgt cggtggcctg gtctcctggg ccggcctctt cccctcaggg gggcggcggg    4620
tgccgctgcc cacgtaccct tggcagcgcg agcgctactg gatcgacacg aaagccgacg    4680
acgcggcgcg tggcgaccgc cgtgctccgg gagcgggtca cgacgaggtc gagaagggg    4740
gcgcggtgcg cggcggcgac cggcgcagcg ctcggctcga ccatccgccg cccgagagcg    4800
gacgccggga gaaggtcgag gccgccgcg accgtccgtt ccggctcgag atcgatgagc    4860
caggcgtgct cgatcgcctg gtgcttcggg tcacggagcg gcgcgcccct ggtcttggcg    4920
aggtcgagat cgccgtcgac gcggcgggc tcagcttcaa tgatgtccag ctcgcgctgg    4980
gcatggtgcc cgacgacctg ccgggaaagc ccaaccctcc gctgctgctc ggaggcgagt    5040
gcgccgggcg catcgtcgcc gtgggcgagg gcgtgaacgg ccttgtggtg gccaaccgg    5100
tcatcgccct ttcggcggga gcgtttgcta cccacgtcac cacgtcggct gcgctggtgc    5160
tgcctcggcc tcaggcgctc tcggcgaccg aggcggccgc catgcccgtc gcgtacctga    5220
cggcatggta cgcgctcgac ggaatagccc gccttcagcc gggggagcgg gtgctgatcc    5280
```

```
acgcggcgac cggcggggtc ggtctcgccg cggtgcagtg ggcgcagcac gtgggagccg    5340
aggtccatgc gacggccggc acgcccgaga agcgcgccta cctggagtcg ctgggcgtgc    5400
ggtatgtgag cgattcccgc tcggaccggt tcgtcgccga cgtgcgcgcg tggacgggcg    5460
gcgagggagt agacgtcgtg ctcaactcgc tttcgggcga gctgatcgac aagagtttca    5520
atctcctgcg atcgcacggc cggtttgtgg agctcggcaa gcgcgactgt tacgcggata    5580
accagctcgg gctgcggccg ttcctgcgca atctctcctt ctcgctggtg gatctccggg    5640
ggatgatgct cgagcggccg gcgcgggtcc gtgcgctctt cgaggagctc ctcggcctga    5700
tcgcggcagg cgtgttcacc cctcccccca tcgcgacgct cccgatcgct cgtgtcgccg    5760
atgcgttccg gagcatggcg caggcgcagc atcttgggaa gctcgtactc acgctgggtg    5820
acccggaggt ccagatccgt attccgaccc acgcaggcgc cggcccgtcc accggggatc    5880
gggatctgct cgacaggctc gcgtcagctc cgccggccgc gcgcgcggcg cgctggaggg    5940
cgttcctccg tacgcaggtc tcgcaggtgc tgcgcacgcc cgaaatcaag gtcggcgcgg    6000
aggcgctgtt cacccgcctc ggcatggact cgctcatggc cgtggagctg cgcaatcgta    6060
tcgaggcgag cctcaagctg aagctgtcga cgacgttcct gtccacgtcc cccaatatcg    6120
ccttgttgac ccaaaacctg ttggatgctc tcgccacagc tctctccttg gagcgggtgg    6180
cggcggagaa cctacgggca ggcgtgcaaa gcgacttcgt ctcatcgggc gcagatcaag    6240
actgggaaat cattgcccta tgacgatcaa tcagcttctg aacgagctcg agcaccaggg    6300
tgtcaagctg gcgccgatg gggagcgcct ccagatacag gcccccaaga acgccctgaa    6360
cccgaacctg ctcgctcgaa tctccgagca caaaagcacg atcctgacga tgctccgtca    6420
gagactcccc gcagagtcca tcgtgcccgc cccagccgag cggcacgttc cgtttcctct    6480
cacagacatc caaggatcct actggctggg tcggacagga gcgtttacgg tccccagcgg    6540
gatccacgcc tatcgcgaat acgactgtac ggatctcgac gtggcgaggc tgagccgcgc    6600
cttttcggaaa gtcgtcgcgc ggcacgacat gcttcgggcc cacacgctgc ccgacatgat    6660
gcaggtgatc gagcctaaag tcgacgccga catcgagatc atcgatctgc gcgggctcga    6720
ccggagcaca cgggaagcga ggctcgtatc gttgcgagat gcgatgtcgc accgcatcta    6780
tgacaccgag cgccctccgc tctatcacgt cgtcgccgtt cggctggacg agcagcaaac    6840
ccgtctcgtg ctcagtatcg atctcattaa cgttgaccta ggcagcctgt ccatcatctt    6900
caaggattgg ctcagcttct acgaagatcc cgagacctct ctccctgtcc tggagctctc    6960
gtaccgcgac tatgtgctcg cgctggagtc tcgcaagaag tctgaggcgc atcaacgatc    7020
gatggattac tggaagcggc gcgtcgccga gctccacct ccgccgatgc ttccgatgaa    7080
ggccgatcca tctaccctga gggagatccg cttccggcac acggagcaat ggctgccgtc    7140
ggactcctgg agtcgattga agcagcgtgt cggggagcgc gggctgaccc cgacgggcgt    7200
cattctggct gcattttccg aggtgatcgg gcgctggagc gcgagccccc ggtttacgct    7260
caacataacg ctcttcaacc ggctcccgt ccatccgcgc gtgaacgata tcaccgggga    7320
cttcacgtcg atggtcctcc tggacatcga caccactcgc gacaagagct tcgaacagcg    7380
cgctaagcgt attcaagagc agctgtggga agcgatggat cactgcgacg taagcggtat    7440
cgaggtccag cgagaggccg cccgggtcct ggggatccaa cgaggcgcat tgttcccccgt    7500
ggtgctcacg agcgcgctca accagcaagt cgttggtgtc acctcgctgc agaggctcgg    7560
cactccggtg tacaccagca cgcagactcc tcagctgctg ctggatcatc agctctacga    7620
```

```
gcacgatggg gacctcgtcc tcgcgtggga catcgtcgac ggagtgttcc cgcccgacct   7680
tctggacgac atgctcgaag cgtacgtcgc ttttctccgg cggctcactg aggaaccatg   7740
gagtgaacag atgcgctgtt cgcttccgcc tgcccagcta aagcgcggg cgagcgcaaa    7800
cgagaccaac tcgctgctga gcgagcatac gctgcacggc ctgttcgcgg cgcgggtcga   7860
gcagctgcct atgcagctcg ccgtggtgtc ggcgcgcaag acgctcacgt acgaagagct   7920
ttcgcgccgt tcgcggcgac ttggcgcgcg gctgcgcgag caggggggcac gcccgaacac   7980
attggtcgcg gtggtgatgg agaaaggctg ggagcaggtt gtcgcggttc tcgcggtgct   8040
cgagtcaggc gcggcctacg tgccgatcga tgccgaccta ccggcggagc gtatccacta   8100
cctcctcgat catggtgagg taaagctcgt gctgacgcag ccatggctgg atggcaaact   8160
gtcatggccg ccggggatcc agcggctgct cgtgagcgat gccggcgtcg aaggcgacgg   8220
cgaccagctt ccgatgatgc ccattcagac accttcggat ctcgcgtatg tcatctacac   8280
ctcgggatcc acagggttgc caaggggggt gatgatcgat catcggggtg ccgtcaacac   8340
catcctggac atcaacgagc gcttcgaaat agggcccgga gacagagtgc tggcgctctc   8400
ctcgctgagc ttcgatctct cggtctacga tgtgttcggg atcctggcgg cgggcggtac   8460
gatcgtggtg ccggacgcgt ccaagctgcg cgatccggcg cattgggcag cgttgatcga   8520
acgagagaag gtgacggtgt ggaactcggt gccggcgctg atgcggatgc tcgtcgagca   8580
ttccgagggt cgccccgatt cgctcgctag gtctctgcgg cttttcgctgc tgagcggcga   8640
ctggatcccg gtgggcctgc ctggcgagct ccaggccatc aggcccggcg tgtcggtgat   8700
cagcctgggc ggggccaccg aagcgtcgat ctggtccatc gggtaccccg tgaggaacgt   8760
cgatccatcg tgggcgagca tccctacgg ccgtccgctg cgcaaccaga cgttccacgt    8820
gctcgatgag gcgctcgaac cgcgcccggt ctgggttccg gggcaactct acattggcgg   8880
ggtcggactg gcactgggct actgcgcgca tgaagagaag acgcgcaaca gcttcctcgt   8940
gcaccccgag accggggagc gcctctacaa gaccggcgat ctgggccgct acctgcccga   9000
tggaaacatc gagttcatgg ggcgggagga caaccaaatc aagcttcgcg gataccgcgt   9060
tgagctcggg gaaatcgagg aaacgctcaa gtcgcatccg aacgtacgcg acgcggtgat   9120
tgtgcccgtc gggaacgacg cggcgaacaa gctccttcta gcctatgtgg tcccggaagg   9180
cacacggaga cgcgctgccg agcaggacgc gagcctcaag accgagcggg tcgacgcgag   9240
agcacacgcc gccaaagcgg acggattgag cgacggcgag agggtgcagt tcaagctcgc   9300
tcgacacgga ctccggaggg atctggacgg aaagcccgtc gtcgatctga ccgggctggt   9360
tccgcgggag gcggggctgg acgtctacgc gcgtcgccgt agcgtccgaa cgttcctcga   9420
ggccccgatt ccatttgttg aattcggccg attcctgagc tgcctgagca gcgtggagcc   9480
cgacggcgcg gcccttccca aattccgtta tccatcggct ggcagcacgt acccggtgca   9540
aacctacgcg tacgccaaat ccggccgcat cgagggcgtg gacgagggct tctattatta   9600
ccacccgttc gagcaccgtt tgctgaaggt ctccgatcac gggatcgagc gcggagcgca   9660
cgttccgcaa aacttcgacg tgttcgatga agcggcgttc ggcctcctgt tcgtgggcag   9720
gatcgatgcc atcgagtcgc tgtatggatc gttgtcacga gaattctgcc tgctggaggc   9780
cggatatatg gcgcagctcc tgatggagca ggcgccttcc tgcaacatcg gcgtctgtcc   9840
ggtgggtcaa ttcgattttg aacaggttcg gccggttctc gacctgcggc attcggacgt   9900
ttacgtgcac ggcatgctgg gcgggcgggt agacccgcgg cagttccagg tctgtacgct   9960
cggtcaggat tcctcaccga ggcgcgccac gacgcgcggc gcccctcccg gccgcgatca  10020
```

```
gcacttcgcc gatatccttc gcgacttctt gaggaccaaa ctacccgagt acatggtgcc    10080
tacagtcttc gtggagctcg atgcgttgcc gctgacgtcc aacggcaagg tcgatcgtaa    10140
ggccctgcgc gagcggaagg atacctcgtc gccgcggcat tcggggcaca cggcgccacg    10200
ggacgccttg gaggagatcc tcgttgcggt cgtacgggag gtgctcgggc tggaggtggt    10260
tgggctccag cagagcttcg tcgatcttgg tgcgacatcg attcacatcg ttcgcatgag    10320
gagtctgttg cagaagaggc tggatagggga gatcgccatc accgagttgt tccagtaccc    10380
gaacctcggc tcgctggcgt ccggtttgcg ccgagactcg aaagatctag agcagcggcc    10440
gaacatgcag gaccgagtgg aggctcggcg caagggcagg agacgtagct aagagcgccg    10500
aacaaaacca ggccgagcgg gccaatgaac cgcaagcccg cctgcgtcac cctgggactc    10560
atctgatctg atcgcgggta cgcgtcgcgg gtgtgcgcgt tgagccgtgt tgctcgaacg    10620
ctgaggaacg gtgagctcat ggaagaacaa gagtcctccg ctatcgcagt catcggcatg    10680
tcgggccgtt ttccggggggc gcgggatctg gacgaattct ggaggaacct tcgagacggc    10740
acggaggccg tgcagcgctt ctccgagcag gagctcgcgg cgtccggagt cgacccagcg    10800
ctggtgctgg acccgaacta cgtccgggcg ggcagcgtgc tggaagatgt cgaccggttc    10860
gacgctgctt tcttcggcat cagcccgcgc gaggcagagc tcatggatcc gcagcaccgc    10920
atcttcatgg aatgcgcctg ggaggcgctg gagaacgccg gatacgaccc gacagcctac    10980
gagggctcta tcggcgtgta cgccggcgcc aacatgagct cgtacttgac gtcgaacctc    11040
cacgagcacc cagcgatgat gcggtggccc ggctggtttc agacgttgat cggcaacgac    11100
aaggattacc tcgcgaccca cgtctcctac aggctgaatc tgagagggcc gagcatctcc    11160
gttcaaactg cctgctctac ctcgctcgtg gcggttcact tggcgtgcat gagcctcctg    11220
gaccgcgagt gcgacatggc gctggccggc gggattaccg tccggatccc ccatcgagcc    11280
ggctatgtat atgctgaggg gggcatcttc tctcccgacg gccattgccg ggccttcgac    11340
gccaaggcga acggcacgat catgggcaac ggctgcgggg ttgtcctcct gaagccgctg    11400
gacccgggcg ctctccgatgg tgatcccgtc cgcgcggtca tccttgggtc tgccacaaac    11460
aacgacggag cgaggaagat cgggttcact gcgcccagtg aggtgggcca ggcgcaagcg    11520
atcatggagg cgctggcgct ggcagggtc gaggcccgt ccatccaata catcgagacc    11580
cacgggaccg gcacgctgct cggagacgcc atcgagacgg cggcgttgcg gcgggtgttc    11640
gatcgcgacg cttcgacccg gaggtcttgc gcgatcggct ccgtgaagac cggcatcgga    11700
cacctcgaat cggcggctgg catcgccggt ttgatcaaga cggtcttggc gctggagcac    11760
cggcagctgc cgcccagcct gaacttcgag tctcctaacc catcgatcga tttcgcgagc    11820
agcccgttct acgtcaatac ctctcttaag gattggaata ccggctcgac tccgcggcgg    11880 gccgcgtca gctcgttcgg gatcggcggc accaacgccc atgtcgtgct ggaggaagca    11940
cccgcggcga agcttccagc cgcggcgccg gcgcgctctg ccgagctctt cgtcgtctcg    12000
gccaagagcg cagcggcgct ggatgccgcg cggcacggc tacgagatca tctgcaggcg    12060 caccagggc tttcgttggg cgacgtcgcc ttcagcctgg cgacgacgcg cagtcccatg    12120
gagcaccggc tcgcgatggc ggcaccgtcg cgcgaggcgt tgcgagaggg gctcgacgca    12180
gcggcgcgag gccagacccc gccgggcgcc gtgcgtggcc gctgctcccc aggcaacgtg    12240
ccgaaggtgg tcttcgtctt tcccggccag ggctctcagt gggtcggtat gggccgtcag    12300
ctcctggctg aggaacccgt cttccacgcg gcgctttcgg cgtgcgaccg ggccatccag    12360
```

```
gccgaagctg gttggtcgct gctcgccgag ctcgccgccg acgaagggtc gtcccagatc   12420
gagcgcatcg acgtggtgca gccggtgctg ttcgcgctcg cggtggcatt tgcggcgctg   12480
tggcggtcgt ggggtgtcgg gcccgacgtc gtgatcggcc acagcatggg cgaggtagcc   12540
gccgcgcatg tggccggggc gctgtcgctc gaggatgcgg tggcgatcat ctgccggcgc   12600
agccggctgc tccggcgcat cagcggtcag ggcgagatgg cggtgaccga gctgtcgctg   12660
gccgaggccg aggcagcgct ccgaggctac gaggatcggt tgagcgtggc cgtgagcaac   12720
agcccgcgct cgacggtgct ctcgggcgag ccggcagcga tcggcgaggt gctgtcgtcc   12780
ctgaacgcga aggggtgtt ctgccgtcgg gtgaaggtga tgtcgccag ccacagcccg     12840
caggtcgacc cgctgcgcga ggacctcttg gcagcgctgg gcgggctccg gccgcgtgcg   12900
gctgcggtgc cgatgcgctc gacggtgacg ggcgccatgg tagcgggccc ggagctcgga   12960
gcgaattact ggatgaacaa tctcaggcag cctgtgcgct tcgccgaggt agtccaggcg   13020
cagctccaag gcgccacgg tctgttcgtg gagatgagcc cgcatccgat cctaacgact    13080
tcggtcgagg agatgcggcg cgcggcccag cgggcgggcg cagcggtggg ctcgctgcgg   13140
cgagggcagg acgagcgccc ggcgatgctg gaggcgctgg gcgcgctgtg ggcgcagggc   13200
taccctgtac cctgggggcg gctgtttccc gcggggggc ggcgggtacc gctgccgacc    13260
tatccctggc agcgcgagcg gtactggatc gaagcgccgg ccaagagcgc cgcgggcgat   13320
cgccgcggcg tgcgtgcggg cggtcacccg ctcctcggtg aaatgcagac cctatcaacc   13380
cagacgagca cgcggctgtg ggagacgacg ctggatctca gcggctgcc gtggctcggc    13440
gaccaccggg tgcagggagc ggtcgtgttt ccggcgcgg cgtacctgga gatggcgatt     13500
tcgtcggggg ccgaggcttt gggcgatggc ccattgcaga taaccgacgt ggtgctcgcc   13560
gaggcgctgg ccttcgcggg cgacgcggcg tgttggtcc aggtggtgac gacggagcag    13620
ccgtcgggac ggctgcagtt ccagatcgcg agcggggcgc cgggcgctgg ccacgcgtcc   13680
ttccgggtcc acgctcgcgg cgcgttgctc cgagtggagc gcaccgaggt cccggctggg   13740
cttacgcttt ccgccgtgcg cgcacggctc caggccagca tgcccgccgc ggccacctac   13800
gcggagctga ccgagatggg gctgcagtac ggccctgcct tccaggggat tgctgagcta   13860
tggcgcggtg agggcgaggc gctgggacgg gtacgcctgc ccgacgcggc cggctcggca   13920
gcggagtatc ggttgcatcc tgcgctgctg gacgcgtgct tccaggtcgt cggcagcctc   13980
ttcgccggcg gtggcgaggc gacgccgtgg gtgcccgtgg aagtgggctc gctgcggctc   14040
ttgcagcggc cttcggggga gctgtggtgc catgcgcgcg tcgtgaacca cgggcgccaa   14100
accccgatc ggcagggcgc cgacttttgg gtggtcgaca gctcgggtgc agtggtcgcc    14160
gaagtcagcg ggctcgtggc gcagcggctt ccggagggg tgcgccggcg cgaagaagac    14220
gattggttcc tggagctcga gtgggaaccc gcagcggtcg gcacagccaa ggtcaacgcg   14280
ggccggtggc tgctcctcgg cggcggcggt gggctcggcg ccgcgttgcg ctcgatgctg   14340
gaggccggcg gccatgccgt cgtccatgcg gcagagagca acacgagcgc tgccggcgta   14400
cgcgcgctcc tggcaaaggc ctttgacggc caggctccga cggcggtggt gcacctcggc   14460
agcctcgatg ggggtggcga gctcgaccca gggctcgggg cgcaaggcgc attggacgcg   14520
ccccggagcg ccgacgtcag tcccgatgcc ctcgatccgg cgctggtacg tggctgtgac   14580
agcgtgctct ggaccgtgca ggcccctggcc ggcatgggct ttcgagacgc cccgcgattg   14640
tggcttctga cccgcggcgc acaggccgtc ggcgccggcg acgtctccgt gacacaggca   14700
ccgctgctgg ggctgggccg cgtcatcgcc atggagcacg cggatctgcg ctgcgctcgg   14760
```

-continued

```
gtcgacctcg atccgacccg gcccgatggg gagctcggtg ccctgctggc cgagctgctg    14820
gccgacgacg ccgaagcgga agtcgcgttg cgcggtggcg agcgatgcgt cgctcggatc    14880
gtccgccggc agcccgagac ccggcccggg gggaggatcg agagctgcgt tccgaccgac    14940
gtcaccatcc gcgcggacag cacctacctt gtgaccggcg gtctgggtgg gctcggtctg    15000
agcgtggccg gatggctggc cgagcgcggc gctggtcacc tggtgctggt gggccgctcc    15060
ggcgcggcga gcgtggagca acgggcagcc gtcgcggcgc tcgaggcccg cggcgcgcgc    15120
gtcaccgtgg cgaaggcaga tgtcgccgat cgggcgcagc tcgagcggat cctccgcgag    15180
gttaccacgt cggggatgcc gctgcggggc gtcgtccatg cggccggcat cttggacgac    15240
gggctgctga tgcagcagac tcccgcgcgg tttcgtaagg tgatggcgcc caaggtccag    15300
ggggccttgc acctgcacgc gttgacgcgc gaagcgccgc tttccttctt cgtgctgtac    15360
gcttcgggag tagggctctt gggctcgccg ggccagggca actacgccgc ggccaacacg    15420
ttcctcgacg ctctggcgca ccaccggagg gcgcaggggc tgccagcgtt gagcgtcgac    15480
tggggcctgt tcgcggaggt gggcatggcg gccgcgcagg aagatcgcgg cgcgcggctg    15540
gtctcccgcg gaatgcggag cctcaccccc gacgagggc tgtccgctct ggcacggctg    15600
ctcgaaagcg gccgcgtgca ggtgggggtg atgccggtga acccgcggct gtgggtggag    15660
ctctaccccg cggcggcgtc ttcgcgaatg ttgtcgcgcc tggtgacggc gcatcgcgcg    15720
agcgccggcg ggccagccgg ggacggggac ctgctccgcc gcctcgctgc tgccgagccg    15780
agcgcgcgga gcgggctcct ggagccgctc ctccgcgcgc agatctcgca ggtgctgcgc    15840
ctccccgagg gcaagatcga ggtggacgcc ccgctcacga gctgggcat gaactcgctg    15900
atggggctcg agctgcgcaa ccgcatcgag gccatgctgg gcatcaccgt accggcaacg    15960
ctgttgtgga cctatcccac ggtggcggcg ctgagcgggc atctggcgcg ggaggcatgc    16020
gaagccgctc ctgtggagtc accgcacacc accgccgatt ctgctgtcga gatcgaggag    16080
atgtcgcagg acgatctgac gcagttgatc gcagcaaaat tcaaggcgct tacatgacta    16140
ctcgcggtcc tacggcacag cagaatccgc tgaaacaagc ggccatcatc attcagcggc    16200
tggaggagcg gctcgctggg ctcgcacagg cggagctgga acggaccgag ccgatcgcca    16260
tcgtcggtat cggctgccgc ttccctggcg gtgcggacgc tccggaagcg tttttgggagc    16320
tgctcgacgc ggagcgcgac gcggtccagc cgctcgacag gcgctgggcg ctggtaggtg    16380
tcgctcccgt cgaggccgtg ccgcactggg cggggctgct caccgagccg atagattgct    16440
tcgatgctgc gttcttcggc atctcgcctc gggaggcgcg atcgctcgac ccgcagcatc    16500
gtctgttgct ggaggtcgct tgggaggggc tcgaggacgc cggtatcccg ccccggtcca    16560
tcgacgggag ccgcaccggt gtgttcgtcg gcgctttcac ggcggactac gcgcgcacgg    16620
tcgctcggtt gccgcgcgag gagcgagacg cgtacagcgc caccggcaac atgctcagca    16680
tcgccgccgg acggctgtcg tacacgctgg ggctgcaggg accttgcctg accgtcgaca    16740
cggcgtgctc gtcatcgctg gtggcgattc acctcgcctg ccgcagcctg cgcgcaggag    16800
agagcgatct cgcgttggcg ggaggggtca gcacgctcct ctcccccgac atgatggaag    16860
ccgcggcgcg cacgcaagcg ctgtcgcccg atggtcgttg ccggaccttc gatgcttcgg    16920
ccaacgggtt cgtccgtggc gagggctgtg gcctggtcgt cctcaaacgg ctctccgacg    16980
cgcaacggga tggcgaccgc atctgggcgc tgatccgggg ctcggccatc aaccatgatg    17040
gccggtcgac cgggttgacc gcgcccaacg tgctggctca ggagacggtc ttgcgcgagg    17100
```

```
cgctgcggag cgcccacgtc gaagctgggg ccgtcgatta cgtcgagacc cacggaacag   17160
ggacctcgct gggcgatccc atcgaggtcg aggcgctgcg ggcgacggtg gggccggcgc   17220
gctccgacgg cacacgctgc gtgctgggcg cggtgaagac caacatcggc catctcgagg   17280
ccgcggcagg cgtagcgggc ctgatcaagg cagcgctttc gctgacgcac gagcgcatcc   17340
cgagaaacct caacttccgc acgctcaatc cgcggatccg gctcgagggc agcgcgctcg   17400
cgttggcgac cgagccggtg ccgtggccgc gcacggaccg tccgcgcttc gcgggggtga   17460
gctcgttcgg gatgagcgga acgaacgcgc atgtggtgct ggaagaggcg ccggcggtgg   17520
agctgtggcc tgccgcgccg gagcgctcgg cggagctttt ggtgctgtcg ggcaagagcg   17580
aggggcgct cgacgcgcag gcggcgcggc tgcgcgagca cctggacatg cacccggagc   17640
tcgggctcgg ggacgtggcg ttcagcctgg cgacgacgcg cagcgcgatg acccaccggc   17700
tcgcggtggc ggtgacgtcg cgcgaggggc tgctggcggc gctttcggcc gtggcgcagg   17760
ggcagacgcc ggcgggggcg cgcgcgctgca tcgcgagctc ctcgcgcggc aagctggcgt   17820
tgctgttcac cggacagggc gcgcagacgc cgggcatggg ccgggggctc tgcgcggcgt   17880
ggccagcgtt ccgggaggcg ttcgaccggt gcgtgacgct gttcgaccgg gagctggacc   17940
gcccgctgcg cgaggtgatg tgggcggagg cggggagcgc cgagtcgttg ttgctggacc   18000
agacggcgtt cacccagccc cgcgctcttcg cggtggagta cgcgctgacg gcgctgtggc   18060
ggtcgtgggg cgtagagccg gagctcctgg ttgggcatag catcggggag ctggtggcgg   18120
cgtgcgtggc ggggtgttc tcgctggaag atggggtgag gctcgtggcg gcgcgcgggc   18180
ggctgatgca ggggctctcg gcgggcggcg cgatggtgtc gctcggagcg ccggaggcgg   18240
aggtggccgc ggcggtggcg ccgcacgcgg cgtgggtgtc gatcgcggcg gtcaatgggc   18300
cggagcaggt ggtgatcgcg ggcgtggagc aagcggtgca ggcgatcgcg gcggggttcg   18360
cggcgcgcgg cgtgcgcacc aagcggctgc atgtctcgca cgcgttccac tcgccgctga   18420
tggaaccgat gctggaggag ttcgggcggg tggcggcgtc ggtgacgtac cggcggccaa   18480
gcgtttcgct ggtgagcaac ctgagcggga aggtggtcac ggacgagctg agcgcgccgg   18540
gctactgggt gcggcacgtg cgggaggcgg tgcgcttcgc ggacggggtg aaggcgctgc   18600
acgaagccgg cgcgggcacg ttcctcgaag tgggcccgaa gccgacgctg ctcggcctgt   18660
tgccagcttg cctgccggag gcggagccga cgttgctggc gtcgttgcgc gccgggcgcg   18720
aggaggctgc ggggggtgctc gaggcgctgg gcaggctgtg ggccgctggc ggctcggtca   18780
gctggccggg cgtcttcccc acggctgggc ggcggtgcc gctgccgacc tatccgtggc   18840
agcggcagcg gtactggatc gaggcgccgg ccgaagggct cggagccacg gccgccgatg   18900
cgctggcgca gtggttctac cgggtggact ggcccgagat gcctcgctca tccgtggatt   18960
cgcggcgagc ccggtccggc gggtggctgg tgctggccga ccggggtgga gtcggggagg   19020
cggccgcggc ggcgctttcg tcgcagggat gttcgtgcgc cgtgctccat gcgcccgccg   19080
aggcctccgc ggtcgccgag caggtgaccc aggccctcgg tggccgcaac gactggcagg   19140
gggtgctgta cctgtggggt ctggacgccg tcgtggaggc ggggcatcg gccgaagagg   19200
tcggcaaagt cacccatctt gccacggcgc cggtgctcgc gctgattcag gcggtgggca   19260
cggggccgc ctcaccccgg ctctggatcg tgacccgagg ggcctgcacg gtgggcggcg   19320
agcctgacgc tgccccctgt caggcggcgc tgtggggtat gggccgggtc gcggcgctgg   19380
agcatcccgg ctcctgggc gggctcgtgg acctggatcc ggaggagagc ccgacggagg   19440
tcgaggccct ggtggccgag ctgctttcgc cggacgccga ggatcagctg gcattccgcc   19500
```

```
aggggcgccg gcgcgcagcg cggctcgtgg ccgccccacc ggagggaaac gcagcgccgg    19560
tgtcgctgtc tgcggagggg agttacttgg tgacgggtgg gctgggcgcc cttggcctcc    19620
tcgttgcgcg gtggttggtg gagcgcgggg cggggcacct tgtgctgatc agccggcacg    19680
gattgcccga ccgcgaggaa tggggccgag atcagccgcc agaggtgcgc gcgcgcattg    19740
cggcgatcga ggcgctggag gcgcaggcg cgcgggtcac cgtggcggcg gtcgacgtgg     19800
ccgatgccga aggcatggcg gcgctcttgg cggccgtcga gccgccgctg cgggggggtcg   19860
tgcacgccgc gggtctgctc gacgacgggc tgctggccca ccaggacgcc ggtcggctcg    19920
cccgggtgtt gcgccccaag gtggaggggg catgggtgct gcacaccctt acccgcgagc    19980
agccgctgga cctcttcgta ctgttttcct cggcgtcggg cgtcttcggc tcgatcggcc    20040
agggcagcta cgcggcaggc aatgcctttt tggacgcgct ggcggacctc cgtcgaacgc    20100
aggggctcgc cgccctgagc atcgcctggg gcctgtgggc ggagggggg atgggctcgc     20160
aggcgcagcg ccgggaacat gaggcatcgg gaatctgggc gatgccgacg agtcgtgccc    20220
tggcggcgat ggaatggctg ctcggtacgc gcgcgacgca gcgcgtggtc atccagatgg    20280
attgggccca tgcgggagcg gctccgcgcg acgcgagccg aggccgcttc tgggatcggc    20340
tggtaactgt cacgaaagcg gcctcctcct cggccgtgcc agctgtagag cgctggcgca    20400
acgcgtctgt tgtggagacc cgctcggcgc tctacgagct tgtgcgcggc gtggtcgccg    20460
gggtgatggg ctttaccgac caaggcacgc tcgacgtgcg acgaggcttc gccgagcagg    20520
gcctcgactc cctgatggct gtggagatcc gcaaacggct tcaggtgag ctgggtatgc     20580
cgctgtcggc gacgctggcg ttcgaccatc cgaccgtgga gcggctggtg gaatacttgc    20640
tgagccaggc gctggagctg caggaccgca ccgacgtgcg aagcgttcgg ttgccggcga    20700
cagaggaccc gatcgccatc gtgggtgccg cctgccgctt cccgggcggg gtcgaggacc    20760
tggagtccta ctggcagctg ttgaccgagg gcgtggtggt cagcaccgag gtgccggccg    20820
accggtggaa tggggcagac gggcgcggcc ccggctcggg agaggctccg agacagacct    20880
acgtgcccag gggtggcttt ctgcgcgagg tggagacgtt cgatgcggcg ttcttccaca    20940
tctcgcctcg ggaggcgatg agcctggacc cgcaacagcg gctgctgctg gaagtgagct    21000
gggaggcgat cgacgcgcgc ggccaggacc cgtcggcgct cgcgagagc cccacggggcg    21060
tgttcgtggg cgcgggcccc aacgaatatg ccgagcgggt gcaggacctc gccgatgagg    21120
cggcggggct ctacagcggc accggcaaca tgctcagcgt tgcggcggga cggctgtcat    21180
ttttcctggg cctgcacggg ccgaccctgg ctgtggatac ggcgtgctcc tcgtcgctcg    21240
tggcgctgca cctcggctgc cagagcttgc gacggggcga gtgcgaccaa gccctggttg    21300
gcggggtcaa catgctgctc tcgccgaaga ccttcgcgct gctctcacgg atgcacgcgc    21360
tttcgcccgg cggcgtgc aagacgttct cggccgacgc ggacggctac gcgcgggccc     21420
agggctgcgc cgtggtggtg ctcaagcggc tctccgacgc gcagcgcgac cgcgaccccca   21480
tcctggcggt gatccggggt acggcgatca atcatgatgg cccgagcagc gggctgacag    21540
tgcccagcgg ccctgcccag gaggcgctgt acgccaggc gctggcgcac gcaggggtgg     21600
ttccggccga cgtcgatttc gtggaatgcc acgggaccgg gacggcgctg ggcgacccga    21660
tcgaggtgcg ggcgctgagc gacgtgtacg ggcaagcccg ccctgcggac cgaccgctga    21720
tcctgggagc cgccaaggcc aaccttgggc acatggagcc cgcggcgggc ctggccggct    21780
tgctcaaggc ggtgctcgcg ctggggcaag agcaaatacc agcccagccg gagctgggcg    21840
```

```
agctcaaccc gctcttgccg tgggaggcgc tgccggtggc ggtggcccgc gcagcggtgc   21900
cgtggccgcg cacggaccgt ccgcgcttcg cggggggtgag ctcgttcggg atgagcggaa   21960
cgaacgcgca tgtggtgctg aagaggcgc cggcggtgga gctgtggcct gccgcgccgg   22020
agcgctcggc ggagctttg tgctgtcgg gcaagagcga gggggcgctc gacgcgcagg   22080
cggcgcggct gcgcgagcac ctggacatgc acccggagct cgggctcggg gacgtggcgt   22140
tcagcctggc gacgacgcgc agcgcgatga accaccggct cgcggtggcg gtgacgtcgc   22200
gcgaggggct gctggcggcg ctttcggccg tggcgcaggg gcagacgccg ccggggggcgg   22260
cgcgctgcat cgcgagctcg tcgcgcggca agctggcgtt cctgttcacc ggacagggcg   22320
cgcagacgcc gggcatgggc cgggggcttt gcgcggcgtg gccagcgttc cgagaggcgt   22380
tcgaccggtg cgtggcgctg ttcgaccggg agctggaccg cccgctgtgc gaggtgatgt   22440
gggcggagcc ggggagcgcc gagtcgttgt tgctcgacca cgacggcgttc acccagcccg   22500
cgctcttcac ggtggagtac gcgctgacgg cgctgtggcg gtcgtggggc gtagagccgg   22560
agctggtggc tgggcatagc gccggggagc tggtggcggc gtgcgtggcg ggggtgttct   22620
cgctggaaga tgggggtgagg ctcgtggcgg cgcgcgggcg gctgatgcag gggctctcgg   22680
cgggcggcgc gatggtgtcg ctcggagcgc cggaggcgga ggtggccgcg gcggtggcgc   22740
cgcacgcggt gtgggtgtcg atcgcggcgg tcaatgggcc ggagcaggtg gtgatcgcgg   22800
gcgtggagca agcggtgcag gcgatcgcgg cggggttcgc ggcgcgcggc gtgcgcacca   22860
agcggctgca tgtctcgcac gcatcccact cgccgctgat ggaaccgatg ctggaggagt   22920
tcgggcgggt ggcggcgtcg gtgacgtacc ggcggccaag cgtttcgctg gtgagcaacc   22980
tgagcgggaa ggtggtcacg gacgagctga gcgcgccggg ctactgggtg cggcacgtgc   23040
gggaggcggt gcgcttcgcg gacgggggtga aggcgctgca cgaagccggc gcggggacgt   23100
tcctcgaagt ggggcccgaag ccgacgctgc tcggcctgtt gccagcttgc ctgccggagg   23160
cggagccgac gctgctggcg tcgttgcgcg ccgggcgcga ggaggctgcg ggggtgctcg   23220
aggcgctggg caggctgtgg gccgccggcg gctcggtcag ctggccgggc gtcttcccca   23280
cggctgggcg gcgggtgccg ctgccgacct atccgtggca gcggcagcgg tactggcccg   23340
acatcgagcc tgacagccgt cgccacgcag ccgcggatcc gacccaaggc tggttctatc   23400
gcgtggactg gccggagata cctcgcagcc tccagaaatc agaggaggcg agccgcggga   23460
gctggctggt attggcggat aagggtggag tcggcgaggc ggtcgctgca gcgctgtcga   23520
cacgtggact tccatgcgtc gtgctccatg cgccggcaga gacatccgcg accgccgagc   23580
tggtgaccga ggctgccggc ggtcgaagcg attggcaggt agtgctctac ctgtgggggtc   23640
tggacgccgt cgtcggcgcg gaggcgtcga tcgatgagat cggcgacgcg acccgtcgtg   23700
ctaccgcgcc ggtgctcggc ttggctcggt ttctgagcac cgtgtcttgt tcgccccgac   23760
tctgggtcgt gacccggggg gcatgcatcg ttggcgacga gcctgcgatc gccccttgtc   23820
aggcggcgtt atgggcatg ggccgggtgg cggcgctcga gcatcccggg gcctggggcg   23880
ggctcgtgga cctggatccc cgagcgagcc cgccccaagc cagcccgatc gacggcgaga   23940
tgctcgtcac cgagctattg tcgcaggaga ccgaggacca gctcgccttc gccatgggc   24000
gccggcacgc ggcacggctg gtggccgccc gccacgggg ggaagcggca ccggcgtcgc   24060
tgtctgcgga ggcgagctac ctggtgacgg gaggcctcgg tgggctgggc ctgatcgtgg   24120
cccagtggct ggtggagctg ggagcgcggc acttggtgct gaccagccgg cgcgggttgc   24180
ccgaccggca ggcgtggcgc gagcagcagc cgcctgagat ccgcgcgcgg atcgcagcgg   24240
```

```
tcgaggcgct ggaggcgcgg ggtgcacggg tgaccgtggc agcggtggac gtggccgacg   24300
tcgaaccgat gacagcgctg gtttcgtcgg tcgagccccc gctgcgaggg gtggtgcacg   24360
ccgctggcgt cagcgtcatg cgtccactgg cggagacgga cgagaccctg ctcgagtcgg   24420
tgctccgtcc caaggtggcc gggagctggc tgctgcaccg gctgctgcac ggccggcctc   24480
tcgacctgtt cgtgctgttc tcgtcgggcg cagcggtgtg gggtagccat agccagggtg   24540
cgtacgcggc ggccaacgct ttcctcgacg ggctcgcgca tcttcggcgt tcgcaatcgc   24600
tgcctgcgtt gagcgtcgcg tggggtctgt gggccgaggg aggcatggcg gacgcggagg   24660
ctcatgcacg tctgagcgac atcggggttc tgcccatgtc gacgtcggca gcgttgtcgg   24720
cgctccagcg cctggtggag accggcgcgg ctcagcgcac ggtgacccgg atggactggg   24780
cgcgcttcgc gccggtgtac accgctcgag ggcgtcgcaa cctgctttcg gcgctggtcg   24840
cagggcgcga catcatcgcg ccttcccctc cggcggcagc aacccggaac tggcgtggcc   24900
tgtccgttgc ggaagcccgc atggctctgc acgaggtcgt ccatggggcc gtcgctcggg   24960
tgctgggctt cctcgacccg agcgcgctcg atcctgggat ggggttcaat gagcagggcc   25020
tcgactcgtt gatggcggtg gagatccgca acctccttca ggctgagctg gacgtgcggc   25080
tttcgacgac gctggccttt gatcatccga cggtacagcg gctggtggag catctgctcg   25140
tcgatgtact gaagctggag gatcgcagcg acacccagca tgttcggtcg ttggcgtcag   25200
acgagcccat cgccatcgtg ggagccgcct gccgcttccc gggcgggtg gaggacctgg   25260 agtcctactg gcagctgttg gccgagggcg tggtggtcag cgccgaggtg ccggccgacc   25320
ggtgggatgc ggcggactgg tacgaccctg atccggagat cccaggccgg acttacgtga   25380
ccaaaggcgc cttcctgcgc gatttgcaga gattggatgc gaccttcttc cgcatctcgc   25440
ctcgcgaggc gatgagcctc gacccgcagc agcggttgct cctggaggta agctgggagg   25500
cgctcgagag cgcgggtatc gctccggata cgctgcgaga tagccccacc ggggtgttcg   25560
tgggtgcggg gcccaatgag tactacacgc agcggctgcg aggcttcacc gacggagcgg   25620
cagggctgta cggcggcacc gggaacatgc tcagcgttgc ggctggacgg ctgtcgtttt   25680
tcctgggtct gcacggcccg acgctggcca tggatacggc gtgctcgtcc tccctggtcg   25740
cgctgcacct cgcctgccag agcctgcgac tgggcgagtg cgatcaagcg ctggttggcg   25800
gggtcaacgt gctgctcgcg ccggagacct tcgtgctgct ctcacggatg cgcgcgcttt   25860
cgcccgacgg gcggtgcaag acgttctcgg ccgacgcgga cggctacgcg cggggcgagg   25920
ggtgcgccgt ggtggtgctc aagcggctgc gcgatgcgca gcgcgccggc gactccatcc   25980
tggcgctgat ccggggaagc gcggtgaacc acgacgcccc gagcagcggg ctgaccgtgc   26040
ccaacggacc cgcccagcaa gcattgctgc gccaggcgct ttcgcaagca ggcgtgtctc   26100
cggtcgacgt tgattttgtg gagtgtcacg ggacagggac ggcgctgggc gacccgatcg   26160
aggtgcaggc gctgagcgag gtgtatggtc cagggcgctc cgaggatcga ccgctggtgc   26220
tgggggccgt caaggccaac gtcgcgcatc tggaggcggc atccggcttg gccagcctgc   26280
tcaaggccgt gcttgcgctg cggcacgagc agatcccggc ccagccggag ctgggggagc   26340
tcaacccgca cttgccgtgg aacacgctgc cggtggcggt gccacgtaag gcggtgccgt   26400
gggggcgcgg cgcacggccg cgtcgggccg gcgtgagcgc gttcggggttg agcggaacca   26460 acgtgcatgt cgtgctggag gaggcaccgg aggtggagct ggtgcccgcg cgccgcggcg   26520
gaccggtgga gctggttgtg ctatcggcca agagcgcggc ggcgctggac gccgcggcgg   26580
```

```
aacggctctc ggcgcacctg tccgcgcacc cggagctgag cctcggcgac gtggcgttca   26640
gcctggcgac gacgcgcagc ccgatggagc accggctcgc catcgcgacg acctcgcgcg   26700
aggccctgcg aggcgcgctg gacgccgcgg cgcagcggca gacgccgcag ggcgcggtgc   26760
gcggcaaggc cgtgtcctca cgcggtaagt tggctttcct gttcaccgga cagggcgcgc   26820
aaatgccggg catgggccgt gggctgtacg aggcgtggcc agcgttccgg gaggcgttcg   26880
accggtgcgt ggcgctcttc gatcgggagc tcgaccagcc tctgcgcgag gtgatgtggg   26940
ctgcgccggg cctcgctcag gcggcgcggc tcgatcagac cgcgtacgcg cagccggctc   27000
tctttgcgct ggagtacgcg ctggctgccc tgtggcgttc gtggggcgtg gagccgcacg   27060
tactcctcgg tcatagcatc ggcgagctgg tcgccgcctg cgtggcgggc gtgttctcgc   27120
tcgaagacgc ggtgaggttg gtggccgcgc gcgggcggct gatgcaggcg ctgcccgccg   27180
gcggtgccat ggtcgccatc gcagcgtccg aggccgaggt ggccgcctcc gtggcacccc   27240
acgccgccac ggtgtcgatc gccgcggtca acggtcctga cgccgtcgtg atcgctggcg   27300
ccgaggtaca ggtgctcgcc ctcggcgcga cgttcgcggc gcgtgggata cgcacgaaga   27360
ggctcgccgt ctcccatgcg ttccactcgc cgctcatgga tccgatgctg gaagacttcc   27420
agcgggtcgc tgcgacgatc gcgtaccgcg cgccagaccg cccggtggtg tcgaatgtca   27480
ccggccacgt cgcaggcccc gagatcgcca cgcccgagta ttgggtccgg catgtgcgaa   27540
gcgccgtgcg cttcggcgat ggggcaaagg cgttgcatgc cgcgggtgcc gccacgttcg   27600
tcgagattgg cccgaagccg gtcctgctcg ggctattgcc agcgtgcctc ggggaagcgg   27660
acgcggtcct cgtgccgtcg ctacgcgcgg accgctcgga atgcgaggtg gtcctcgcgg   27720
cgctcgggac ttggtatgcc tgggggggtg cgctcgactg gaagggcgtg ttccccgatg   27780
gcgcgcgccg cgtggctctg cccatgtatc catggcagcg tgagcgccat tggatggacc   27840
tcaccccgcg aagcgccgcg cctgcaggga tcgcaggtcg ctggccgctg gctggtgtcg   27900
ggctctgcat gcccggcgct gtgttgcacc acgtgctctc gatcggacca cgccatcagc   27960
ccttcctcgg tgatcacctc gtgtttggca aggtggtggt gcccggcgcc tttcatgtcg   28020
cggtgatcct cagcatcgcc gccgagcgct ggcccgagcg ggcgatcgag ctgacaggcg   28080
tggagttcct gaaggcgatc gcgatggagc ccgaccagga ggtcgagctc cacgccgtgc   28140 tcaccccccga agccgccggg gatggctacc tgttcgagct ggcgaccctg gcggcgccgg   28200
agaccgaacg ccgatggacg acccacgccc gcggtcgggt gcagccgaca gacggcgcgc   28260
ccggcgcgtt gccgcgcctc gaggtgctgg aggaccgcgc gatccagccc ctcgacttcg   28320
ccggattcct cgacaggtta tcggcggtgc ggatcggctg gggtccgctt tggcgatggc   28380
tgcaggacgg gcgcgtcggc gacgaggcct cgcttgccac cctcgtgccg acctatccga   28440
acgcccacga cgtggcgccc ttgcacccga tcctgctgga caacggcttt gcggtgagcc   28500
tgctggcaac ccggagcgag ccggaggacg acggacgcc cccgctgccg ttcgccgtgg   28560
aacgggtgcg gtggtggcgg gcgccggttg gaagggtgcg gtgtggcggc gtgccgcggt   28620
cgcaggcatt cggtgtctcg agcttcgtgc tggtcgacga aactggcgag gtggtcgctg   28680
aggtggaggg atttgtttgc cgccgggcgc cgcgagaggt gttcctgcgg caggagtcgg   28740
gcgcgtcgac tgcagccttg taccgcctcg actggcccga agcccccttg cccgatcgcg   28800
ctgcggaacg gatggaggag agctgggtcg tggtggcagc acctggctcg gagatggccg   28860
cggcgctcgc aacacggctc aaccgctgcg tactcgccga acccaaaggc ctcgaggcgg   28920
ccctcgcggg ggtgtctccc gcaggtgtga tctgcctctg ggaacctgga gcccacgagg   28980
```

```
aagctccggc ggcggcgcag cgtgtggcga ccgagggcct ttcggtggtg caggcgctca   29040
gggatcgcgc ggtgcgcctg tggtgggtga ccacgggcgc cgtggctgtc gaggccggtg   29100
agcgggtgca ggtcgccaca cgcgcggtat ggggcctggg ccggacagtg atgcaggagc   29160
gcccggagct cagctgcact ctggtggatt tggagccgga ggtcgatgcc gcgcgttcag   29220
ctgacgttct gctgcgggag ctcggtcgcg ctgacgacga gacccaggtg gttttccgtt   29280
ccggagagcg ccgcgtagcg cggctggtca aagcgacaac ccccgaaggg ctcttggtcc   29340
ctgacgcaga atcctatcga ctggaggctg gcagaaggg cacattggac cagctccgcc   29400
tcgcgccggc acagcgccgg gcacccggcc cgggcgaggt cgagatcaag gtaaccgcct   29460
cggggctcaa cttccggacc gtcctcgctg tgctgggaat gtatccgggc gacgctgggc   29520
cgatgggcgg agattgtgcc ggtatcgtca cggcggtggg ccaggggtg caccacctct   29580 cggtcggcga tgctgtcatg acgctgggga cgttgcatcg attcgtcacg gtcgacgcgc   29640
ggctggtggt ccggcagcct gcagggctga ctcccgcgca ggcagctacg gtgccggttg   29700
cgttcctgac ggcctggctc gctctgcacg acctggggaa tctgcggcgc ggcgagcggg   29760
tgctgatcca tgctgcggcc ggcggcgtgg gcatggccgc ggtgcaaatc gcccgatgga   29820
taggggccga ggtgttcgcc acggcgagcc cgtccaagtg ggcagcggtt caggccatgg   29880
gcgtgccgcg cacgcacatc gccagctcgc ggacgctgga gtttgctgag acgttccggc   29940
aggtcaccgg cggccgggc gtggacgtgg tgctcaacgc gctggccggc gagttcgtgg   30000
acgcgagcct gtccctgctg acgacgggcg ggcggttcct cgagatgggc aagaccgaca   30060
tacgggatcg agccgcggtc gcggcggcgc atcccggtgt tcgctatcgg gtattcgaca   30120
tcctggagct cgctccggat cgaactcgag agatcctcga gcgcgtggtc gagggctttg   30180
ctgcgggaca tctgcgcgca ttgccggtgc atgcgttcgc gatcaccaag gccgaggcag   30240
cgtttcggtt catggcgcaa gcgcggcatc agggcaaggt cgtgctgctg ccggcgccct   30300
ccgcagcgcc cttggcgccg acgggcaccg tactgctgac cggtgggctg ggagcgttgg   30360
ggctccacgt ggcccgctgg ctcgcccagc agggcgcgcc gcacatggtg ctcacaggtc   30420
ggcggggcct ggatacgccg ggcgctgcca aagccgtcgc ggagatcgaa gcgctcggcg   30480
ctcgggtgac gatcgcggcg tcggatgtcg ccgatcggaa cgcgctggag ctgtgctcc   30540 aggccattcc ggcggagtgg ccgttacagg gcgtgatcca tgcagccgga gcgctcgatg   30600
atggtgtgct tgatgagcag accaccgacc gcttctcgcg ggtgctggca ccgaaggtga   30660
ctggcgcctg gaatctgcat gagctcacgg cgggcaacga tctcgctttc ttcgtgctgt   30720
tctcctccat gtcggggctc ttgggctcgg ccgggcagtc caactatgcg gcggccaaca   30780
ccttcctcga cgcgctggcc gcgcatcggc gggccgaagg cctggcggcg cagagcctcg   30840 cgtgggccc atggtcggac ggaggcatgg cagcggggct cagcgcggcg ctgcaggcgc   30900
ggctcgctcg gcatgggatg ggagcgctgt cgcccgctca gggcaccgcg ctgctcgggc   30960
aggcgctggc tcggccggaa acgcagctcg gggcgatgtc gctcgacgtg cgtgcggcaa   31020
gccaagcttc gggagcggca gtgccgcctg tgtggcgcgc gctggtgcgc gcggaggcgc   31080
gccatgcggc ggctggggcg cagggggcat tggccgcgcg ccttggggcg ctgcccgagg   31140
cgcgtcgcgc cgacgaggtg cgcaaggtcg tgcaggccga gatcgcgcgc gtgctttcat   31200
ggggcgccgc gagcgccgtg cccgtcgatc ggccgctgtc ggacttgggc ctcgactcgc   31260
tcacggcggt ggagctgcgc aacgtgctcg gccagcgggt gggtgcgacg ctgccggcga   31320
```

```
cgctggcatt cgatcacccg acggtcgacg cgctcacgcg ctggctgctc gataaggtcc   31380
tggccgtggc cgagccgagc gtatcgcccg caaagtcgtc gccgcaggtc gccctcgacg   31440
agcccattgc ggtgatcggc atcggctgcc gttccccagg cggcgtgacc gatccggagt   31500
cgttttggcg gctgctcgaa gagggcagcg atgccgtcgt cgaggtgccg catgagcgat   31560
gggacatcga cgcgttctat gatccggatc cggatgtgcg cggcaagatg acgacacgct   31620
ttggcggctt cctgtccgat atcgaccggt tcgagccggc cttcttcggc atctcgccgc   31680
gcgaagcgac gaccatggat ccgcagcagc ggctgctcct ggagacgagc tgggaggcgt   31740
tcgagcgcgc cgggattttg cccgagcggc tgatgggcag cgataccggc gtgttcgtgg   31800
ggctcttcta ccaggagtac gctgcgctcg ccggcggcat cgaggcgttc gatggctatc   31860
taggcaccgg caccacggcc agcgtcgcct cgggcaggat ctcttatgtg ctcgggctaa   31920
aggggccgag cctgacggtg gacaccgcgt gctcctcgtc gctggtcgcg gtgcacctgg   31980
cctgccaggc gctgcggcgg ggcgagtgtt cggtggcgct ggccggcggc gtggcgctga   32040
tgctcacgcc ggcgacgttc gtggagttca gccggctgcg aggcctggct cccgacggac   32100
ggtgcaagag cttctcggcc gcagccgacg cgtgggggtg gagcgaaggc tgcgccatgc   32160
tcctgctcaa accgcttcgc gatgctcagc gcgatgggga tccgatcctg cggtgatcc    32220 gcggcaccgc ggtgaaccag gatgggcgca gcaacgggct gacggcgccc aacgggtcgt   32280
cgcagcaaga ggtgatccgt cgggccctgg agcaggcggg gctggctccg gcggacgtca   32340
gctacgtcga gtgccacggc accggcacga cgttgggcga ccccatcgaa gtgcaggccc   32400
tgggcgccgt gctggcacag gggcgaccct cggaccggcc gctcgtgatc gggtcggtga   32460
agtccaatat cggacatacg caggctgcgg cgggcgtggc cggtgtcatc aaggtggcgc   32520
tggcgctcga gcgcgggctt atcccgagga gcctgcattt cgacgcgccc aatccgcaca   32580
ttccgtggtc ggagctcgcc gtgcaggtgg ccgccaaacc cgtcgaatgg acgagaaacg   32640
gcgcgccgcg acgagccggg gtgagctcgt ttggcgtcag cgggaccaac gcgcacgtgg   32700
tgctggagga ggcgccagcg gcggcgttcg cgcccgcggc ggcgcgttca gcggagcttt   32760
tcgtgctgtc ggcgaagagc gccgcggcgc tggacgcgca ggcggcgcgg ctttcggcgc   32820
atgtcgttgc gcacccggag ctcggcctcg gcgacctggc gttcagcctg gcgacgaccc   32880
gcagcccgat gacgtaccgg ctcgcggtgg cggcgacctc gcgcgaggcg ctgtctgcgg   32940
cgctcgacac agcggcgcag gggcaggcgc cgcccgcagc ggctcgcggc cacgcttcca   33000
caggcagcgc cccaaaggtg gttttcgtct ttcctggcca gggctcccag tggctgggca   33060
tgggccaaaa gctcctctcg gaggagcccg tcttccgcga cgcgctctcg gcgtgtgacc   33120
gagcgattca ggccgaagcc ggctggtcgc tgctcgccga gctcgcggcc gatgagacca   33180
cctcgcagct cggccgcatc gacgtggtgc agccggcgct gttcgcgatc gaggtcgcgc   33240
tgtcggcgct gtgcggtcg tggggcgtcg agccggatgc agtggtaggc cacagcatgg   33300
gcgaagtggc ggccgcgcac gtcgccggcg ccctgtcgct cgaggatgct gtagcgatca   33360
tctgccggcg cagcctgctg ctgcggcgga tcagcggcca aggcgagatg gcggtcgtcg   33420
agctctccct ggccgaggcc gaggcagcgc tcctgggcta cgaagatcgg ctcagcgtgg   33480
cggtgagcaa cagcccgcga tcgacggtgc tggcgggcga gccggcagcg ctcgcagagg   33540
tgctggcgat ccttgcggca aagggggtgt tctgccgtcg agtcaaggtg gacgtcgcca   33600
gccacagccc acagatcgac ccgctgcgcg acgagctatt ggcagcattg ggcgagctcg   33660
agccgcgaca agcgaccgtg tcgatgcgct cgacggtgac gagcacgatc gtggcgggcc   33720
```

```
cggagctcgt ggcgagctac tgggcggaca acgttcgaca gccggtgcgc ttcgccgaag    33780
cggtgcaatc gttgatggaa ggcggtcatg ggctgttcgt ggagatgagc ccgcatccga    33840
tcctgacgac gtcggtcgag gagatccgac gggcgacgaa gcgggaggga gtcgcggtgg    33900
gctcgttgcg gcgtggacag gacgagcgcc tgtccatgtt ggaggcgctg ggagcgctct    33960
gggtacacgg ccaggcggtg ggctgggagc ggctgttctc cgcgggcggc gcgggcctcc    34020
gtcgcgtgcc gctgccgacc tatccctggc agcgcgagcg gtactgggtc gaagcgccga    34080
ccggcggcgc ggcgagcggc agccgctttg ctcatgcggg cagtcacccg ctcctgggtg    34140
aaatgcagac cctgtcgacc cagaggagca cgcgcgtgtg ggagacgacg ctggatctca    34200
aacggctgcc gtggctcggc gatcaccggg tgcaggggc ggtcgtgttc ccggcgcgg     34260
cgtacctgga gatggcgctt tcgtctgggg ccgaggcctt gggtgacggt ccgctccagg    34320
tcagcgatgt ggtgctcgcc gaggcgctgg ccttcgcgga tgatacgccg gtggcggtgc    34380
aggtcatggc gaccgaggag cgaccaggcc gcctgcaatt ccacgttgcg agccgggtgc    34440
cgggccacgg ccgtgctgcc tttcgaagcc atgcccgcgg ggtgctgcgc cagaccgagc    34500
gcgccgaggt cccggcgagg ctggatctgg ccgcgcttcg tgcccggctt caggccagcg    34560
cacccgctgc ggctacctat gcggcgctgg ccgagatggg gctcgagtac ggcccagcgt    34620
tccaggggct tgtcgagctg tggcgggggg agggcgaggc gctgggacgt gtgcggctcc    34680
ccgaggccgc cggctcccca gccgcgtgcc ggctccaccc cgcgctcttg gatgcgtgct    34740
tccacgtgag cagcgccttc gctgaccgcg gcgaggcgac gccatgggta cccgtcgaaa    34800
tcggctcgct gcggtggttc cagcggccgt cggggagct gtggtgtcat gcgcggagcg     34860
tgagccacgg aaagccaaca cccgatcggc ggagtaccga cttttgggtg gtcgacagca    34920
cgggcgcgat cgtcgccgag atctccgggc tcgtggcgca gcggctcgcg ggaggtgtac    34980
gccggcgcga agaagacgac tggttcatgg agccggcttg ggaaccgacc gcggtccccg    35040
gatccgaggt cacggcgggc cggtggctgc tcatcggctc gggcggcggg ctcggcgctg    35100
cgctctactc ggcgctgacg gaagctggcc attccgtcgt ccacgcgaca gggcacggca    35160
cgagcgccgc cgggttgcag gcactcctga cggcgtcctt cgacggccag gccccgacgt    35220
cggtggtgca cctcggcagc ctcgatgagc gtggcgtgct cgacgcggat gccccttcg     35280
acgccgatgc cctcgaggag tcgctggtgc gcggctgcga cagcgtgctc tggaccgtgc    35340
aggccgtggc cggggcgggc ttccgagatc ctccgcggtt gtggctcgtg acacgcggcg    35400
ctcaggccat cggcgccggc gacgtctccg tggcgcaagc gccgctcctg gggctgggcc    35460
gcgttatcgc cttggagcac gccgagctgc gctgcgctcg gatcgacctc gatccagcgc    35520
ggcgcgacgg agaggtcgat gagctgcttg ccgagctgtt ggccgacgac gccgaggagg    35580
aagtcgcgtt tcgcggcggt gagcggcgcg tggcccggct cgtccgaagg ctgcccgaga    35640
ccgactgccg agagaaaatc gagcccgcgg aaggccggcc gttccggctg gagatcgatg    35700
ggtccggcgt gctcgacgac ctggtgctcc gagccacgga gcggcgccct cctggccgg     35760
gcgaggtcga gatcgccgtc gaggcggcgg ggctcaactt tctcgacgtg atgagggcca    35820
tggggatcta ccctgggccc ggggacggtc cggttgcgct gggcgccgag tgctccggcc    35880
gaattgtcgc gatgggcgaa ggtgtcgaga gccttcgtat cggccaggac gtcgtggccg    35940
tcgcgcccct tcagtttcgg cacccacgtca ccatcgacgc ccggatggtc gcacctcgcc    36000
ccgcggcgct gacggccgcg caggcagccg cgctgcccgt cgcattcatg acggcctggt    36060
```

-continued

```
acggtctcgt ccatctgggg aggctccggg ccggcgagcg cgtgctcatc cactcggcga    36120
cgggggcac cgggctcgct gctgtgcaga tcgcccgcca cctcggcgcg agatatttg     36180
cgaccgctgg tacgccggag aagcgggcgt ggctgcgcga gcaggggatc gcgcacgtga    36240
tggactcgcg gtcgctggac ttcgccgagc aagtgctggc cgcgacgaag ggcgaggggg    36300
tcgacgtcgt gttgaactcg ctgtctggcg ccgcgatcga cgcgagcctt gcgaccctcg    36360
tgccggacgg ccgcttcatc gagctcggca agacggacat ctatgcagat cgctcgctgg    36420
ggctcgctca ctttaggaag agcctgtcct acagcgccgt cgatcttgcg ggtttggccg    36480
tgcgtcggcc cgagcgcgtc gcagcgctgc tggcggaggt ggtggacctg ctcgcacggg    36540
gagcgctgca gccgcttccg gtagagatct tcccctctc gcgggccgcg gacgcgttcc     36600
ggaaaatggc gcaagcgcag catctcggga agctcgtgct cgcgctggag gacccggacg    36660
tgcggatccg cgttccgggc gaatccggcg tcgccatccg cgcggacggc acctacctcg    36720
tgaccggcgg tctgggtggg ctcggtctga gcgtggctgg atggctggcc gagcaggggg    36780
ctgggcatct ggtgctggtg ggccgctccg gtgcggtgag cgcggagcag cagacggctg    36840
tcgccgcgct cgaggcgcac ggcgcgcgtg tcacggtagc gagggcagac gtcgccgatc    36900
gggcgcagat cgagcggatc ctccgcgagg ttaccgcgtc ggggatgccg ctccgcggcg    36960
tcgttcatgc ggccggtatc ctggacgacg ggctgctgat gcagcaaacc cccgcgcggt    37020
tccgcgcggt catggcgccc aaggtccgag gggccttgca cctgcatgcg ttgacacgcg    37080
aagcgccgct ctccttcttc gtgctgtacg cttcgggagc agggctcttg ggctcgccgg    37140
gccagggcaa ctacgccgcg gccaacacgt tcctcgacgc tctggcacac caccggaggg    37200
cgcagggct gccagcattg agcatcgact ggggcctgtt cgcggacgtg ggtttggccg     37260
ccgggcagca aaatcgcggc gcacggctgg tcacccgcgg gacgcggagc ctcaccccg     37320
acgaagggct gtgggcgctc gagcgtctgc tcgacggcga tcgcacccag gccggggtca    37380
tgccgttcga cgtgcggcag tgggtggagt tctacccggc ggcggcatct tcgcggaggt    37440
tgtcgcggct ggtgacggca cggcgcgtgg cttccggtcg gctcgccggg gatcgggacc    37500
tgctcgaacg gctcgccacc gccgaggcgg gcgcgcgggc aggaatgctg caggaggtcg    37560
tgcgcgcgca ggtctcgcag gtgctgcgcc tccccgaagg caagctcgac gtggatgcgc    37620
cgctcacgag cctgggaatg gactcgctga tgggctaga gctgcgcaac cgcatcgagg     37680
ccgtgctcgg catcaccatg ccggcgaccc tgctgtggac ctaccccacg gtggcagcgc    37740
tgagtgcgca tctggcttct catgtcgtct ctacgggga tggggaatcc gcgcgcccgc     37800
cggatacagg gaacgtggct ccaatgaccc acgaagtcgc ttcgctcgac gaagacgggt    37860
tgttcgcgtt gattgatgag tcactcgcgc gtgcgggaaa gaggtgattg cgtgacagac    37920
cgagaaggcc agctcctgga gcgcttgcgt gaggttactc tggcccttcg caagacgctg    37980
aacgagcgcg ataccctgga gctcgagaag accgagccga tcgccatcgt ggggatcggc    38040
tgccgcttcc ccggcggagc gggcactccg gaggcgttct gggagctgct cgacgacggg    38100
cgcgacgcga tccggccgct cgaggagcgc tgggcgctcg taggtgtcga cccaggcgac    38160
gacgtaccgc gctgggcggg gctgctcacc gaagccatcg acggcttcga cgccgcgttc    38220
ttcggtatcg cccccggga ggcacggtcg ctcgacccgc agcatcgctt gctgctggag     38280
gtcgcctggg aggggttcga agacgccggc atcccgccta ggtccctcgt cgggagccgc    38340
accggcgtgt tcgtcggcgt ctgcgccacg gagtatctcc acgccgccgt cgcgcaccag    38400
ccgcgcgaag agcgggacgc gtacagcacc accggcaaca tgctcagcat cgccgccgga    38460
```

```
cggctatcgt acacgctggg gctgcaggga ccttgcctga ccgtcgacac ggcgtgctcg    38520
tcatcgctgg tggccattca cctcgcctgc cgcagcctgc gcgctcgaga gagcgatctc    38580
gcgctggcgg gaggggtcaa catgcttctc tcccccgaca cgatgcgagc tctggcgcgc    38640
acccaggcgc tgtcgcccaa tggccgttgc cagaccttcg acgcgtcggc aacgggttc     38700 gtccgtgggg agggctgcgg tctgatcgtg ctcaagcgat tgagcgacgc gcggcgggat    38760
ggggaccgga tctgggcgct gatccgagga tcggccatca atcaggacgg ccggtcgacg    38820
gggttgacgg cgcccaacgt gctcgcccag ggggcgctct tgcgcgaggc gctgcggaac    38880
gccggcgtcg aggccgaggc catcggttac atcgagaccc acggggcggc gacctcgctg    38940
ggcgacccca tcgagatcga agcgctgcgc accgtggtgg ggccggcgcg agccgacgga    39000
gcgcgctgcg tgctgggcgc ggtgaagacc aacctcggcc acctggaggg cgctgccggc    39060
gtggcgggcc tgatcaaggc tacactttcg ctacatcacg agcgcatccc gaggaacctc    39120
aactttcgta cgctcaatcc gcggatccgg atcgagggga ccgcgctcgc gttggcgacc    39180
gaaccggtgc cctggccgcg gacgggccgg acgcgcttcg cgggagtgag ctcgttcggg    39240
atgagcggga ccaacgcgca tgtggtgttg gaggaggcgc cggcggtgga gcctgaggcc    39300
gcggcccccg agcgcgctgc ggagctgttc gtcctgtcgg cgaagagcgt ggcggcgctg    39360
gatgcgcagg cagcccggct gcgggaccac ctggagaagc atgtcgagct tggcctcggc    39420
gatgtggcgt tcagcctggc gacgacgcgc agcgcgatgg agcaccggct ggcggtggcc    39480
gcgagctcgc gcgaggcgct gcgaggggcg cttttcggccg cagcgcaggg gcatacgccg    39540
ccgggagccg tgcgtgggcg ggcctccggc ggcagcgcgc cgaaggtggt cttcgtgttt    39600 cccgccagg gctcgcagtg ggtgggcatg ggccgaaagc tcatggccga agagccggtc    39660
ttccgggcgg cgctggaggg ttgcgaccgg gccatcgagg cggaagcggg ctggtcgctg    39720 ctcgggggagc tctccgccga cgaggccgcc tcgcagctcg ggcgcatcga cgtggttcag    39780
ccggtgctct tcgccatgga agtagcgctt tctgcgctgt ggcggtcgtg gggagtggag    39840
ccggaagcgg tggtgggcca cagcatgggc gaggtggcgg cggcgcacgt ggccggcgcg    39900
ctgtcgctcg aggacgcggt ggcgatcatc tgccggcgca gccggctgct gcggcggatc    39960
agcggtcagg gcgagatggc gctggtcgag ctgtcgctgg aggaggccga ggcggcgctg    40020
cgtggccatg agggtcggct gagcgtggcg gtgagcaaca gcccgcgctc gaccgtgctc    40080
gcaggcgagc cggcggcgct ctcggaggtg ctggcggcgc tgacggccaa gggggtgttc    40140
tggcggcagg tgaaggtgga cgtcgccagc catagcccgc aggtcgaccc gctgcgcgaa    40200
gagctgatcg cggcgctggg ggcgatccgg ccgcgagcgg ctgcggtgcc gatgcgctcg    40260
acggtgacgg gcggggtgat cgcgggtccg gagctcggtc cgagctactg ggcggacaat    40320
cttcggcagc cggtgcgctt cgctgcgcg gcgcaagcgc tgctggaagg tggccccacg    40380
ctgttcatcg agatgagccc gcacccgatc ctggtgccgc ccctggacga gatccagacg    40440
gcggtcgagc aagggggcgc tgcgtgtggc tcgctgcggc gagggcagga cgagcgcgcg    40500
acgctgctgg aggcgctggg gacgctgtgg gcgtccggct atccggtgag ctgggctcgg    40560
ctgttccccg cgggcggcag gcgggttccg ctgccgacct atccctggca gcacgagcgg    40620
tgctggatcg aggtcgagcc tgacgcccgc cgcctcgccg cagccgaccc caccaaggac    40680
tggttctacc ggacggactg gcccgaggtg ccccgcgccg ccccgaaatc ggagacagct    40740
catgggagct ggctgctgtt ggccgacagg ggtgggtcg gcgaggcggt cgctgcagcg    40800
```

```
ctgtcgacgc gcggactttc ctgcaccgtg ctttcatgcgt cggctgacgc ctccaccgtc   40860
gccgagcagg tatccgaagc tgccagtcgc cgaaacgact ggcagggagt cctctacctg   40920
tggggcctcg acgccgtcgt cgatgctggg gcatcggccg acgaagtcag cgaggctacc   40980
cgccgtgcca ccgcacccgt ccttgggctg gttcgattcc tgagcgctgc gccccatcct   41040
cctcgcttct gggtggtgac ccgcggggca tgcacggtgg gcggcgagcc agaggtctct   41100 cttttgccaag cggcgttgtg gggcctcgcg cgcgtcgtgg cgctggagca tcccgctgcc   41160
tggggtggcc tcgtggacct ggatcctcag aagagcccga cggagatcga gccctggtg    41220 gccgagctgc tttcgccgga cgccaggat caactggcgt tccgcagcgg tcgccggcac    41280
gcagcacgcc ttgtagccgc cccgccggag ggcgacgtcg caccgatatc gctgtccgcg   41340
gagggaagct acctggtgac gggtgggctg ggtggccttg gtctgctcgt ggctcggtgg   41400
ctggtggagc ggggagctcg acatctggtg ctcaccagcc ggcacgggct gccagagcga   41460
caggcgtcgg gcggagagca gccgccggag gcccgcgcgc gcatcgcagc ggtcgagggg   41520
ctggaagcgc agggcgcgcg ggtgaccgtg gcagcggtgg atgtcgccga ggccgatccc   41580 atgacgcgc tgctggccgc catcgagccc ccgttgcgcg gggtggtgca cgccgccggc    41640
gtcttccccg tgcgtcccct ggcggagacg gacgaggccc tgctggagtc ggtgctccgt   41700
cccaaggtgg ccgggagctg gctgctgcac cggctgctgc gcgaccggcc tctcgacctg   41760
ttcgtgctgt tctcgtcggg cgcggcggtg tggggtggca aaggccaagg cgcatacgcc   41820
gcggccaatg cgttcctcga cgggctcgcg caccatcgcc gcgcgcactc cctgccggcg   41880
ttgagcctcg cctgggcct atgggccgag ggaggcgtgg ttgatgcaaa ggctcatgca    41940
cgtctgagcg acatcggagt cctgcccatg gccacggggc cggccttgtc ggcgctggag   42000
cgcctggtga acaccagcgc tgtccagcgt tcggtcacac ggatggactg ggcgcgcttc   42060
gcgccggtct atgccgcgcg agggcggcgc aacttgcttt cggctctggt cgcggaggac   42120
gagcgcactg cgtctccccc ggtgccgacg gcaaaccgga tctggcgcgg cctgtccgtt   42180
gcggagagcc gctcagccct ctacgagctc gttcgcggca tcgtcgcccg ggtgctgggc   42240
ttctccgacc cgggcgcgct cgacgtcggc cgaggcttcg ccgagcaggg gctcgactcc   42300
ctgatggctc tggagatccg taaccgcctt cagcgcgagc tgggcgaacg gctgtcggcg   42360
actctggcct tcgaccaccc gacggtggag cggctggtgg cgcatctcct caccgacgtg   42420
ctgaagctgg aggaccggag cgacacccgg cacatccgt cggtggcggc ggatgacgac    42480
atcgccatcg tcggtgccgc ctgccggttc ccggcgggg atgagggcct ggagacatac    42540
tggcggcatc tggccgaggg catggtggtc agcaccgagg tgccagccga ccggtggcgc   42600
gcggcggact ggtacgaccc cgatccggag gttccgggcc ggacctatgt ggccaagggg   42660
gccttcctcc gcgatgtgcg cagcttggat gcggcgttct tctccatctc ccctcgtgag   42720
gcgatgagcc tggacccgca acagcggctg ttgctggagg tgagctggga ggcgatcgag   42780
cgcgctggcc aggacccgat ggcgctgcgc gagagcgcca cgggcgtgtt cgtgggcatg   42840
atcgggagcg agcacgccga gcgggtgcag ggcctcgacg acgacgcggc gttgctgtac   42900
ggcaccaccg gcaacctgct cagcgtcgcc gctggacggc tgtcgttctt cctgggtctg   42960
cacgcccgga cgatgacggt ggacaccgcg tgctcgtcgt cgctggtggc gttgcacctc   43020
gcctgccaga gctgcgatt gggcgagtgc gaccaggcac tggccggcgg gtccagcgtg   43080
cttttgtcgc cgcggtcatt cgtcgcggca tcgcgcatgc gtttgctttc gccagatggg   43140
cggtgcaaga cgttctcggc cgctgcagac ggctttgcgc gggccgaggg ctgcgccgtg   43200
```

```
gtggtgctca agcggctccg tgacgcgcag cgcgaccgcg accccatcct ggcggtggtc   43260
cggagcacgg cgatcaacca cgatggcccg agcagcgggc tcacggtgcc cagcggtcct   43320
gcccagcagg cgttgctagg ccaggcgctg gcgcaagcgg gcgtggcacc ggccgaggtc   43380
gatttcgtgg agtgccacgg gacggggaca gcgctgggtg acccgatcga ggtgcaggcg   43440
ctgggcgcgt tgtatggccg gggccgcccc cgggagcggc cgctctggct gggcgctgtc   43500
aaggccaacc tcggccacct ggaggccgcg gcgggcttgg ccggcgtgct caaggtgctc   43560
ttggcgctgg agcacgagca gattccggct caaccggagc tcgacgagct caacccgcac   43620
atcccgtggg cagagctgcc agtggccgtt gtccgcgcgg cggtcccctg gccgcgcggc   43680
gcgcgcccgc gtcgtgcagg cgtgagcgct ttcggcctga gcgggaccaa cgcgcatgtg   43740
gtgttggagg aggcgccggc ggtggagcct gaggccgcgc ccccgagcg cgctgcggag   43800 ctgttcgtcc tgtcggcgaa gagcgtggcg gcgctggatg cgcaggcagc ccggctgcgg   43860
gatcatctgg agaagcatgt cgagcttggc ctcggcgatg tggcgttcag cctggcgacg   43920
acgcgcagcg cgatggagca ccggctggcg gtggccgcga gctcgcgcga ggcgctgcga   43980
ggggcgcttt cggccgcagc gcaggggcat acgccgccgg gagccgtgcg tgggcgggcc   44040
tccggcggca gcgcgccgaa ggtggtcttc gtgtttcccg gccagggctc gcagtgggtg   44100
ggcatgggcc gaaagctcat ggccgaagag ccggtcttcc gggcggcgct ggagggttgc   44160
gaccgggcca tcgaggcgga agcgggctgg tcgctgctcg gggagctctc cgccgacgag   44220
gccgcctcgc agctcgggcg catcgacgtg gttcagccgg tgctcttcgc cgtggaagta   44280 gcgcttcag cgctgtggcg gtcgtgggga gtggagccgg aagcggtggt gggccacagc   44340
atgggcgagg ttgcggcggc gcacgtggcc ggcgcgctgt cgctcgagga tgcggtggcg   44400
atcatctgcc ggcgcagccg gctgctgcgg cggatcagcg gtcagggcga gatggcgctg   44460
gtcgagctgt cgctggagga ggccgaggcg gcgctgcgtg gccatgaggg tcggctgagc   44520
gtggcggtga gcaacagccc gcgctcgacc gtgctcgcag gcgagccggc ggcgctctcg   44580
gaggtgctgg cggcgctgac ggccaagggg gtgttctggc ggcaggtgaa ggtggacgtc   44640
gccagccata gcccgcaggt cgacccgctg cgcgaagagc tggtcgcggc gctgggagcg   44700
atccggccgc gagcggctgc ggtgccgatg cgctcgacgg tgacgggcgg ggtgattgcg   44760
ggtccggagc tcggtgcgag ctactgggcg gacaatcttc ggcagccggt gcgcttcgct   44820
gcggcggcgc aagcgctgct ggaaggtggc cccacgctgt tcatcgagat gagcccgcac   44880
ccgatcctgg tgccgcctct ggacgagatc cagacggcgg tcgagcaagg gggcgctgcg   44940
gtgggctcgc tgcggcgagg gcaggacgag cgcgcgacgc tgctgaggc gctggggacg   45000 ctgtgggcgt ccggctatcc ggtgagctgg gctcggctgt tccccgcggg cggcaggcgg   45060
gttccgctgc cgacctatcc ctggcagcac gagcggtact ggatcgagga cagcgtgcat   45120
gggtcgaagc cctcgctgcg gcttcggcag cttcataacg gcgccacgga ccatccgctg   45180 ctcgggctc cattgctcgt ctcggcgcga cccggagctc acttgtggga gcaagcgctg   45240
agcgacgaga ggctatccta tctttcggaa catagggtcc atggcgaagc cgtgttgccc   45300
agcgcggcgt atgtagagat ggcgctcgcc gccggcgtag atctctatgg cgcggcgacg   45360
ctggtgctgg agcagctggc gctcgagcga gccctcgccg tgccttccga aggcggacgc   45420
atcgtgcaag tggccctcag cgaagaaggg cccggtcggg cctcattcca ggtatcgagc   45480
cgtgaggagg caggtagaag ctgggttcgg cacgccacgg ggcacgtgtg tagcgaccag   45540
```

```
agctcagcag tgggagcgtt gaaggaagct ccgtgggaga ttcaacagcg atgtccgagc   45600
gtcctgtcgt cggaggcgct ctatccgctg ctcaacgagc acgccctcga ctatggcccc   45660
tgcttccagg gtgtggagca ggtgtggctc ggcacggggg aggtgctcgg ccgggtacgc   45720
ttgccagaag acatggcatc ctcaagtggc gcctatcgga ttcatcccgc cttgttggat   45780
gcatgttttc aagtgctgac cgcgctgctc accacgccgg aatccatcga gattcggagg   45840
cggctgacgg atctccacga accggatctc ccgcggtcca gggctccggt gaatcaagcg   45900
gtgagtgaca cctggctgtg ggacgccgcg ctggacggtg gacggcgcca gagcgcgagc   45960
gtgcccgtcg acctggtgct cggcagcttc cacgcgaagt gggaggtcat ggatcgcctc   46020
gcgcagacgt acatcatccg cactctccgc acatggaacg tcttctgcgc tgctggagag   46080
cgtcacacga tagacgagtt gctcgtcagg ctccaaatct ctgctgtcta caggaaggtc   46140
atcaagcgat ggatggatca ccttgtcgcg atcggcgtcc ttgtagggga cggagagcat   46200
cttgtgagct ctcagccgct gccggagcat gattgggcgg cggtgctcga ggaggccgcg   46260
acggtgttcg ccgacctccc agtcctactt gagtggtgca agtttgccgg gaacggctc    46320 gcggacgtgt tgaccgggaa gacgctggcg ctcgagatcc tcttccctgg cggctcgttc   46380
gatatggcgg agcgaatcta tcaagattcg cccatcgccc gttactcgaa cggcatcgtg   46440
cgcggtgtcg tcgagtcggc ggcgcgggtg gtagcaccgt cgggaacgtt cagcatcttg   46500
gagatcggag cagggacggg cgcgaccacc gccgccgtcc tcccggtgtt gctgcctgac   46560
cggacagaat accatttcac cgatgttcct ccgctcttcc ttgctcgtgc ggagcaaaga   46620
tttcgagatc atccattcct gaagtatggt attctggata tcgaccagga gccagctggc   46680
cagggatacg cacatcagaa gttcgacgtc atcgtcgcgg ccaacgtcat ccatgcgacc   46740
cgcgatataa gagccacggc gaagcgtctc ctgtcgttgc tcgcgcccgg aggccttctg   46800
gtgctggtcg agggcacagg gcatccgatc tggttcgata tcaccacggg attgatcgag   46860
gggtggcaga agtacgaaga tgatcttcgt accgaccatc cgctcctgcc tgctcggacc   46920
tggtgtgacg tcctgcgccg ggtaggcttt gcggatgccg tgagtctgcc aggcgacgga   46980
tctccggcgg ggatcctcgg acagcacgtg atcctctcgc gcgctccggg catagcagga   47040
gccgcttgtg acagctccgg tgagtcggcg accgaatcgc cggccgcgcg tgcagtacgg   47100
caggaatggg ccgatggctc cgctgacggc gtccatcgga tggcgttgga gagaatgtac   47160
ttccaccgcc ggccgggccg gcaggtttgg gtccacggtc gattgcgtac cggtggaggc   47220
gcgttcacga aggcgctcac tggagatctg ctcctgttcg aagagaccgg gcaggtcgtg   47280
gcagaggttc agggctccg cctgccgcag ctcgaggctt ctgctttcgc gccgcgggac    47340
ccgcgggaag agtggttgta cgcgttggaa tggcagcgca aagaccctat accagaggct   47400
ccggcagccg cgtcttcttc caccgcgggg gcttggctcg tgctgatgga ccagggcggg   47460
acaggcgctg cgctcgtatc gctgctggaa gggcgaggcg aggcgtgcgt gcgcgtcgtc   47520
gcgggtacgg catacgcctg cctcgcgccg gggctgtatc aagtcgatcc ggcgcagcca   47580
gatggctttc ataccctgct ccgcgatgca ttcggcgagg accggatgtg ccgcgcgta    47640 gtgcatatgt ggagccttga tgcgaaggca gcagggagga ggacgacagc ggagtcgctt   47700
caggccgatc aactcctggg gagcctgagc gcgctttctc tggtgcaggc gctggtcgcg   47760
cggaggtggc gcaacatgcc gcgactttgg ctcttgaccc gcgccgtgca tgcggtgggc   47820
gcggaggacg cagcggcctc ggtggcgcag gcgccggtgt ggggcctcgg tcggacgctc   47880
gcgctcgagc atccagagct gcggtgcacg ctcgtggacg tgaacccggc gccgtctcca   47940
```

```
gaggacgcag ctgcactcgc ggtggagctc ggggcgagcg acagagagga ccagatcgca    48000
ttgcgctcga atggccgcta cgtggcgcgc ctcgtgcgga gctccttttc cggcaagcct    48060
gctacggatt gcggcatccg ggcggacggc agttatgtga tcaccgatgg catggggaga    48120
gtggggctct cggtcgcgca atggatggtg atgcagggg cccgccatgt ggtgctcgtg     48180
gatcgcggcg gcgcttccga cgcctcccgg gatgccctcc ggtccatggc cgaggctggc    48240
gcagaggtgc agatcgtgga ggccgacgtg gctcggcgcg tcgatgtcgc tcggcttctc    48300
tcgaagatcg aaccgtcgat gccgccgctt cggggatcg tgtacgtgga cgggaccttc     48360
cagggcgact cctcgatgct ggagctggat gcccatcgct tcaaggagtg gatgtatccc    48420
aaggtgctcg gagcgtggaa cctgcacgcg ctgaccaggg atagatcgct ggacttcttc    48480
gtcctgtact cctcgggcac ctcgcttctg ggcttgcccg gacagggag ccgcgccgcc     48540 ggtgacgcct tcttggacgc catcgcgcat accggtgta ggctgggcct cacagcgatg     48600
agcatcaact ggggattgct ctccgaagca tcatcgccgg cgaccccgaa cgacggcggc    48660
gcacggctcc aataccgggg gatggaaggt ctcacgctgg agcagggagc ggaggcgctc    48720
gggcgcttgc tcgcacaacc cagggcgcag gtaggggtaa tgcggctgaa tctgcgccag    48780
tggctggagt tctatcccaa cgcggcccga ctggcgctgt gggcggagtt gctgaaggag    48840
cgtgaccgca ccgaccggag cgcgtcgaac gcatcgaacc tgcgcgaggc gctgcagagc    48900
gccaggcccg aagatcgtca gttggttctg gagaagcact tgagcgagct gttgggggcgg   48960 gggctgcgcc ttccgccgga gaggatcgag cggcacgtgc cgttcagcaa tctcggcatg    49020
gactcgttga taggcctgga gctccgcaac cgcatcgagg ccgcgctcgg catcaccgtg    49080
ccggcgaccc tgctatggac ttaccctacc gtagcagctc tgagcgggaa cctgctagat    49140
attctgttcc cgaatgccgg cgcgactcac gctccggcca ccgagcggga aagagcttc    49200 gagaacgatg ccgcagatct cgaggctctg cggggtatga cggacgagca aaggacgcg    49260 ttgctcgccg aaaagctggc gcagctcgcg cagatcgttg gtgagtaagg gactgaggga    49320
gtatggcgac cacgaatgcc gggaagcttg agcatgccct tctgctcatg gacaagcttg    49380
cgaaaaagaa cgcgtctttg gagcaagagc ggaccgagcc gatcgccatc ataggtattg    49440
gctgccgctt ccccggcgga gcggacactc cggaggcatt ctgggagctg ctcgactcgg    49500
gccgagacgc ggtccagccg ctcgaccggc gctgggcgct ggtcggcgtc catcccagcg    49560
aggaggtgcc gcgctgggcc ggactgctca ccgaggcggt ggacggcttc gacgccgcgt    49620
tctttggcac ctcgcctcgg gaggcgcggt cgctcgatcc tcagcaacgc ctgctgctgg    49680
aggtcacctg ggaagggctc gaggacgccg gcatcgcacc ccagtccctc gacggcagcc    49740
gcaccggggt attcctgggc gcatgcagca gcgactactc gcataccgtt gcgcaacagc    49800
ggcgcgagga gcaggacgcg tacgacatca ccggcaatac gctcagcgtc gccgccggac    49860
ggttgtctta tacgctaggg ctgcagggac cctgcctgac cgtcgacacg gcctgctcgt    49920
cgtcgctcgt ggccatccac cttgcctgcc gcagcctgcg cgctcgcgag agcgatctcg    49980
cgctggcggg gggcgtcaac atgctccttt cgtccaagac gatgataatg ctggggcgca    50040
tccaggcgct gtcgcccgat ggccactgcc ggacattcga cgcctcggcc aacgggttcg    50100
tccgtgggga gggctgcggt atggtcgtgc tcaaacggct ctccgacgcc cagcgacatg    50160
gcgatcggat ctgggctctg atccggggtt cggccatgaa tcaggatggc cggtcgacag    50220
ggttgatggc acccaatgtg ctcgctcagg aggcgctctt acgccaggcg ctgcagagcg    50280
```

```
ctcgcgtcga cgccggggcc atcgattatg tcgagaccca cggaacgggg acctcgctcg   50340
gcgacccgat cgaggtcgat gcgctgcgtg ccgtgatggg gccggcgcgg gccgatggga   50400
gccgctgcgt gctgggcgca gtgaagacca acctcggcca cctggagggc gctgcaggcg   50460
tggcgggttt gatcaaggcg gcgctggctc tgcaccacga atcgatcccg cgaaacctcc   50520
attttcacac gctcaatccg cggatccgga tcgaggggac cgcgctcgcg ctggcgacgg   50580
agccggtgcc gtggccgcgg gcgggccgac cgcgcttcgc ggggtgagc gcgttcggcc   50640
tcagcggcac caacgtccat gtcgtgctgg aggaggcgcc ggccacggtg ctcgcaccgg   50700
cgacgccggg gcgctcagca gagcttttgg tgctgtcggc gaagagcacc gccgcgctgg   50760
acgcacaggc ggcgcggctc tcagcgcaca tcgccgcgta cccggagcag ggcctcggag   50820
acgtcgcgtt cagcctggta gcgacgcgga gcccgatgga gcaccggctc gcggtggcgg   50880
cgacctcgcg cgaggcgctg cgaagcgcgc tggaagctgc ggcgcagggg cagaccccgg   50940
caggcgcggg gcgcggcagg gccgcttcct cgcccggcaa gctcgccttc ctgttcgccg   51000
ggcagggcgc gcaggtgccg ggcatgggcc gtgggttgtg ggaggcgtgg ccggcgttcc   51060
gcgagacctt cgaccggtgc gtcacgctct tcgaccggga gctccatcag ccgctctgcg   51120
aggtgatgtg ggccgagccg ggcagcagca ggtcgtcgtt gctggaccag acggcattca   51180
cccagccggc gctctttgcg ctggagtacg cgctggccgc gctcttccgg tcgtggggcg   51240
tggagccgga gctcatcgct ggccatagcc tcggcgagct ggtggccgcc tgcgtggcgg   51300
gtgtgttctc cctcgaggac gccgtgcgct tggtggtcgc gcgcggccgg ttgatgcagg   51360
cgctgccggc cggcggtgcg atggtatcga tcgccgcgcc ggaggccgac gtggctgccg   51420
cggtggcgcc gcacgcagcg tcggtgtcga tcgcggcagt caatgggccg gagcaggtgg   51480
tgatcgcggg cgccgagaaa ttcgtgcagc agatcgcggc ggcgttcgcg gcgcgggggg   51540
cgcgaaccaa accgctgcat gtttcgcacg cgttccactc gccgctcatg gatccgatgc   51600
tggaggcgtt ccggcgggtg accgagtcgg tgacgtatcg gcggccttcg atggcgctgg   51660
tgagcaacct gagcgggaag ccctgcacgg atgaggtgtg cgcgccgggt tactgggtgc   51720
gtcacgcgcg agaggcggtg cgcttcgcgg acggcgtgaa ggcgctgcac gcggccggtg   51780
cgggcatctt cgtcgaggtg ggcccgaagc cggcgctgct cggccttttg ccggcctgcc   51840
tgccggatgc caggccggtg ctgctcccag cgtcgcgcgc cggcgtgac gaggctgcga   51900
gcgcgctgga ggcgctgggt gggttctggg tcgtcggtgg atcggtcacc tggtcgggtg   51960
tcttcccttc gggcggacgg cgggtaccgc tgccaaccta tccctggcag cgcgagcgtt   52020
actggatcga agcgccggtc gatggtgagg cggacggcat cggccgtgct caggcggggg   52080
accaccccct tctgggtgaa gccttttccg tgtcgaccca tgccggtctg cgcctgtggg   52140
agacgacgct ggaccgaaag cggctgccgt ggctcggcga gcaccgggcg caggggagg    52200
tcgtgtttcc tggcgccggg tacctggaga tggcgctgtc gtcgggggcc gagatcttgg   52260
gcgatggacc gatccaggtc acggatgtgg tgctcatcga gacgctgacc ttcgcgggcg   52320
atacggcggt accggtccag gtggtgacga ccgaggagcg accgggacgg ctgccggttcc  52380
aggtagcgag tcgggagccg ggggcacgtc gcgcgtcctt ccggatccac gcccgcggcg   52440
tgctgcgccg gtcgggcgc gccgagaccc cggcgaggtt gaacctcgcc gccctgcgcg   52500
cccggcttca tgccgccgtg cccgctgcgg ctatctatgg ggcgctcgcc gagatggggc   52560
ttcaatacgg cccggcgttg cggggggctcg ccgagctgtg gcggggtgag gcgaggcgc    52620
tgggcagagt gagactgcct gagtccgccg gctccgcgac agcctaccag ctgcatccgg   52680
```

```
tgctgctgga cgcgtgcgtc caaatgattg ttggcgcgtt cgccgatcgc gatgaggcga    52740
cgccgtgggc gccggtggag gtgggctcgg tgcggctgtt ccagcggtct cctggggagc    52800
tatggtgcca tgcgcgcgtc gtgagcgatg gtcaacaggc ccccagccgg tggagcgccg    52860
actttgagtt gatggacggt acgggcgcgg tggtcgccga gatctcccgg ctggtggtgg    52920
agcggcttgc gagcggtgta cgccggcgcg acgcagacga ctggttcctg gagctggatt    52980
gggagcccgc ggcgctcgag gggcccaaga tcacagccgg ccggtggctg ctgctcggcg    53040
agggtggtgg gctcgggcgc tcgttgtgct cagcgctgaa ggccgccggc catgtcgtcg    53100
tccacgccgc gggggacgac acgagcgctg caggaatgcg cgcgctcctg gccaacgcgt    53160
tcgacggcca ggccccgacg gccgtggtgc acctcagcag cctcgacggg gcggccagc    53220 tcgacccggg gctcggggcg cagggcgcgc tcgacgcgcc ccggagccca gatgtcgatg    53280
ccgatgccct cgagtcggcg ctgatgcgtg gttgcgacag cgtgctctcc ctggtgcaag    53340
cgctggtcgg catggacctc cgaaatgcgc cgcggctgtg gcttttgacc cgcggggctc    53400
aggcggccgc cgccggcgat gtctccgtgg tgcaagcgcc gctgttgggg ctgggccgca    53460
ccatcgcctt ggagcacgcc gagctgcgct gtatcagcgt cgacctcgat ccagcccagc    53520
ctgaagggga agccgatgct ttgctggccg agctacttgc agatgatgcc gaggaggagg    53580
tcgcgctgcg cggtggcgag cggtttgttg cgcggctcgt ccaccggctg cccgaggctc    53640
aacgccggga gaagatcgcg cccgccggtg acaggccgtt ccggctagag atcgatgaac    53700
ccggcgtgct ggaccaactg gtgctccggg ccacggggcg cgcgcgctcct ggtccgggcg    53760 aggtcgagat cgccgtcgaa gcggcggggc tcgactccat cgacatccag ctggcggtgg    53820
gcgttgctcc caatgacctg cctggaggag aaatcgagcc gtcggtgctc ggaagcgagt    53880
gcgccgggcg catcgtcgct gtgggcgagg gcgtgaacgg ccttgtggtg ggccagccgg    53940
tgatcgccct tgcggcggga gtatttgcta cccatgtcac cacgtcggcc acgctggtgt    54000
tgcctcggcc tctgggctc tcggcgaccg aggcggccgc gatgcccctc gcgtatttga    54060
cggcctggta cgccctcgac aaggtcgccc acctgcaggc gggggagcgg gtgctgatcc    54120
gtgcggaggc cggtggtatc ggtctttgcg cggtgcgatg ggcgcagcgc gtgggcgccg    54180
aggtgtatgc gaccgccgac acgcccgaga acgtgccta cctggagtcg ctgggcgtgc    54240
ggtacgtgag cgattcccgc tcgggccggt tcgccgcaga cgtgcatgca tggacggacg    54300
gcgagggtgt ggacgtcgtg ctcgactcgc tttcgggcga gcacatcgac aagagcctca    54360
tggtcctgcg cgcctgtggc cgccttgtga agctgggcag gcgcgacgac tgcgccgaca    54420
cgcagcctgg gctgccgccg ctcctacgga atttttcctt ctcgcaggtg gacttgcggg    54480
gaatgatgct cgatcaaccg gcgaggatcc gtgcgctcct cgacgagctg ttcgggttgg    54540
tcgcagccgt tgccatcagc ccactgggt cggggttgcg cgttggcgga tccctcacgc    54600
caccgccggt cgagaccttc ccgatctctc gcgcagccga ggcattccgg aggatggcgc    54660
aaggacagca tctcgggaag ctcgtgctca cgctggacga cccggaggtg cggatccgcg    54720
ctccggccga atccagcgtc gccgtccgcg cggacggcac ctaccttgtg accggcggtc    54780
tgggtgggct cggtctgcgc gtggccggat ggctggccga gcggggcgcg ggcaactgg    54840 tgctggtggg ccgctccggt gcggcgagcg cagagcagcg agccgccgtg gcggcgctag    54900
aggcccacgg cgcgcgcgtc acggtggcga aagcggatgt cgccgatcgg tcacagatcg    54960
agcgggtcct ccgcgaggtt accgcgtcgg ggatgccgct gcggggtgtc gtgcatgcgg    55020
```

```
caggtcttgt ggatgacggg ctgctgatgc agcagactcc ggcgcggctc cgcacggtga   55080
tgggacctaa ggtccaggga gccttgcact tgcacacgct gacacgcgaa gcgcctcttt   55140
ccttcttcgt gctgtacgct tctgcagctg ggctgttcgg ctcgccaggc cagggcaact   55200
atgccgcagc caacgcgttc ctcgacgccc tttcgcatca ccgcagggcg cacggcctgc   55260
cggcgctgag catcgactgg ggcatgttca cggaggtggg gatggccgtt gcgcaagaaa   55320
accgtggcgc gcggctgatc tctcgcggga tgcgggcat caccccgat gagggtctgt    55380 cagctctggc gcgcttgctc gagggtgatc gcgtgcagac ggggtgata ccgatcactc    55440 cgcggcagtg ggtggagttc tacccggcaa cagcggcctc acggaggttg tcgcggctgg   55500
tgaccacgca gcgcgcggtt gctgatcgga ccgccgggga tcgggacctg ctcgaacagc   55560
ttgcctcggc tgagccgagc gcgcgggcgg ggctgctgca ggacgtcgtg cgcgtgcagg   55620
tctcgcatgt gctgcgtctc cctgaagaca agatcgaggt ggatgccccg ctctcgagca   55680
tgggcatgga ctcgctgatg agcctggagc tgcgcaaccg catcgaggct gcgctgggcg   55740
tcgccgcgcc tgcagccttg gggtggacgt acccaacggt agcagcgata acgcgctggc   55800
tgctcgacga cgcccctcgcc gtccggcttg gggcgggtc ggacacggac gaatcgacgg   55860
caagcgccgg atcgttcgtc cacgtcctcc gctttcgtcc tgtcgtcaag ccgcgggctc   55920
gtctcttctg ttttcacggt tctggcggct cgcccgaggg cttccgttcc tggtcggaga   55980
agtctgagtg gagcgatctg gaaatcgtgg ccatgtggca cgatcgcagc ctcgcctccg   56040
aggacgcgcc tggtaagaag tacgtccaag aggcggcctc gctgattcag cactatgcag   56100
acgcaccgtt tgcgttagta gggttcagcc tgggtgtccg gttcgtcatg gggacagccg   56160
tggagctcgc tagtcgttcc ggcgcaccgg ctccgctggc cgttttttgcg ttgggcggca   56220 gcttgatctc ttcttcagag atcacccccgg agatggagac cgatataata gccaagctct   56280
tcttccgaaa tgccgcgggt ttcgtgcgat ccacccaaca agttcaggcc gatgctcgcg   56340
cagacaaggt catcacagac accatggtgg ctccggcccc cggggactcg aaggagccgc   56400
cctcgaagat cgcggtccct atcgtcgcca tcgccggctc ggacgatgtg atcgtgcctc   56460
caagcgacgt tcaggatcta caatctcgca ccacggagcg cttctatatg catctccttc   56520
ccggagatca cgagtttctc gtcgatcgag ggcgcgagat catgcacatc gtcgactcgc   56580
atctcaatcc gctgctcgcc gcgaggacga cgtcgtcagg ccccgcgttc gaggcaaaat   56640
gatggcagcc tccctcgggc gcgcgagatg gttgggagca gcgtgggtgc tggtggccgg   56700
cggcaggcag cggaggctca tgagccttcc tggaagtttg cagcatagga gattttatga   56760
cacaggagca agcgaatcag agtgagacga agcctgcttt cgacttcaag ccgttcgcgc   56820
ctgggtacgc ggaggacccg tttccgcgca tcgagcgcct gagagaggca accccatct   56880 tctactggga tgaaggccgc tcctgggtcc tcacccgata ccacgacgtg tcggcggtgt   56940
tccgcgacga acgcttcgcg gtcagtcgag aagaatggga atcgagcgcg gagtactcgt   57000
cggccattcc cgagctcagc gatatgaaga agtacggatt gttcgggctg ccgccggagg   57060
atcacgctcg ggtccgcaag ctcgtcaacc catcgtttac gtcacgcgcg atcgacctgc   57120
tgcgcgccga aatacagcgc accgtcgacc agctgctcga tgctcgctcc ggacaagagg   57180
agttcgacgt tgtgcgggat tacgcggagg gaatcccgat gcgtgcgatc agcgctctgt   57240
tgaaggttcc ggccgagtgt gacgagaagt tccgtcgctt cggctcggcg actgcgcgcg   57300
cgctcggcgt gggtttggtg ccccgggtcg atgaggagac caagaccctg gtcgcgtccg   57360
tcaccgaggg gctcgcgctg ctccatggcg tcctcgatga gcggcgcagg aacccgctcg   57420
```

```
aaaatgacgt cttgacgatg ctgcttcagg ccgaggccga cggcagcagg ctgagcacga    57480
aggagctggt cgcgctcgtg ggtgcgatta tcgctgctgg caccgatacc acgatctacc    57540
ttatcgcgtt cgctgtgctc aacctgctgc ggtcgcccga ggcgctcgag ctggtgaagg    57600
ccgagcccgg gctcatgagg aacgcgctcg atgaggtgct ccgcttcgac aatatcctca    57660
gaataggaac tgtgcgtttc gccaggcagg acctggagta ctgcggggca tcgatcaaga    57720
aaggggagat ggtctttctc ctgatcccga gcgccctgag agatgggact gtattctcca    57780
ggccagacgt gttgatgtg cgacgggaca cgagcgcgag cctcgcgtac ggtagaggcc    57840
cccatgtctg ccccgggtg tcccttgctc gcctcgaggc ggagatcgcc gtgggcacca    57900
tcttccgtag gttccccgag atgaagctga aagaaactcc cgtgtttgga taccaccccg    57960
cgttccggaa catcgaatca ctcaacgtca tcttgaagcc ctccaaagct ggataactcg    58020
cgggggcatc gcttcccgaa cctcattctt tcatgatgca actcgcgcgc gggtgctgtc    58080
tgccgcgggt gcgattcgat ccagcggaca agcccattgt cagcgcgcga agatcgaatc    58140
cacggcccgg agaagagccc gatggcgagc ccgtccgggt aacgtcggaa gaagtgccgg    58200
gcgccgccct gggagcgcaa agctcgctcg ctcgcgctca gcgcgccgct tgccatgtcc    58260
ggccctgcac ccgcaccgag gagccacccg ccctgatgca cggcctcacc gagcggcagg    58320
ttctgctctc gctcgtcgcc ctcgcgctcg tcctcctgac cgcgcgcgcc ttcggcgagc    58380
tcgcgcggcg gctgcgccag cccgaggtgc tcggcgagct cttcggcggc gtggtgctgg    58440
gcccgtccgt cgtcggcgcg ctcgctcctg ggttccatcg agtcctcttc caggatccgg    58500
cggtcggggg cgtgctctcc ggcatctcct ggataggcgc gctcgtcctg ctgctcatgg    58560
cgggtatcga ggtcgatgtg agcattctac gcaaggaggc gcgcccgggg gcgctctcgg    58620
cgctcggcgc gatcgcgccc ccgctgcgca cgccgggccc gctggtgcag cgcatgcagg    58680
gcacgttgac gtgggatctc gacgtctcgc cgcgacgctc tgcgcaagcc tgagcctcgg    58740
cgcctgctcg tacacctcgc cggtgctcgc tccgcccgcg gacatccggc cgcccccgc    58800 ggcccagctc gagccggact cgccggatga cgaggccgac gaggcgctcc gcccgttccg    58860
cgacgcgatc gccgcgtact cggaggccgt tcggtgggcg gaggcggcgc agcggccgcg    58920
gctggagagc ctcgtgcggc tcgcgatcgt cggctgggc aaggcgctcg acaaggcacc    58980
tttcgcgcac acgacggccg gcgtctccca gatcgccggc agacttcccc agaaaacgaa    59040
tgcggtctgg ttcgatgtcg ccgcccggta cgcgagcttc cgcgcggcga cggagcacgc    59100
gctccgcgac gcggcgtcgg ccacggaggc gctcgcggcc ggcccgtacc gcggatcgag    59160
cagcgtgtcc gctgccgtag gggagttttcg ggggaggcg gcgcgccttc accccgggga    59220
ccgcgtaccc gcgtccgacc agcagatcct gaccgcgctg cgcgcagccg agcgggcgct    59280
catcgcgctc tacaccgcgt tcgcccgtga ggagtgagcc tctctcgggc gcagccgagc    59340
ggcggcgtgc cggttgttcc ctcttcgcaa ccatgaccgg agccgcgccc ggtccgcgca    59400
gcggctagcg cgcgtcgagg cagagagcgc tggagcgaca ggcgacgacc cgcccgaggg    59460
tgtcgaacgg attccgcag ccctcattgc ggatccctc cagacactcg ttcagcgcct    59520
tggcgtcgat gccgctgggc cactcgccga aggtcagctc gtcgcgccag tcggatcgga    59580
tcttgttcga gcacgcatcc ttgctcgaat actcccggtc ttgtccgatg ttgttgcacc    59640
gcgcctcgcg gtcgcaccgc gccgccacga tgctatcgac ggcgctgccg actggcaccg    59700
gcgcctcgcc ttgcgcgcca cccggggttt gcgcctcccc gcctgaccgc ttttcgccgc    59760
```

-continued

| | |
|---|---|
| cgcacgccgc cgcgagcagg ctcattcccg acatcgagat caggcccacg accagtttcc | 59820 |
| cagcaatctt ttgcatggct tcccctccct cacgacacgt cacatcagag attctccgct | 59880 |
| cggctcgtcg gttcgacagc cggcgacggc cacgagcaga accgtccccg accagaacag | 59940 |
| ccgcatgcgg gtttctcgca gcatgccacg acatccttgc gactagcgtg cctccgctcg | 60000 |
| tgccgagatc ggctgtcctg tgcgacggca atgtcctgcg atcggccggg caggatcgac | 60060 |
| cgacacgggc gccgggctgg aggtgccgcc acgggctcga aatgcgctgt ggcaggcgcc | 60120 |
| tccatgcccg ctgccgggaa cgcagcgccc ggccagcctc ggggcgacgc tgcgaacggg | 60180 |
| agatgctccc ggagaggcgc cgggcacagc cgagcgccgt caccaccgtg cgcactcgtg | 60240 |
| agcgctagct cctcggcata gaagagaccg tcactcccgg tccgtgtagg cgatcgtgct | 60300 |
| gatcagcgcg tcctccgcct gacgcgagtc gagccgggta tgctgcacga cgatgggcac | 60360 |
| gtccgattcg atcacgctgg catagtccgt atcgcgcggg atcggctcgg ggtcggtcag | 60420 |
| atcgttgaac cggacgtgcc gggtgcgcct cgctggaacg gtcacccggt acggccggc | 60480 |
| ggggtcgcgg tcgctgaagt agacggtgat ggcgacctgc gcgtcccggt ccgacgcatt | 60540 |
| caacaggcag gccgtctcat ggctcgtcat ctgcggctca ggtccgttgc tccggcctgg | 60600 |
| gatgtagccc tctgcgattg cccagcgcgt ccgcccgatc ggcttgtcca tgtgtcctcc | 60660 |
| ctcctggctc tctttggca gcctccctct gctgtccagg tgcgacggcc tcttcgctcg | 60720 |
| acgcgctcgg ggctccatgg ctgagaatcc tcgccgagcg ctccttgccg accggcgcgc | 60780 |
| tgagcgccga cgggccttga aagcacgcga ccggacacgg gatgccggcg cgacgaggcc | 60840 |
| gccccgcgtc tgatcccgat cgtggcatca cgacgtccgc cgacgcctcg gcaggccggc | 60900 |
| gtgagcgctg cgcggtcatg gtcgtcctcg cgtcaccgcc acccgccgat tcacatccca | 60960 |
| ccgcggcacg acgcttgctc aaaccgcgac gacacggccg ggcggctgtg gtaccggcca | 61020 |
| gcccggacgc gaggcccgag agggacagtg ggtccgccgt gaagcagaga ggcgatcgag | 61080 |
| gtggtgagat gaaacacgtt gacacgggcc gacgagtcgg ccgccggata gggctcacgc | 61140 |
| tcggtctcct cgcgagcatg gcgctcgccg gctgcggcgg cccgagcgag aagaccgtgc | 61200 |
| agggcacgcg gctcgcgccc ggcgccgatg cgcacgtcac cgccgacgtc gacgccgacg | 61260 |
| ccgcgaccac gcggctggcg gtggacgtcg ttcacctctc gccgcccgag cggatcgagg | 61320 |
| ccggcagcga gcggttcgtc gtctggcagc gtccgaactc cgagtccccg tggctacggg | 61380 |
| tcggagtgct cgactacaac gctgccagcc gaagaggcaa gctggccgag acgaccgtgc | 61440 |
| cgcatgccaa cttcgagctg ctcatcaccg tcgagaagca gagcagccct cagtcgccat | 61500 |
| cgtctgccgc cgtcatcggg ccgacgtccg tcgggtaaca tcgcgctatc agcagcgctg | 61560 |
| agcccgccag catgccccag agccctgcct cgatcgcttt ccccatcatc cgtgcgcact | 61620 |
| cctccagcga cggccgcgtc aaagcaaccg ccgtgccggc gcggctctac gtgcgcgaca | 61680 |
| ggagagcgtc ctagcgcggc ctgcgcatcg ctggaaggat cggcggagca tggagaaaga | 61740 |
| atcgaggatc gcgatctacg gcgccgtcgc cgccaacgtg gcgatcgcgg cggtcaagtt | 61800 |
| catcgccgcc gccgtgaccg gcagctctgc gatgctctcc gagggcgtgc actccctcgt | 61860 |
| cgataccgca gacgggctcc tcctcctgct cggcaagcac cggagcgccc gccgcccga | 61920 |
| cgccgagcat ccgttcggcc acggcaagga gctctatttc tggacgctga tcgtcgccat | 61980 |
| catgatcttc gccgcgggcg gcggcgtctc gatctacgaa gggatcttgc acctcttgca | 62040 |
| cccgcgctcg atcgaggatc cgacgttgaa ctacgttgtc ctcggcgcag cggccgtctt | 62100 |
| cgaggggacg tcgctcgcca tctcgatcca cgagttcaag aagaaagacg gacagggcta | 62160 |

```
cgtcgcggcg atgcggtcca gcaaggaccc gacgacgttc acgatcgtcc tggaggattc   62220
cgcggcgctc gccgggctcg ccatcgcctt cctcggcgtc tggcttgggc accgcctggg   62280
aaacccctac ctcgacggcg cggcgtcgat cggcatcggc ctcgtgctcg ccgcggtcgc   62340
ggtcttcctc gccagccaga gccgtggact cctcgtaggg gagagcgcgg acagggagct   62400
cctcgccgcg atccgcgcgc tcgccagcgc agatcctggc gtgtcggcgg tggggcggcc   62460
cctgacgatg cacttcggtc cgcacgaagt cctggtcgtg ctgcgcatcg agttcgacgc   62520
cgcgctcacg gcgtccgggg tcgcggaggc gatcgagcga atcgagacac ggatacggag   62580
cgagcgaccc gacgtgaagc acatctacgt cgaggccagg tcgctccacc agcgcgcgag   62640
ggcgtgacgc gccgtggaga gaccgctcgc ggcctccgcc atcctccgcg gcgcccgggc   62700
tcgggtagcc ctcgcagcag ggcgcgcctg gcggcaaaac cgtgaagacg tcgtccttcg   62760
acgcgaggta cgctggttgc aagttgtcac gccgtatcgc gaggtccggc agcgccgag   62820 cccgggcggt ccgggcgcac gaaggcccgg cgagcgcggg cttcgagggg gcgacgtcat   62880
gaggaagggc agggcgcatg gggcgatgct cggcgggcga gaggacggct ggcgtcgcgg   62940
cctccccggc gccggcgcgc ttcgcgccgc gctccagcgc ggtcgctcgc gcgatctcgc   63000
ccggcgccgg ctcatcgccg ccgtgtccct caccggcggc gccagcatgg cggtcgtctc   63060
gctgttccag ctcgggatca tcgagcacct gcccgatcct ccgcttccag ggttcgattc   63120
ggccaaggtg acgagctccg atatcgcgtt cgggctcacg atgccggacg cgccgctcgc   63180
gctcaccagc ttcgcgtcca acctggcgct ggctggctgg ggaggcgccg agcgcgccag   63240
gaacaccccc tggatccccg tcgccgtggc ggccaaggcg gccgtcgagg cggccgtgtc   63300
cggatggctc ctcgtccaga tgcgacggcg ggagagggcc tggtgcgcgt actgcctggt   63360
cgccatggcg gccaacatgg ccgtgttcgc gctctcgctc ccggaagggt gggcggcgct   63420
gaggaaggcg cgagcgcgct cgtgacaggg ccgtgcgggc gccgcggcca tcggaggccg   63480
gcgtgcaccc gctccgtcac gccccggccc gcgccgcggt gagctgccgc ggacagggcg   63540
cgtaccgtgg accccgcacg cgccgcgtcg acggacatcc ccggcggctc gcgcggcgcg   63600
gccggcgcaa ctccggcccg ccgccgggca tcgacatctc ccgcgagcaa gggcactccg   63660
ctcctgcccg cgtccgcgaa cgatggctgc gctgtttcca ccctggagca actccgttta   63720
ccgcgtggcg ctcgtcgggc tcatcgcctc ggcgggcggc gccatcctcg cgctcatgat   63780
ctacgtccgc acgccgtgga agcgatacca gttcgagccc gtcgatcagc cggtgcagtt   63840
cgatcaccgc catcacgtgc aggacgatgg catcgattgc gtctactgcc acaccacggt   63900
gacccgctcg ccgacggcgg ggatgccgcc gacggccacg tgcatggggt gccacagcca   63960
gatctggaat cagagcgtca tgctcgagcc cgtgcggcgg agctggttct ccggcatgcc   64020
gatcccgtgg aaccgggtga actccgtgcc cgacttcgtt tatttcaacc acgcgattca   64080
cgtgaacaag ggcgtgggct gcgtgagctg ccacgggcgc gtggacgaga tggcggccgt   64140
ctacaaggtg gcgccgatga cgatgggctg gtgcctggag tgccatcgcc tgccggagcc   64200
gcacctgcgc ccgctctccg cgatcaccga catgcgctgg gacccggggg aacggaggga   64260
cgagctcggg gcgaagctcg gaaggagta cggggtccgg cggctcacgc actgcacagc   64320
gtgccatcga tgaacgatga acaggggatc tccgtgaaag acgcagatga gatgaaggaa   64380
tggtggctag aagcgctcgg gccggcggga gagcgcgcgt cctacaggct gctgcgccg   64440 ctcatcgaga gcccggagct ccgcgcgctc gccgcgggcg aaccgcccg gggcgtggac   64500
```

```
gagccggcgg gcgtcagccg ccgcgcgctg ctcaagctgc tcggcgcgag catggcgctc    64560
gccggcgtcg cgggctgcac cccgcatgag cccgagaaga tcctgccgta caacgagacc    64620
ccgcccggcg tcgtgccggg tctctcccag tcctacgcga cgagcatggt gctcgacggg    64680
tatgccatgg gcctcctcgc caagagctac gcggggcggc ccatcaagat cgagggcaac    64740
cccgcgcacc cggcgagcct cggcgcgacc ggcgtccacg agcaggcctc gatcctctcg    64800
ctgtacgacc cgtaccgcgc gcgcgcgccg acgcgcggcg gccaggtcgc gtcgtgggag    64860
gcgctctccg cgcgcttcgg cggcgaccgc gaggacggcg gcgctggcct ccgcttcgtc    64920
ctccagccca cgagctcgcc cctcatcgcc gcgctgatcg agcgcgtccg gcgcaggttc    64980
cccggcgcgc ggttcacctt ctggtcgccg gtccacgccg agcaagcgct cgaaggcgcg    65040
cgggcggcgc tcggcctcag gctcttgcct cagctcgact tcgaccaggc cgaggtgatc    65100
ctcgccctgg acgcggactt cctcgcggac atgccgttca gcgtgcgcta tgcgcgcgac    65160
ttcgccgcgc gccgccgacc cgcgagcccg gcggcggcca tgaaccgcct ctacgtcgcg    65220
gaggcgatgt tcacgcccac ggggacgctc gccgaccacc ggctccgcgt gcggcccgcc    65280
gaggtcgcgc gcgtcgcggc cggcgtcgcg cgggagctcg tgcacggcct cggcctgcgc    65340
ccgcgcggga tcacggacgc cgacgccgcc gcgctgcgcg cgctccgccc cccggacggc    65400
gagggggcacg gcgccttcgt ccgggcgctc gcgcgcgatc tcgcgcgcgc gggggggcgcc    65460
ggcgtcgccg tcgtcggcga cggccagccg cccatcgtcc acgccctcgg gcacgtcatc    65520
aacgccgcgc tccgcagccg ggcggcctgg atggtcgatc ctgtgctgat cgacgcgggc    65580
ccctccacgc agggcttctc cgagctcgtc ggcgagctcg ggcgcggcgc ggtcgacacc    65640
tgatcctcct cgacgtgaac cccgtgtacg ccgcgccggc cgacgtcgat ttcgcgggcc    65700
tcctcgcgcg cgtgcccacg agcttgaagg ccgggctcta cgacgacgag accgcccgcg    65760
cttgcacgtg gttcgtgccg accggcatt acctcgagtc gtgggggac gcgcgggcgt    65820
acgacgggac ggtctcgttc gtgcaacccc tcgtccggcc gctgttcgac ggccgggcgg    65880
tgcccgagct gctccgccgtc ttcgcggggg acgagcgccc ggatccccgg ctgctgctgc    65940
gcgagcactg gcgcggcgcg cgcggagagg cggatttcga ggccttctgg ggcgaggcat    66000
tgaagcgcgg cttcctccct gacagcgccc ggccgaggca gacaccggat ctcgcgccgg    66060
ccgacctcgc caaggagctc gcgcggctcg ccgccgcgcc gcggccggcc ggcggcgcgc    66120
tcgacgtggc gttcctcagg tcgccgtcgg tccacgacgg caggttcgcc aacaacccct    66180
ggctgcaaga gctcccgcgg ccgatcacca ggctcacctg gggcaacgcc gccatgatga    66240
gcgcggcgac cgcggcgcgg ctcggcgtcg agcgcggcga tgtcgtcgag ctcgcgctgc    66300
gcggccgtac gatcgagatc ccggccgtcg tcgtccgcgg gcacgccgac gacgtgatca    66360
gcgtcgacct cggctacggg cgcgacgccg gcgaggaggt cgcgcgcggg gtgggcgtgt    66420
cggcgtatcg gatccgcccg tccgacgcgc ggtggttcgc ggggggcctc tccgtgagga    66480
agaccggcgc cacggccgcg ctcgcgctgg ctcagatcga gctgtcccag cacgaccgtc    66540
ccatcgcgct ccggaggacg ctgccgcagt accgtgaaca gcccggtttc gcggaggagc    66600
acaaggggcc ggtccgctcg atcctgccgg aggtcgagta caccggcgcg caatgggcga    66660
tgtccatcga catgtcgatc tgcaccgggt gctcctcgtg cgtcgtggcc tgtcaggccg    66720
agaacaacgt cctcgtcgtc ggcaaggagg aggtgatgca cggccgcgag atgcagtggt    66780
tgcggatcga tcagtacttc gagggtggag gcgacgaggt gagcgtcgtc aaccagccga    66840
tgctctgcca gcactgcgag aaggcgccgt gcgagtacgt ctgtccggtg aacgcgacgg    66900
```

```
tccacagccc cgatggcctc aacgagatga tctacaaccg atgcatcggg acgcgctttt   66960
gctccaacaa ctgtccgtac aagatccggc ggttcaattt cttcgactac aatgcccacg   67020
tcccgtacaa cgccggcctc cgcaggctcc agcgcaaccc ggacgtcacc gtccgcgccc   67080
gcggcgtcat ggagaaatgc acgtactgcg tgcagcggat ccgagaggcg gacatccgcg   67140
cgcagatcga gcgcggccg ctccggccgg gcgaggtggt caccgcctgc cagcaggcct   67200
gtccgaccgg cgcgatccag ttcgggtcgc tggatcacgc ggatacaaag atggtcgcgt   67260
ggcgcaggga gccgcgcgcg tacgccgtgc tccacgacct cggcacccgg ccgcggacgg   67320
agtacctcgc caagatcgag aacccgaacc cggggctcgg ggcggagggc gccgagaggc   67380
gacccggagc cccgagcgtc aaacccgcgc tcggggcgga gggcgccgag aggcgacccg   67440
gagccccgag cgtcaaaccg agattgaat gagccatggc gggcccgctc atcctggacg   67500
caccgaccga cgatcagctg tcgaagcagc tcctcgagcc ggtatggaag ccgcgctccc   67560
ggctcggctg gatgctcgcg ttcgggctcg cgctcggcgg cacgggcctg ctcttcctcg   67620
cgatcaccta caccgtcctc accgggatcg gcgtgtgggg caacaacatc ccggtcgcct   67680
gggccttcgc gatcaccaac ttcgtctggt ggatcgggat cggccacgcc gggacgttca   67740
tctccgcgat cctcctcctg ctcgagcaga agtggcggac gagcatcaac cgcttcgccg   67800
aggcgatgac gctcttcgcg gtcgtccagg ccggcctctt tccggtcctc cacctcggcc   67860
gccctggtt cgcctactgg atcttcccgt accccgcgac gatgcaggtg tggccgcagt   67920
tccggagcgc gctgccgtgg gacgccgccg cgatcgcgac ctacttcacg gtgtcgctcc   67980
tgttctggta catgggcctc gtcccggatc tggcggcgct gcgcgaccac gccccgggcc   68040
gcgtccggcg ggtgatctac gggctcatgt cgttcggctg gcacggcgcg ccgaccact   68100
tccggcatta ccgggtgctg tacgggctgc tcgcggggct cgcgacgccc ctcgtcgtct   68160
cggtgcactc gatcgtgagc agcgatttcg cgatcgccct ggtgcccggc tggcactcga   68220
cgctctttcc gccgttcttc gtcgcgggcg cgatcttctc cgggttcgcg atggtgctca   68280
cgctgctcat cccggtgcgg cggatctacg ggctccataa cgtcgtgacc gcgcgccacc   68340
tcgacgatct cgcgaagatg acgctcgtga ccggctggat cgtcatcctc tcgtacatca   68400
tcgagaactt cctcgcctgg tacagcggct cggcgtacga gatgcatcag tttttccaga   68460
cgcgcctgca cggcccgaac agcgccgcct actgggccca gcacgtctgc aacgtgctcg   68520
tcatccagct cctctggagc gagcggatcc ggacagcccc cgtcgcgctc tggctcatct   68580
ccctcctggt caacgtcggg atgtggagcg agcggttcac gctcatcgtg atgtcgctcg   68640
agcaagagtt cctcccgtcc aagtggcacg gctacagccc gacgtgggtg gactggagcc   68700
tcttcatcgg gtcaggcggc ttcttcatgc tcctgttcct gagcttttg cgcgtctttc   68760
cgttcatccc cgtcgcggag gtcaaggagc tcaaccatga agagctggag aaggctcggg   68820
gcgagggggg ccgctgatgg agaccggaat gctcggcgag ttcgatgacc cggaggcgat   68880
gctccatgcg atccgagagc tcaggcggcg cggctaccgc cgggtggaag cgttcacgcc   68940
ctatccggtg aaggggctcg acgaggcgct cggcctcccg cgctcgaacc tcaaccggat   69000
ggtgctgccc ttcgcgatcc tggggtcgt gggcggctac ttcgtccagt ggttctgcaa   69060
cgctttccac tatccgctga acgtgggcgg gcgcccgctg aactcggcgc cggcgttcat   69120
cccgatcacg ttcgagatgg gggtgctctc cacctcgatc ttcggcgtgc tcatcggctt   69180
ttacctgacg aggctgccga ggctctacct cccgctcttc gacgccccgg gcttcgagcg   69240
```

```
cgtcacgctg gatcggtttc tggtcgggct cgacgacacg gaaccttcct tctcgagcgc    69300
ccaggcggag cgcgacctcc tcgcgctcgg cgcccggcgc gtcgtcgtcg cgaggaggcg    69360
cgaggagcca tgagggccgg cgccccggct cgccctctcg ggcgcgcgct cgcgccgttc    69420
gccctcgtcc tgctcgccgg gtgccgcgag aaggtgctgc ccgagccgga cttcgagcgg    69480
atgatccgcc aggagaaata cggactctgg gagccgtgcg agcacttcga cgacggccgc    69540
gcgatgcagc acccgcccga ggggaccgtc gcgcgcgggc gcgtcaccgg gccgcccggc    69600
tatctccagg gcgtcctcga cggggcgtac gtcacggagg tgccgctctt gctcacggtc    69660
gagctcgtgc agcgcggccg gcagcgcttc gagaccttct cgcgcgccgt gccacgggatc    69720 ctcggcgacg gcagctcgcg cgtggcgacg aacatgacgc tgcgcccgcc cccgtcgctc    69780 atcgacccg aggcgcggag cttcccgccg ggcaggatct accaggtcat catcgagggc    69840
tacggcctga tgccgcgcta ctcggacgat ctgcccgaca tcgaagagcg ctgggccgtg    69900
gtcgcctacg tgaaggcgct tcagctgagc gcggagtgg ccgcgggcgc cctcccgcca    69960
gcgctccgcg gccgggcaga gcaggagctg cgatgaacag ggatgccatc gagtacaagg    70020
gcggcgcgac gatcgcggcc tcgctcgcga tcgcggcgct cggcgcggtc gccgcgatcg    70080
tcggcggctt cgtcgatctc cgccggttct tcttctcgta cctcgccgcg tggtcgttcg    70140
cggtgtttct gtccgtgggc gcgctcgtca cgctcctcac ctgcaacgcc atgcgcgcg    70200 gctggcccac ggcggtgcgc cgcctcctcg agacgatggt ggcgccgctg cctctgctcg    70260
cggcgctctc cgcgccgatc ctggtcggcc tggacacgct gtatccgtgg atgcaccccg    70320
agcggatcgc cggcgagcac gcgcggcgca tcctcgagca cagggcgccc tacttcaatc    70380
caggcttctt cgtcgtgcgc tcggcgatct acttcgcgat ctggatcgcc gtcgccctcg    70440
tgctccgccg gcgatcgttc gcgcaggacc gtgagccgag ggccgacgtc aaggacgcga    70500
tgtatggcct gagcggcgcc atgctgccgg tcgtggcgat cacgatcgtc ttctcgtcgt    70560
tcgactggct catgtccctc gacgcgacct ggtactcgac gatgttcccg gtctacgtgt    70620
tcgcgagcgc cttcgtgacc gccgtcggcg cgctcacggt cctctcgtat gccgcgcaga    70680
cgtccggcta cctcgcgagg ctgaacgact cgcactatta cgcgctcggg cggctgctcc    70740
tcgcgttcac gatattctgg gcctatgcgc cctatttcca gttcatgttg atctggatcg    70800
cgaacaagcc cgatgaggtc gccttcttcc tcgaccgctg ggaagggccc tggcggccga    70860
cctccgtgct cgtcgtcctc acgcggttcg tcgtcccgtt cctgatcctg atgtcgtacg    70920
cgatcaagcg gcgcccgcgc cagctctcgt ggatggcgct ctgggtcgtc gtctccggct    70980
acatcgactt tcactggctc gtggtgccgg cgacagggcg ccacggttc gcctatcact    71040 ggctcgacct cgcgaccctg tgcgtcgtgg gcggcctctc gaccgcgttc gccgcgtggc    71100
ggctgcgagg gcggccggtg gtcccggtcc acgacccgcg gctcgaagag gcctttgcgt    71160 accgagcat atgatgttcc gtttccgtca cagcgaggtt cgccaggagg aggacacgct    71220
ccctgggggg cgcgtgatcc tcgcgttcgc cgtcgtgctc gcgatcggcg gcgcgctgac    71280
gctctgggcc tggctcgcga tgcgggcccg cgaggcggat ctgcggccct ccctcgcgtt    71340
ccccgagaag gatctcgggc gcggcgcgca ggtcggcatg gtccagcagt cgctgttcga    71400
cgaggcgcgc ctgggccagc agctcgtcga cgcgcagcgc gcggagctcc gccgcttcgg    71460
cgtcgtcgat cgggagaggg gcatcgtgag catcccgatc gacgacgcga tcgagctcat    71520
ggtggcgggg ggcgcgcgat gagccgggcc gtcgccgtgg ccctcctgct ggcagccggc    71580
ctcgtgtcgc gcccgggcgc cgcgtccgag cccgagcgcg cgcgccccgc gctgggcccg    71640
```

```
tccgcggccg acgccgcgcc ggcgagcgac ggctccggcg cggaggagcc gcccgaaggc      71700
gccttcctgg agcccacgcg cggggtggac atcgaggagc gcctcggccg cccggtggac      71760
cgcgagctcg ccttcaccga catgacgggc cggcgggtgc gcctcggcga ctacttcgcc      71820
gacggcaagc ccctcctcct cgtcctcgcg tactaccggt gtcccgcgct gtgcggcctc      71880
gtgctgcgcg gcgccgtcga ggggctgaag ctcctcccgt accggctcgg cgagcagttc      71940
cacgcgctca cggtcagctt cgacccgcgc gagcgcccgg cggccgcdd                  71989

<210> SEQ ID NO 3
<211> LENGTH: 30
<212> TYPE: DNA
<213> ORGANISM: Artificial
<220> FEATURE:
<223> OTHER INFORMATION: Synthetic Construct

<400> SEQUENCE: 3
agcggataac aatttcacac aggaaacagc                                        30

<210> SEQ ID NO 4
<211> LENGTH: 29
<212> TYPE: DNA
<213> ORGANISM: Artificial
<220> FEATURE:
<223> OTHER INFORMATION: Synthetic Construct

<400> SEQUENCE: 4
ttaattaaga gaaggttgca acgggggc                                          29

<210> SEQ ID NO 5
<211> LENGTH: 848
<212> TYPE: DNA
<213> ORGANISM: Artificial
<220> FEATURE:
<223> OTHER INFORMATION: Synthetic Construct

<400> SEQUENCE: 5
cgacgcaggt gaagctgctt cgtgtgctcc aggagcggaa ggtgaagccg gtcggcagcg       60
ccgcggagat tcccttccag gcgcgtgtca tcgcggcaac gaaccggcgg ctcgaagccg      120
aagtaaaggc cggacgcttt cgtgaggacc tcttctaccg gctcaacgtc atcacgttgg      180
agctgcctcc actgcgcgag cgttccggcg acgtgtcgtt gctggcgaac tacttcctgt      240
ccagactgtc ggaggagttg gggcgacccg gtctgcgttt ctcccccgag acactggggc      300
tattggagcg ctatcccttc ccaggcaacg tgcggcagct gcagaacatg gtggagcggg      360
ccgcgaccct gtcggattca gacctcctgg ggccctccac gcttccaccc gcagtgcggg      420
gcgatacaga ccccgccgtg cgtcccgtgg agggcagtga gccagggctg gtggcgggct      480
tcaacctgga gcggcatctc gacgacagcg agcggcgcta tctcgtcgcg gcgatgaagc      540
aggccggggg cgtgaagacc cgtgctgcgg agttgctggg cctttcgttc cgttcattcc      600
gctaccggtt ggccaagcat gggctgacgg atgacttgga gcccgggagc gcttcggatg      660
cgtaggctga tcgacagtta tcgtcagcgt cactgccgaa ttttgtcagc cctggaccca      720
tcctcgccga ggggattgtt ccaagccttg agaattgggg ggcttggagt gcgcacctgg      780
gttggcatgc gtagtgctaa tcccatccgc gggcgcagtg cccccgttg caaccttctc      840 ttaattaa                                                              848

<210> SEQ ID NO 6
```

```
<211> LENGTH: 44
<212> TYPE: DNA
<213> ORGANISM: Artificial
<220> FEATURE:
<223> OTHER INFORMATION: Synthetic Construct

<400> SEQUENCE: 6
gcttaattaa ggaggacaca tatgcccgtc gtggcggatc gtcc              44

<210> SEQ ID NO 7
<211> LENGTH: 27
<212> TYPE: DNA
<213> ORGANISM: Artificial
<220> FEATURE:
<223> OTHER INFORMATION: Synthetic Construct

<400> SEQUENCE: 7
gcggatcctc gaatcaccgc caatatc                                 27

<210> SEQ ID NO 8
<211> LENGTH: 50
<212> TYPE: DNA
<213> ORGANISM: Artificial
<220> FEATURE:
<223> OTHER INFORMATION: Synthetic Construct

<400> SEQUENCE: 8
gcttaattaa ggaggacaca tatgaccgac cgagaaggcc agctcctgga        50

<210> SEQ ID NO 9
<211> LENGTH: 25
<212> TYPE: DNA
<213> ORGANISM: Artificial
<220> FEATURE:
<223> OTHER INFORMATION: Synthetic Construct

<400> SEQUENCE: 9
ggacctaggc gggatgccgg cgtct                                   25

<210> SEQ ID NO 10
<211> LENGTH: 38
<212> TYPE: DNA
<213> ORGANISM: Artificial
<220> FEATURE:
<223> OTHER INFORMATION: Synthetic Construct

<400> SEQUENCE: 10
aggcatgcat atgacccagg agcaagcgaa tcagagtg                     38

<210> SEQ ID NO 11
<211> LENGTH: 32
<212> TYPE: DNA
<213> ORGANISM: Artificial
<220> FEATURE:
<223> OTHER INFORMATION: Synthetic Construct

<400> SEQUENCE: 11
ccaagcttta tccagctttg gagggcttca ag                           32

<210> SEQ ID NO 12
<211> LENGTH: 43
<212> TYPE: DNA
<213> ORGANISM: Artificial
<220> FEATURE:
<223> OTHER INFORMATION: Synthetic Construct

<400> SEQUENCE: 12
```
gtaagcttag gaggacacat atgatgcaac tcgcgcgcgg gtg            43

<210> SEQ ID NO 13
<211> LENGTH: 29
<212> TYPE: DNA
<213> ORGANISM: Artificial
<220> FEATURE:
<223> OTHER INFORMATION: Synthetic Construct

<400> SEQUENCE: 13
gcctgcaggc tcaggcttgc gcagagcgt                            29

<210> SEQ ID NO 14
<211> LENGTH: 24
<212> TYPE: DNA
<213> ORGANISM: Artificial
<220> FEATURE:
<223> OTHER INFORMATION: Synthetic Construct

<400> SEQUENCE: 14
ccggtatcca ccgcgacaca cggc                                 24

<210> SEQ ID NO 15
<211> LENGTH: 27
<212> TYPE: DNA
<213> ORGANISM: Artificial
<220> FEATURE:
<223> OTHER INFORMATION: Synthetic Construct

<400> SEQUENCE: 15
gccagtcgtc ctcgctcgtg gccgttc                              27

<210> SEQ ID NO 16
<211> LENGTH: 59
<212> TYPE: DNA
<213> ORGANISM: Artificial
<220> FEATURE:
<223> OTHER INFORMATION: Synthetic Construct

<400> SEQUENCE: 16
aaaaacatat gcaccaccac caccaccaca tgacacagga gcaagcgaat cagagtgag   59

<210> SEQ ID NO 17
<211> LENGTH: 33
<212> TYPE: DNA
<213> ORGANISM: Artificial
<220> FEATURE:
<223> OTHER INFORMATION: Synthetic Construct

<400> SEQUENCE: 17
aaaaaggatc cttaatccag ctttggaggg ctt                       33

<210> SEQ ID NO 18
<211> LENGTH: 29
<212> TYPE: DNA
<213> ORGANISM: Artificial
<220> FEATURE:
<223> OTHER INFORMATION: Synthetic Construct

<400> SEQUENCE: 18
aaaaacatat gacacaggag caagcgaat                            29

<210> SEQ ID NO 19
<211> LENGTH: 59
<212> TYPE: DNA

<213> ORGANISM: Artificial
<220> FEATURE:
<223> OTHER INFORMATION: Synthetic Construct

<400> SEQUENCE: 19
aaaaaggatc cttagtggtg gtggtggtgg tgtccagctt tggagggctt caagatgac        59

<210> SEQ ID NO 20
<211> LENGTH: 7
<212> TYPE: PRT
<213> ORGANISM: Artificial
<220> FEATURE:
<223> OTHER INFORMATION: Synthetic Construct

<400> SEQUENCE: 20

Thr Ala Tyr Ser Ser Ser Leu
1               5

<210> SEQ ID NO 21
<211> LENGTH: 24
<212> TYPE: PRT
<213> ORGANISM: Artificial
<220> FEATURE:
<223> OTHER INFORMATION: Synthetic Construct

<400> SEQUENCE: 21

Cys Thr Ser Gly Thr Ser Lys Cys Ser Ser Thr Asx Cys Ala Cys Cys
1               5                   10                  15

Thr Ser Gly Cys Ser Thr Gly Cys
            20

<210> SEQ ID NO 22
<211> LENGTH: 24
<212> TYPE: PRT
<213> ORGANISM: Artificial
<220> FEATURE:
<223> OTHER INFORMATION: Synthetic Construct

<400> SEQUENCE: 22

Thr Gly Ala Tyr Arg Thr Gly Ser Gly Cys Gly Thr Thr Ser Gly Thr
1               5                   10                  15

Ser Cys Cys Gly Ser Trp Gly Ala
            20

<210> SEQ ID NO 23
<211> LENGTH: 292
<212> TYPE: DNA
<213> ORGANISM: Artificial
<220> FEATURE:
<223> OTHER INFORMATION: Synthetic Construct

<400> SEQUENCE: 23
tcctgggtct gcacggcccg acgctggcca tggatacggc gtgctcgtcc tccctggtcg        60
cgctgcacct cgcctgccag agcctgcgac tgggcgagtg cgatcaagcg ctggttggcg       120
gggtcaacgt gctgctcgcg ccggagacct cgtgctgct ctcacggatg cgcgcgcttt        180
cgcccgacgg gcggtgcaag acgttctcgg ccgacgcgga cggctacgcg cggggcgagg       240
ggtgcgccgt ggtggtgctc aagcggctgc gcaatgcgca gcgcgctcgg cg              292

<210> SEQ ID NO 24
<211> LENGTH: 96
<212> TYPE: PRT
<213> ORGANISM: Artificial
<220> FEATURE:

<223> OTHER INFORMATION: Synthetic Construct

<400> SEQUENCE: 24

Leu Gly Leu His Gly Pro Thr Leu Ala Met Asp Thr Ala Cys Ser Ser
1               5                   10                  15

Ser Leu Val Ala Leu His Leu Ala Cys Gln Ser Leu Arg Leu Gly Glu
            20                  25                  30

Cys Asp Gln Ala Leu Val Gly Gly Val Asn Val Leu Leu Ala Pro Glu
        35                  40                  45

Thr Phe Val Leu Leu Ser Arg Met Arg Ala Leu Ser Pro Asp Gly Arg
    50                  55                  60

Cys Lys Thr Phe Ser Ala Asp Ala Asp Gly Tyr Ala Arg Gly Glu Gly
65                  70                  75                  80

Cys Ala Val Val Val Leu Lys Arg Leu Arg Asn Ala Gln Arg Ala Arg
                85                  90                  95

<210> SEQ ID NO 25
<211> LENGTH: 435
<212> TYPE: DNA
<213> ORGANISM: Artificial
<220> FEATURE:
<223> OTHER INFORMATION: Synthetic Construct

<400> SEQUENCE: 25
catagatcgt aagctgtgct agtgatctgc cttacgttac gtcttccgca cctcgagcga     60
attctctcgg ataactttca agttttctga gggggcttgg tctctggttc ctcaggaagc    120
ctgatcggga cgagctaatt cccatccatt tttttgagac tctgctcaaa gggattagac    180
cgagtgagac agttcttttg cagtgagcga agaacctggg gctcgaccgg aggacgatcg    240
acgtccgcga gcgggtcagc cgctgaggat gtgcccgtcg tggcggatcg tcccatcgag    300
cgcgcagccg aagatccgat tgcgatcgtc ggagcgggct gccgtctgcc cggtggcgtg    360
atcgatctga gcgggttctg gacgctcctc gagggctcgc gcgacaccgt cgggcaagtc    420
cccgccgaac gctgg                                                    435

<210> SEQ ID NO 26
<211> LENGTH: 25
<212> TYPE: PRT
<213> ORGANISM: Artificial
<220> FEATURE:
<223> OTHER INFORMATION: Synthetic Construct

<400> SEQUENCE: 26

Ala Val Leu Val Ile Cys Leu Thr Leu Arg Leu Pro His Leu Glu Arg
1               5                   10                  15

Ile Leu Ser Asp Asn Phe Gln Val Phe
            20                  25

<210> SEQ ID NO 27
<211> LENGTH: 15
<212> TYPE: PRT
<213> ORGANISM: Artificial
<220> FEATURE:
<223> OTHER INFORMATION: Synthetic Construct

<400> SEQUENCE: 27

Gly Gly Leu Val Ser Gly Ser Gly Ser Leu Ile Gly Thr Ser
1               5                   10                  15

<210> SEQ ID NO 28

<211> LENGTH: 99
<212> TYPE: PRT
<213> ORGANISM: Artificial
<220> FEATURE:
<223> OTHER INFORMATION: Synthetic Construct

<400> SEQUENCE: 28

Phe Pro Ser Ile Phe Leu Arg Leu Cys Ser Lys Gly Leu Asp Arg Val
1               5                   10                  15

Arg Gln Phe Phe Cys Ser Glu Arg Thr Trp Gly Ser Thr Gly Gly
            20                  25                  30

Arg Ser Thr Ser Ala Ser Gly Ser Ala Ala Glu Asp Val Pro Val Val
        35                  40                  45

Ala Asp Arg Pro Ile Glu Arg Ala Ala Glu Asp Pro Ile Ala Ile Val
50                  55                  60

Gly Ala Gly Cys Arg Leu Pro Gly Gly Val Ile Asp Leu Ser Gly Phe
65                  70                  75                  80

Trp Thr Leu Leu Glu Gly Ser Arg Asp Thr Val Gly Gln Val Pro Ala
                85                  90                  95

Glu Arg Trp

<210> SEQ ID NO 29
<211> LENGTH: 366
<212> TYPE: DNA
<213> ORGANISM: Artificial
<220> FEATURE:
<223> OTHER INFORMATION: Synthetic Construct

<400> SEQUENCE: 29
gacgcgcgga ctttcctgca cggtgcttca tgcgtcggct gacgcctcca ccgtcgccga     60
gcaggtatcc gaagctgcca gtcgccgaaa cgactggcag ggagtcctct acctgtgggg    120
cctcgacgcc gtcgtcgatg ctggggcatc ggccgacgaa gtcagcgagg ctacccgccg    180
tgccaccgca cccgtccttg gctggttcg attcctgagc gctgcgcccc atcctcctcg     240
cttctgggtg gtgacccgcg gggcatgcac ggtgggcggc gagccagagg tctctctttg    300
ccaagcggcg ttgtggggcc tcgcgcgcgt cgtggcgctg agcatcccg ctgcctgtgg     360 gtggcc                                                              366

<210> SEQ ID NO 30
<211> LENGTH: 121
<212> TYPE: PRT
<213> ORGANISM: Artificial
<220> FEATURE:
<223> OTHER INFORMATION: Synthetic Construct

<400> SEQUENCE: 30

Thr Arg Gly Leu Ser Cys Thr Val Leu His Ala Ser Ala Asp Ala Ser
1               5                   10                  15

Thr Val Ala Glu Gln Val Ser Glu Ala Ala Ser Arg Arg Asn Asp Trp
            20                  25                  30

Gln Gly Val Leu Tyr Leu Trp Gly Leu Asp Ala Val Val Asp Ala Gly
        35                  40                  45

Ala Ser Ala Asp Glu Val Ser Glu Ala Thr Arg Ala Thr Ala Pro
50                  55                  60

Val Leu Gly Leu Val Arg Phe Leu Ser Ala Ala Pro His Pro Pro Arg
65                  70                  75                  80

Phe Trp Val Val Thr Arg Gly Ala Cys Thr Val Gly Gly Glu Pro Glu
                85                  90                  95

Val Ser Leu Cys Gln Ala Ala Leu Trp Gly Leu Ala Arg Val Val Ala
          100                 105                 110

Leu Glu His Pro Ala Ala Cys Gly Trp
        115                 120

<210> SEQ ID NO 31
<211> LENGTH: 455
<212> TYPE: DNA
<213> ORGANISM: Artificial
<220> FEATURE:
<223> OTHER INFORMATION: Synthetic Construct

<400> SEQUENCE: 31
cgtccagcct gcgcgatccg gcgcattggg cgcgttgatc gaacgagaga aggtgacggt    60
gtggaactcg gtgccggcgc tgatgcggat gctcgtcgag cattccgagg gtcgccccga   120
ttcgctcgct aggtctcctg cggctttcgc tgctgagcgg cgactggatc ccggtggggcc  180 tgcctggcga gctccaggcc atcaggcccg gcgtgtcggt gatcagcctg gcggggcca   240 ccgaagcgtc gatctggtcc atcgggtacc ccgtgaggaa cgtcgatcca tcgtgggcga   300
gcatccccta cggccgtccg ctgcgcaacc agacgttcca cgtgctcgat gaggcgctcg   360
aaccgcgccc ggtctgggtt ccggggcaac tctacattgg cggggtcgga ctggcactgg   420
gctactggcg cgatgaagag aagacgcgca cagct                              455

<210> SEQ ID NO 32
<211> LENGTH: 151
<212> TYPE: PRT
<213> ORGANISM: Artificial
<220> FEATURE:
<223> OTHER INFORMATION: Synthetic Construct

<400> SEQUENCE: 32

Val Gln Pro Ala Arg Ser Gly Ala Leu Gly Ala Leu Ile Glu Arg Glu
1               5                   10                  15

Lys Val Thr Val Trp Asn Ser Val Pro Ala Leu Met Arg Met Leu Val
            20                  25                  30

Glu His Ser Glu Gly Arg Pro Asp Ser Leu Ala Arg Ser Leu Arg Leu
        35                  40                  45

Ser Leu Leu Ser Gly Asp Trp Ile Pro Val Gly Leu Pro Gly Glu Leu
    50                  55                  60

Gln Ala Ile Arg Pro Gly Val Ser Val Ile Ser Leu Gly Gly Ala Thr
65                  70                  75                  80

Glu Ala Ser Ile Trp Ser Ile Gly Tyr Pro Val Arg Asn Val Asp Pro
                85                  90                  95

Ser Trp Ala Ser Ile Pro Tyr Gly Arg Pro Leu Arg Asn Gln Thr Phe
            100                 105                 110

His Val Leu Asp Glu Ala Leu Gly Pro Arg Pro Val Trp Val Pro Gly
        115                 120                 125

Gln Leu Tyr Ile Gly Gly Val Gly Leu Ala Leu Gly Tyr Trp Arg Asp
    130                 135                 140

Glu Glu Lys Thr Arg Thr Ala
145                 150

<210> SEQ ID NO 33
<211> LENGTH: 383
<212> TYPE: DNA
<213> ORGANISM: Artificial
<220> FEATURE:

```
<223> OTHER INFORMATION: Synthetic Construct

<400> SEQUENCE: 33
ggcccggtcg ggcctcattc caggtatcga gccgtgagga ggcaggtaga agctgggttc    60
ggcacgccac ggggcacgtg tgtagcgacc agagctcagc agtgggagcg ttgaaggaag   120
ctccgtggga gattcaacag cgatgtccga gcgtcctgtc gtcggaggcg ctctatccgc   180
tgctcaacga gcacgcctc gactatgcc cctgcttcca gggtgtggag caggtgtggc    240
tcggcacggg ggaggtgctg ggccgggtac gcttgccaga agacatggca tcctcaagtg   300
gcgcctatcg gattcatccc gccttgttgg atgcagtttt catagtgctg accgcgctgc   360
tcgaccacgc cggaatccat cgt                                           383

<210> SEQ ID NO 34
<211> LENGTH: 127
<212> TYPE: PRT
<213> ORGANISM: Artificial
<220> FEATURE:
<223> OTHER INFORMATION: Synthetic Construct

<400> SEQUENCE: 34

Pro Gly Arg Ala Ser Phe Gln Val Ser Ser Arg Glu Glu Ala Gly Arg
1               5                   10                  15

Ser Trp Val Arg His Ala Thr Gly His Val Cys Ser Asp Gln Ser Ser
            20                  25                  30

Ala Val Gly Ala Leu Lys Glu Ala Pro Trp Glu Ile Gln Gln Arg Cys
        35                  40                  45

Pro Ser Val Leu Ser Ser Glu Ala Leu Tyr Pro Leu Leu Asn Glu His
    50                  55                  60

Ala Leu Asp Tyr Gly Pro Cys Phe Gln Gly Val Glu Gln Val Trp Leu
65                  70                  75                  80

Gly Thr Gly Glu Val Leu Gly Arg Val Arg Leu Pro Glu Asp Met Ala
                85                  90                  95

Ser Ser Ser Gly Ala Tyr Arg Ile His Pro Ala Leu Leu Asp Ala Val
            100                 105                 110

Phe Ile Val Leu Thr Ala Leu Leu Asp His Ala Gly Ile His Arg
        115                 120                 125
```